United States Patent
Nakano et al.

(10) Patent No.: US 10,333,085 B2
(45) Date of Patent: Jun. 25, 2019

(54) POLYCYCLIC COMPOUND AND ORGANIC ELECTROLUMINESCENCE DEVICE INCLUDING THE SAME

(71) Applicant: SAMSUNG DISPLAY CO., LTD., Yongin-si, Gyeonggi-do (KR)

(72) Inventors: Hiromi Nakano, Yokohama (JP); Nobutaka Akashi, Yokohama (JP)

(73) Assignee: SAMSUNG DISPLAY CO., LTD., Yongin-si, Gyeonggi-Do (KR)

( * ) Notice: Subject to any disclaimer, the term of this patent is extended or adjusted under 35 U.S.C. 154(b) by 4 days.

(21) Appl. No.: 15/476,120

(22) Filed: Mar. 31, 2017

(65) Prior Publication Data
US 2018/0019415 A1    Jan. 18, 2018

(30) Foreign Application Priority Data
Jul. 13, 2016 (KR) .................. 10-2016-0088682

(51) Int. Cl.
*H01L 51/00* (2006.01)
*C07F 5/02* (2006.01)
(Continued)

(52) U.S. Cl.
CPC .......... *H01L 51/0094* (2013.01); *C07F 5/027* (2013.01); *C07F 7/0803* (2013.01);
(Continued)

(58) Field of Classification Search
None
See application file for complete search history.

(56) References Cited

FOREIGN PATENT DOCUMENTS
WO    2015072537    5/2015

OTHER PUBLICATIONS

Numata, et al., "High Efficiency Pure Blue Thermally Activated Delayed Fluorescence Molecules Having 10H-phenoxaborin and Acridan Units", Electronic Supplementary Material (ESI) for Chemcomm., The Royal Society of Chemistry 2015, pp. 1-37.

*Primary Examiner* — Jay Yang
(74) *Attorney, Agent, or Firm* — F. Chau & Associates, LLC

(57) ABSTRACT

Provided are a polycyclic compound and an organic electroluminescence device including the same. The polycyclic compound according to an exemplary embodiment of the present disclosure is represented by the following formula 1.

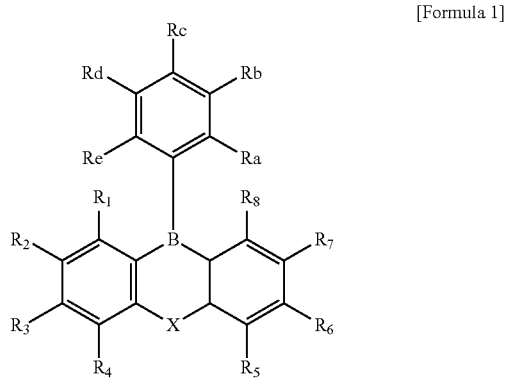

[Formula 1]

In Formula 1, X is O, SiR'R", S, or $BAr_1$. At least one of $R_1$ to $R_8$ is an aryl amine-containing electron donor. When X is O, SiR'R", or S, the aryl amine-containing electron donor further includes a Si.

23 Claims, 1 Drawing Sheet

(51) Int. Cl.
*C07F 7/08* (2006.01)
*C09K 11/06* (2006.01)
*H01L 51/50* (2006.01)
*H05B 33/14* (2006.01)

(52) U.S. Cl.
CPC ............ *C09K 11/06* (2013.01); *H01L 51/008* (2013.01); *H05B 33/14* (2013.01); *C09K 2211/104* (2013.01); *C09K 2211/1007* (2013.01); *C09K 2211/1029* (2013.01); *C09K 2211/1096* (2013.01); *H01L 51/5012* (2013.01)

POLYCYCLIC COMPOUND AND ORGANIC ELECTROLUMINESCENCE DEVICE INCLUDING THE SAME

CROSS-REFERENCE TO RELATED APPLICATIONS

This application claims priority under 35 U.S.C. § 119 to Korean Patent Application No. 10-2016-0088682, filed on Jul. 13, 2016, the entire content of which is hereby incorporated by reference.

TECHNICAL FIELD

The present disclosure relates to a polycyclic compound and an organic electroluminescence device including the same.

DISCUSSION OF RELATED ART

The development of an organic electroluminescence display as an image display is being actively conducted recently. The organic electroluminescence display is different from a liquid crystal display, and is a self-luminescent display capable of displaying images via the recombination of holes and electrons injected from a first electrode (anode) and a second electrode (cathode) in an emission layer and then the emission of light from a luminescent material which is an organic compound included in the emission layer.

The organic electroluminescence device may include, for example, a first electrode, a hole transport layer disposed on the first electrode, an emission layer disposed on the hole transport layer, an electron transport layer disposed on the emission layer, and a second electrode disposed on the electron transport layer. Holes injected from the first electrode move via the hole transport layer and are injected to the emission layer. Meanwhile, electrons injected from the second electrode move via the electron transport layer and are injected to the emission layer. The holes and the electrons injected to the emission layer recombine to produce excitons in the emission layer. The organic electroluminescence device may emit light when the excitons transit from an excited state to a ground state.

SUMMARY

The present disclosure provides a polycyclic compound and an organic electroluminescence device including the same. In detail, the present disclosure provides a polycyclic compound for emitting thermally activated delayed fluorescence, and an organic electroluminescence device including the same.

An exemplary embodiment of the present disclosure provides a polycyclic compound represented by the following Formula 1.

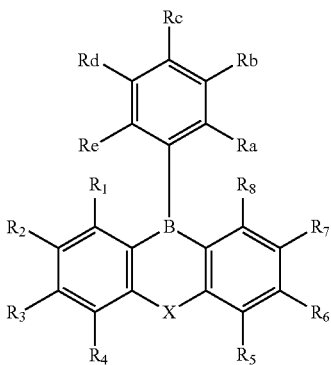

[Formula 1]

In Formula 1, X is O, SiR'R", S, or $BAr_1$; $Ar_1$ is substituted or unsubstituted aryl group having 6 to 30 carbon atoms for forming a ring, or substituted or unsubstituted heteroaryl group having 2 to 30 carbon atoms for forming a ring; R' and R" are each independently substituted or unsubstituted alkyl group having 1 to 30 carbon atoms, substituted or unsubstituted aryl group having 6 to 30 carbon atoms for forming a ring, or substituted or unsubstituted heteroaryl group having 2 to 30 carbon atoms for forming a ring, where R' and R" may optionally be combined with each other to form a ring; Ra to Re and $R_1$ to $R_8$ are each independently hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring; and when X is $BAR_1$, at least one of $R_1$ to $R_8$ is represented by one of the following Formulae 2 to 4, and when X is O, SiR'R", or S, at least one of $R_1$ to $R_8$ is represented by the following Formula 3 or 4.

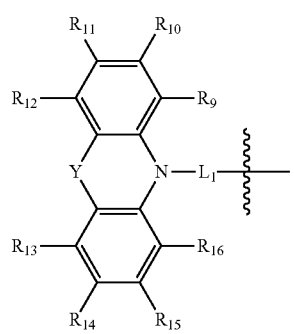

[Formula 2]

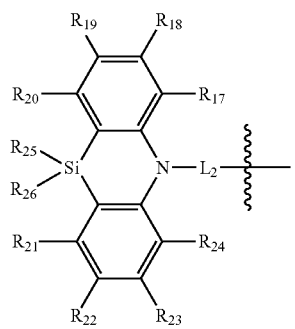

[Formula 3]

[Formula 4]

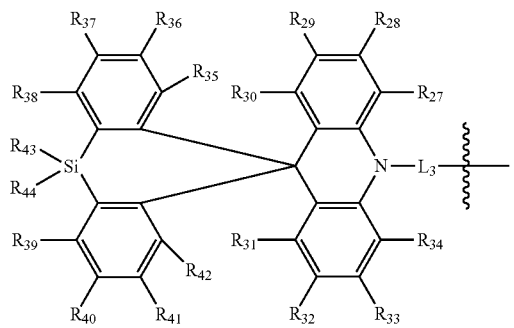

[Formula 3-1]

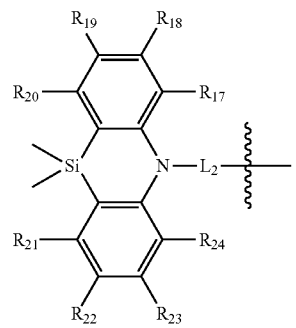

[Formula 3-2]

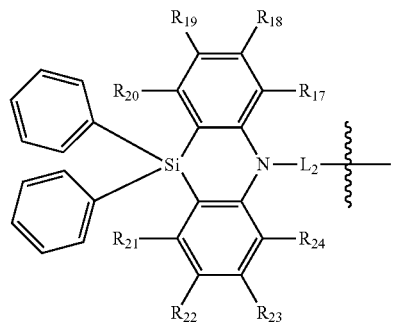

[Formula 3-3]

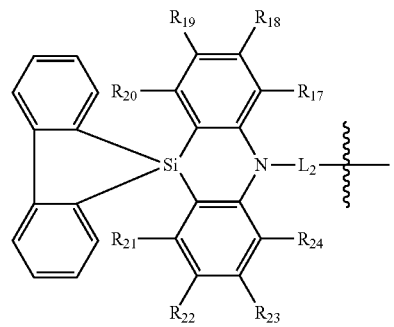

In Formulae 2 to 4, Y is a direct linkage, $CZ_1Z_2$, $NZ_3$, O, or S; $Z_1$ to $Z_3$ and $R_9$ to $R_{44}$ are each independently hydrogen atom, deuterium atom, halogen atom, cyano group, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring; optionally, $R_{25}$ and $R_{26}$, $R_{43}$ and $R_{44}$, and $Z_1$ and $Z_2$ may each two groups independently combine with each other to form a ring; and $L_1$ to $L_3$ are each independently a direct linkage, or substituted or unsubstituted arylene group having 6 to 30 carbon atoms for forming a ring.

In an exemplary embodiment of the present disclosure, Formula 1 may be represented by the following Formula 1-1.

[Formula 1-1]

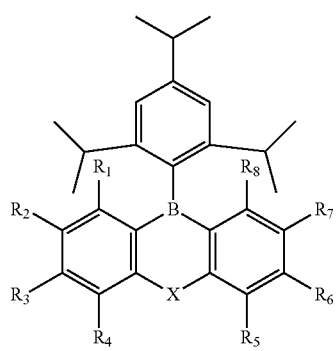

In Formula 1-1, X and $R_1$ to $R_8$ are as described above.

In an exemplary embodiment of the present disclosure, $L_1$ to $L_3$ may be each independently a direct linkage, or substituted or unsubstituted phenylene group.

In an exemplary embodiment of the present disclosure, Formula 3 may be represented by one of the following Formulae 3-1 to 3-4.

[Formula 3-4]

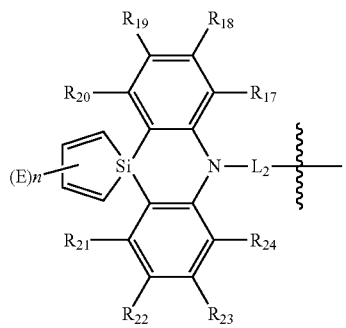

In Formulae 3-1 to 3-4, $L_2$, and $R_{17}$ to $R_{24}$ are as described above, E is hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, where E may optionally combine with an adjacent group to form a ring, and n is an integer of 0 to 4.

In an exemplary embodiment of the present disclosure, Formula 4 may be represented by one of the following Formulae 4-1 to 4-4.

[Formula 4-1]

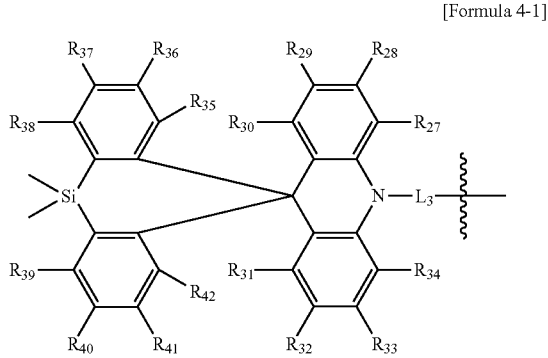

[Formula 4-2]

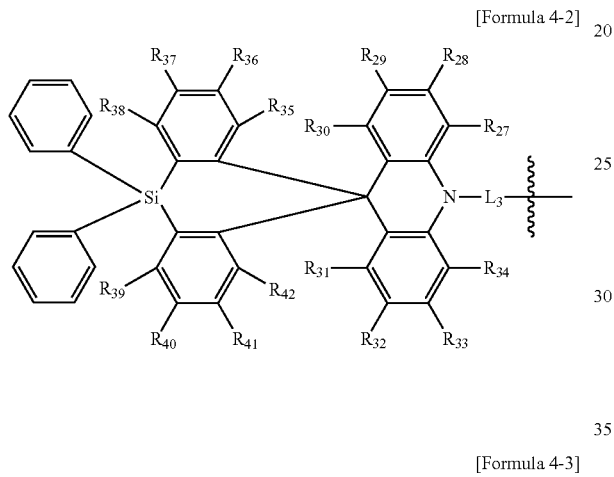

[Formula 4-3]

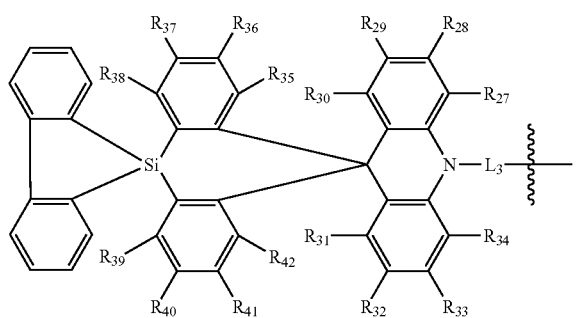

[Formula 4-4]

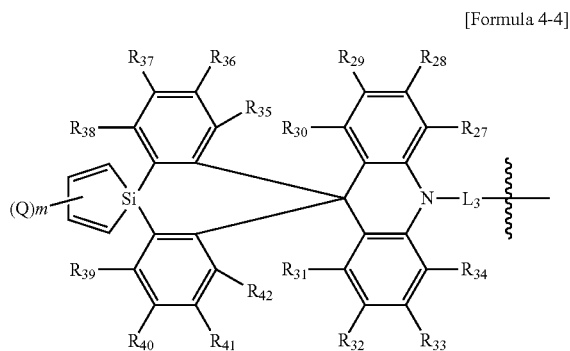

In Formulae 4-1 to 4-4, $L_3$, and $R_{27}$ to $R_{42}$ are as described above, Q is hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, where Q may optionally combine with an adjacent group to form a ring, and m is an integer of 0 to 4.

In an exemplary embodiment of the present disclosure, X may be $BAr_1$, and $Ar_1$ may be substituted or unsubstituted phenyl group.

In an exemplary embodiment of the present disclosure, Formula 1 may be represented by the following Formula 1-2.

[Formula 1-2]

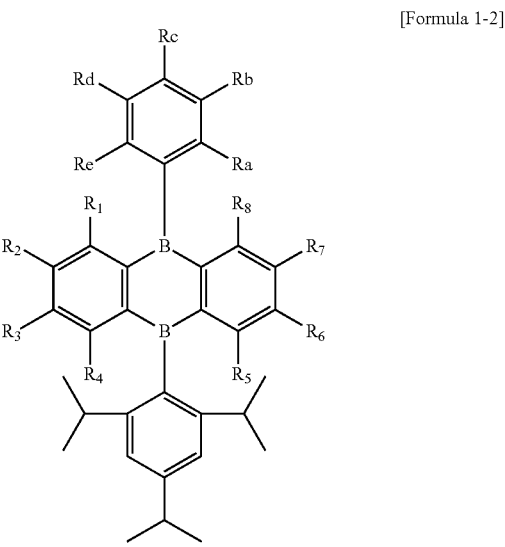

In Formula 1-2, Ra to Re, and $R_1$ to $R_8$ are as described above.

In an exemplary embodiment of the present disclosure, an organic electroluminescence device includes a first electrode, a hole transport region provided on the first electrode, an emission layer provided on the hole transport region, an electron transport region provided on the emission layer, and a second electrode provided on the electron transport region, wherein the emission layer includes the above-described polycyclic compound according to an exemplary embodiment of the present disclosure.

In an exemplary embodiment of the present disclosure, the polycyclic compound represented by Formula 1 and included in the emission layer may have an absolute value of about 0.2 eV or less energy gap between a singlet energy level and a triplet energy level.

In an exemplary embodiment of the present disclosure, the polycyclic compound represented by Formula 1 may be a material for emitting thermally activated delayed fluorescence.

In an exemplary embodiment of the present disclosure, an organic electroluminescence device includes a first electrode, a hole transport region provided on the first electrode, an emission layer provided on the hole transport region, an electron transport region provided on the emission layer, and a second electrode provided on the electron transport region, in which the emission layer includes a polycyclic compound represented by the following Formula 1.

[Formula 1]

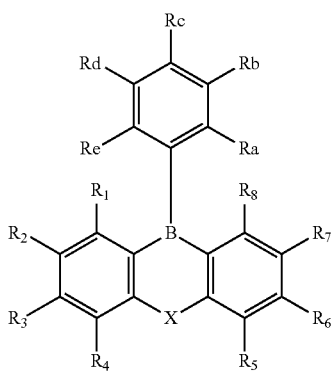

In Formula 1, X is O, SiR'R", S, or $BAr_1$; $Ar_1$ is substituted or unsubstituted aryl group having 6 to 30 carbon atoms for forming a ring, or substituted or unsubstituted heteroaryl group having 2 to 30 carbon atoms for forming a ring; R' and R" are each independently substituted or unsubstituted alkyl group having 1 to 30 carbon atoms, substituted or unsubstituted aryl group having 6 to 30 carbon atoms for forming a ring, or substituted or unsubstituted heteroaryl group having 2 to 30 carbon atoms for forming a ring, where R' and R" may optionally be combined with each other to form a ring; Ra to Re and $R_1$ to $R_8$ are each independently hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring; and at least one of $R_1$ to $R_8$ is represented by the following Formula 2.

[Formula 2]

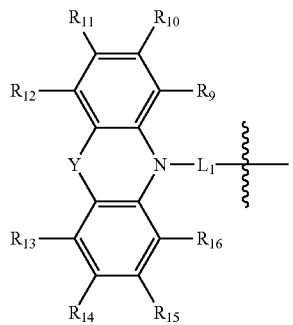

When X is $BAr_1$, in Formulae 2, Y is a direct linkage, $CZ_1Z_2$, $NZ_3$, $SiZ_4Z_5$, O, S or $CZ_6Z_7$ of which $Z_6$ and $Z_7$ combine with each other through Si to form a ring, and when X is O, SiR'R", or S, Y is $SiZ_4Z_5$, or $CZ_6Z_7$ of which $Z_6$ and $Z_7$ combine with each other through Si to form a ring; $Z_1$ to $Z_5$, and $R_9$ to $R_{16}$ are each independently hydrogen atom, deuterium atom, halogen atom, cyano group, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring; $Z_6$ and $Z_7$ are each independently substituted or unsubstituted phenyl group; optionally, $Z_1$ and $Z_2$, and $Z_4$ and $Z_5$ each two groups may independently combine with each other to form a ring; and $L_1$ is a direct linkage, or substituted or unsubstituted arylene group having 6 to 30 carbon atoms for forming a ring.

In an exemplary embodiment of the present disclosure, the polycyclic compound represented by Formula 1 may be a material for emitting thermally activated delayed fluorescence with wavelength from about 440 nm to about 460 nm.

BRIEF DESCRIPTION OF THE FIGURES

The accompanying drawings are included to provide a further understanding of the present disclosure, and are incorporated in and constitute a part of this specification. The drawings illustrate exemplary embodiments of the present disclosure and, together with the description, serve to explain principles of the present disclosure, in which.

Figure 1:
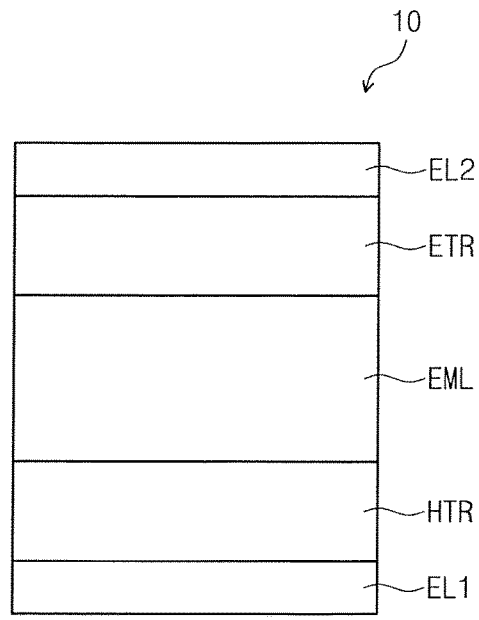
FIG. 1 is a cross-sectional view schematically illustrating an organic electroluminescence device according to an exemplary embodiment of the present disclosure.
Figure 2:
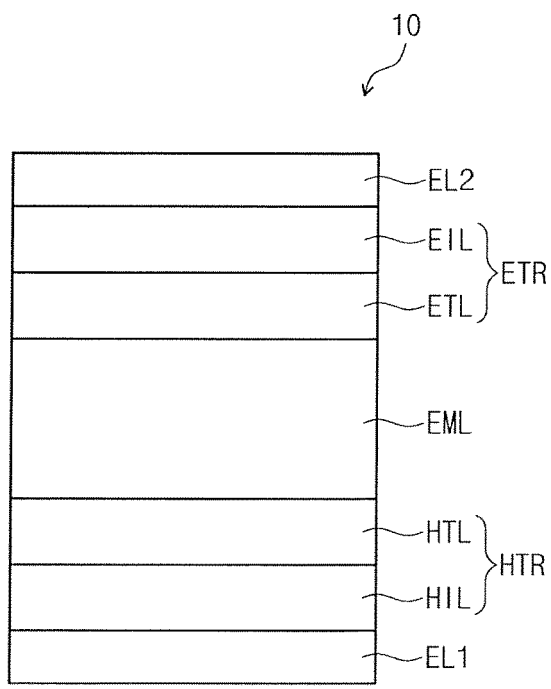
FIG. 2 is a cross-sectional view schematically illustrating an organic electroluminescence device according to an exemplary embodiment of the present disclosure.

Since the drawings in FIGS. 1-2 are intended for illustrative purposes, the elements in the drawings are not necessarily drawn to scale. For example, some of the elements may be enlarged or exaggerated for clarity purpose.

DETAILED DESCRIPTION OF THE EMBODIMENTS

The features of the present disclosure will be easily understood from preferred exemplary embodiments with reference to the accompanying drawings. The present disclosure may, however, be embodied in different forms and should not be construed as limited to the specific exemplary embodiments set forth herein. Rather, these exemplary embodiments are provided so that this disclosure will be thorough and complete, and will fully convey the scope of the present disclosure to those skilled in the art.

Like reference numerals refer to like elements for explaining each drawing. It will be understood that, although the terms "first", "second", etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprise" or "comprising", when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being 'on' another part, it can be directly on the other part, or intervening layers, films, regions, plates, etc. may also be present. On the contrary, when a layer, a film, a region, a plate, etc. is referred to as being 'under' another part, it can be directly under the other part, or intervening layers, films, regions, plates, etc. may also be present.

In the present disclosure,

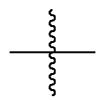

means a position to be connected.

In the present disclosure, "substituted or unsubstituted" may mean substituted with at least one substituent of deuterium atom, halogen atom, cyano, nitro, amino, silyl, boron, arylamine, phosphine oxide, phosphine sulfide, alkyl, alkenyl, aryl, and heteroaryl, or unsubstituted. In addition, each of the substituent illustrated above may be substituted or unsubstituted. For example, biphenyl may be interpreted as aryl, or phenyl substituted with phenyl.

In the present disclosure, the term "forming a ring by combining adjacent groups with each other" may mean forming a substituted or unsubstituted hydrocarbon ring, or substituted or unsubstituted heterocycle by combining adjacent groups with each other. The hydrocarbon ring may include an aliphatic hydrocarbon ring and an aromatic hydrocarbon ring. The heterocycle may include an aliphatic heterocycle and aromatic heterocycle. The hydrocarbon ring and heterocycle may be a monocycle or polycycle. In addition, the ring formed by combining adjacent groups may be connected with another ring to form a spiro structure.

In the present disclosure, the term "adjacent groups" may mean a substituent substituted with an atom directly connected with another atom substituted with a corresponding substituent, a different substituent substituted with an atom substituted with a corresponding substituent, or a substituent disposed stereoscopically at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, halogen may include a fluorine atom, a chlorine atom, a bromine atom, or an iodine atom.

In the present disclosure, the alkyl group may have a linear or branched chain or a cycle shape. The carbon number of the alkyl group may be 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group means an optional functional group or substituent derived from an aromatic hydrocarbon ring. The aryl group may be monocyclic aryl group or polycyclic aryl group. The carbon number of the aryl group for forming a ring may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc., without limitation.

In the present disclosure, the fluorenyl may be substituted, or two substituents may be combined to form a Spiro structure.

In the present disclosure, the heteroaryl group may be heteroaryl group including at least one of O, N, P, Si, and S as a heteroatom. The carbon number of the heteroaryl group for forming a ring may be 2 to 30, or 2 to 20. Examples of the heteroaryl group may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzofuranyl, etc., without limitation.

In the present disclosure, the explanation on the aryl group may be applied to the arylene group, except for the case where the arylene group is divalent.

In the present disclosure, the silyl may include alkyl silyl and aryl silyl. Examples of the silyl may include trimethylsilyl, triethylsilyl, t-butyl dimethylsilyl, vinyl dimethylsilyl, propyl dimethylsilyl, triphenylsilyl, diphenylsilyl, phenyl silyl, etc., without limitation.

In the present disclosure, the boron may include alkyl boron and aryl boron. Examples of the boron may include trimethyl boron, triethyl boron, t-butyl dimethyl boron, triphenyl boron, diphenyl boron, phenyl boron, etc., without limitation.

In the present disclosure, the alkenyl may be linear or branched. The carbon number is not specifically limited, however may be 2 to 30, 2 to 20, or 2 to 10. Examples of the alkenyl may include vinyl, 1-butenyl, 1-pentenyl, 1,3-butadienyl aryl, styrenyl, styrylvinyl, etc., without limitation.

In the present disclosure, the carbon number of the amine is not specifically limited, however may be 1 to 30. The amine may include alkylamine and arylamine. Examples of the amine may include methylamine, dimethylamine, phenylamine, diphenylamine, naphthylamine, 9-methyl-anthracenylamine, triphenylamine, etc., without limitation.

Hereinafter, the polycyclic compound according to an exemplary embodiment of the present disclosure will be explained.

The polycyclic compound according to an exemplary embodiment of the present disclosure is represented by the following Formula 1.

[Formula 1]

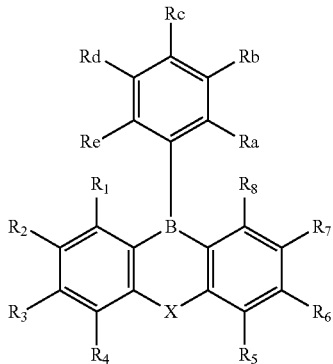

In Formula 1, X is O, SiR'R", S, or BAr₁, in which Ar₁ is substituted or unsubstituted aryl group having 6 to 30 carbon atoms for forming a ring, or substituted or unsubstituted heteroaryl group having 2 to 30 carbon atoms for forming a ring.

In Formula 1, Ra to Re and $R_1$ to $R_8$ are each independently hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring.

In Formula 1, R' and R" are each independently substituted or unsubstituted alkyl group having 1 to 30 carbon atoms, substituted or unsubstituted aryl group having 6 to 30 carbon atoms for forming a ring, or substituted or unsubstituted heteroaryl group having 2 to 30 carbon atoms for forming a ring, or R' and R" may be combined with each other to form a ring.

In Formula 1, R' and R" may be each independently methyl group, or substituted or unsubstituted phenyl group.

In Formula 1, R' and R" may combine with each other to form a fluorene ring.

In Formula 1, at least one of $R_1$ to $R_8$ is substituted with a substituent other than hydrogen atom. Particularly, when X is BAr₁, at least one of $R_1$ to $R_8$ is represented by one of the following Formulae 2 to 4, and when X is O, SiR'R", or S, at least one of $R_1$ to $R_8$ is represented by the following Formula 3 or 4.

[Formula 2]

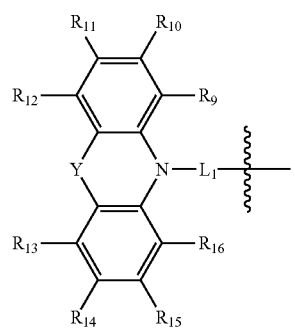

[Formula 3]

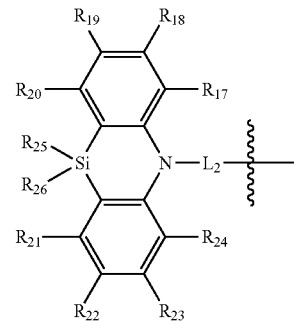

[Formula 4]

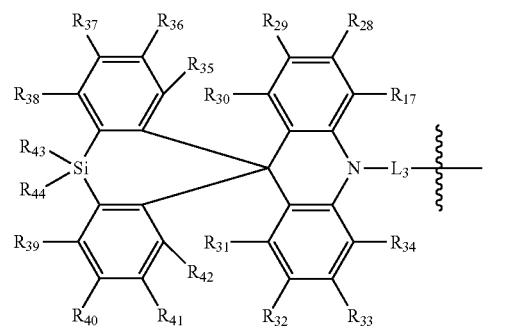

In Formulae 2, $R_9$ to $R_{16}$ are each independently hydrogen atom, deuterium atom, halogen atom, cyano group, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring.

In Formula 2, $L_1$ is a direct linkage, or substituted or unsubstituted arylene group having 6 to 30 carbon atoms for forming a ring.

In the present disclosure, the direct linkage may include a single bond.

In Formula 2, Y is a direct linkage, $CZ_1Z_2$, $NZ_3$, O, or S, in which $Z_1$ to $Z_3$ are each independently hydrogen atom, deuterium atom, halogen atom, cyano group, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring. $Z_1$ and $Z_2$ may be combined with each other to form a ring.

In Formula 3, $R_{17}$ to $R_{26}$ are each independently hydrogen, deuterium, halogen atom, cyano group, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring. $R_{25}$ and $R_{26}$ may combine with each other to form a ring.

In Formula 3, $L_2$ is a direct linkage, or substituted or unsubstituted arylene group having 6 to 30 carbon atoms for forming a ring.

Formula 3 may be a subgroup of Formula 2, if Y includes $SiZ_4Z_5$, in which $Z_4$ and $Z_5$ may include structures as defined for $Z_1$ and $Z_2$, respectively, more particularly as defined for $R_{25}$ and $R_{26}$, respectively.

In Formula 4, $R_{27}$ to $R_{44}$ are each independently hydrogen atom, deuterium atom, halogen atom, cyano group, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring. $R_{43}$ and $R_{44}$ may be combined with each other to form a ring.

In Formula 4, $L_3$ is a direct linkage, or substituted or unsubstituted arylene group having 6 to 30 carbon atoms for forming a ring.

Formula 4 may be a subgroup of Formula 2, if Y includes $CZ_6Z_7$, and $Z_6$ and $Z_7$ combine with each other through Si to form a ring, in which $Z_6$ and $Z_7$ are substituted or unsubstituted phenyl group, more particularly substituted or unsubstituted phenylene group. For example, Y may be represented by the following Formula 4-Y.

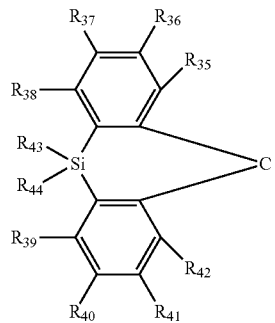

[Formula 4-Y]

The polycyclic compound according to an exemplary embodiment of the present disclosure includes an electron acceptor and an electron donor. Particularly, the polycyclic structure including a boron atom (B) of Formula 1 is an electron acceptor, and Formulae 2 to 4 are electron donors. Generally, the electron acceptor may contain an electron-accepting moiety such as, for example, aryl ketone, aryl sulfone, triazine, benzonitrile, oxadiazole, triazole, or aryl boron. The electron donor may contain aryl amines such as, for example, diphenylamine, triphenylamine, phenoxazine, carbazole, or acridan. For example, Formulae 2 to 4 contain aryl amines.

The polycyclic compound according to an exemplary embodiment of the present disclosure may further include a linker connecting an electron acceptor and an electron donor. The linker may be at least one of $L_1$ of Formula 2, $L_2$ of Formula 3, and $L_3$ of Formula 4.

The polycyclic compound according to an exemplary embodiment of the present disclosure may include one electron donor or a plurality of electron donors.

When X is $BAr_1$, one of $R_1$ to $R_8$ may be represented by one of Formulae 2 to 4. All the remainder of $R_1$ to $R_8$ may be hydrogen atom.

When X is $BAr_1$, two of $R_1$ to $R_8$ may be each independently represented by one of Formulae 2 to 4. The two may be the same or different. However, the present disclosure is not limited thereto. Three or four of $R_1$ to $R_8$ may be each independently represented by one of Formulae 2 to 4. All the remainder of $R_1$ to $R_8$ may be hydrogen atom.

Where X is O, SiR'R", or S, one of $R_1$ to $R_8$ may be represented by Formula 3 or 4. All the remainder of $R_1$ to $R_8$ may be hydrogen. Formulae 3 and 4 contain Si.

Where X is O, SiR'R", or S, two of $R_1$ to $R_8$ may be each independently represented by Formula 3 or 4. The two may be the same or different. However, the present disclosure is not limited thereto. Three or four of $R_1$ to $R_8$ may be each independently represented by one of Formula 3 or 4 if required. All the remainder of $R_1$ to $R_8$ may be hydrogen atom.

$R_3$ of Formula 1 may be represented by at least one of Formulae 2 to 4, and $R_6$ may be hydrogen atom or represented by one of Formulae 2 to 4. However, the present disclosure is not limited thereto. When $R_6$ is represented by one of Formulae 2 to 4, $R_3$ and $R_6$ may be the same.

In Formula 1, Ra to Re may be each independently hydrogen atom or substituted or unsubstituted alkyl group having 1 to 10 carbon atoms.

In Formula 1, Ra, Re and Re may be each independently substituted or unsubstituted alkyl group having 1 to 10 carbon atoms, and Rb and Rd may be hydrogen atom. For example, Formula 1 may be represented by the following Formula 1-1. By introducing a large-sized substituent such as isopropyl, the attack of oxygen, moisture, or nucleophile such as base to the boron atom (B) may be prevented.

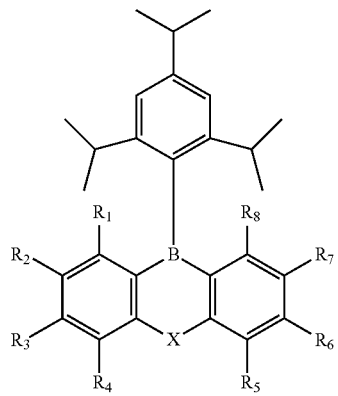

[Formula 1-1]

In Formula 1-1, X and $R_1$ to $R_8$ are the same as described above.

Formula 1 may be represented by Formula 1-1-a.

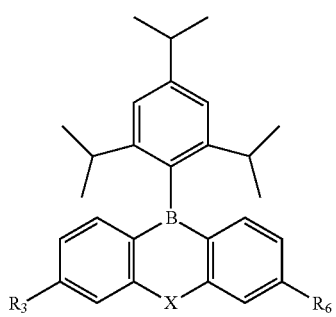

[Formula 1-1-a]

In Formula 1-1-a, when X is $BAr_1$, $R_3$ is represented by one of Formulae 2 to 4, and $R_6$ is a hydrogen atom or represented by one of Formulae 2 to 4. When $R_6$ is represented by one of Formulae 2 to 4, $R_3$ and $R_6$ may be the same, however the present disclosure is not limited thereto.

In Formula 1-1-a, when X is O, $SiR_9R_{10}$, or S, $R_3$ is represented by Formula 3 or 4, and $R_6$ is a hydrogen atom or is represented by Formula 3 or 4.

Formula 1-1-a is only an example, and the present disclosure is not limited thereto. For example, Formula 1 may be represented by Formula 1-1-b,

[Formula 1-1-b]

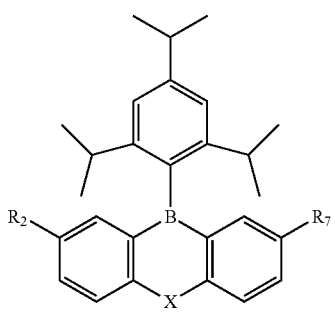

In Formula 1-1-b, when X is BAr$_1$, R$_2$ is represented by one of Formulae 2 to 4, and R$_7$ is a hydrogen atom or is represented by one of Formulae 2 to 4. When R$_7$ is represented by one of Formulae 2 to 4, R$_2$ and R$_7$ may be the same, however the present disclosure is not limited thereto.

In Formula 1-1-b, when X is O, SiR$_9$R$_{10}$, or S, R$_2$ is represented by Formula 3 or 4, and R$_7$ is a hydrogen atom or is represented by Formula 3 or 4.

In Formula 2, L$_1$ may be a direct linkage, or substituted or unsubstituted phenylene group. For example, in Formula 2, L$_1$ may be represented by one of the following structures.

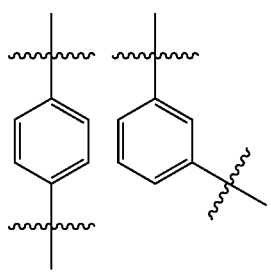

Formula 2 may be represented by one of the following Formulae 2-1 to 2-5.

[Formula 2-1]

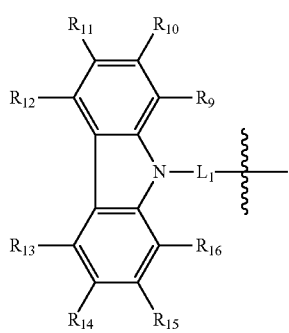

[Formula 2-2]

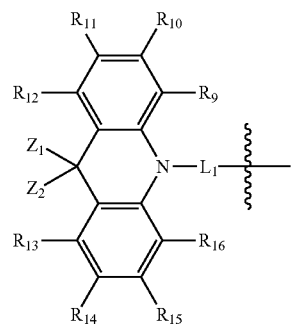

[Formula 2-3]

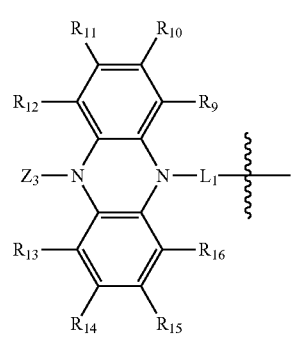

[Formula 2-4]

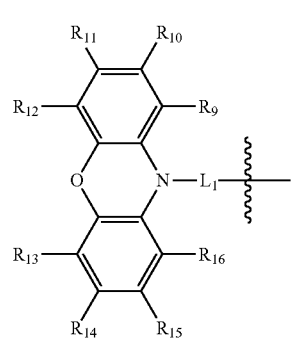

[Formula 2-5]

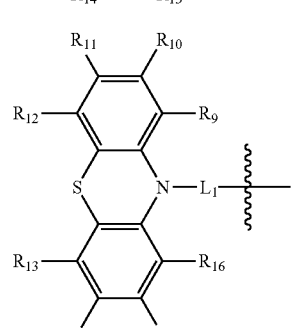

In Formulae 2-1 to 2-5, L$_1$, R$_9$ to R$_{16}$, and Z$_1$ to Z$_3$ are the same as described above.

In Formula 2-1, at least one of R$_9$ to R$_{16}$ may be substituted or unsubstituted heteroaryl group having 2 to 30 carbon atoms for forming a ring.

In Formula 2-1, at least one of R$_9$ to R$_{16}$ may be carbazole group.

In Formula 2-2, Z$_1$ and Z$_2$ are each independently substituted or unsubstituted alkyl group having 1 to 10 carbon atoms, or substituted or unsubstituted aryl group having 6 to 30 carbon atoms for forming a ring. For example, in Formula 2-2, Z$_1$ and Z$_2$ may be each independently methyl group, or may be each independently phenyl group.

In Formula 2-2, $Z_1$ and $Z_2$ may be combined with each other to form a ring as described above. For example, in Formula 2-2, $Z_1$ and $Z_2$ may be combined with each other to form a substituted or unsubstituted hydrocarbon ring, or a substituted or unsubstituted heterocycle. For example, Formula 2-2 may be represented by one of the following Formulae 2-2-1 to 2-2-4.

[Formula 2-2-1]

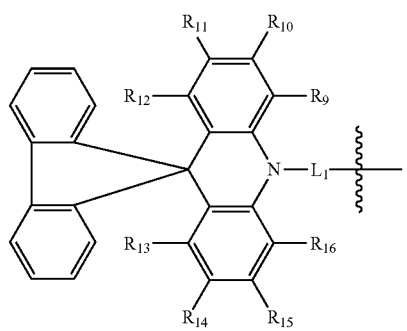

[Formula 2-2-2]

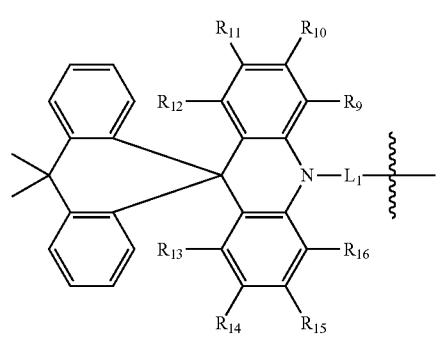

[Formula 2-2-3]

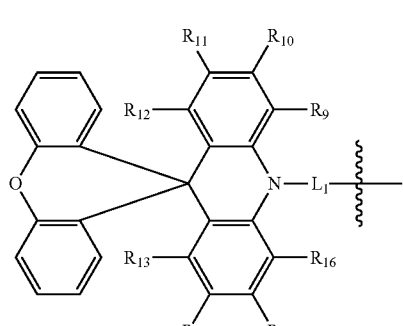

[Formula 2-2-4]

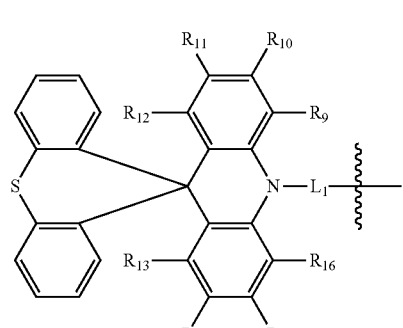

In Formula 2-2, $Z_1$ and $Z_2$ may be combined with each other to form a substituted or unsubstituted heterocycle with Si as the hetero atom, thus a structure represented by Formula 4 may be obtained. For example, $Z_1$ and $Z_2$ are defined as $Z_6$ and $Z_7$ which are substituted or unsubstituted phenyl group, more particularly substituted or unsubstituted phenylene group.

In Formula 2-3, $Z_3$ may be substituted or unsubstituted aryl group having 6 to 30 carbon atoms for forming a ring. For example, in Formula 2-3, $Z_3$ may be substituted or unsubstituted phenyl group.

In Formula 3, $L_2$ may be a direct linkage or substituted or unsubstituted phenylene group. For example, in Formula 3, $L_2$ may be represented by one of the following structures.

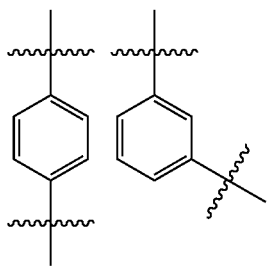

Formula 3 may be represented by one of the following Formulae 3-1 to 3-4.

[Formula 3-1]

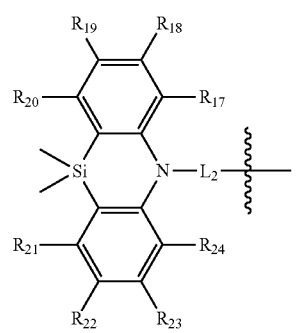

[Formula 3-2]

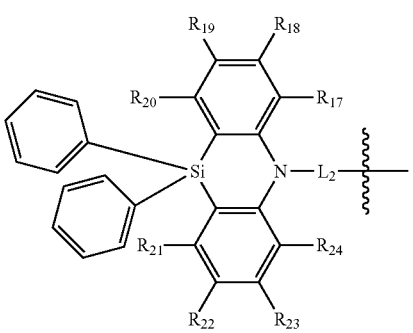

[Formula 3-3]

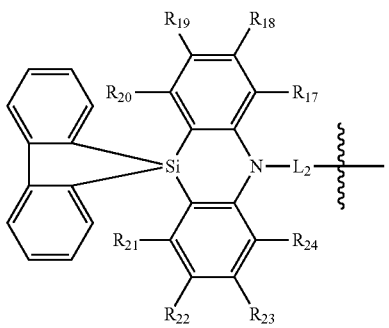

[Formula 3-4]

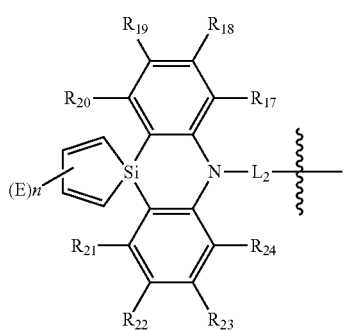

In Formulae 3-1 to 3-4, $L_2$ and $R_{17}$ to $R_{24}$ are the same as described above.

In Formula 3-2, at least one of $R_{17}$ to $R_{24}$ may be substituted or unsubstituted alkyl group having 1 to 10 carbon atoms. For example, in Formula 3-2, at least one of $R_{17}$ to $R_{24}$ may be methyl group.

In Formula 3-3, at least one of $R_{17}$ to $R_{24}$ may be substituted or unsubstituted alkyl group having 1 to 10 carbon atoms. For example, in Formula 3-3, at least one of $R_{17}$ to $R_{24}$ may be methyl group.

In Formula 3-4, E is hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, where E may combine with an adjacent group to form a ring, and n is an integer of 0 to 4.

In Formula 3-4, when n is 2 or more, a plurality of E may be the same or different.

In Formula 3-4, when n is 2 or more, adjacent two Es may combine with each other to form a ring. For example, Formula 3-4 may be represented by the following Formula 3-4-1.

[Formula 3-4-1]

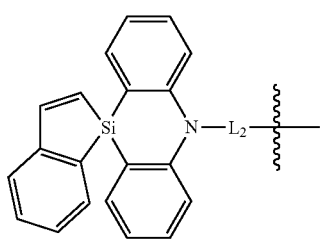

In Formula 3-4, E is hydrogen atom, substituted or unsubstituted alkyl group having 1 to 10 carbon atoms, or substituted or unsubstituted aryl group having 6 to 30 carbon atoms.

In Formula 3-4, n may be 4, and four Es may be the same. However, the present disclosure is not limited thereto. For example, n may be 0.

In Formula 4, $L_3$ may be a direct linkage or substituted or unsubstituted phenylene group. For example, in Formula 4, $L_3$ may be represented by one of the following structures.

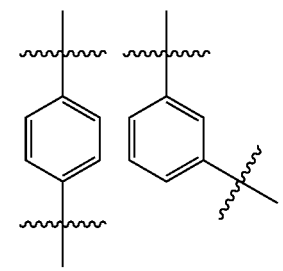

Formula 4 may be represented by one of the following Formulae 4-1 to 4-4.

[Formula 4-1]

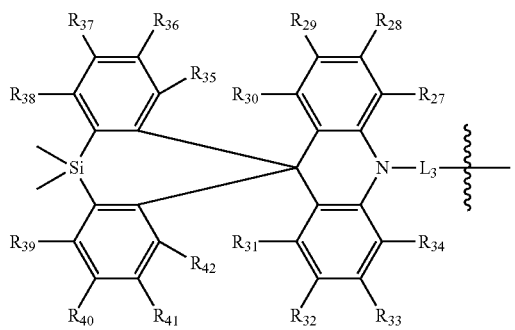

[Formula 4-2]

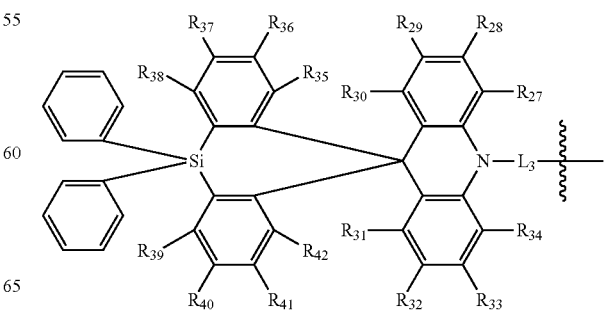

-continued

[Formula 4-3]

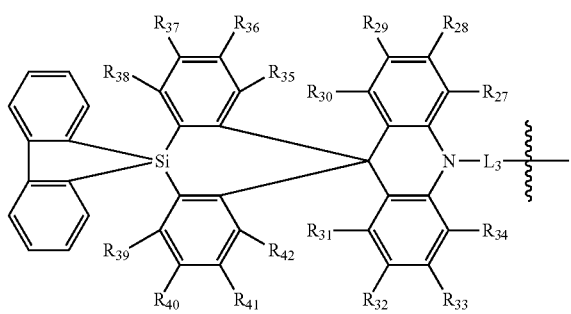

[Formula 4-4]

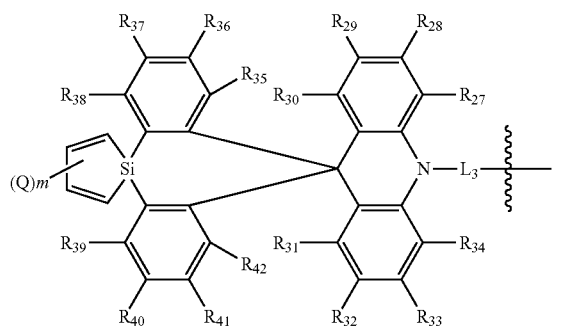

In Formulae 4-1 to 4-4, $L_3$ and $R_{27}$ to $R_{42}$ are the same as described above.

In Formula 4-4, Q is hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, where Q may combine with an adjacent group to form a ring, and m is an integer of 0 to 4.

In Formula 4-4, when m is 2 or more, a plurality of Q is the same or different.

In Formula 4-4, Q may be hydrogen atom, or substituted or unsubstituted alkyl group having 1 to 10 carbon atoms.

In Formula 4-4, m may be 4, and four Qs may be the same. However, the present disclosure is not limited thereto. For example, m may be 0.

In Formula 1, X may be $BAr_1$, and $Ar_1$ may be substituted or unsubstituted phenyl group.

In Formula 1, X may be $BAr_1$, and $Ar_1$ may be phenyl group substituted with at least one alkyl group having 1 to 10 carbon atoms.

Formula 1 may be represented by the following Formula 1-2.

[Formula 1-2]

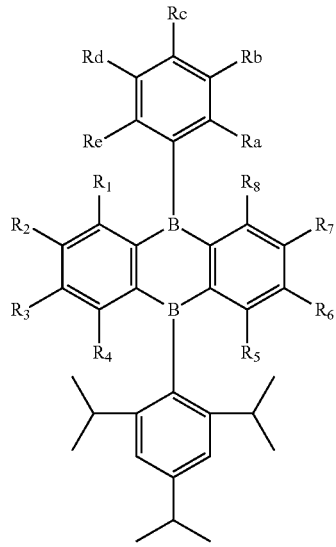

In Formula 1-2, Ra to Re and $R_1$ to $R_8$ are the same as described above.

Formula 1 may be represented by the following Formula 1-2-a.

[Formula 1-2-a]

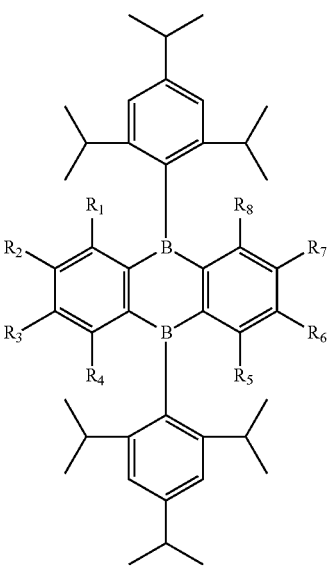

In Formula 1-2-a, $R_1$ to $R_8$ are the same as described above.

In Formula 1-2-a, $R_3$ is represented by one of Formulae 2 to 4, $R_6$ is hydrogen atom or is represented by one of Formulae 2 to 4, and $R_1$, $R_2$, $R_4$, $R_5$, $R_7$ and $R_8$ may be each independently hydrogen atom.

Formula 1 may be represented by t e following 1-2-b.
[Formula 1-2-b]
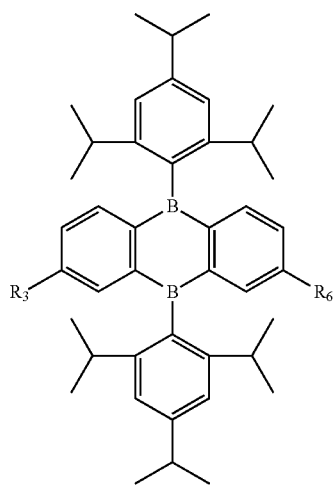
In Formula 1-2-b, $R_3$ is represented by one of Formulae 2 to 4, and $R_6$ is hydrogen atom or is represented by one of Formulae 2 to 4.
The polycyclic compound represented by Formula 1 may be at least one of the following compounds represented in the following Compound Group 1.
[Compound Group 1]
1
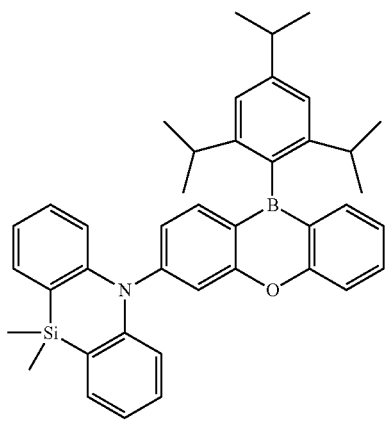
2
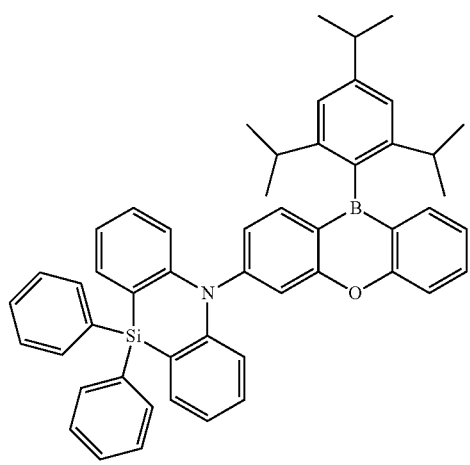
3
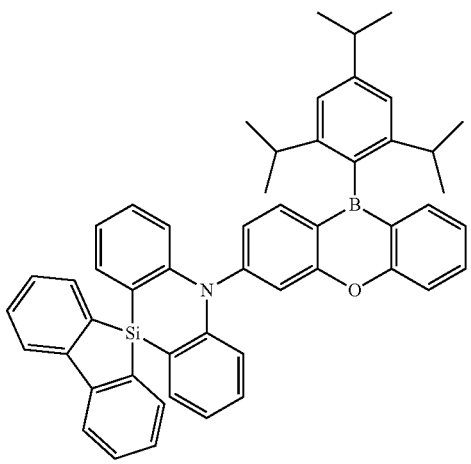
4
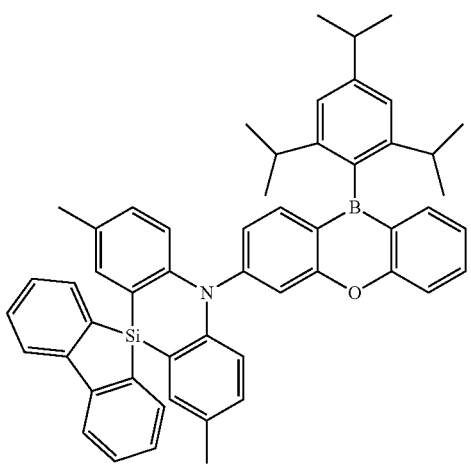
5
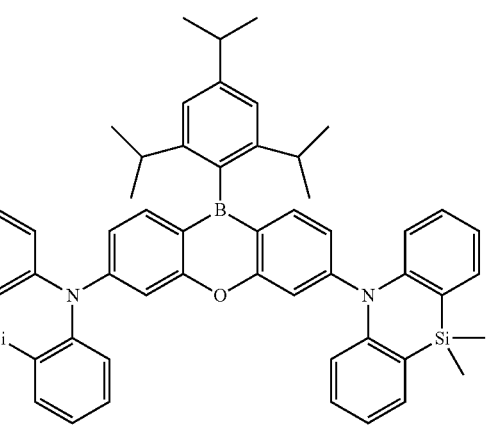

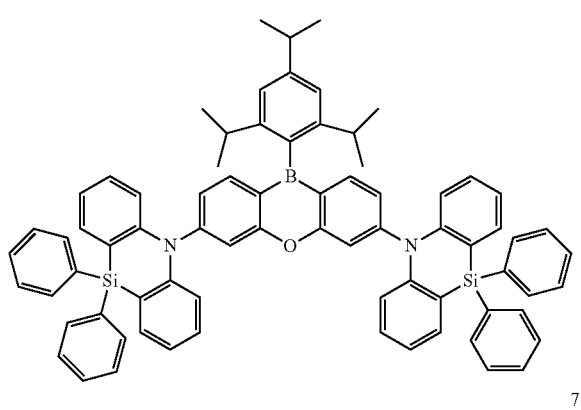
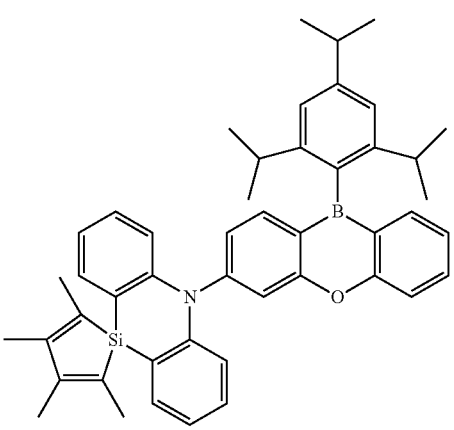
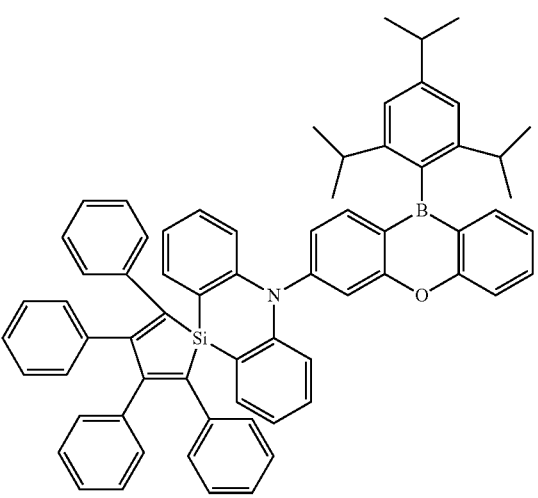
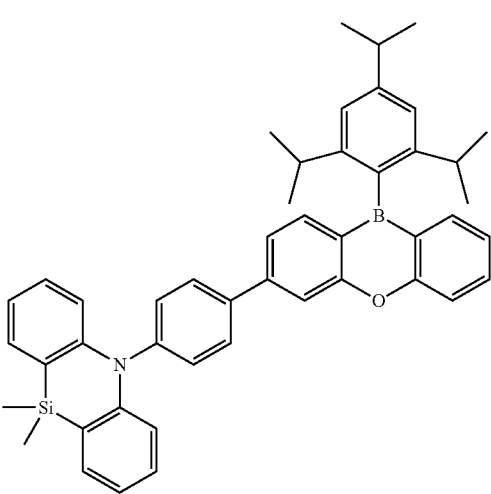

13
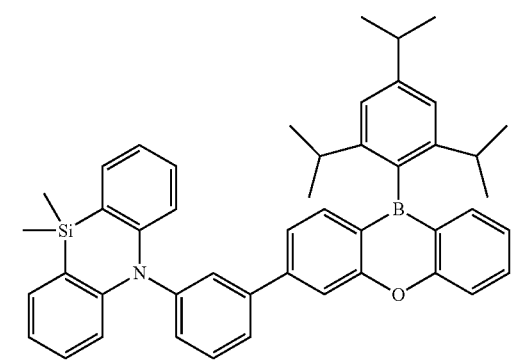
14
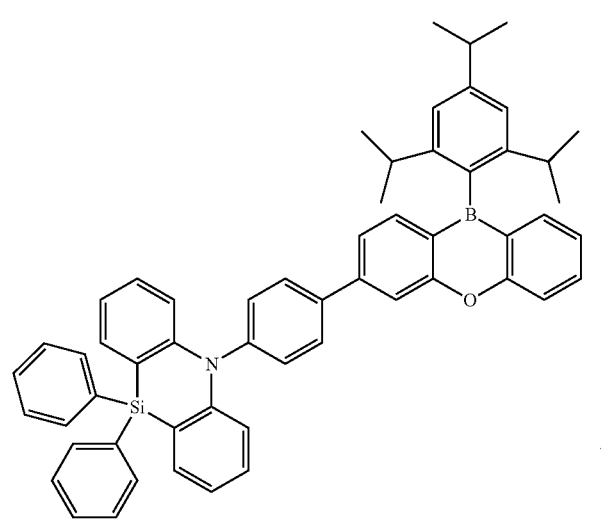
15
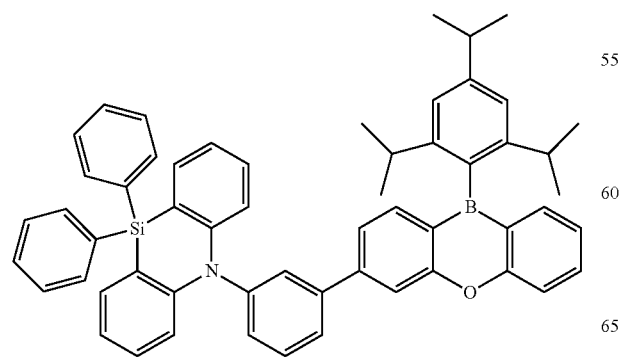
16
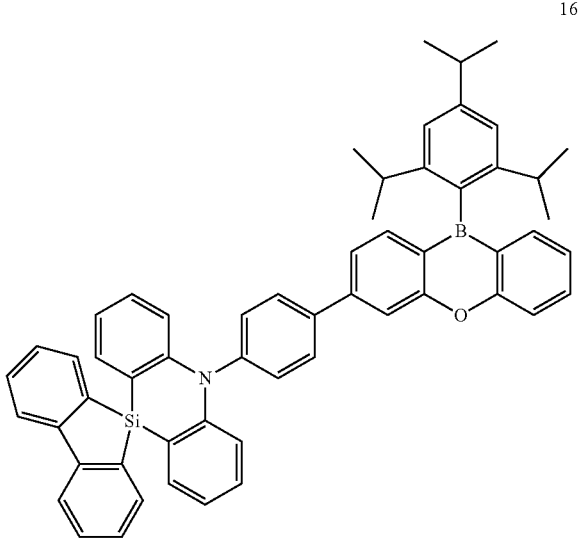
17
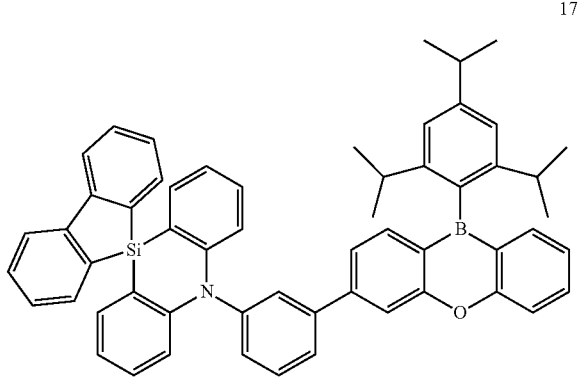
18

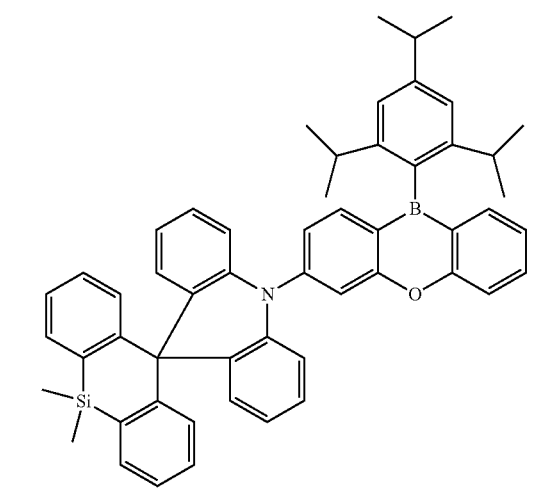
19
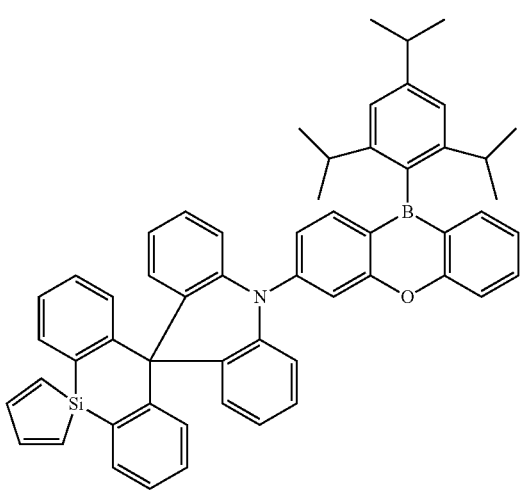
22
20
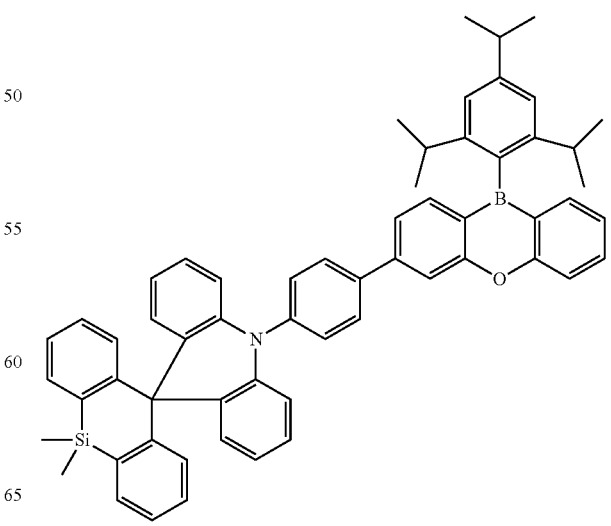
23
21
24

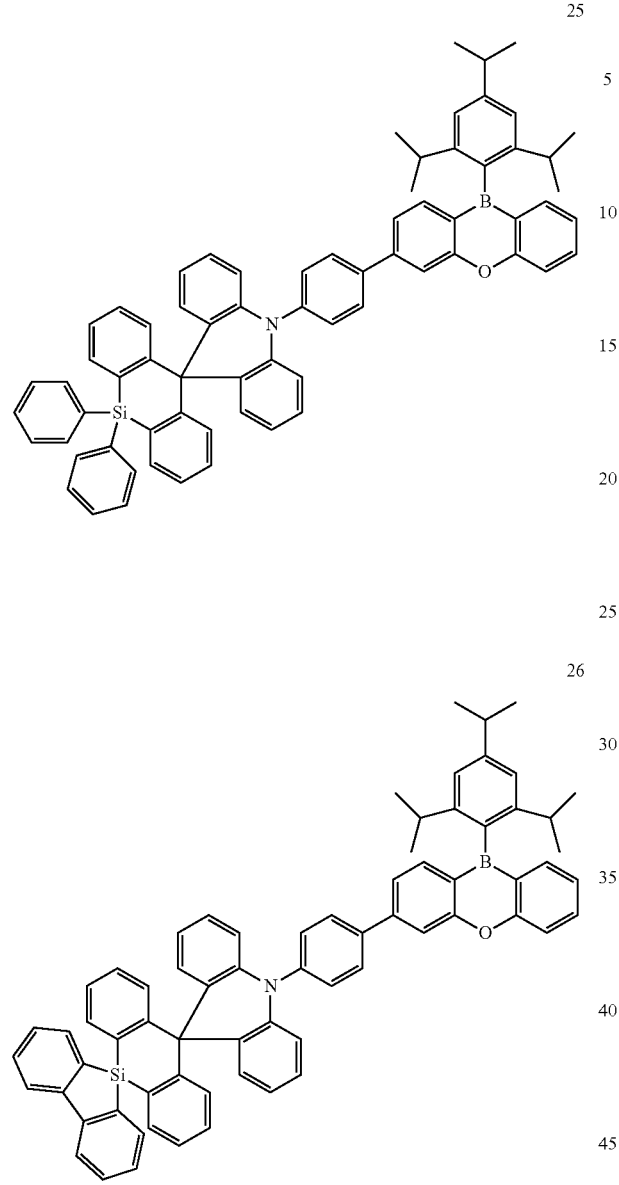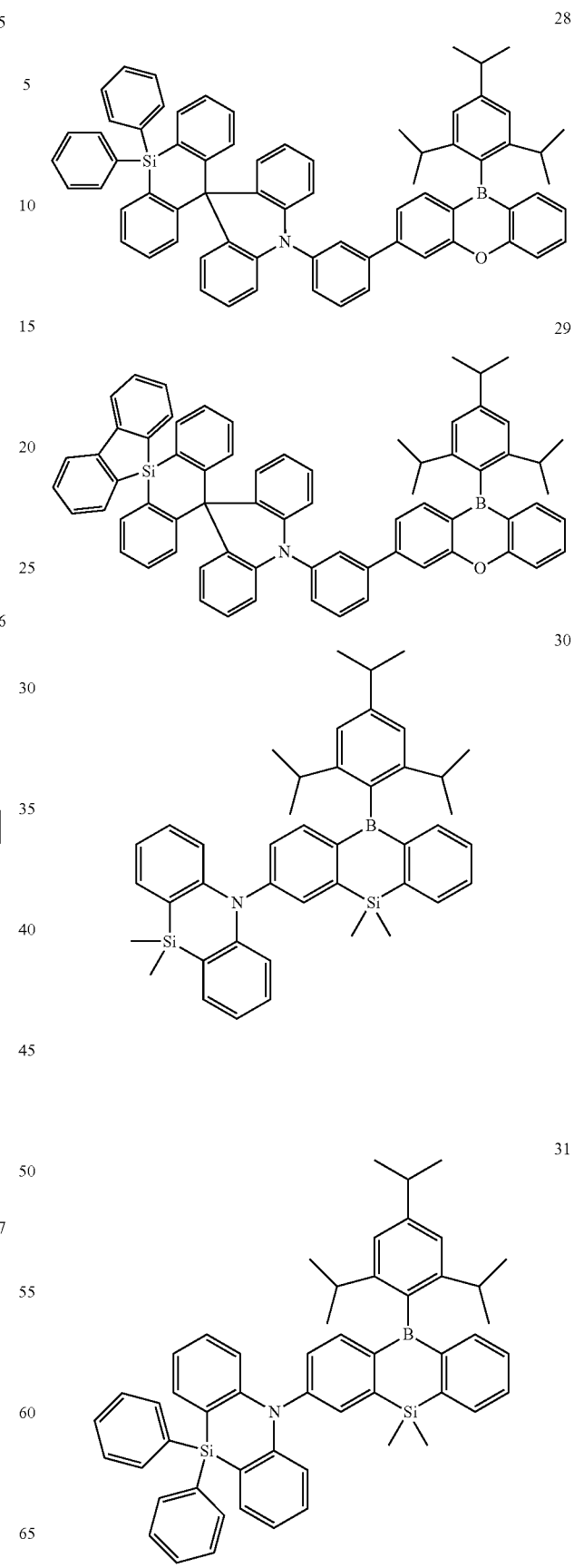

32
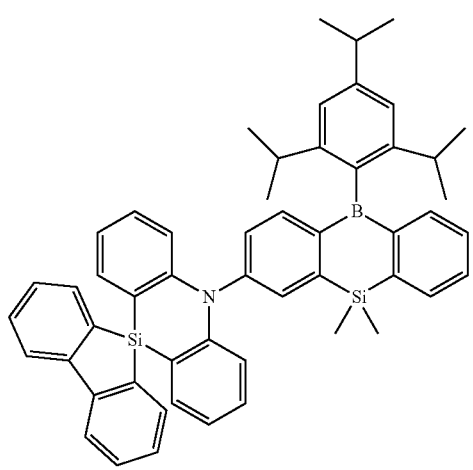
33
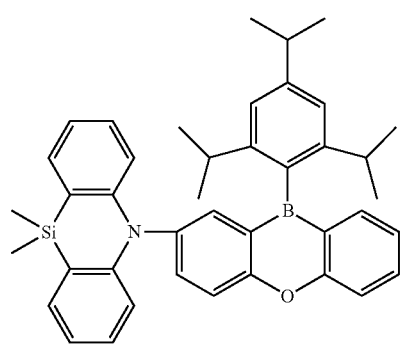
34
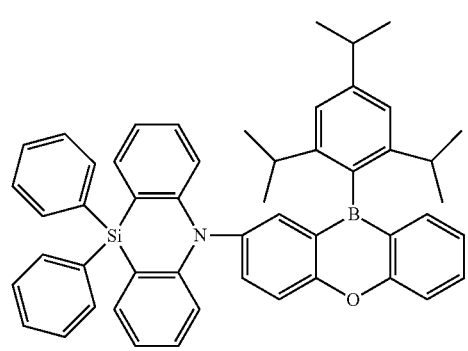
35
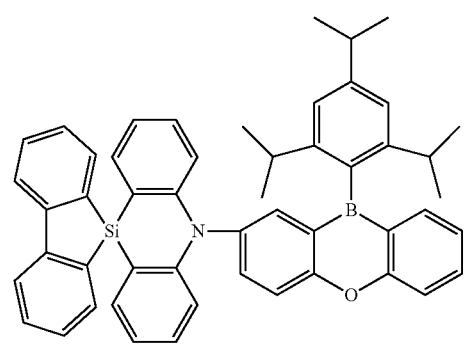
36
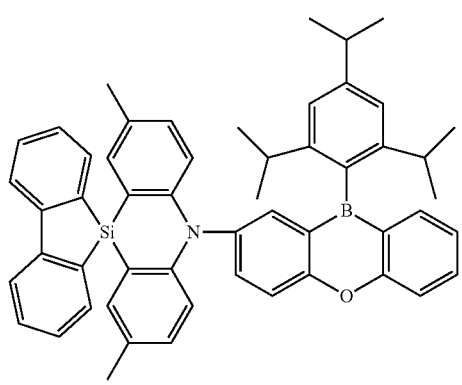
37
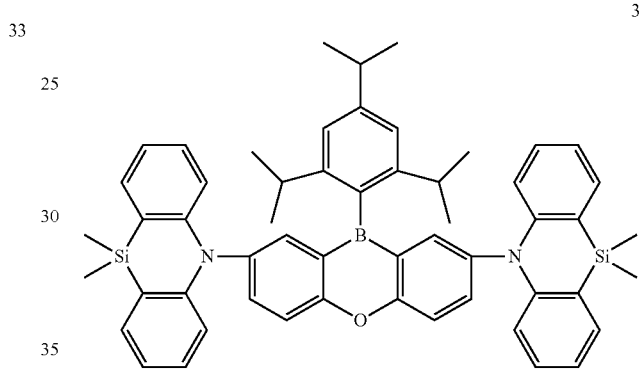
38
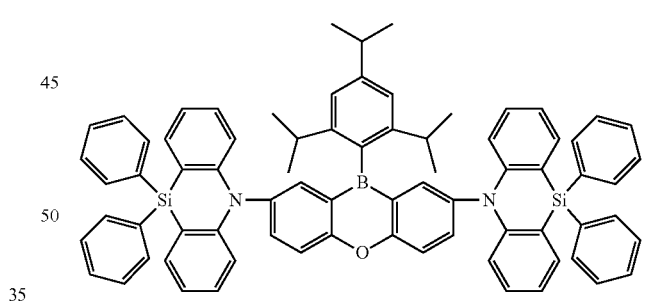
39
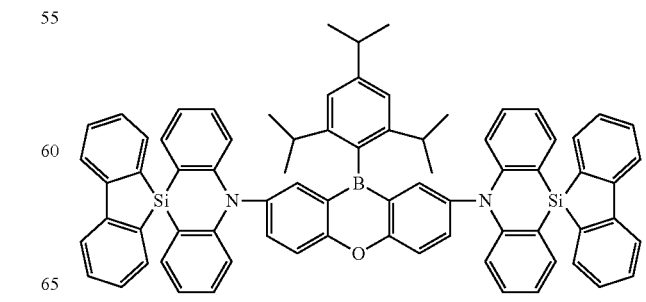

-continued
40
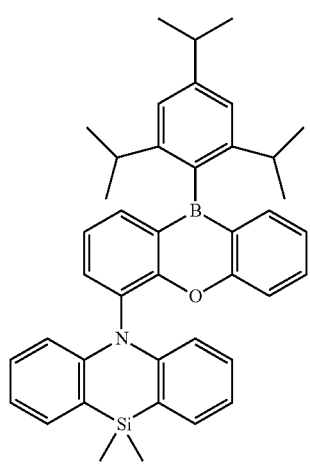
41
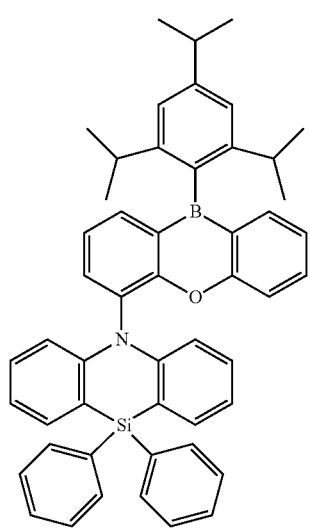
42
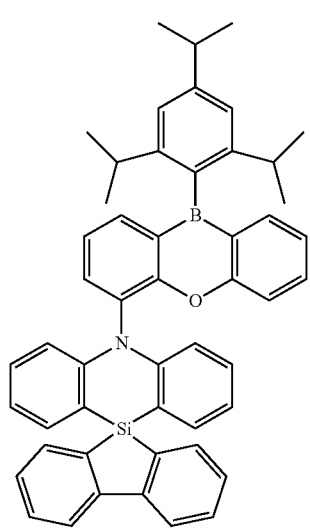
-continued
43
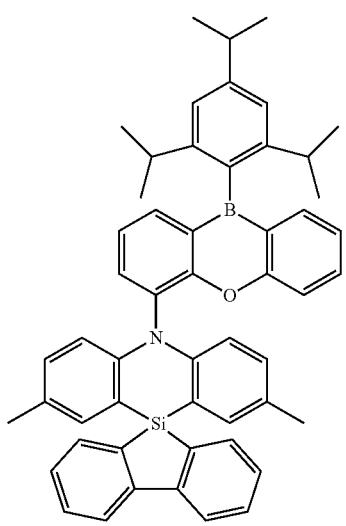
44
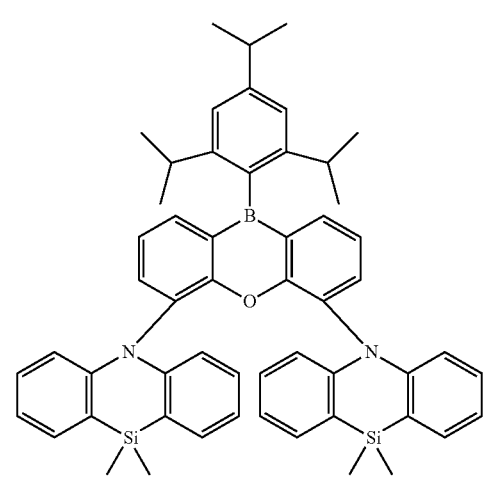
45
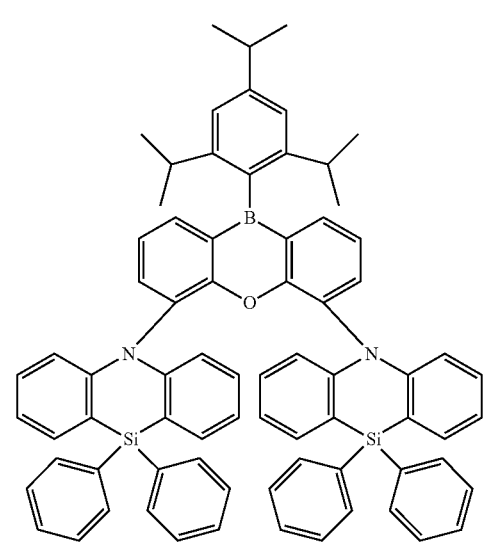

46
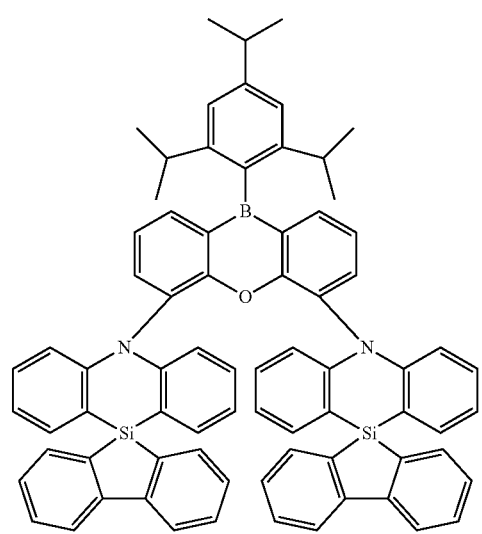
47
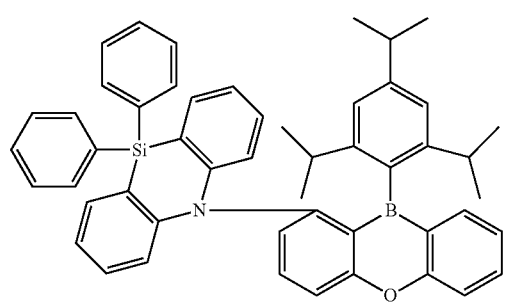
48
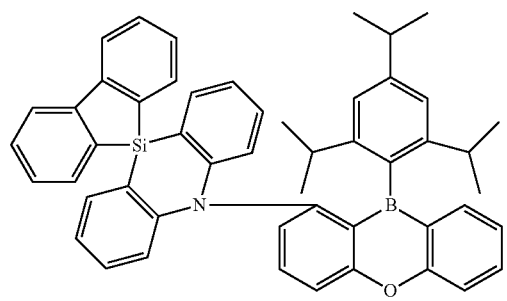
50
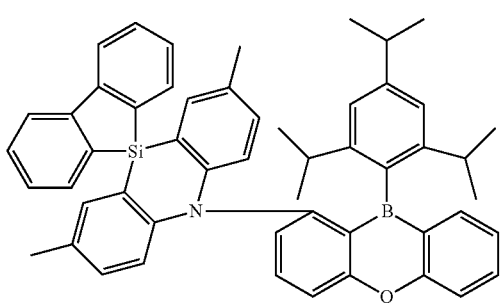
51
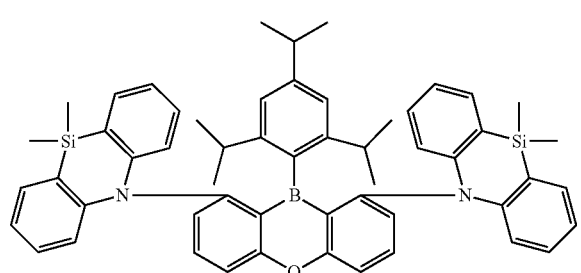
52
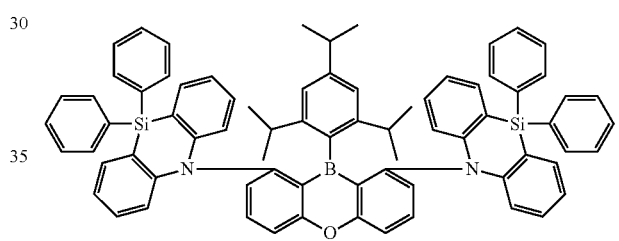
53
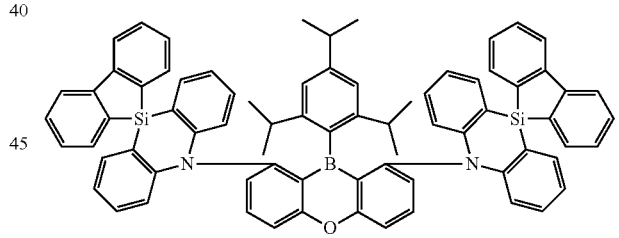
54
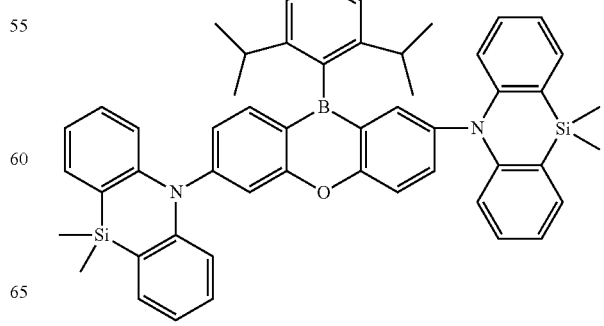

55
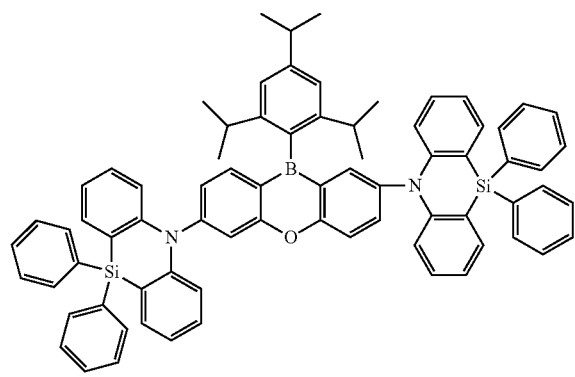
56
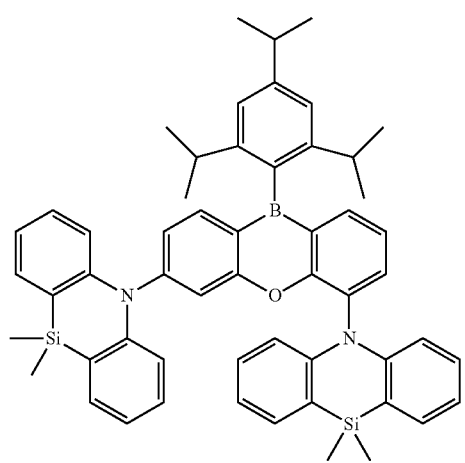
57
58
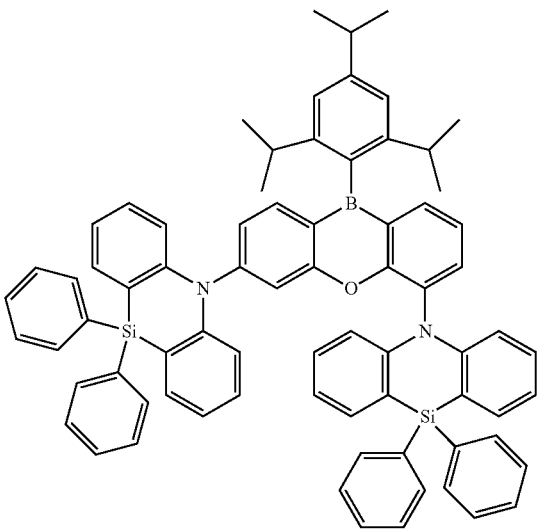
59
60
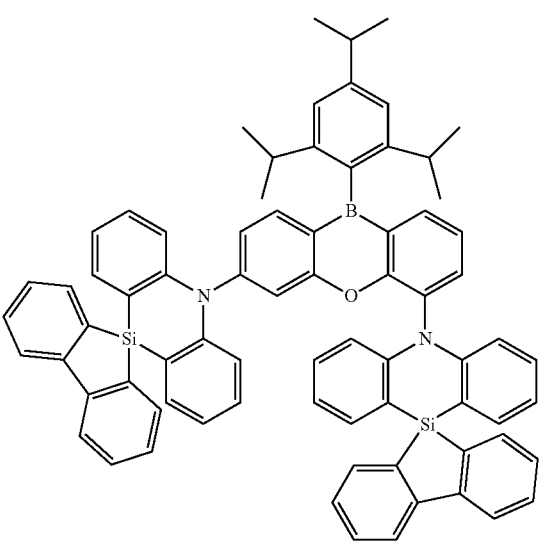

61
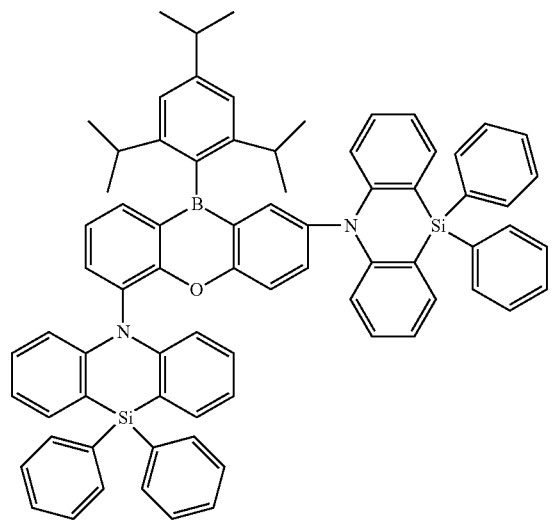
62
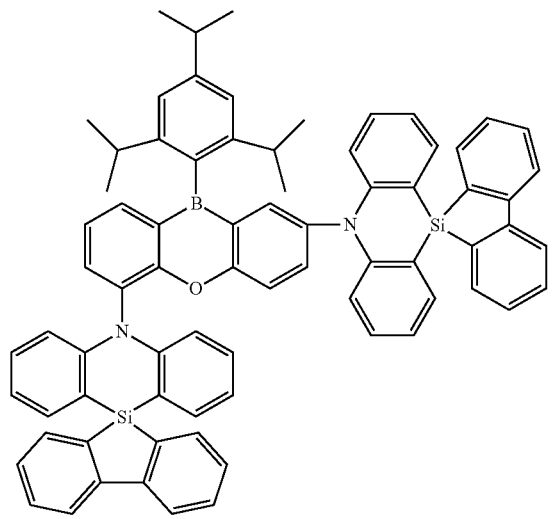
The polycyclic compound represented by Formula 1 may be at least one of the following compounds represented in the following Compound Group 2.
[Compound Group 2]
63
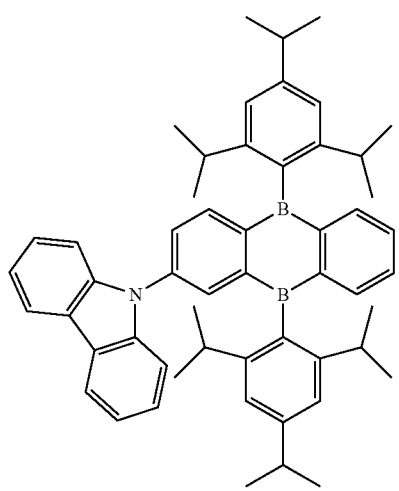
64
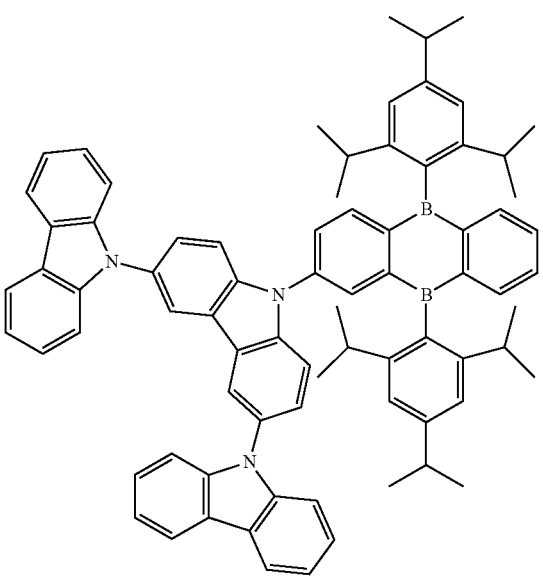

-continued
65
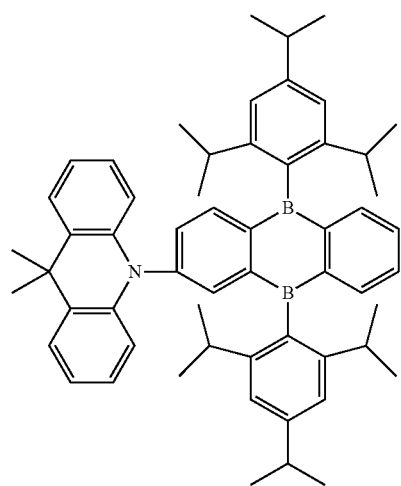
66
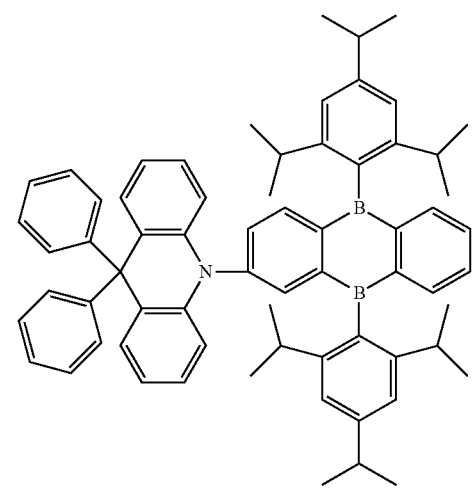
67
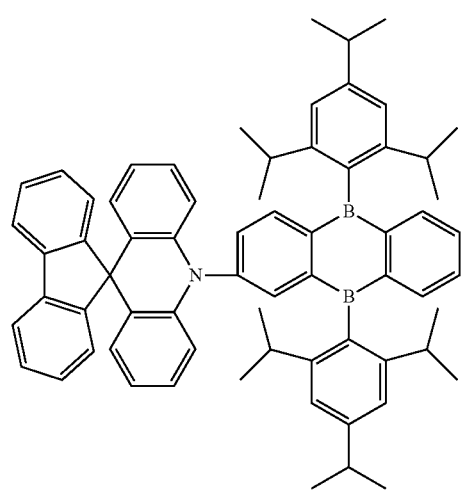
68
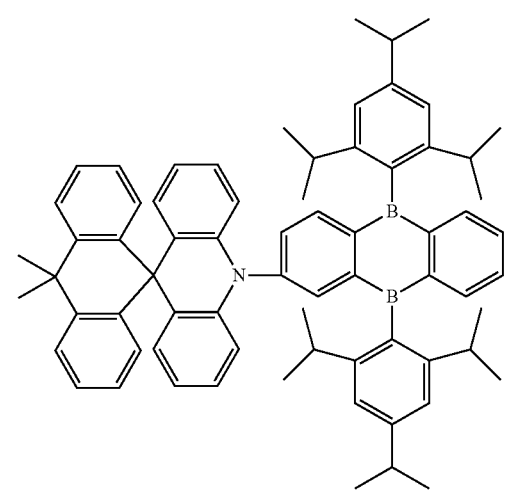
69
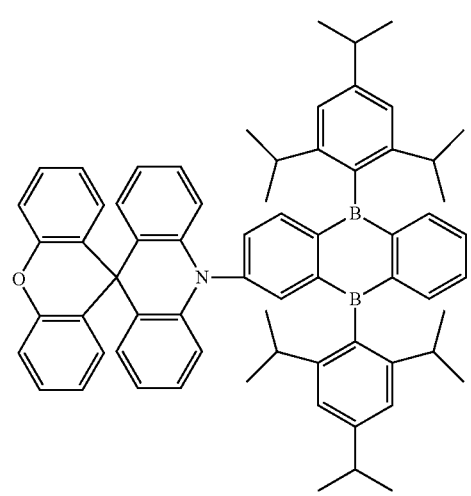
70
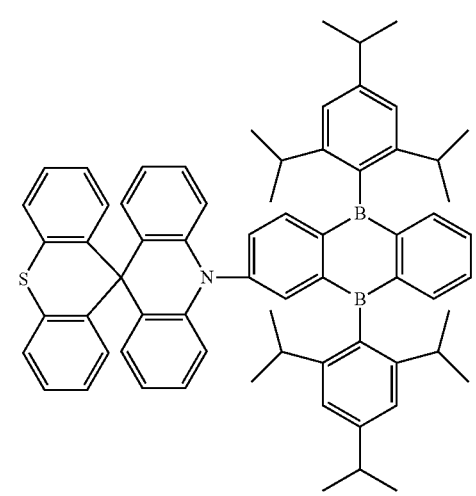

-continued
71
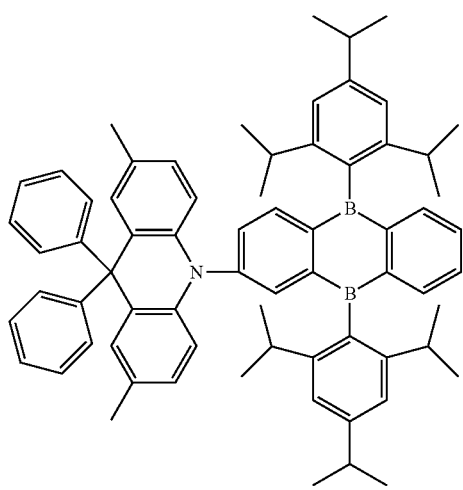
72
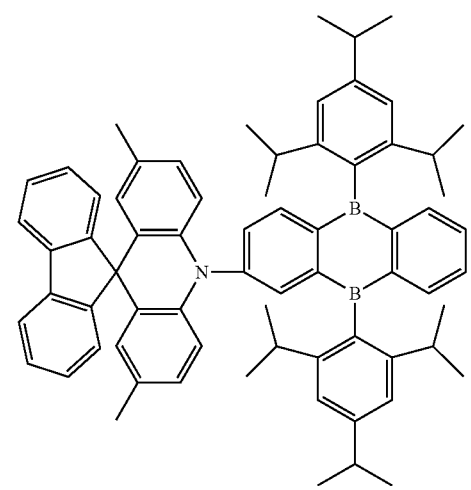
73
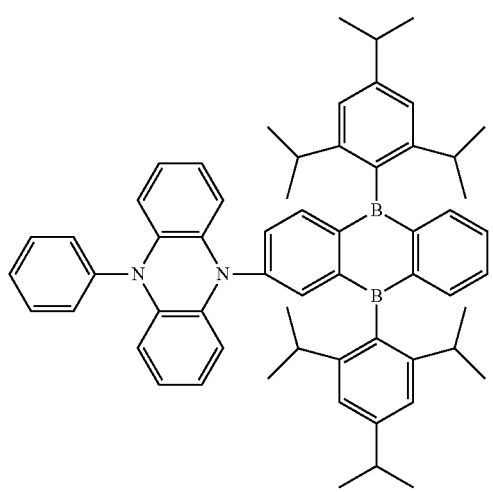
74
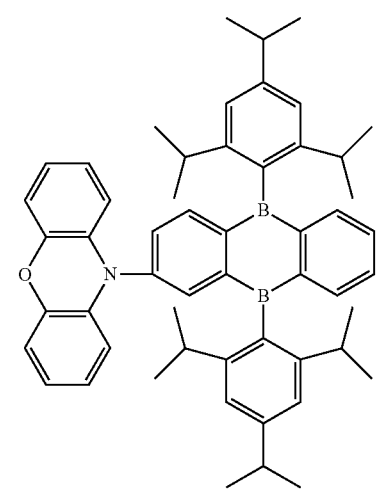
75
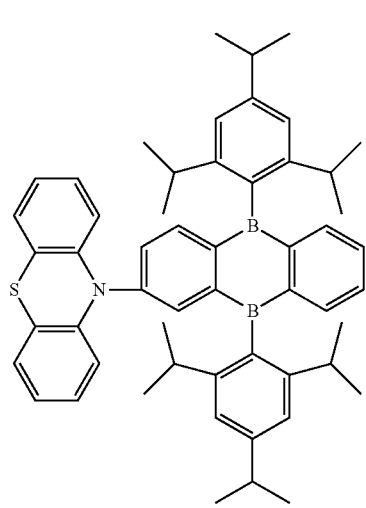
76
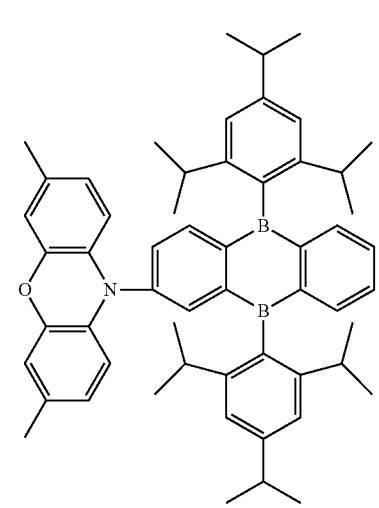

-continued
77
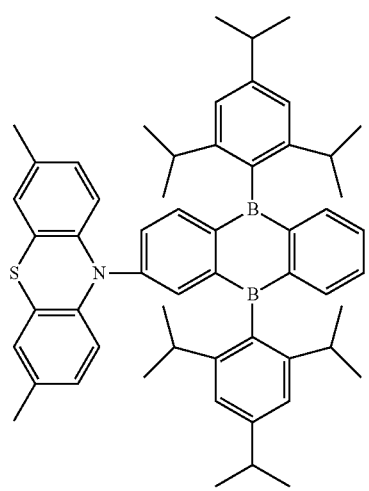
78
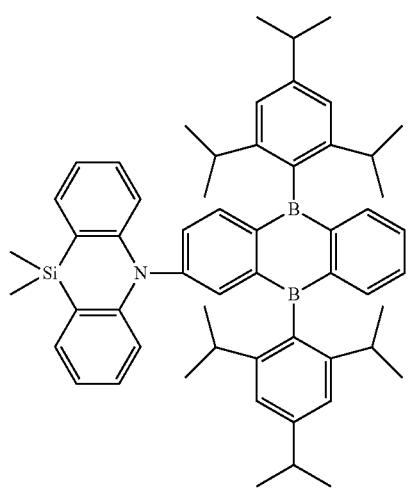
79
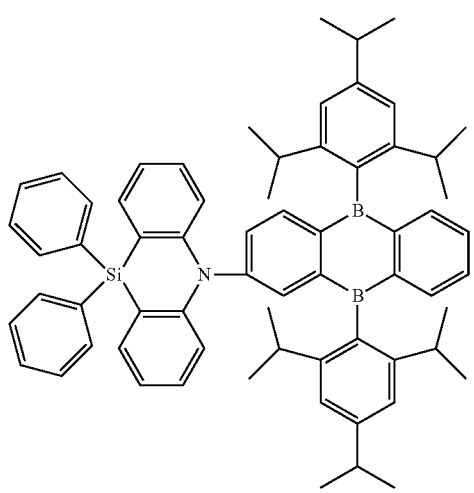
80
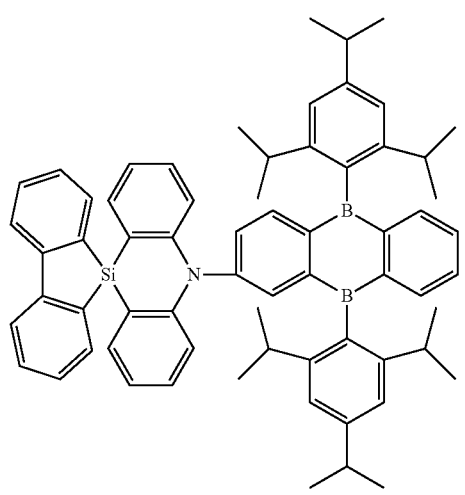
81
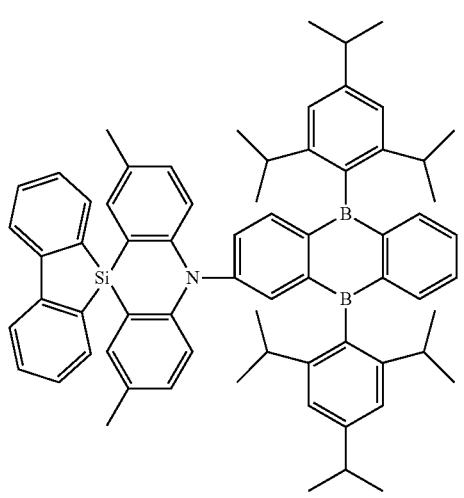
82
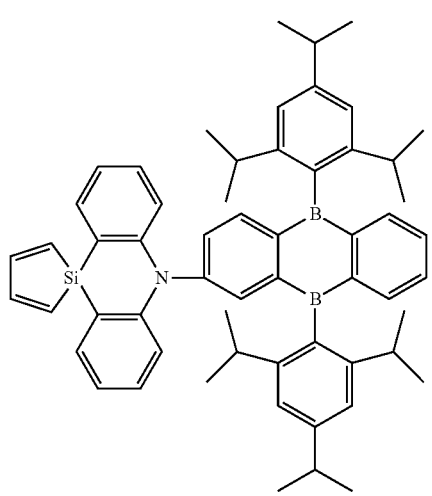

-continued
83
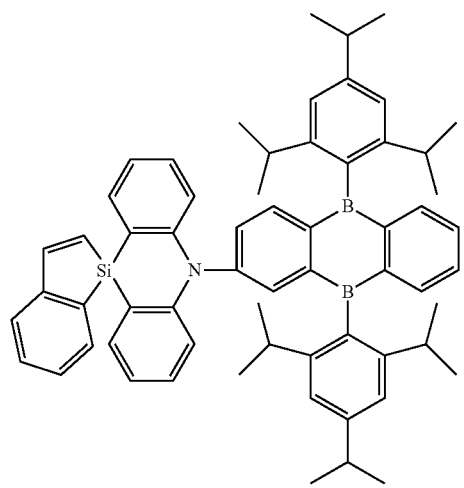
84
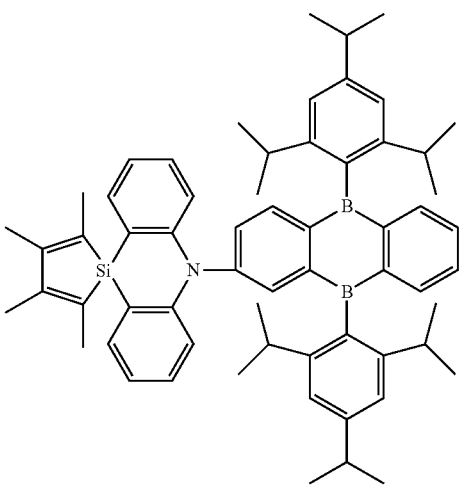
85
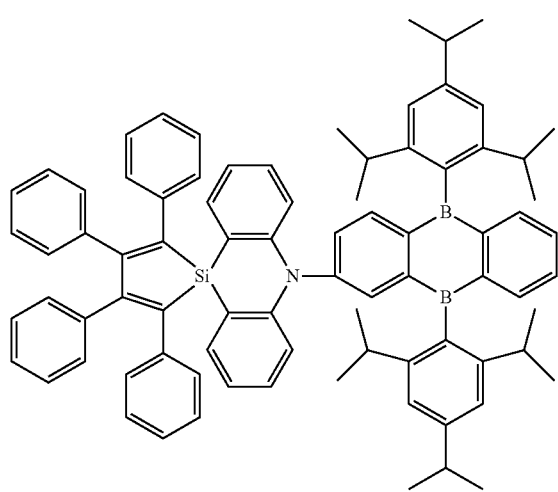
86
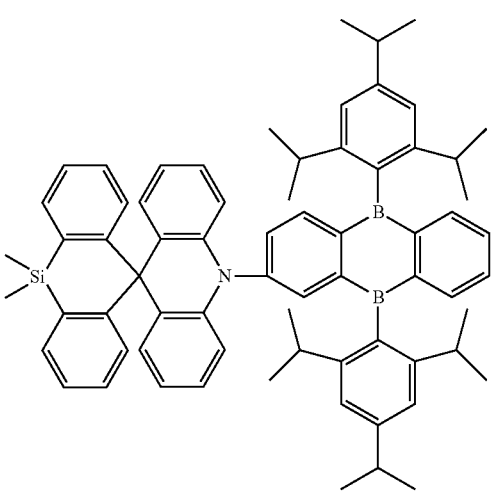
87
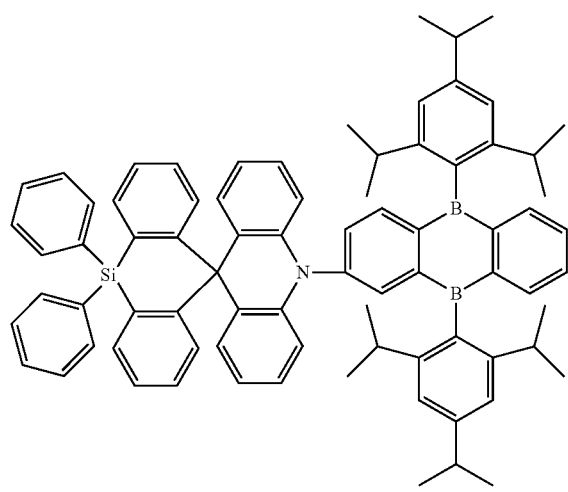
88
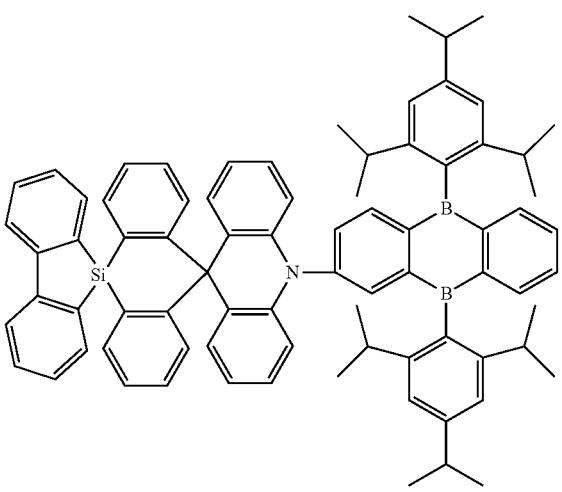

-continued
89
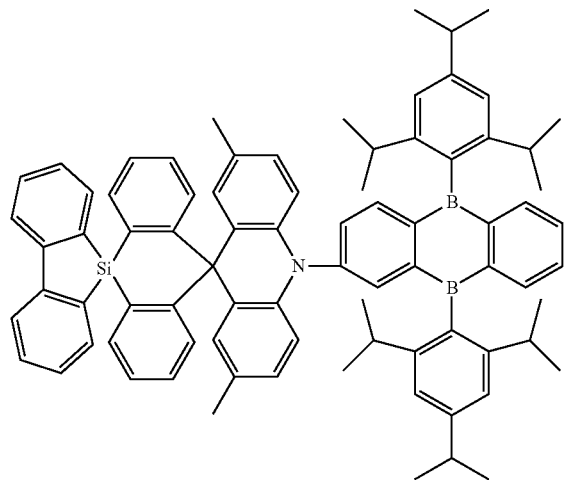
90
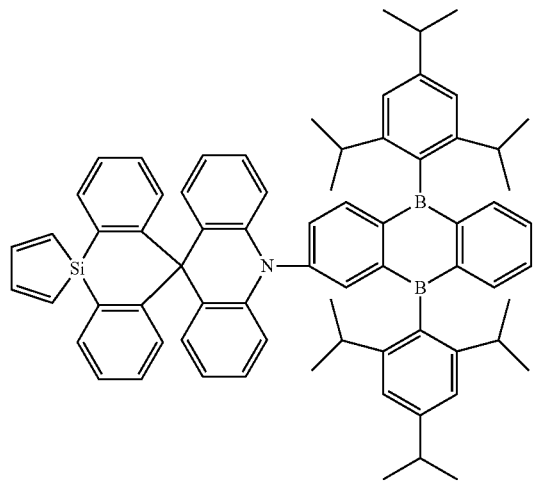
91
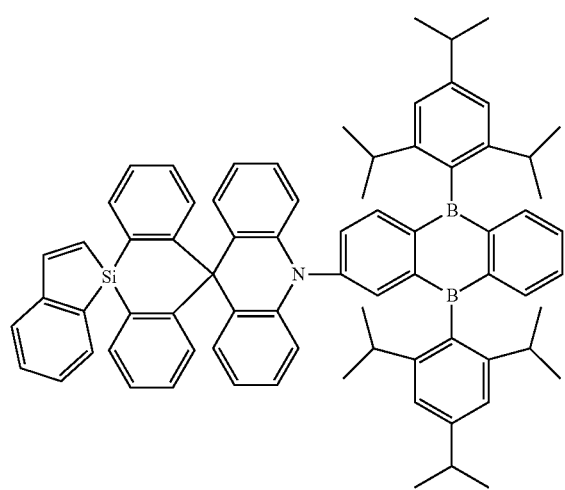
92
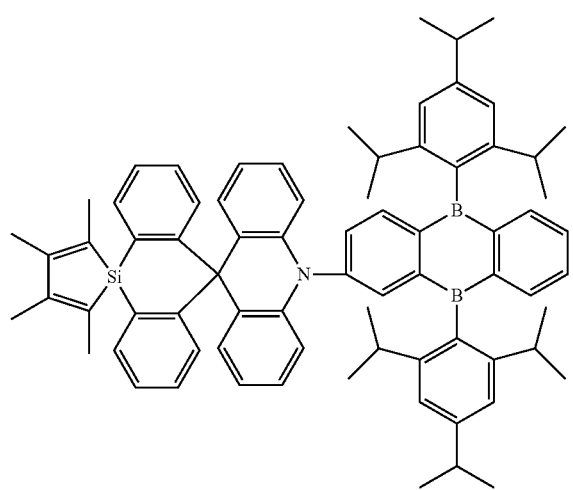
93
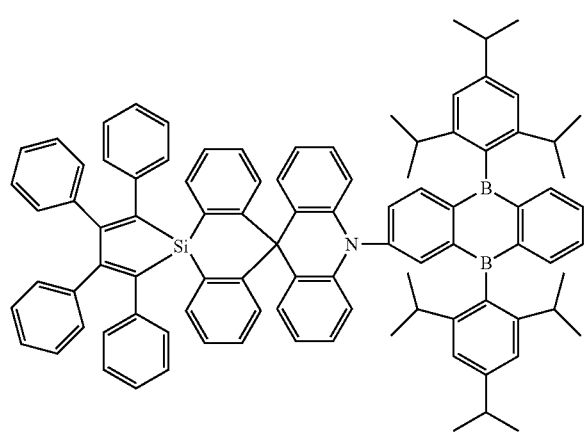
94
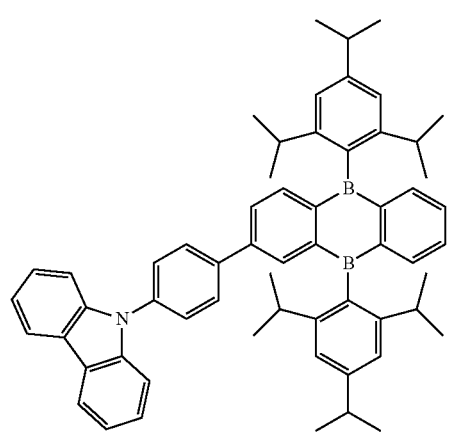

-continued
95
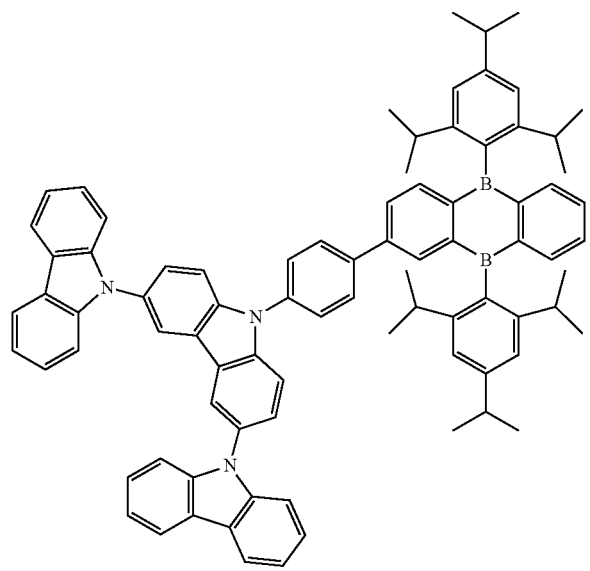
96
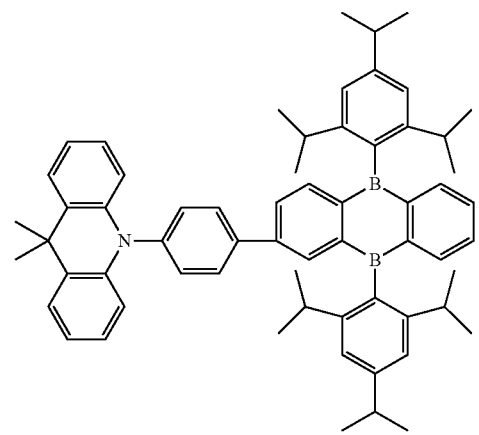
97
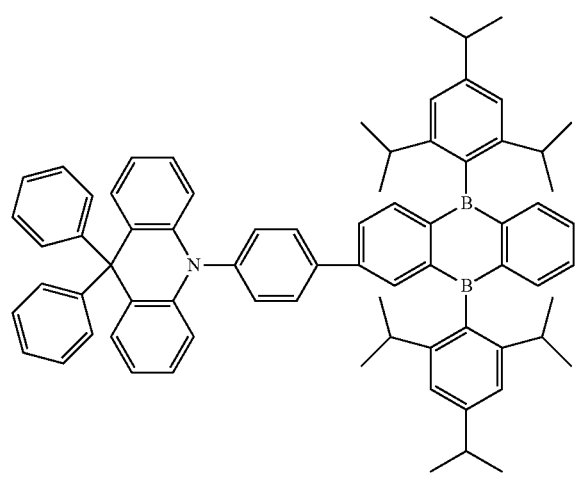
98
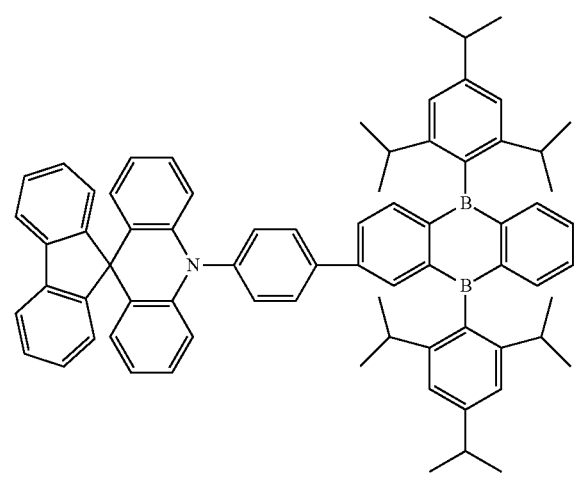
99
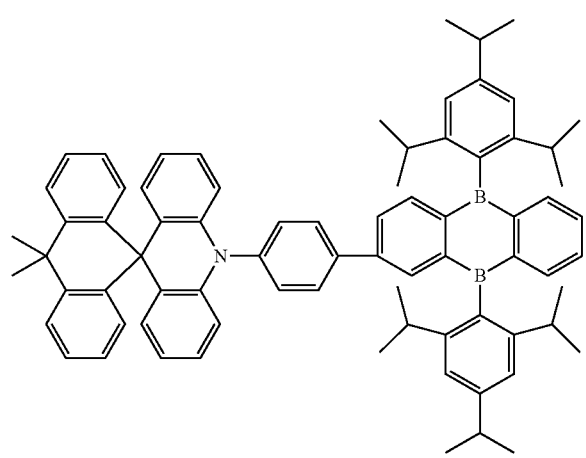
100
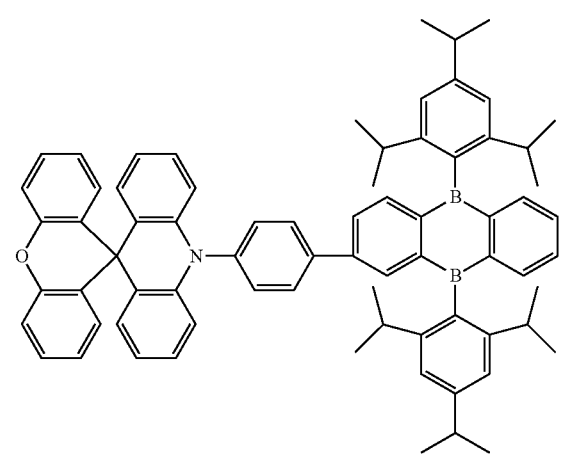

-continued
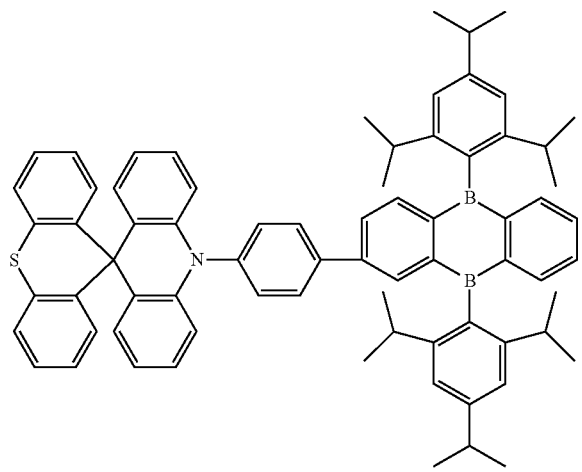
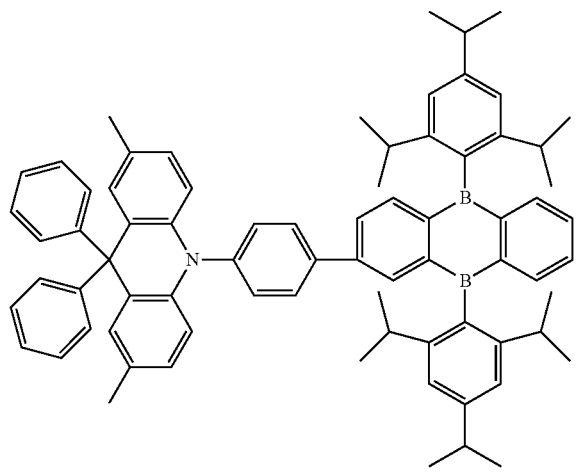
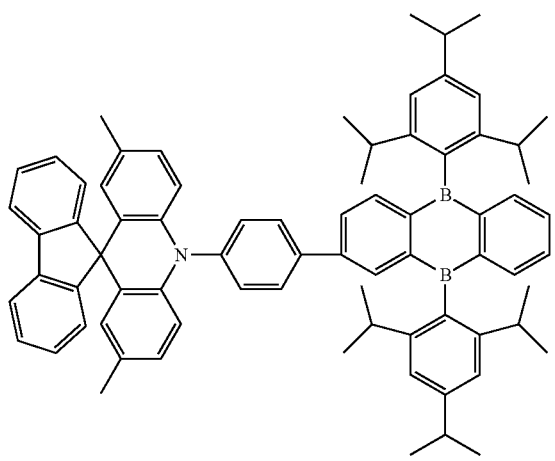
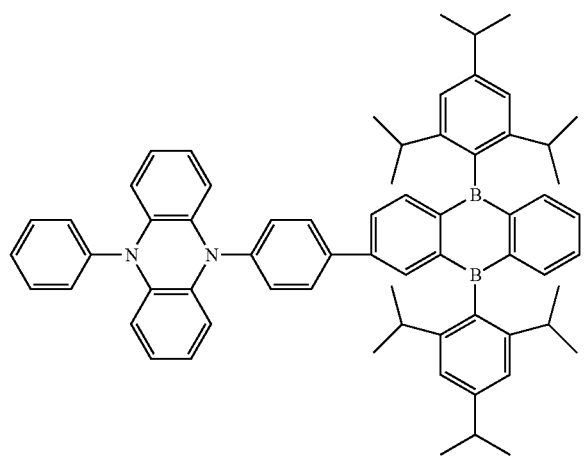
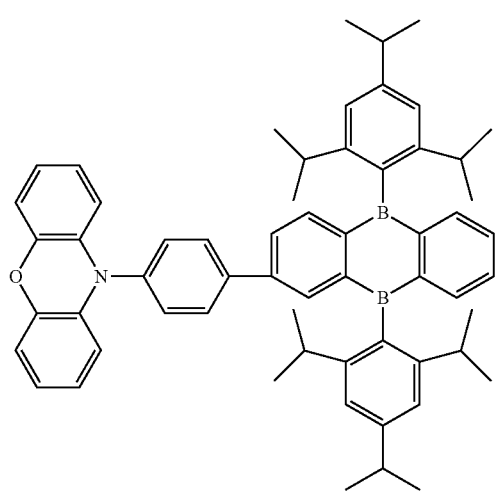
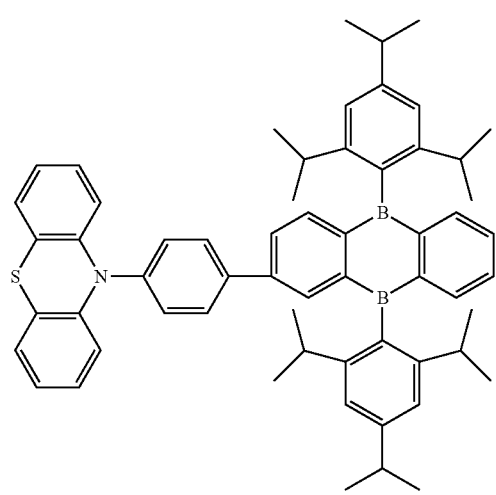

-continued
107
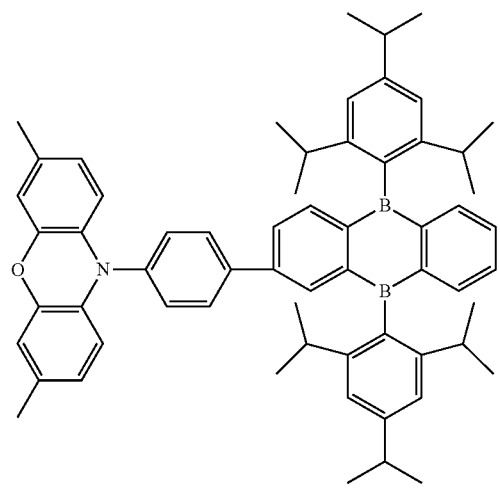
108
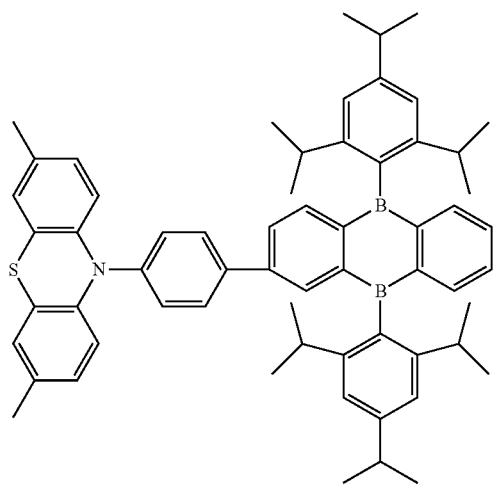
109
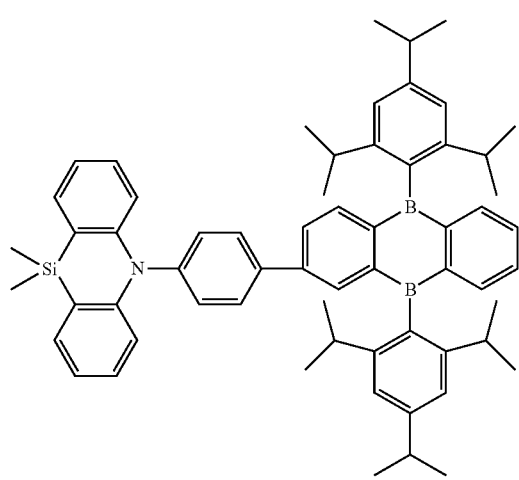
110
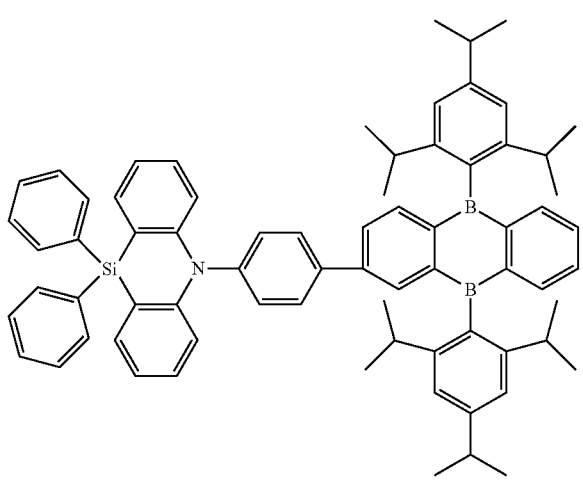
111
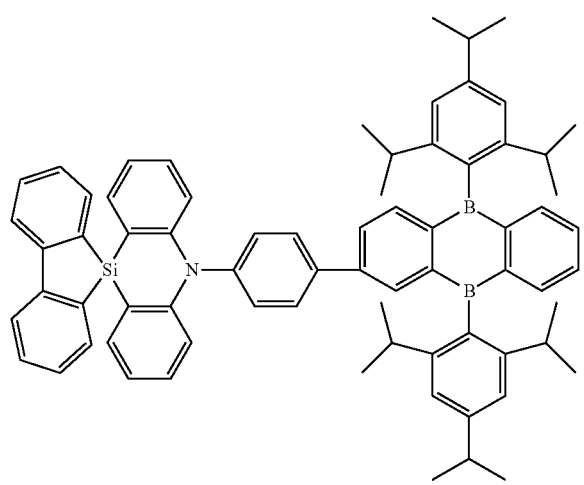
112
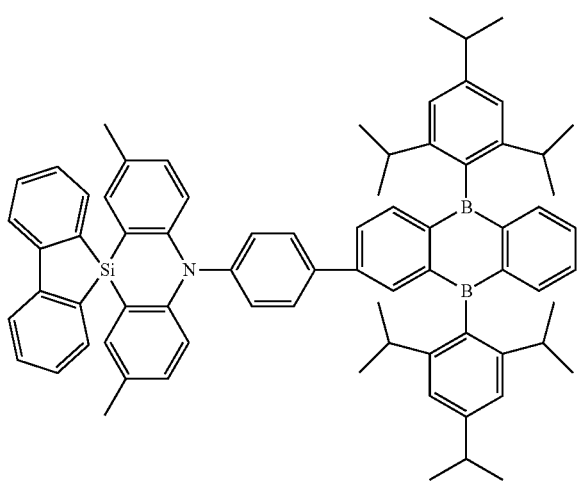

-continued
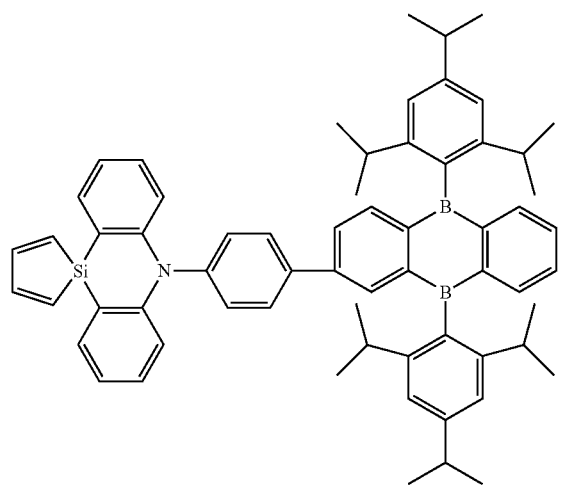
113
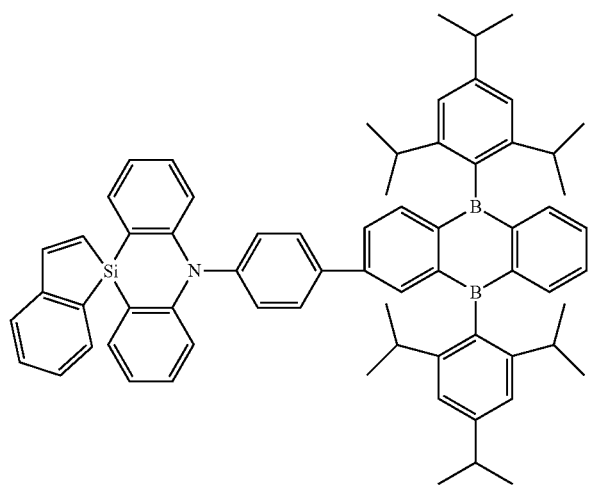
114
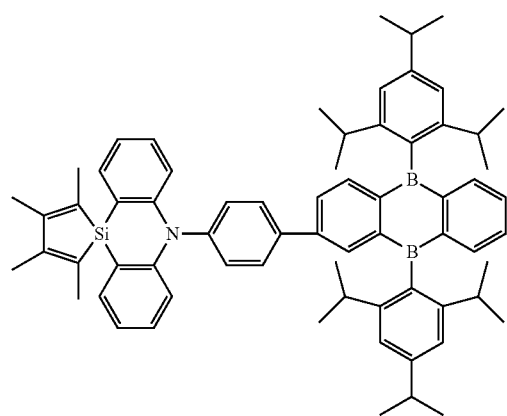
115
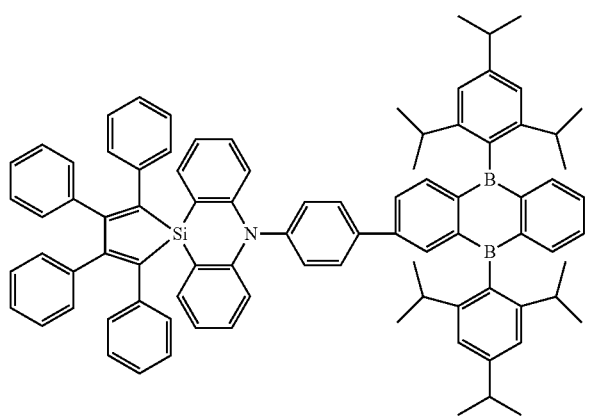
116
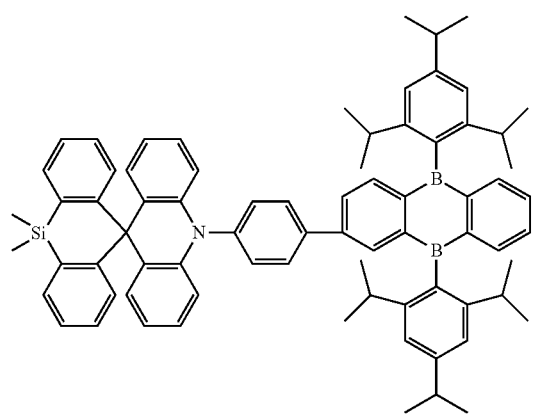
117
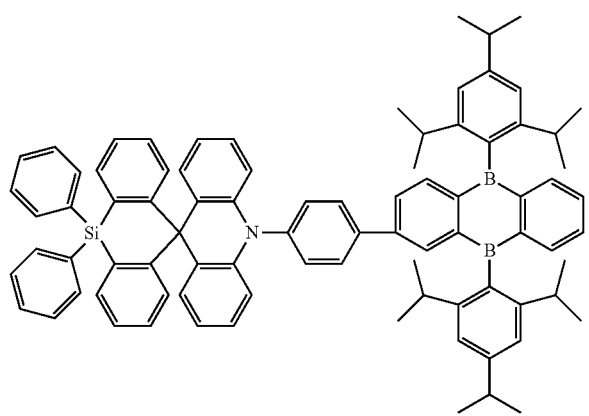
118

-continued
119
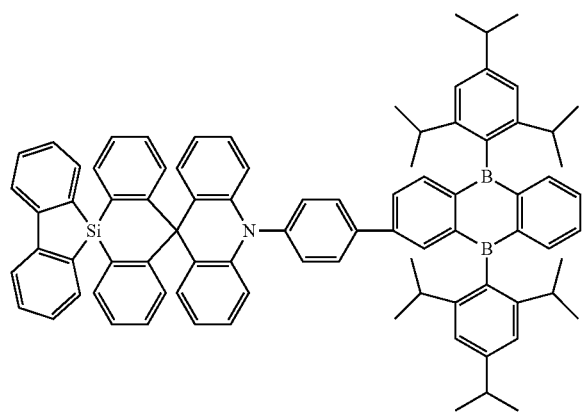
120
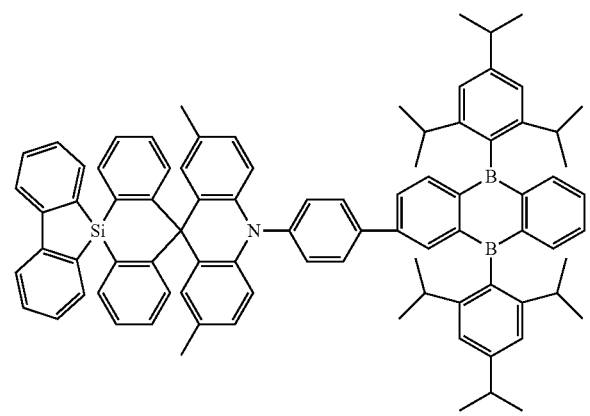
121
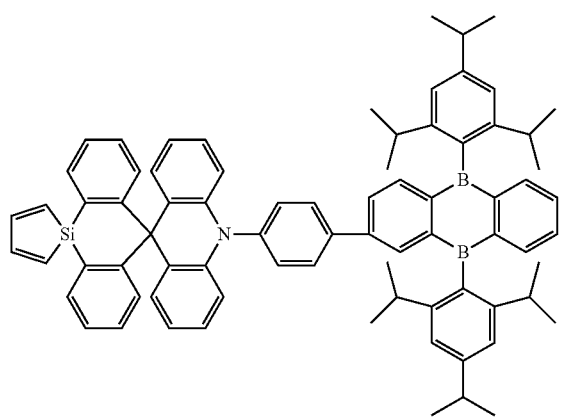
122
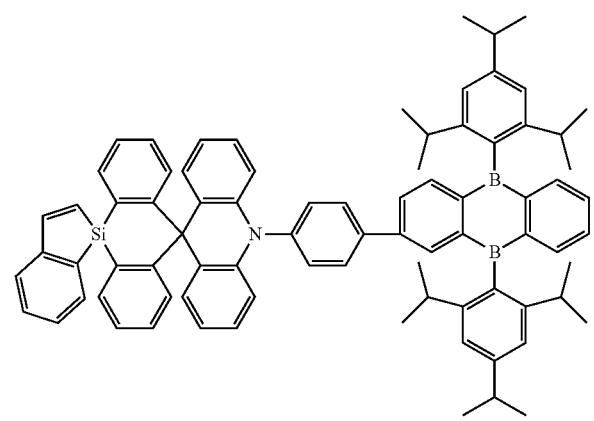
123
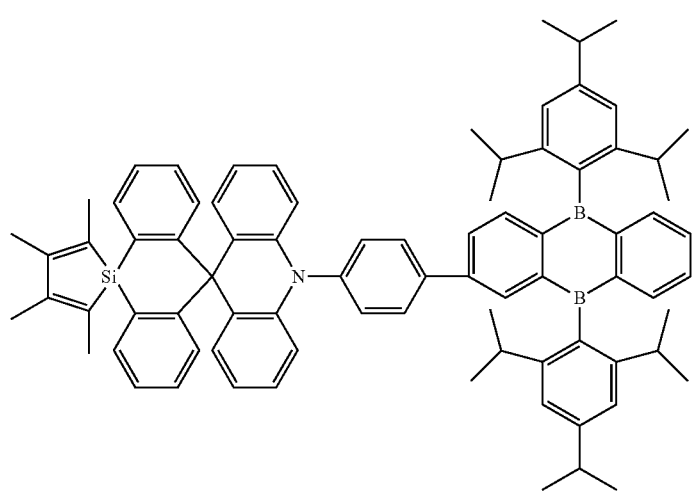

-continued
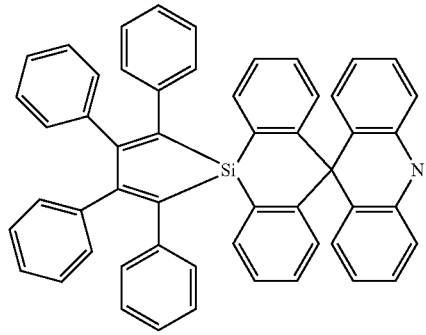
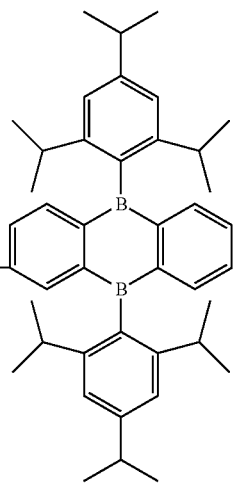
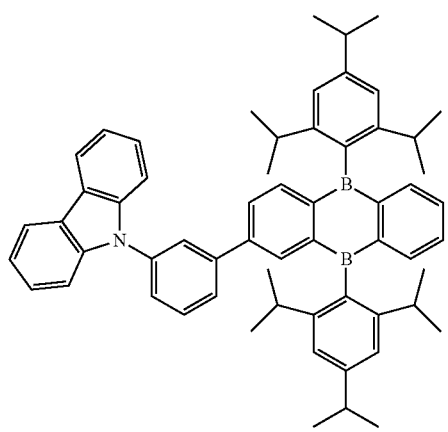
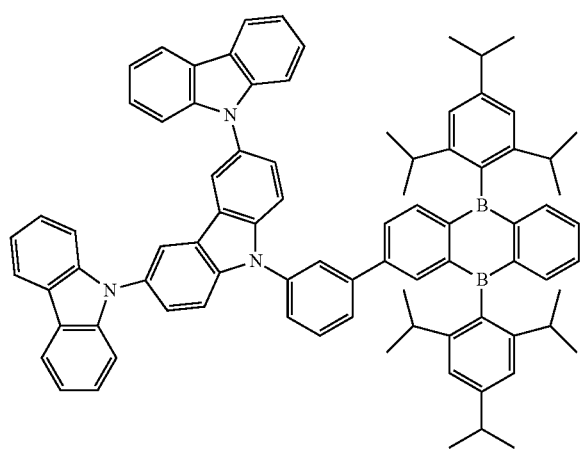
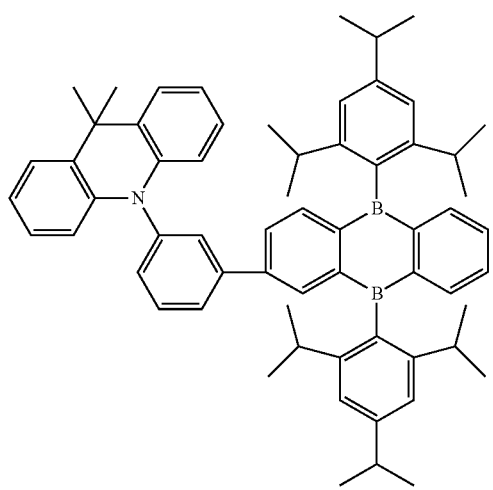
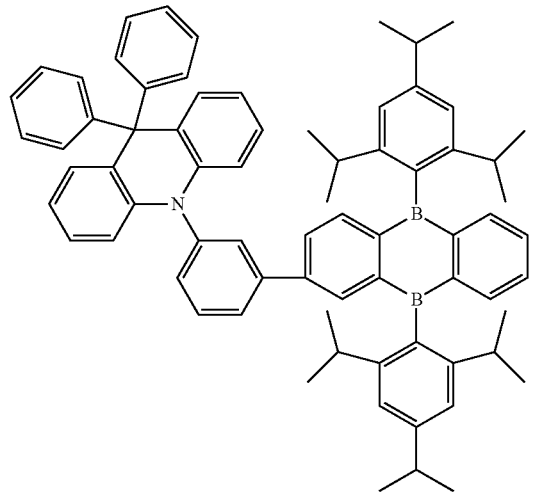

-continued
129
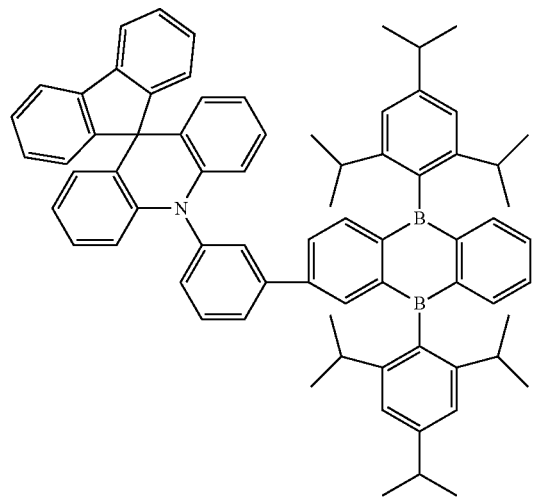
130
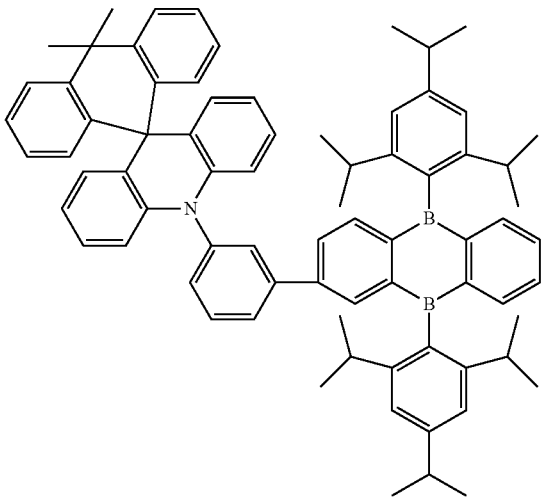
131
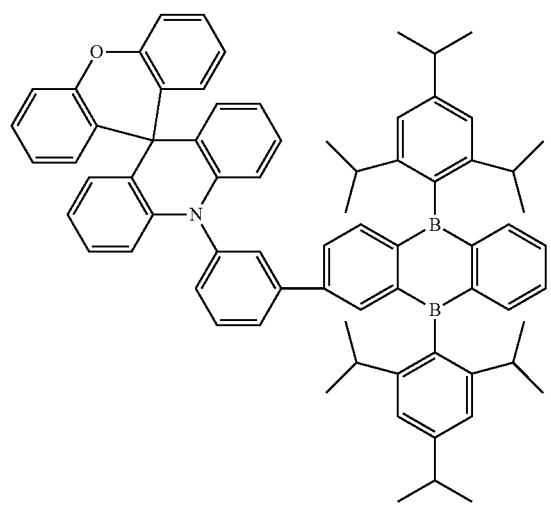
132
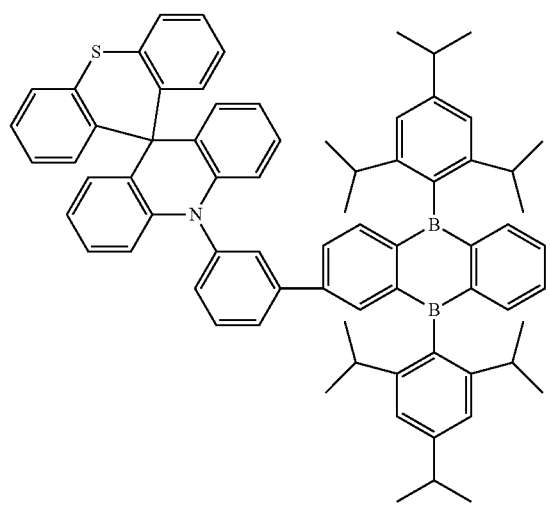
133
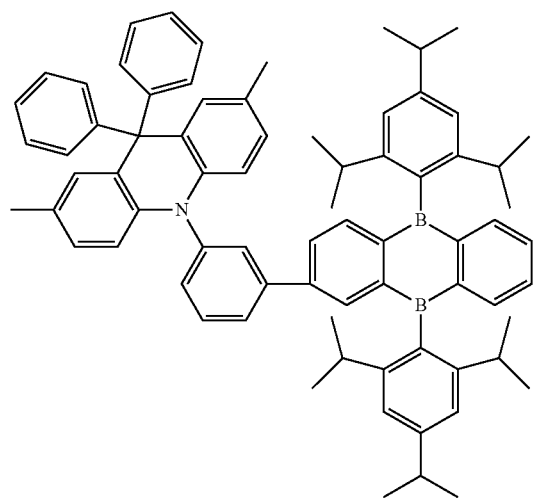
134
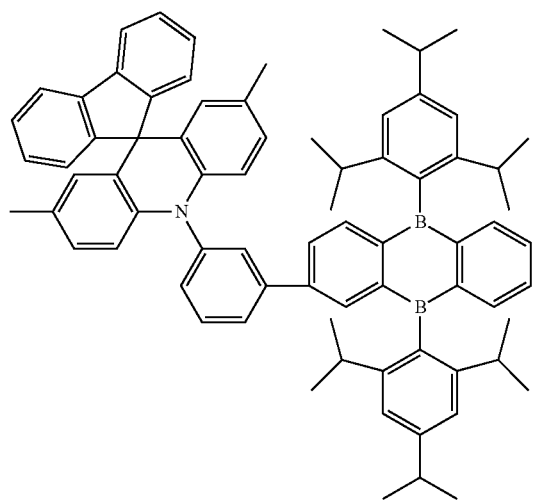

135
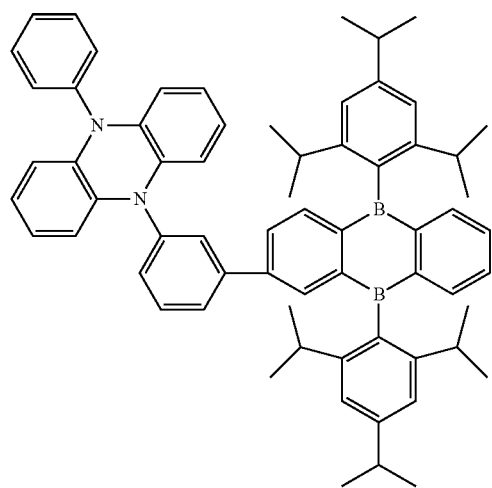
136
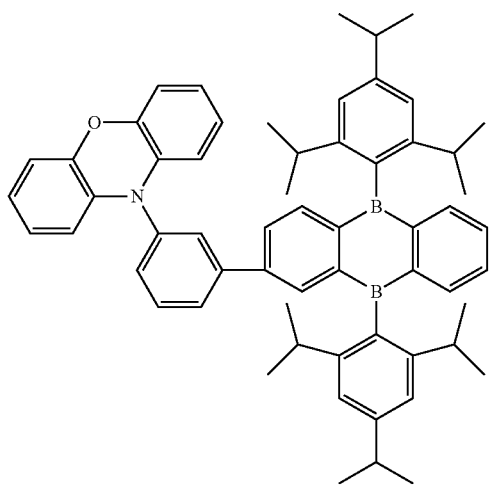
137
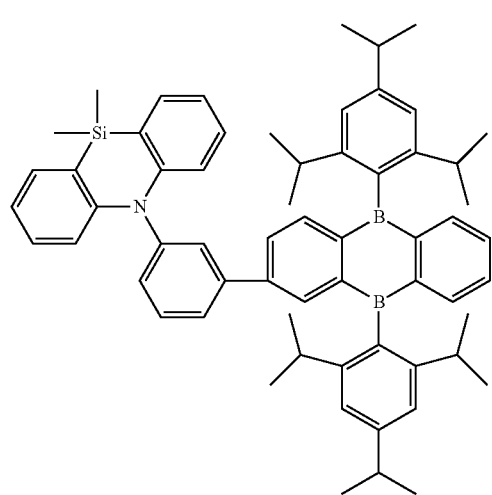
138
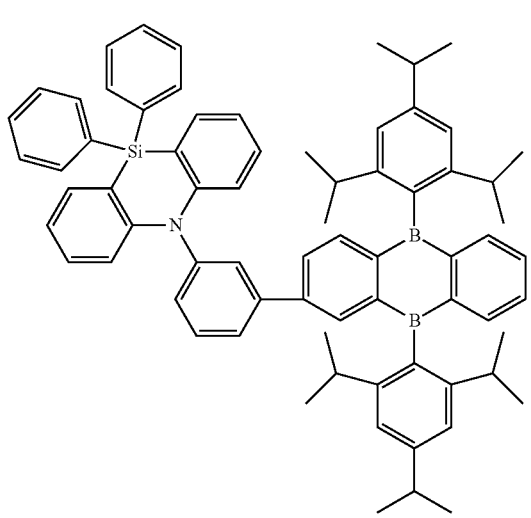
139
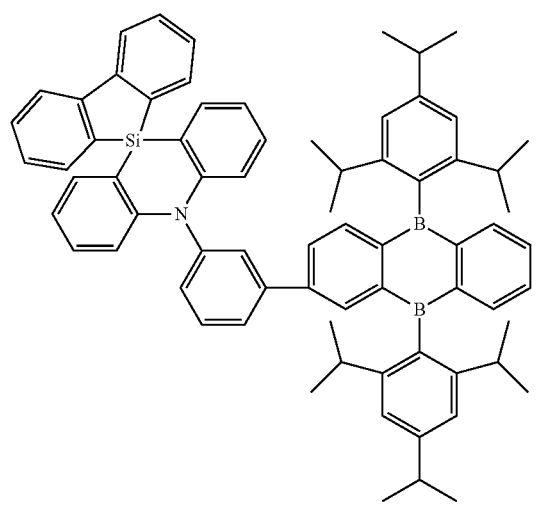
140
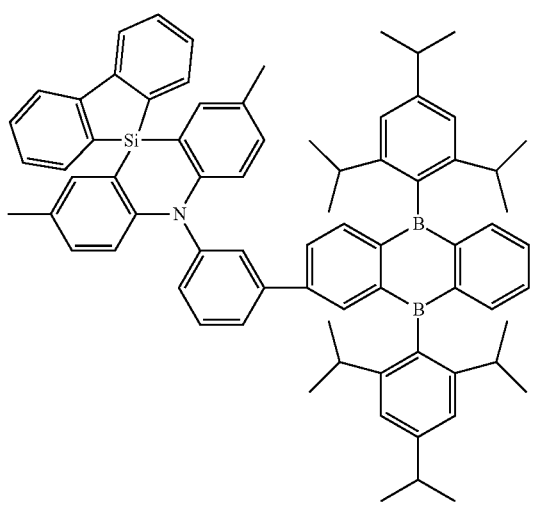

141
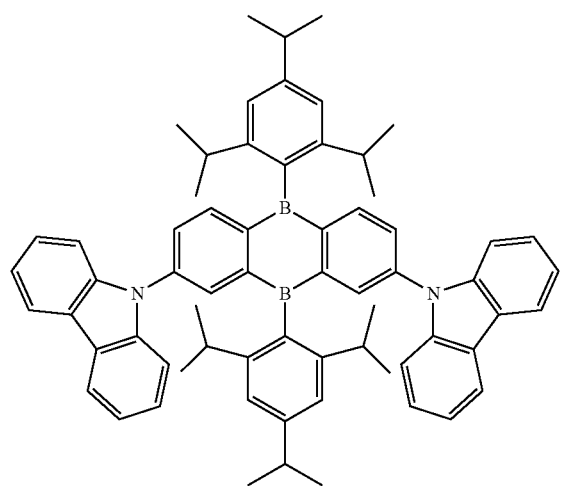
142
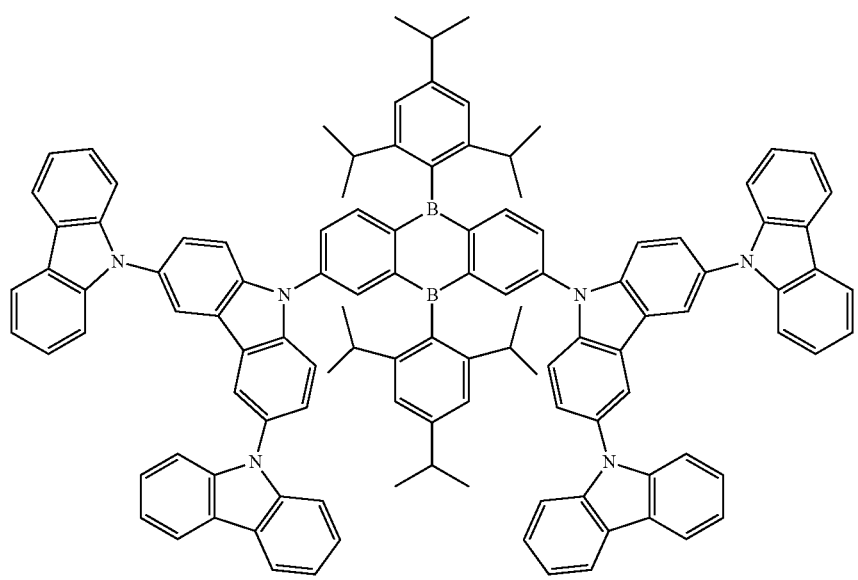
143
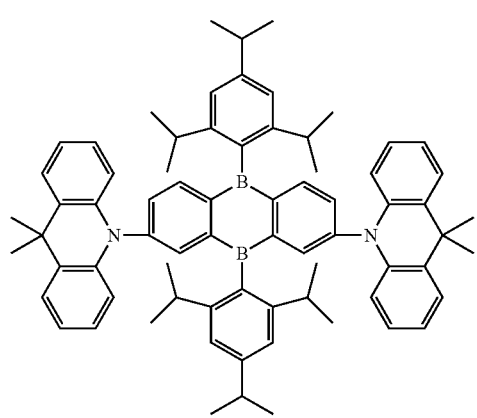
144
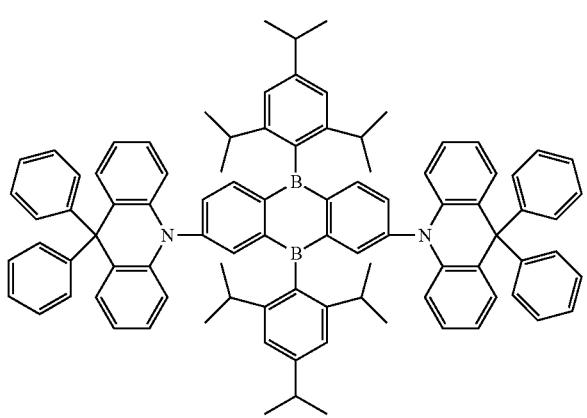

-continued
145
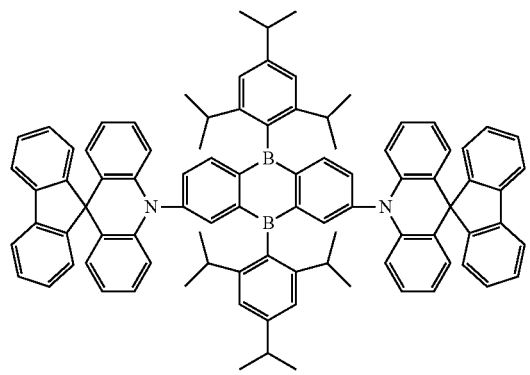
146
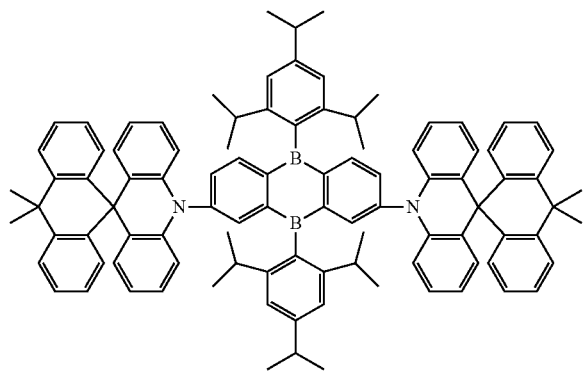
147
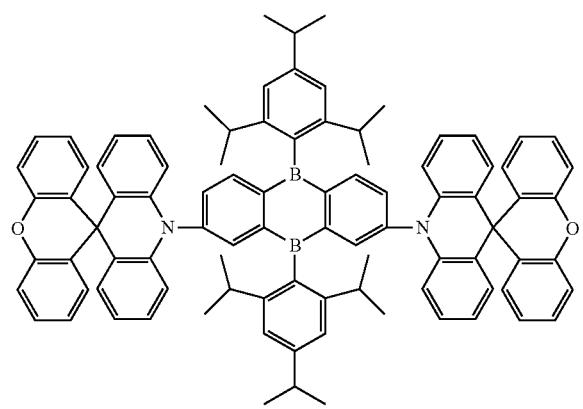
148
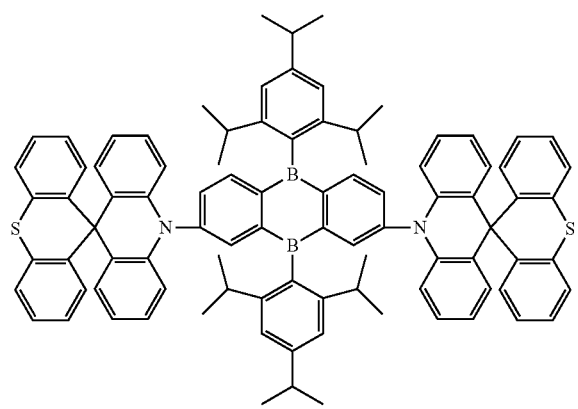
149
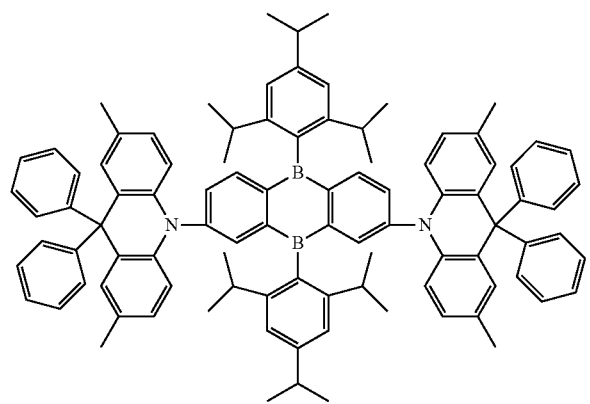
150
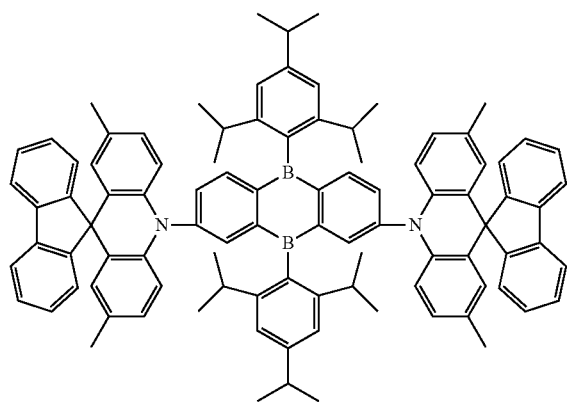
151
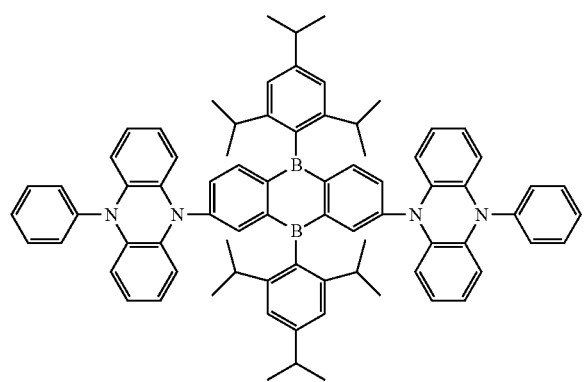
152
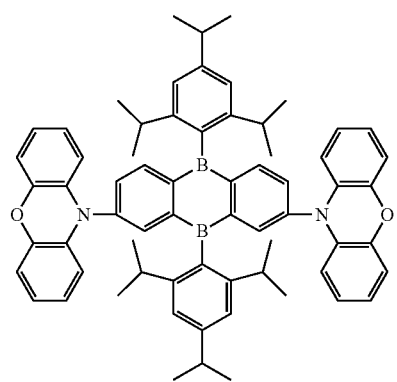

The polycyclic compound represented by Formula 1 may be one of the following compounds represented in the following Compound Group 3.
[Compound Group 3]
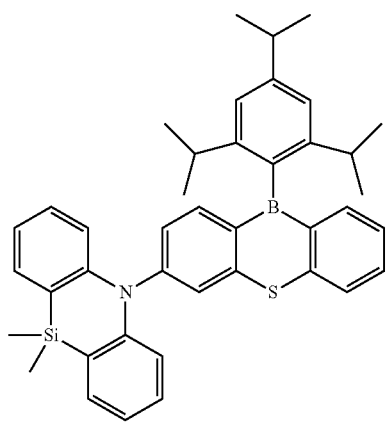
153
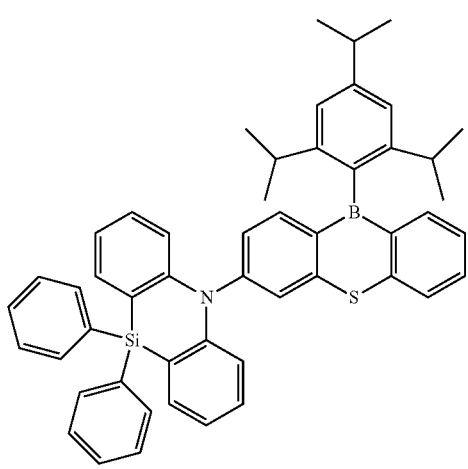
154
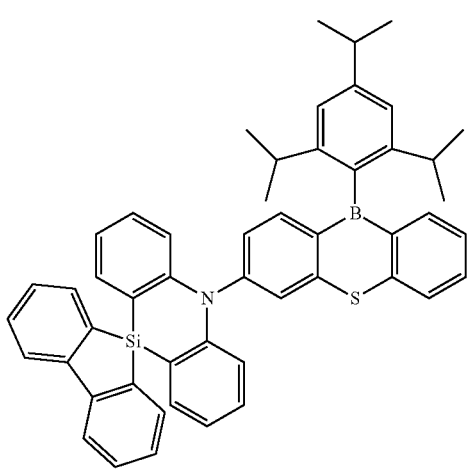
155
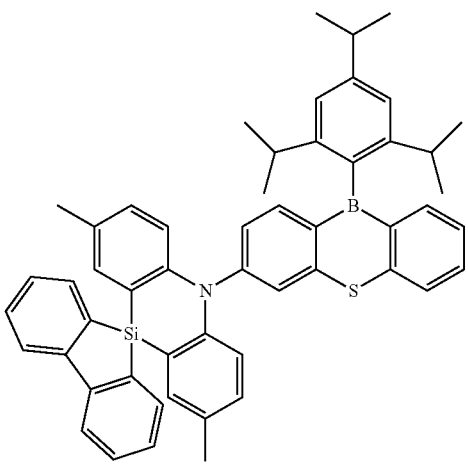
156
157
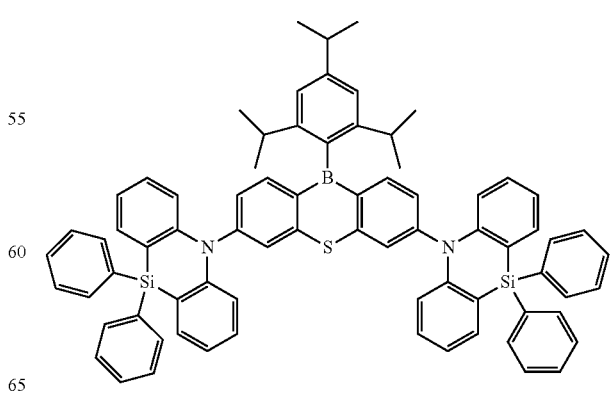
158

159
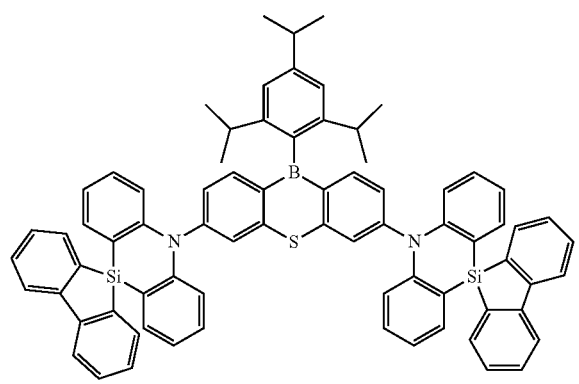
160
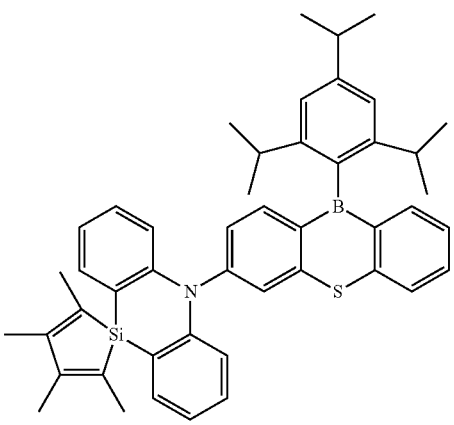
161
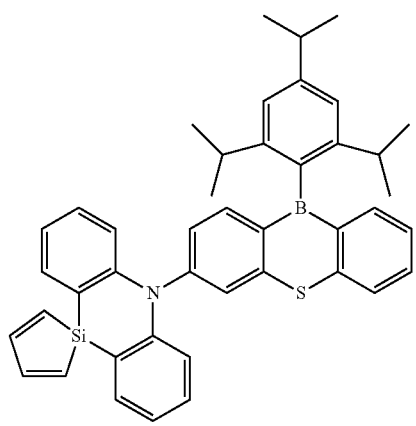
162
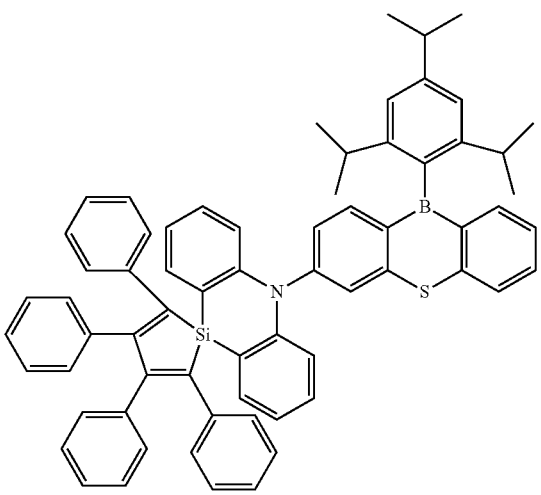
163
164
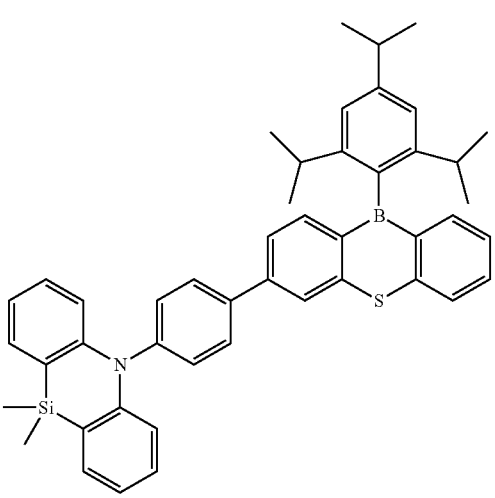

-continued
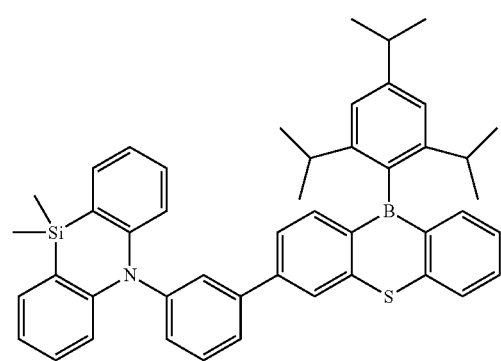
165
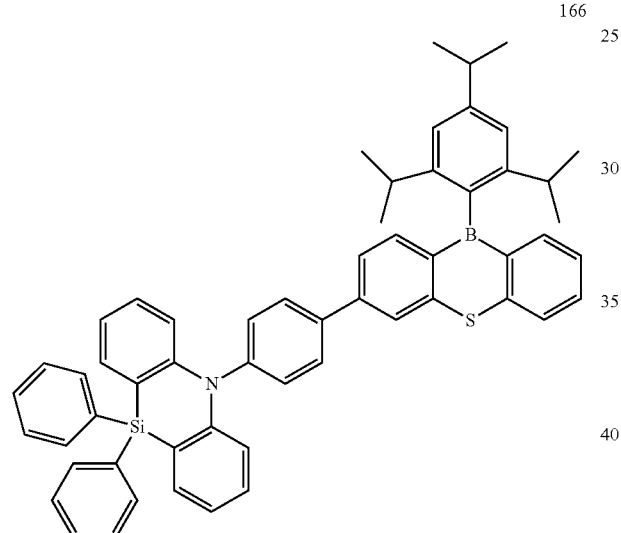
166
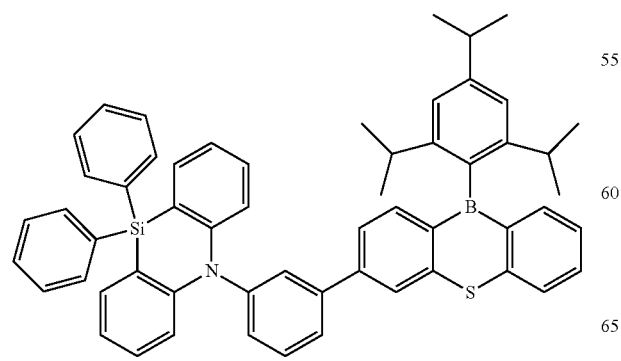
167
-continued
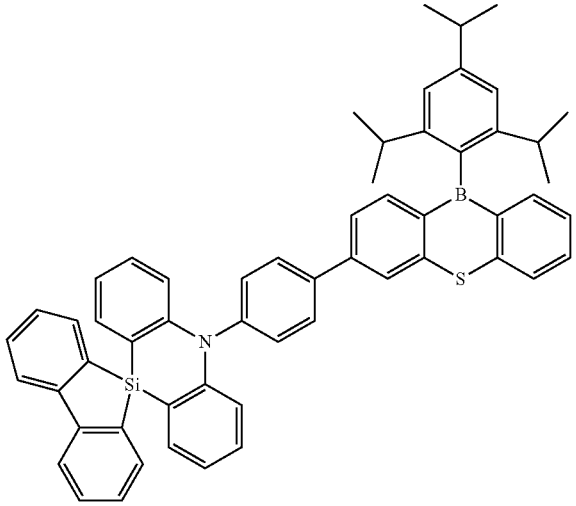
168
169
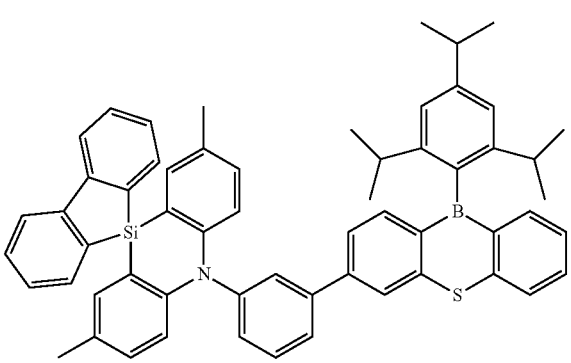
170

-continued
171
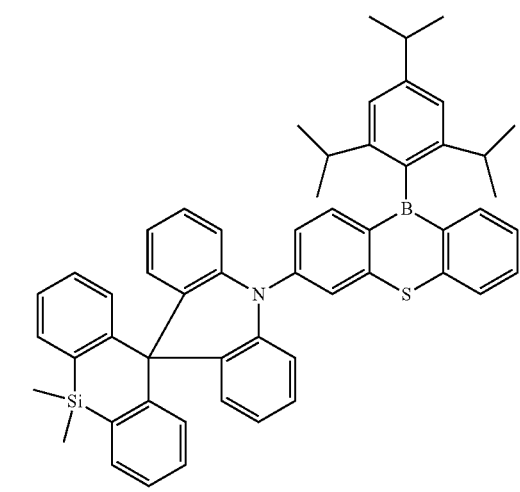
172
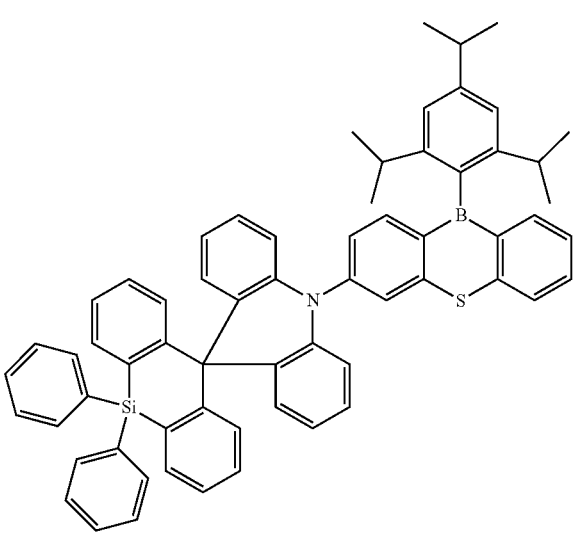
173
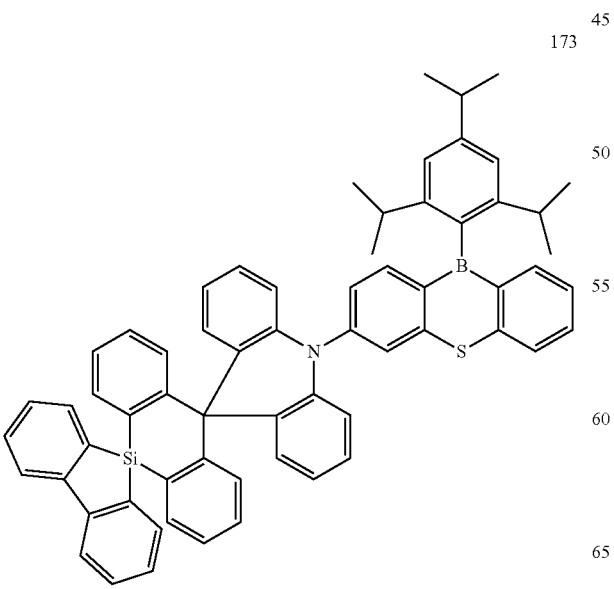
-continued
174
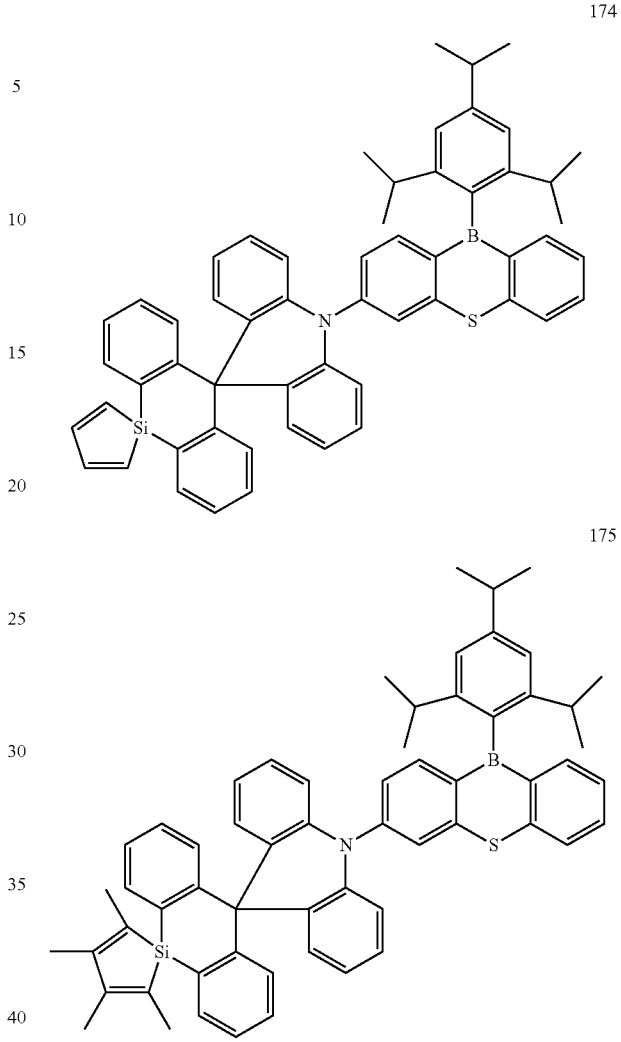
175
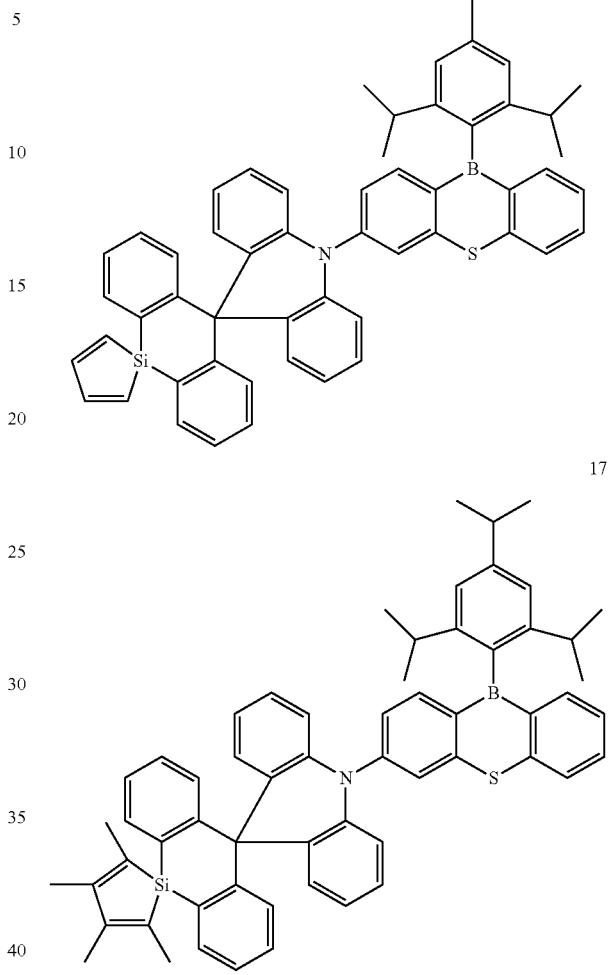
176
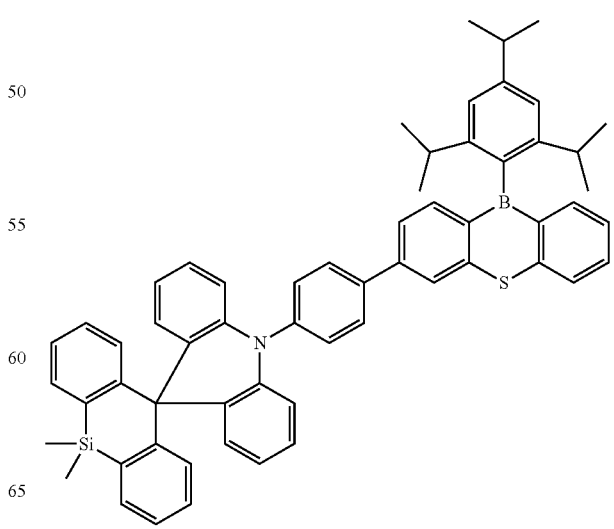

-continued
177
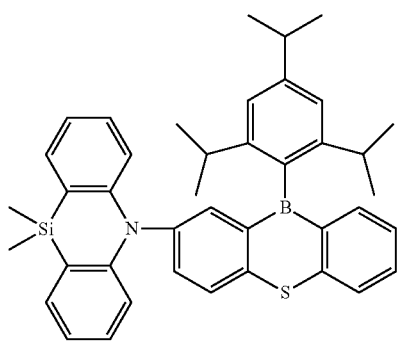
181
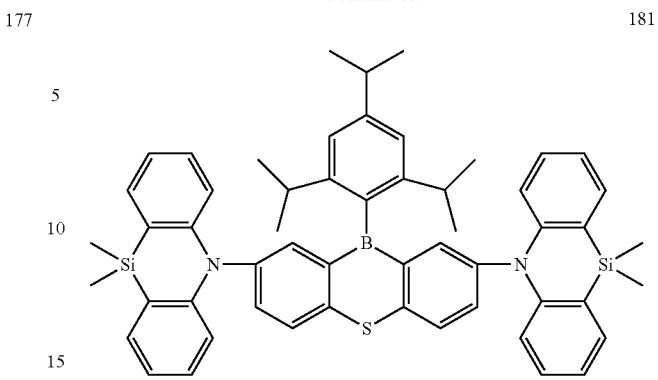
178
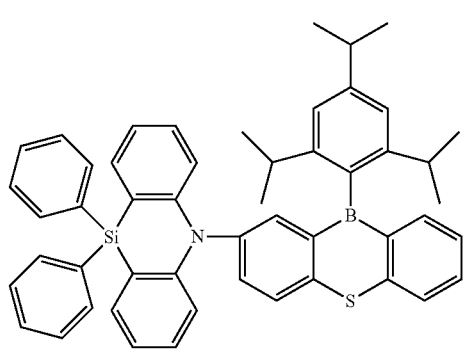
182
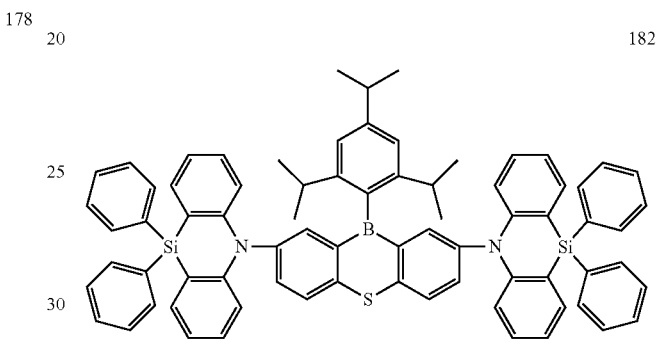
179
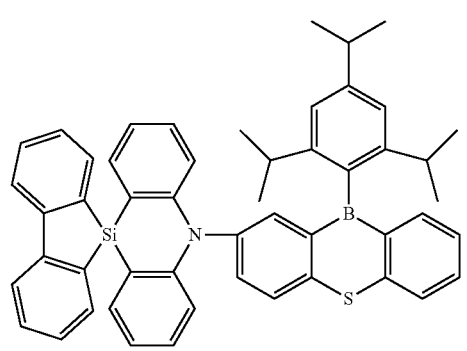
183
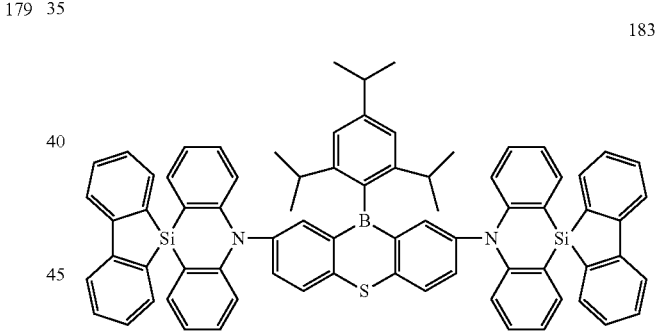
180
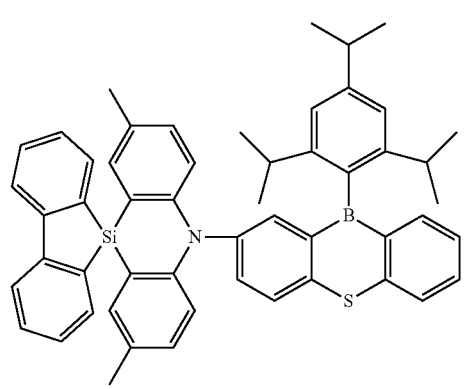
184
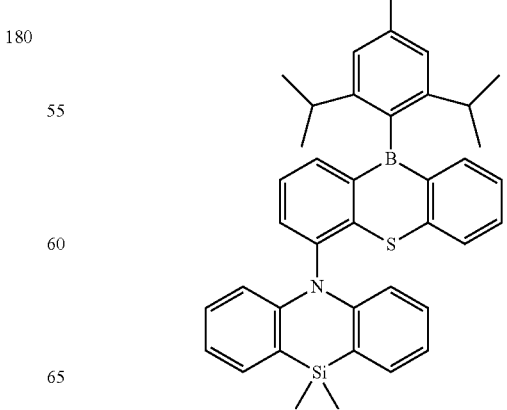

185 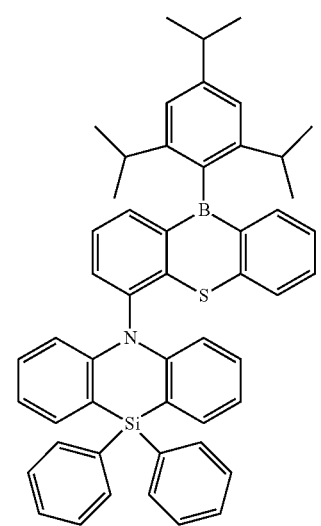
186 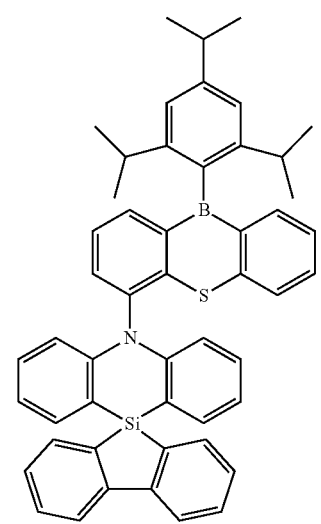
187 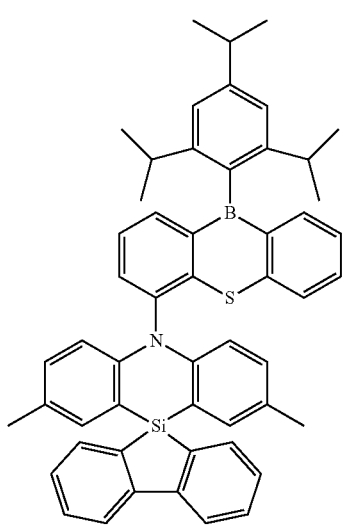
188 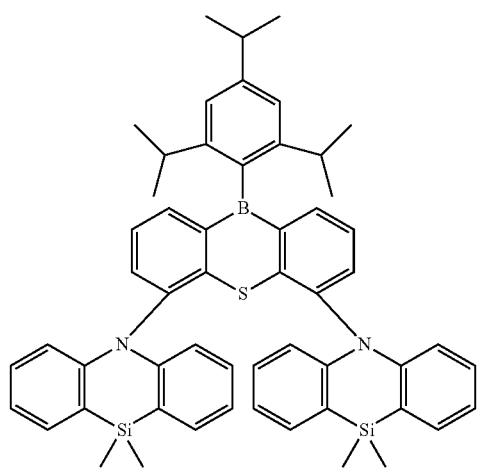
189 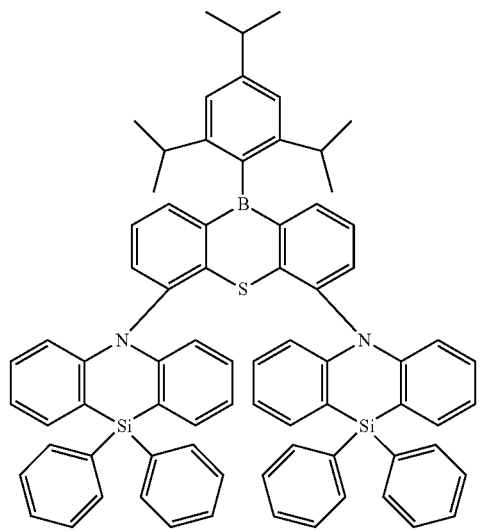
190 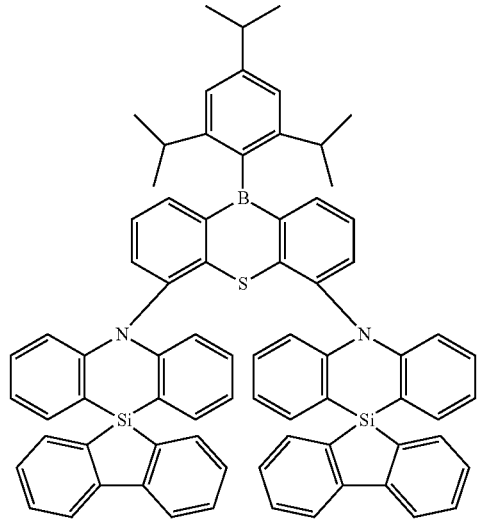

191
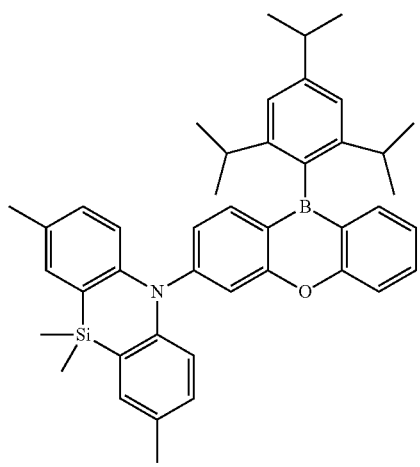
192
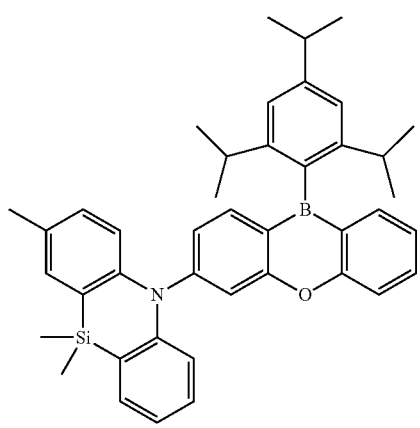
193
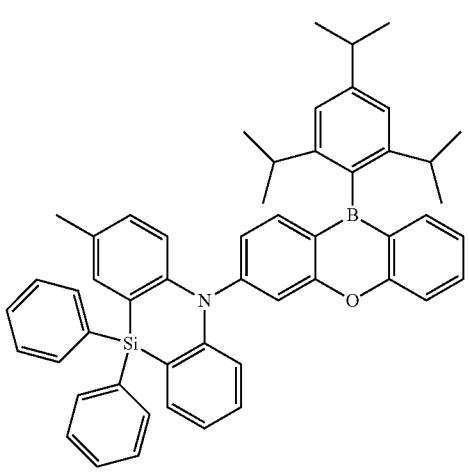
194
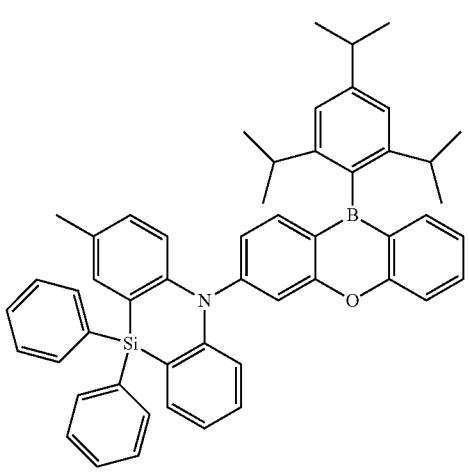
195
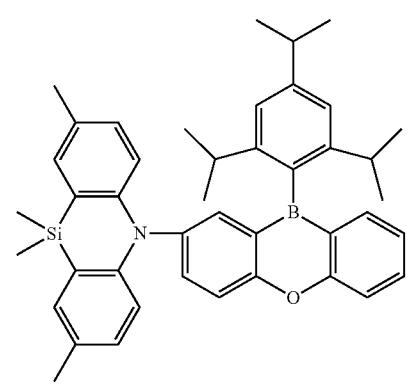
196
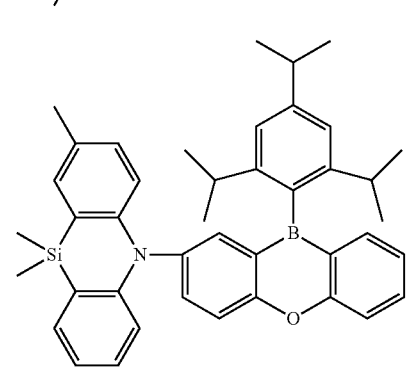
197
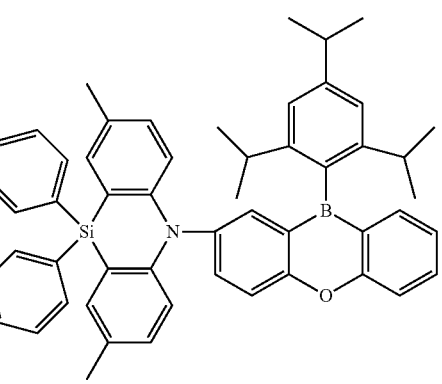

198

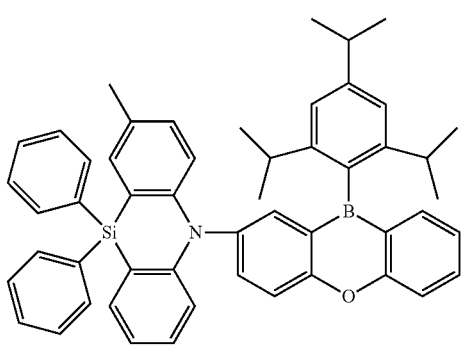

199

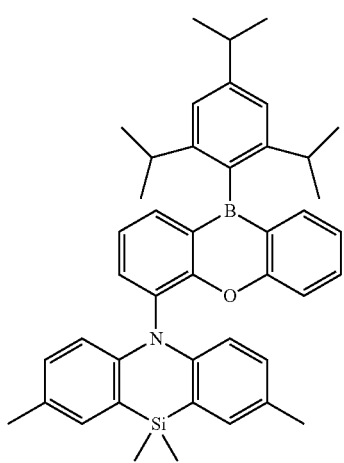

200

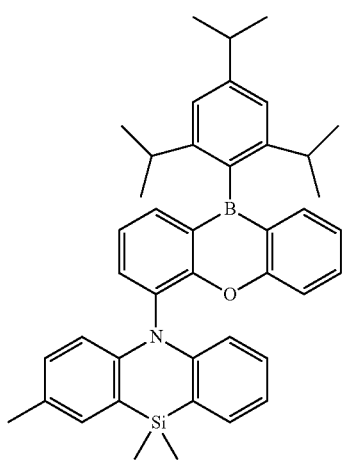

201

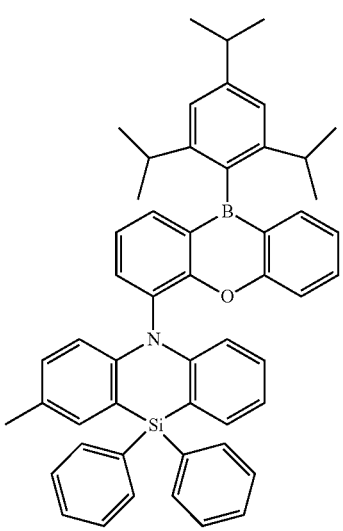

202

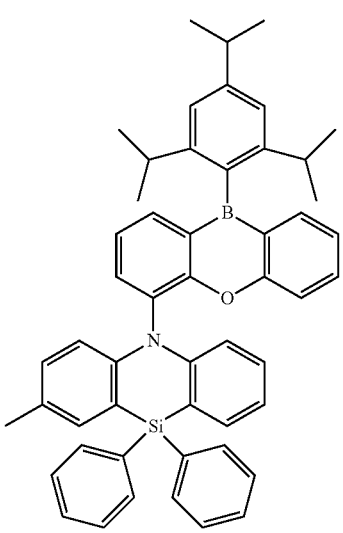

The polycyclic compound according to an exemplary embodiment of the present disclosure may be used as a material for thermally activated delayed fluorescence (TADF). In TADF process, purely organic luminescent compounds with very small singlet-triplet energy splitting (for example ≤0.2 eV gap) enable efficient up-conversion from the lowest triplet excited states to the lowest singlet excited states to enhance light emission. The polycyclic compound according to an exemplary embodiment of the present disclosure may emit blue light via TADF. The polycyclic compound according to an exemplary embodiment of the present disclosure may accomplish blue emission with high efficiency, and more particularly may accomplish deep blue emission with high efficiency. Light with a wavelength between 440 and 495 nm is perceived as blue light with pure blue (in the middle) light having a wavelength of about 470 nm. Deep blue light may have a wavelength from about 440 nm to about 450 nm.

Hereinafter, an organic electroluminescence device according to an exemplary embodiment of the present disclosure will be explained. The explanation will be mainly with the difference in the polycyclic compound according to an exemplary embodiment of the present disclosure, and unexplained part will follow the above-description on the polycyclic compound according to an exemplary embodiment of the present disclosure.

The organic electroluminescence device according to an exemplary embodiment of the present disclosure includes the polycyclic compound according to an exemplary embodiment of the present disclosure.

FIG. 1 is a cross-sectional view schematically illustrating an organic electroluminescence device according to an exemplary embodiment of the present disclosure. FIG. 2 is a cross-sectional view schematically illustrating an organic electroluminescence device according to an exemplary embodiment of the present disclosure.

Referring to FIGS. 1 and 2, an organic electroluminescence device 10 according to an exemplary embodiment of the present disclosure may include a first electrode EL1, a hole transport region HTR, an emission layer EML, an electron transport region ETR, and a second electrode EL2.

The first electrode EL1 has conductivity. The first electrode EL1 may be a pixel electrode or an anode. The first electrode EL1 may be a transmissive electrode, a transflective electrode, or a reflective electrode. When the first electrode EL1 is a transmissive electrode, the first electrode EL1 may be formed of a transparent metal oxide such as, for example, indium tin oxide (ITO), indium zinc oxide (IZO), zinc oxide (ZnO), or indium tin zinc oxide (ITZO). When the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including a reflective layer or a transflective layer formed of the above materials, or a transparent layer formed of ITO, IZO, ZnO, or ITZO.

The hole transport region HTR may be provided on the first electrode EL1. The hole transport region HTR may include at least one of a hole injection layer HIL, a hole transport layer HTL, a hole buffer layer, and an electron blocking layer. The thickness of the hole transport region HTR may be, for example, from about 1,000 Å to about 1,500 Å.

The hole transport region HTR may have a single layer formed of a single material, a single layer formed of a plurality of different materials, or a multilayer structure including a plurality of layers formed of a plurality of different materials.

The hole transport region HTR may be a single layer with a structure having a hole injection layer HIL or a hole transport layer HTL, or may have a structure of a single layer formed of a hole injection material and a hole transport material. In addition, the hole transport region HTR may have a structure of a single layer formed of a plurality of different materials, or a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed by various methods such as, for example, a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenylbenzidine (NPB), triphenylamine-containing polyether ketone (TPAPEK), 4-isopropyl-4'-methyldiphenyliodonium tetrakis(pentafluorophenyl)borate (PPBI), or dipyrazino[2,3-f:2',3'-h]quinoxaline-2,3,6,7,10,11-hexacarbonitrile (HAT-CN).

The hole transport layer HTL may include, for example, a carbazole derivative such as N-phenyl carbazole or polyvinyl carbazole, a fluorine-based derivative, a triphenylamine-based derivative such as N,N'-bis(3-methylphenyl)-N,N'-diphenyl[1,1'-biphenyl]-4,4'-diamine (TPD), 4,4',4"-tris(N-carbazolyl)triphenylamine (TCTA), N,N'-di(naphthalene-1-yl)-N,N'-diphenylbenzidine (NPB), 4,4'-cyclohexylidenebis[N,N-bis(4-methylphenyl)benzenamine] (TAPC), or 4,4'-bis[N,N'-(3-tolyl)amino]-3,3'-dimethylbiphenyl (HMTPD).

The thickness of the hole transport region HTR may be from about 100 Å to about 10,000 Å, for example, from about 100 Å to about 1,000 Å. When the hole transport region HTR includes both the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. When the thicknesses of the hole transport region HTR, the hole injection layer HIL, and the hole transport layer HTL satisfy the above-described ranges, satisfactory hole transport properties may be obtained without a substantial increase of the driving voltage.

The hole transport region HTR may further include a charge generating material in addition to the above-described materials to increase conductivity. The charge generating material may be dispersed in the hole transport region HTR uniformly or non-uniformly. The charge generating material may be, for example, a p-dopant. The p-dopant may be one of a quinone derivative, a metal oxide, and a cyano group-containing compound, without limitation. For example, non-limiting examples of the p-dopant may include a quinone derivative such as tetracyanoquinodimethane (TCNQ) and 2,3,5,6-tetrafluoro-tetracyanoquinodimethane (F4-TCNQ), and a metal oxide such as tungsten oxide and molybdenum oxide.

As described above, the hole transport region HTR may further include at least one of the hole buffer layer and the electron blocking layer in addition to the hole injection layer HIL and the hole transport layer HTL. The hole buffer layer may compensate an optical resonance distance according to the wavelength of light emitted from the emission layer EML to increase light emission efficiency. Materials included in the hole transport region HTR may also be included in the hole buffer layer. The electron blocking layer is a layer preventing electron injection from the electron transport region ETR to the hole transport region HTR.

The emission layer EML may be provided on the hole transport region HTR. The thickness of the emission layer EML may be, for example, from about 100 Å to about 300 Å. The emission layer EML may have a single layer formed of a single material, a single layer formed of a plurality of different materials, or a multilayer structure having a plurality of layers formed of a plurality of different materials.

Hereinafter, an exemplary embodiment of the inclusion of the polycyclic compound according to an exemplary embodiment of the present disclosure in an emission layer EML will be explained. However, the present disclosure is not limited thereto, the polycyclic compound according to an exemplary embodiment of the present disclosure may be included in at least one organic layer provided between the first electrode EL1 and the second electrode EL2. For example, the polycyclic compound according to an exemplary embodiment of the present disclosure may be included in the hole transport region HTR. For example, the polycyclic compound according to an exemplary embodiment of the present disclosure may be included in the hole transport layer HTL.

The emission layer EML may include the polycyclic compound according to an exemplary embodiment of the present disclosure. Particularly, the emission layer EMI, may include a polycyclic compound represented by the following Formula 1.

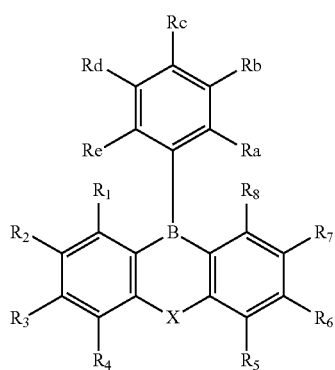

[Formula 1]

Detailed explanation of Ra to Re, $R_1$ to $R_8$, and X is the same as described above and will not be provided.

The emission layer EML may include at least one kind of the polycyclic compound represented by Formula 1. The emission layer EML may further include a known material in addition to the polycyclic compound represented by Formula 1. For example, the emission layer EML may further include a fluorescent material including one of spiro-4,4'-bis(2,2'-diphenylvinyl)-1,1'-biphenyl (spiro-DPVBi), -2,2',7,7''-tetrakis(biphenyl-4-yl)-9,9'-spirobifluorene (spiro-sexiphenyl, spiro-6P), distyryl-benzene (DSB), distyryl-arylene (DSA), a polyfluorene (PFO)-based polymer, and a poly(p-phenylene vinylene) (PPV)-based polymer, without limitation.

The polycyclic compound according to an exemplary embodiment of the present disclosure may be a material included in the emission layer EML and radiating delayed fluorescence. For example, the polycyclic compound represented by Formula 1 may be a material for delayed fluorescence, and may be a material for thermally activated delayed fluorescence (TADF).

The polycyclic compound according to an exemplary embodiment of the present disclosure may be a material for TADF emitting blue light. The polycyclic compound according to an exemplary embodiment of the present disclosure may be a material for TADF emitting deep blue light. The polycyclic compound according to an exemplary embodiment of the present disclosure may emit blue light having a wavelength region less than about 470 nm, for example, from about 440 nm to about 460 nm, or from about 440 nm to about 450 nm.

The polycyclic compound according to an exemplary embodiment of the present disclosure may have an absolute energy difference of about 0.2 eV or less between a singlet energy level and a triplet energy level. By controlling the singlet-triplet energy gap small, the TADF may be efficiently emitted.

The emission layer EML may further include a host. The host may include any commonly used material without specific limitation such as, for example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl) anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl] ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), etc.

The emission layer EML may have a thickness from about 100 Å to about 1,000 Å, for example, from about 100 Å to about 300 Å.

The electron transport region ETR may be provided on the emission layer EML. The electron transport region ETR may include at least one of an electron blocking layer, an electron transport layer ETL, and an electron injection layer EIL, without limitation.

The electron transport region ETR may have a single layer formed of a single material, a single layer formed of a plurality of different materials, or a multilayer structure including a plurality of layers formed of a plurality of different materials.

The electron transport region ETR may be a single layer with a structure having the electron injection layer EIL or the electron transport layer ETL, or a single layer structure formed of an electron injection material and an electron transport material. In addition, the electron transport region ETR may have a single layer structure formed of a plurality of different materials, or a structure laminated from the first electrode EL1 of electron transport layer ETL/electron injection layer EIL, or hole blocking layer/electron transport layer ETL/electron injection layer EIL, without limitation. The thickness of the electron transport region ETR may be, for example, from about 1,000 Å to about 1,500 Å.

The electron transport region ETR may be formed by various methods such as, for example, a vacuum deposition method, a spin coating method, a cast method, a Langmuir-Blodgett (LB) method, an inkjet printing method, a laser printing method, and a laser induced thermal imaging (LITI) method.

When the electron transport region ETR includes the electron transport layer ETL, the electron transport region ETR may include tris(8-hydroxyquinolinato)aluminum ($Alq_3$), 1,3,5-tri[(3-pyridyl)-phen-3-yl]benzene (TmPyPB), 2,4,6-tris(3'-(pyridin-3-yl)biphenyl-3-yl)-1,3,5-triazine (Tm3PyBPZ), 2-(4-(N-phenylbenzoimidazolyl-1-ylphenyl)-9,10-dinaphthylanthracene, 1,3,5-tri(1-phenyl-1H-benzo[d] imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5- diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate) (Bebq$_2$), 9,10-di(naphthalene-2-yl)anthracene (ADN), or a mixture thereof, without limitation. The thickness of the electron transport layer ETL may be from about 100 Å to about 1,000 Å, for example, from about 150 Å to about 500 Å. If the thickness of the electron transport layer ETL satisfies the above-described range, satisfactory electron transport properties may be obtained without a substantial increase of the driving voltage.

When the electron transport region ETR includes the electron injection layer EIL, the electron transport region ETR may include, for example, LiF, lithium quinolate (LiQ), Li$_2$O, BaO, NaCl, CsF, a metal in lanthanoides such as Yb, or a metal halide such as RbCl and RbI, without limitation. The electron injection layer EIL may be formed of a mixture of an electron transport material and an insulating organic metal salt. The organic metal salt may be a material having an energy band gap of about 4 eV or more. Particularly, the organic metal salt may include, for example, a metal acetate, a metal benzoate, a metal acetoacetate, a metal acetylacetonate, or a metal stearate. The thickness of the electron injection layer EIL may be from about 1 Å to about 100 Å, or from about 3 Å to about 90 Å. When the thickness of the electron injection layer EIL satisfies the above described range, satisfactory electron injection property may be obtained without inducing a substantial increase of the driving voltage.

The electron transport region ETR may include a hole blocking layer, as described above. The hole blocking layer may include, for example, at least one of 2,9-dimethyl-4,7-diphenyl-1,10-phenanthroline (BCP) and 4,7-diphenyl-1,10-phenanthroline (Bphen), without limitation.

The second electrode EL2 may be provided on the electron transport region ETR. The second electrode EL2 may be a common electrode or a cathode. The second electrode EL2 may be a transmissive electrode, a transflective electrode or a reflective electrode. When the second electrode EL2 is the transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include, for example, Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed of the above-described materials, and a transparent conductive layer formed of ITO, IZO, ZnO, ITZO, etc.

The second electrode EL2 may be connected with an auxiliary electrode. If the second electrode EL2 is connected with the auxiliary electrode, the resistance of the second electrode EL2 may be reduced.

In the organic electroluminescence device 10, as a voltage is applied to each of the first electrode EL1 and the second electrode EL2, holes injected from the first electrode EL1 may move via the hole transport region HTR to the emission layer EML, and electrons injected from the second electrode EL2 may move via the electron transport region ETR to the emission layer EML. The electrons and holes are then recombined in the emission layer EML to generate excitons, which may emit light via transition from an excited state to a ground state.

When the organic electroluminescence device 10 is a top emission type, the first electrode EL1 may be the reflective electrode, and the second electrode EL2 may be the transmissive electrode or transflective electrode. When the organic electroluminescence device 10 is a bottom emission type, the first electrode EL1 may be the transmissive electrode or the transflective electrode, and the second electrode EL2 may be the reflective electrode.

The organic electroluminescence device according to an exemplary embodiment of the present disclosure includes the polycyclic compound represented by Formula 1, thereby attaining high emission efficiency. Particularly, the polycyclic compound represented by Formula 1 may emit light via a TADF process. Accordingly, the organic electroluminescence device according to an exemplary embodiment of the present disclosure may accomplish high efficiency. More particularly, the organic electroluminescence device according to an exemplary embodiment of the present disclosure may emit blue light via the TADF process and attain high efficiency. The organic electroluminescence device according to an exemplary embodiment of the present disclosure may attain efficiency increase and roll-off decrease as well as blue emission.

Hereinafter, the present disclosure will be explained more particularly referring to preferred embodiments and comparative embodiments. The following embodiments are only for illustration to assist the understanding of the present disclosure, and however the scope of the present disclosure is not limited thereto.

SYNTHESIS EXAMPLES

The polycyclic compound according to an exemplary embodiment of the present disclosure may be synthesized, for example, as follows. However, the present disclosure is not limited thereto.

Synthesis Example 1

Synthesis of Compound 2

Compound 2 which is a polycyclic compound according to an exemplary embodiment of the present disclosure may be synthesized by the following reaction.

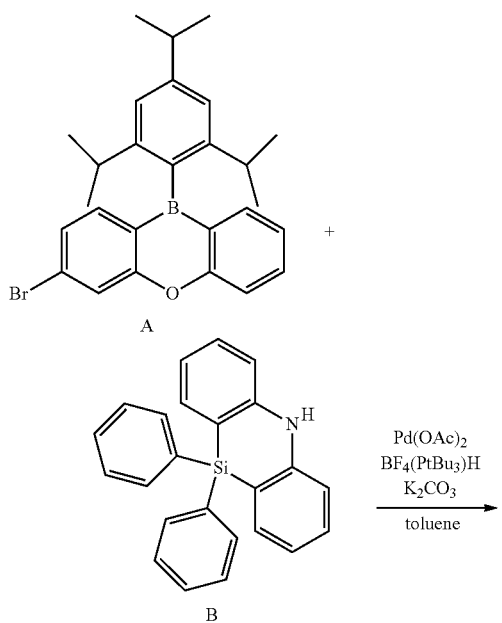

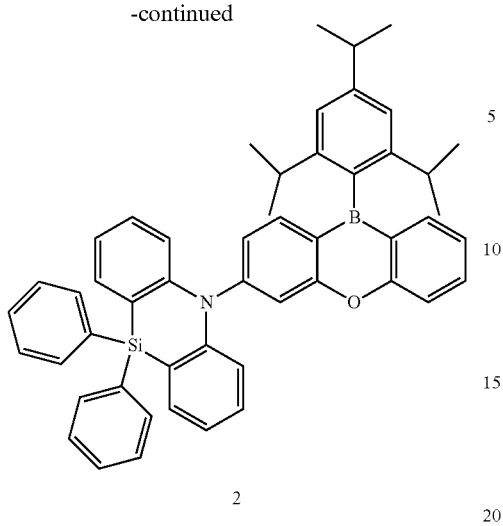

2

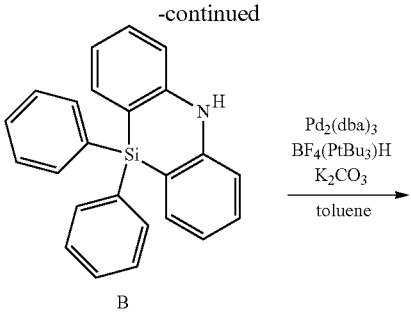

Under an argon (Ar) atmosphere, 3.1 g of Compound A, 1 g of Compound B, 0.1 g of acetic acid palladium, 0.25 g of tri-tert-butylphosphonium tetrafluoroborate (PH(tBu)$_3$/BF$_4$), and 1.77 g of potassium carbonate (K$_2$CO$_3$) were added to a 100 ml three-necked flask, followed by heating and refluxing in 50 ml of a toluene solvent for about 6 hours. After cooling in the air, water was added, an organic layer was separated, and solvents were distilled. The crude product thus obtained was separated by silica gel column chromatography (using a mixture solvent of dichloromethane and hexane) and then, recrystallized using a mixture solvent of toluene and hexane to obtain 2.77 g (yield 82%) of a white solid compound.

The chemical shift values (δ) of the compound measured by $^1$H NMR were 7.99 (d, 1H), 7.90-7.69 (m, 6H), 7.57-7.18 (m, 30H). In addition, the molecular weight of the compound measured by fast-atom bombardment mass spectra (FAB-MS) was 730. Through the results, the white solid compound was identified as Compound 2.

Synthesis Example 2

Synthesis of Compound 79

Compound 79 which is a polycyclic compound according to an exemplary embodiment of the present disclosure may be synthesized by the following reaction.

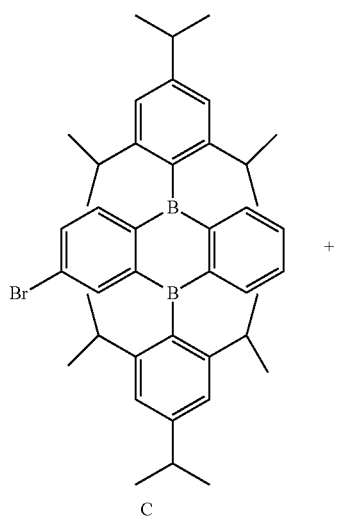

79

Under an argon (Ar) atmosphere, 1.50 g of Compound C, 1.18 g of Compound B, 0.052 g of tris(dibenzylideneacetone)dipalladium (Pd$_2$(dba)$_3$), 0.065 g of PH(tBu)$_3$/BF$_4$, and 0.541 g of sodium tert-butoxide (t-BuONa) were added to a 100 ml three-necked flask, followed by heating and refluxing in 50 ml of a toluene solvent for about 6 hours. After cooling in the air, water was added, an organic layer was separated, and solvents were distilled. The crude product thus obtained was separated by silica gel column chromatography (using a mixture solvent of dichloromethane and hexane) and then, recrystallized using a mixture solvent of toluene and hexane to obtain 2.22 g (yield 85%) of a white solid compound.

The molecular weight of the compound measured by FAB-MS was 927. Through the results, the white solid compound was identified as Compound 79.

Synthesis Example 3

Synthesis of Compound 7

Compound 7 which is a polycyclic compound according to an exemplary embodiment of the present disclosure may be synthesized by the following reaction.

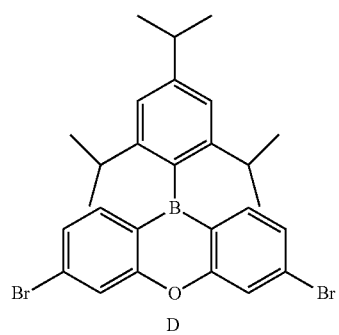

D

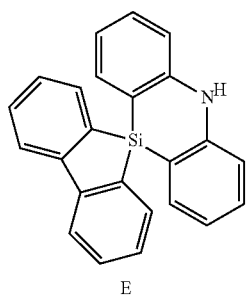

E

Pd(OAc)$_2$
BF$_4$(PtBu$_3$)H
K$_2$CO$_3$
——————→
toluene

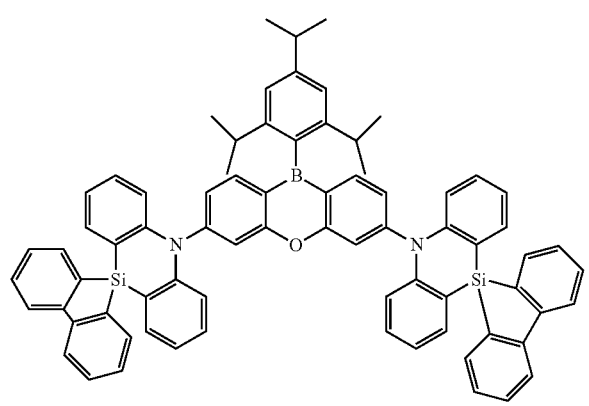

7

Under an argon (Ar) atmosphere, 2.5 g of Compound D, 3.8 g of Compound E, 0.14 g of acetic acid palladium (Pd(OAc)$_2$), 0.38 g of PH(tBu)$_3$/BF$_4$, and 1.8 g of potassium carbonate (K$_2$CO$_3$) were added to a 100 ml three-necked flask, followed by heating and refluxing in 50 ml of a toluene solvent for about 10 hours. After cooling in the air, water was added, an organic layer was separated, and solvents were distilled. The crude product thus obtained was separated by silica gel column chromatography (using a mixture solvent of dichloromethane and hexane) and then, recrystallized using a mixture solvent of toluene and hexane to obtain 3.54 g (yield 71%) of a white solid compound.

The molecular weight of the compound measured by FAB-MS was 1073. Through the results, the white solid compound was identified as Compound 7.

Synthesis Example 4

Synthesis of Compound 29

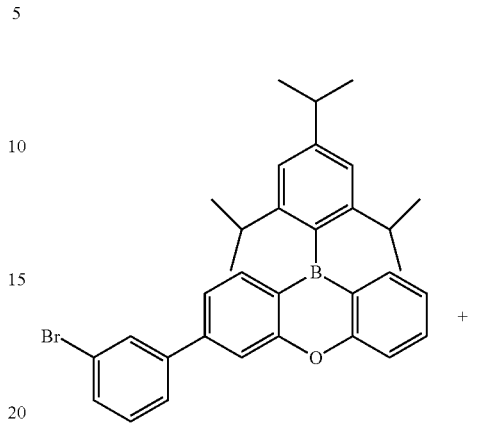

F

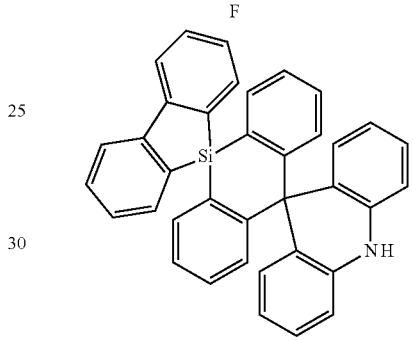

G

Pd(OAc)$_2$
BF$_4$(PtBu$_3$)H
K$_2$CO$_3$
——————→
toluene

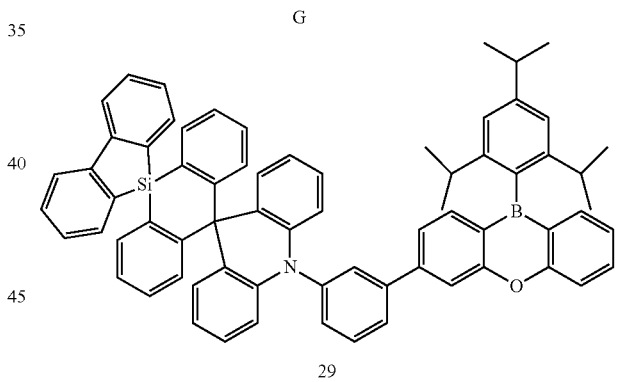

29

Under an argon (Ar) atmosphere, 2.0 g of Compound F, 2.3 g of Compound G, 0.06 g of acetic acid palladium (Pd(OAc)$_2$), 0.15 g of PH(tBu)$_3$/BF$_4$, and 1.0 g of potassium carbonate (K$_2$CO$_3$) were added to a 100 ml three-necked flask, followed by heating and refluxing in 60 ml of a toluene solvent for about 8 hours. After cooling in the air, water was added, an organic layer was separated, and solvents were distilled. The crude product thus obtained was separated by silica gel column chromatography (using a mixture solvent of dichloromethane and hexane) and then, recrystallized using a mixture solvent of toluene and hexane to obtain 2.8 g (yield 77%) of a white solid compound.

The molecular weight of the compound measured by FAB-MS was 968. Through the results, the white solid compound was identified as Compound 29.

Synthesis Example 5

Synthesis of Compound 31

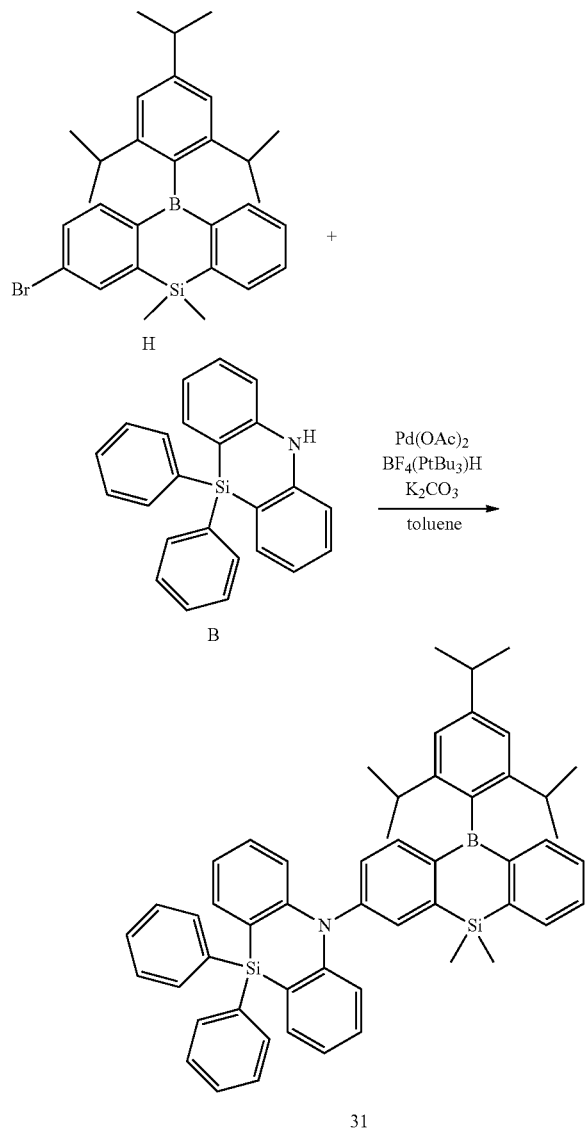

Under an argon (Ar) atmosphere, 3.0 g of Compound H, 2.5 g of Compound B, 0.09 g of acetic acid palladium (Pd(OAc)$_2$), 0.24 g of PH(tBu)$_3$/BF$_4$, and 1.6 g of potassium carbonate (K$_2$CO$_3$) were added to a 100 ml three-necked flask, followed by heating and refluxing in 60 ml of a toluene solvent for about 8 hours. After cooling in the air, water was added, an organic layer was separated, and solvents were distilled. The crude product thus obtained was separated by silica gel column chromatography (using a mixture solvent of dichloromethane and hexane) and then, recrystallized using a mixture solvent of toluene and hexane to obtain 2.8 g (yield 82%) of a white solid compound.

The molecular weight of the compound measured by FAB-MS was 771. Through the results, the white solid compound was identified as Compound 31.

Synthesis Example 6

Synthesis of Compound 34

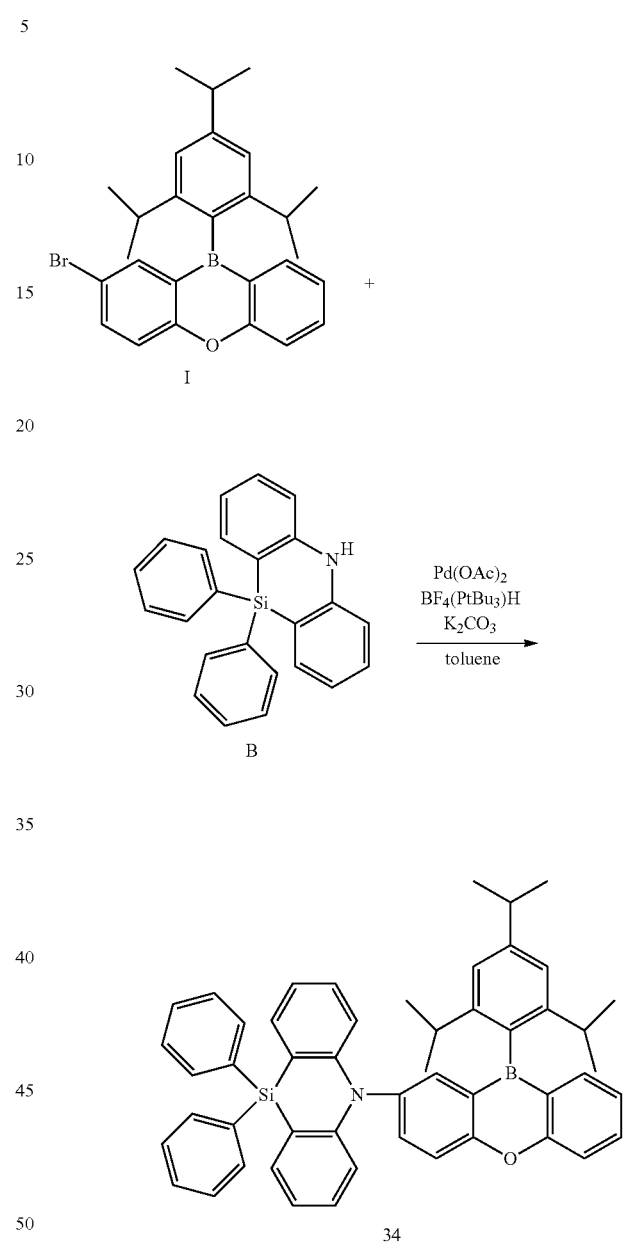

Under an argon (Ar) atmosphere, 4.0 g of Compound I, 3.6 g of Compound B, 0.14 g of acetic acid palladium (Pd(OAc)$_2$), 0.35 g of PH(tBu)$_3$/BF$_4$, and 2.4 g of potassium carbonate (K$_2$CO$_3$) were added to a 100 ml three-necked flask, followed by heating and refluxing in 80 ml of a toluene solvent for about 8 hours. After cooling in the air, water was added, an organic layer was separated, and solvents were distilled. The crude product thus obtained was separated by silica gel column chromatography (using a mixture solvent of dichloromethane and hexane) and recrystallized using a mixture solvent of toluene and hexane to obtain 5.1 g (yield 80%) of a white solid compound.

The molecular weight of the compound measured by FAB-MS was 729. Through the results, the white solid compound was identified as Compound 34.

Synthesis Example 7

Synthesis of Compound 66

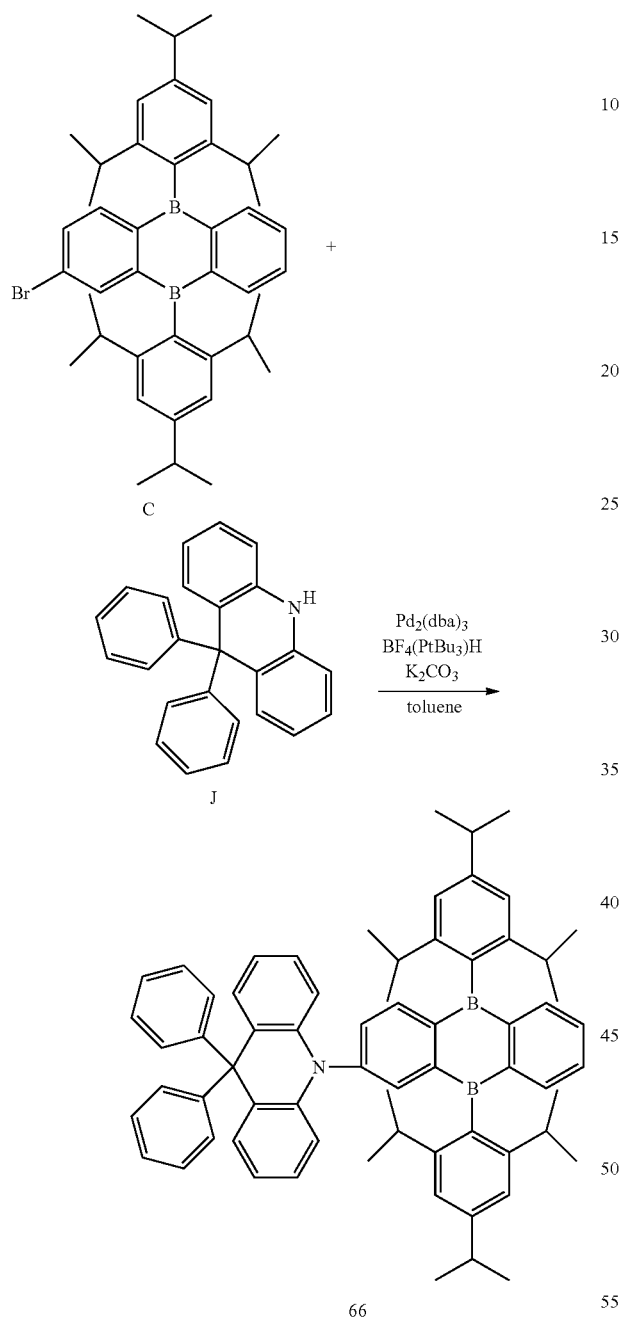

Under an argon (Ar) atmosphere, 1.5 g of Compound C, 0.9 g of Compound J, 0.04 g of acetic acid palladium (Pd(OAc)$_2$), 0.09 g of PH(tBu)$_3$/BF$_4$, and 0.6 g of potassium carbonate (K$_2$CO$_3$) were added to a 100 ml three-necked flask, followed by heating and refluxing in 25 ml of a toluene solvent for about 8 hours. After cooling in the air, water was added, an organic layer was separated, and solvents were distilled. The crude product thus obtained was separated by silica gel column chromatography (using a mixture solvent of dichloromethane and hexane) and recrystallized using a mixture solvent of toluene and hexane to obtain 1.2 g (yield 58%) of a white solid compound.

The molecular weight of the compound measured by FAB-MS was 911. Through the results, the white solid compound was identified as Compound 66.

Synthesis Example 8

Synthesis of Compound 67

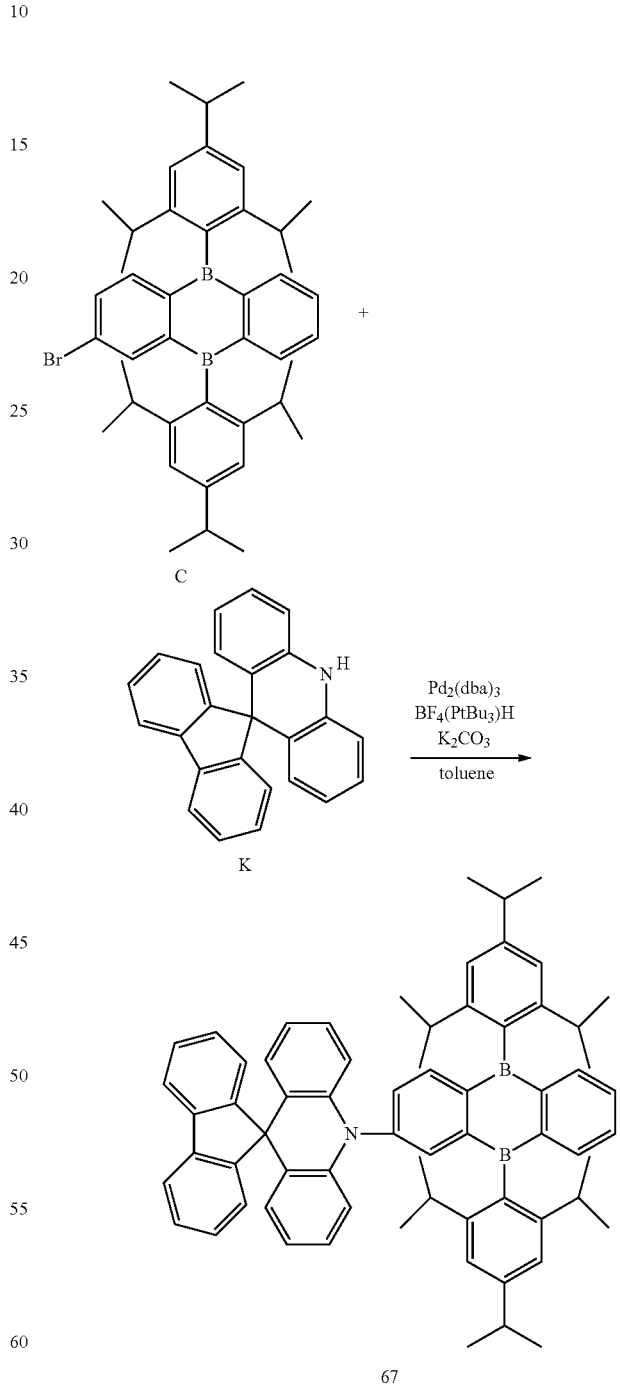

Under an argon (Ar) atmosphere, 1.5 g of Compound C, 0.9 g of Compound K, 0.04 g of acetic acid palladium (Pd(OAc)$_2$), 0.09 g of PH(tBu)$_3$/BF$_4$, and 0.6 g of potassium carbonate (K$_2$CO$_3$) were added to a 100 ml three-necked flask, followed by heating and refluxing in 25 ml of a toluene solvent for about 8 hours. After cooling in the air, water was added, an organic layer was separated, and solvents were distilled. The crude product thus obtained was separated by silica gel column chromatography (using a mixture solvent of dichloromethane and hexane) and recrystallized using a mixture solvent of toluene and hexane to obtain 1.0 g (yield 48%) of a white solid compound.

The molecular weight of the compound measured by FAB-MS was 909. Through the results, the white solid compound was identified as Compound 67.

Synthesis Example 9

Synthesis of Compound 143

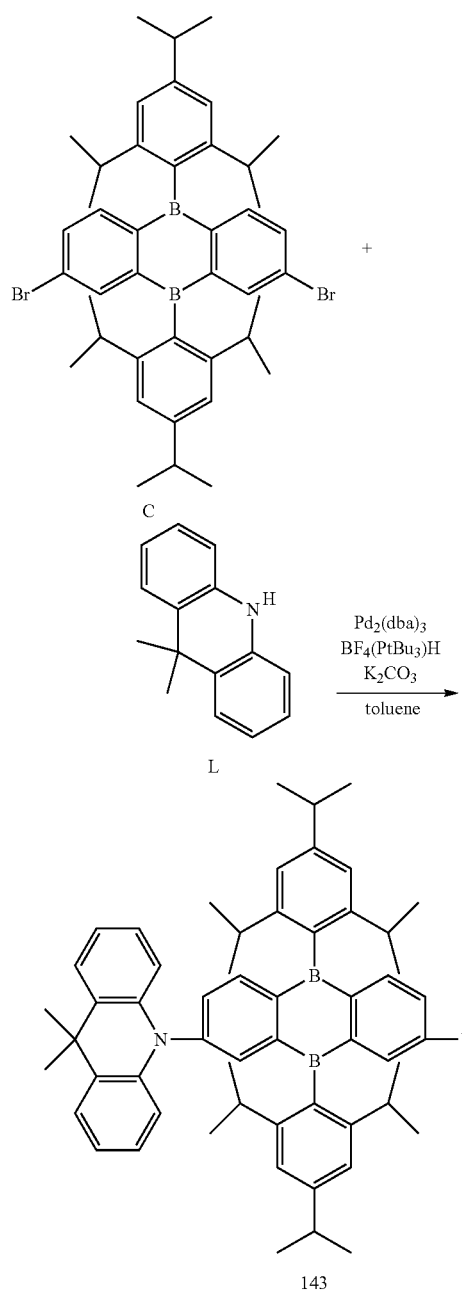

Under an argon (Ar) atmosphere, 1.0 g of Compound C, 0.9 g of Compound L, 0.06 g of acetic acid palladium (Pd(OAc)$_2$), 0.16 g of PH(tBu)$_3$/BF$_4$, and 1.1 g of potassium carbonate (K$_2$CO$_3$) were added to a 100 ml three-necked flask, followed by heating and refluxing in 50 ml of a toluene solvent for about 8 hours. After cooling in the air, water was added, an organic layer was separated, and solvents were distilled. The crude product thus obtained was separated by silica gel column chromatography (using a mixture solvent of dichloromethane and hexane) and recrystallized using a mixture solvent of toluene and hexane to obtain 1.2 g (yield 59%) of a white solid compound.

The molecular weight of the compound measured by FAB-MS was 995. Through the results, the white solid compound was identified as Compound 143.

(Device Manufacturing Examples)

Organic electroluminescence devices of Examples 1 to 6 were manufactured using the above Compounds 2, 7, 29, 31, 34, and 194 as materials for an emission layer.

[Example Compounds]

-continued

29 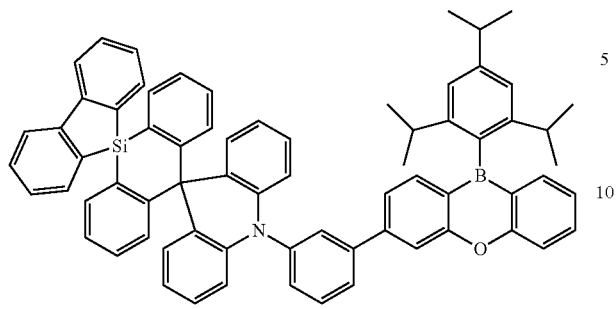

31 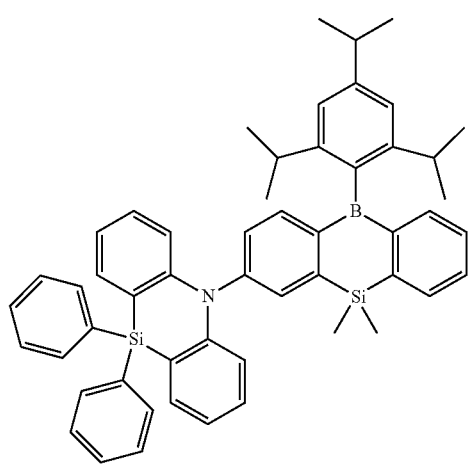

34 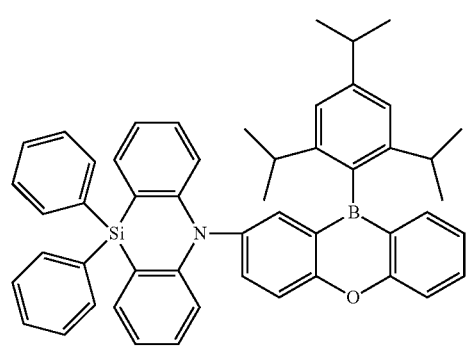

194 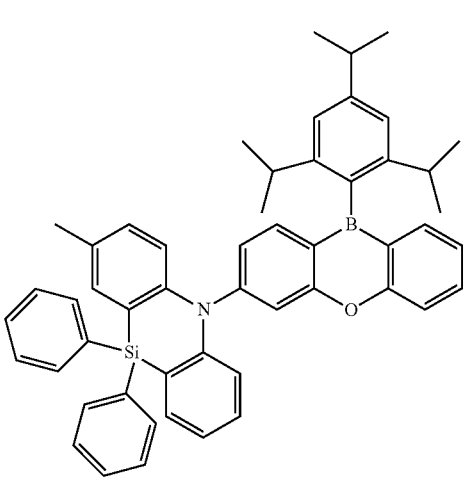

Organic electroluminescence devices of Comparative Examples 1 and 2 were manufactured using the following Comparative Compounds X-1 and X-2 as materials for an emission layer.

[Comparative Compounds]

X-1
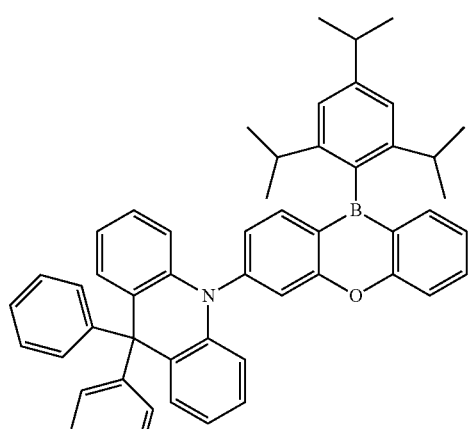

X-2
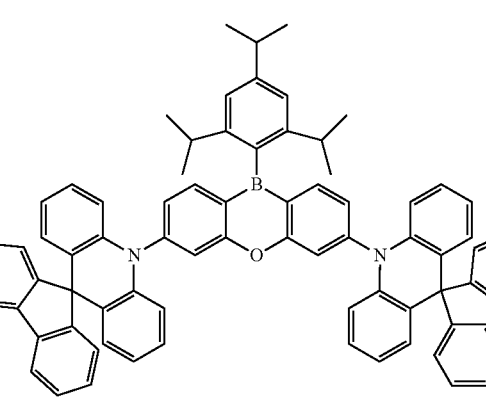

The organic electroluminescence devices of Examples 1 to 6 and Comparative Examples 1 and 2 were manufactured as follows. A first electrode was formed of ITO to a thickness of about 150 nm. After that, a hole injection layer with a thickness of about 10 nm was formed of HAT-CN, a hole transport layer with a thickness of about 80 nm was formed of NPB, an emission layer of DPEPO doped with 18% of the example compound or the comparative compound, and having a layer thickness of about 20 nm was formed, an electron transport layer with a thickness of about 30 nm was formed of TPBi, an electron injection layer with a thickness of about 0.5 nm was formed of LiF, and a second electrode with a thickness of about 100 nm was formed of Al. Each layer and the second electrode were formed using a vacuum deposition apparatus.

After the organic electroluminescence devices of Examples 1 to 6 and Comparative Examples 1 and 2 were manufactured as above, the maximum emission wavelength, delayed life, external quantum efficiency, and roll-off of the organic electroluminescence devices thus manufactured were evaluated. The maximum emission wavelength was obtained by measuring the maximum emission wavelength of an emission spectrum at room temperature (about 300K). The external quantum efficiency of the organic electroluminescence device was measured using an external quantum efficiency measurement apparatus C9920-2-12 manufactured by HAMAMATSU Photonics Co. The evaluation results are shown in Table 1 below.

TABLE 1

| Device manufacturing example | Emission layer | λmax | Delayed fluorescence life (μs) | η ext % | Roll-off ηmax/η (10 mA) |
|---|---|---|---|---|---|
| Example 1 | Example Compound 2 | 445 | 6.02 | 15 | 0.90 |
| Example 2 | Example Compound 7 | 450 | 4.49 | 18 | 0.88 |
| Example 3 | Example Compound 29 | 455 | 5.89 | 17 | 0.82 |
| Example 4 | Example Compound 31 | 450 | 6.50 | 15 | 0.85 |
| Example 5 | Example Compound 34 | 455 | 4.02 | 16 | 0.92 |
| Example 6 | Example Compound 194 | 455 | 3.80 | 15 | 0.95 |
| Comparative Example 1 | Comparative Compound X-1 | 470 | 12.9 | 10 | 0.61 |
| Comparative Example 2 | Comparative Compound X-2 | 475 | 10.6 | 11 | 0.40 |

Referring to Table 1, it may be secured that an organic electroluminescence device including the polycyclic compound according to an exemplary embodiment of the present disclosure may attain deep blue color, high efficiency and low roll-off.

When comparing Examples 1 and 2 with Comparative Examples 1 and 2, the compound according to an exemplary embodiment of the present disclosure succeeded in decreasing the wavelength of emission waves due to Si atomic effect. In addition, delayed fluorescence life was reduced, and thus, roll-off was also reduced.

The π-conjugation system of the donor molecule decreases due to the introduction of a Si atom, and HOMO-LUMO is efficiently separated due to twist effects, thereby decreasing the delayed fluorescence life.

Referring to the results of Example 3, the above-described effects may be sufficiently attained even though a linker was introduced to and a substitution position was changed in Example Compound 29 in comparison to Example Compound 2, and deep blue color, high efficiency, and low roll-off may be attained.

In Example 4, a silicon atom was introduced instead of an oxygen atom to the crosslinking part of an acceptor molecule in Example Compound 31 in comparison to Example Compound 2. When comparing with Example 1, the wavelength was somewhat increased, however a sufficient deep blue emission range may be attained, and the silicon atom may be usefully used instead of the oxygen atom.

Referring to the results of Example 5, it may be found that the above-described effects may be sufficiently attained even though changing the substitution position of a donor in Example Compound 34 in comparison to Example Compound 2.

Referring to the results of Example 6, it may be found that the above-described effects may be sufficiently attained even though introducing a substituent such as an alkyl group to a donor in Example Compound 194 in comparison to Example Compound 2.

(Device Manufacturing Examples)

Organic electroluminescence devices of Examples 7 to 10 were manufactured using the above Compounds 66, 67, 79, and 143 as materials for an emission layer.

[Example Compounds]

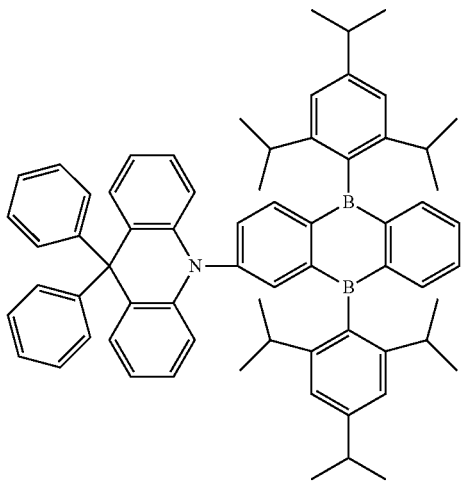

66

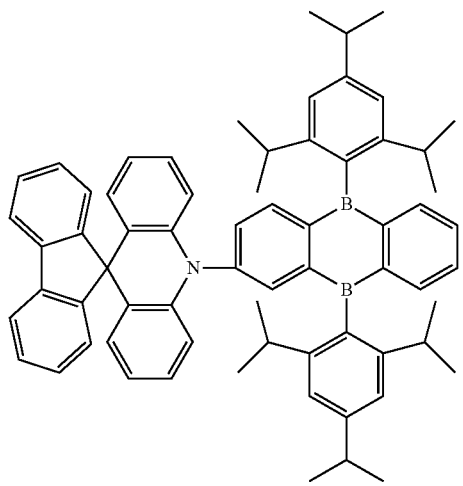

67

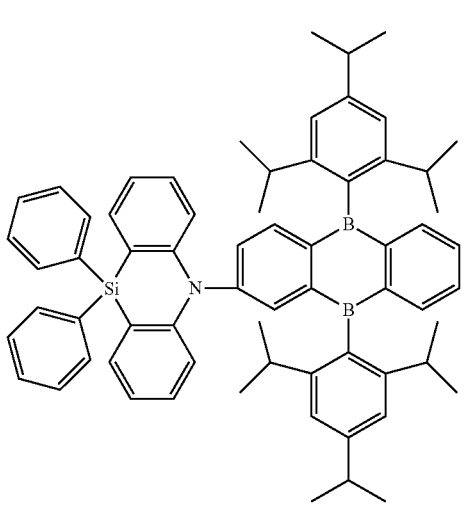

79

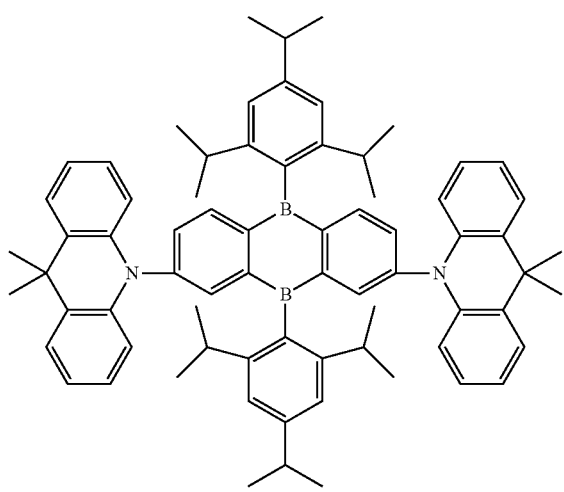

143

Organic electroluminescence devices of Comparative Examples 3 and 4 were manufactured using the following Comparative Compounds X-3 and X-4 as materials for an emission layer.

[Comparative Compounds]

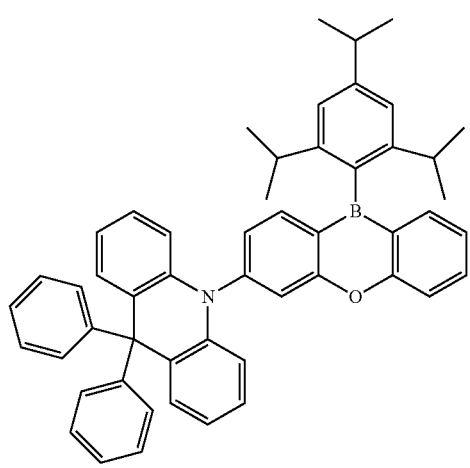

X-3

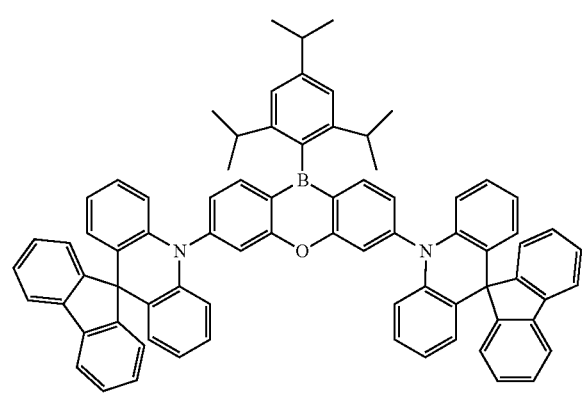

X-4

Organic electroluminescence devices of Examples 7 to 10 and Comparative Examples 3 and 4 were manufactured by the above-described method. Then, the delayed fluorescence life, external quantum efficiency, and roll-off of the organic electroluminescence device thus manufactured were evaluated. The results are shown in Table 2 below.

TABLE 2

| Device manufacturing example | Emission layer | Delayed fluorescence life (μs) | η ext % | Roll-off ηmax/η (10 mA) |
|---|---|---|---|---|
| Example 7 | Example Compound 66 | 7.52 | 15 | 0.90 |
| Example 8 | Example Compound 67 | 8.20 | 18 | 0.88 |
| Example 9 | Example Compound 79 | 6.05 | 17 | 0.82 |
| Example 10 | Example Compound 143 | 6.50 | 15 | 0.85 |
| Comparative Example 3 | Comparative Compound X-3 | 12.9 | 10 | 0.61 |
| Comparative Example 4 | Comparative Compound X-4 | 10.6 | 11 | 0.40 |

From the results of Table 2, it may be found that the organic electroluminescence device including the polycyclic compound according to an exemplary embodiment of the present disclosure may attain efficiency increase, and roll-off decrease.

When comparing the results of Examples 7 and 8 and Comparative Examples 3 and 4, the delayed fluorescence life of the polycyclic compound according to an exemplary embodiment of the present disclosure was reduced, and thus, roll-off was also reduced.

By introducing a boron (B) atom in the structure of an electron acceptor in Example Compounds 66 and 67 in comparison to Comparative Compound X-3, the performance of the acceptor was enhanced, the delayed fluorescence life was decreased, and low roll-off was attained.

From the results of Example 9, the above-described effects may be sufficiently attained even though introducing Si in an electron donor in Example Compound 79 in comparison to Example Compound 66, and high efficiency and low roll-off may be attained.

From the results of Example 10, even in a structure introducing two electron donors in Example Compound 143 in comparison to Example Compound 66, high efficiency and low roll-off may be also attained.

The compound according to an exemplary embodiment of the present disclosure may be used as a material for an organic electroluminescence device.

The compound according to an exemplary embodiment of the present disclosure may be used as a material for emitting delayed fluorescence.

The organic electroluminescence device according to an exemplary embodiment of the present disclosure including the compound according to an exemplary embodiment of the present disclosure may accomplish efficiency enhancement, roll-off decrease, and blue emission.

Although the specific exemplary embodiments of the present disclosure have been described, it is understood that the present disclosure should not be limited to these exemplary embodiments but various changes and modifications can be made by one ordinary skilled in the art within the spirit and scope of the present disclosure as hereinafter claimed.

What is claimed is:

1. A polycyclic compound represented by the following Formula 1:

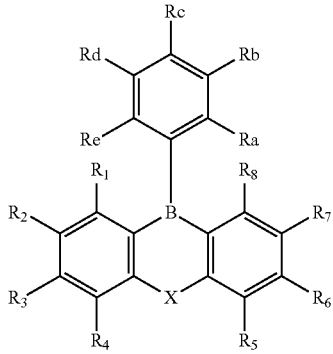

[Formula 1]

in Formula 1, X is O, SiR'R", S, or BAr$_1$,

Ar$_1$ is substituted or unsubstituted aryl group having 6 to 30 carbon atoms for forming a ring, or substituted or unsubstituted heteroaryl group having 2 to 30 carbon atoms for forming a ring, R' and R" are each independently substituted or unsubstituted alkyl group having 1 to 30 carbon atoms, substituted or unsubstituted aryl group having 6 to 30 carbon atoms for forming a ring, or substituted or unsubstituted heteroaryl group having 2 to 30 carbon atoms for forming a ring, where R' and R" are optionally combined with each other to form a ring, Ra to Re and R$_1$ to R$_8$ are each independently hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, when X is BAr$_1$, at least one of R$_1$ to R$_8$ is represented by one of the following Formulae 2 to 4, when X is O, SiR'R", or S, at least one of R$_1$ to R$_8$ is represented by the following Formula 3 or 4:

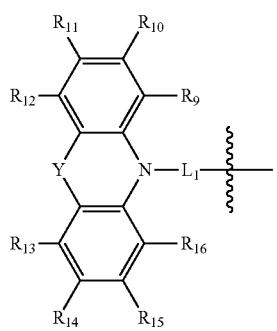

[Formula 2]

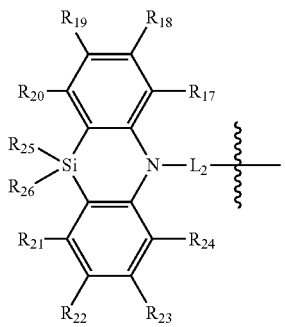

[Formula 3]

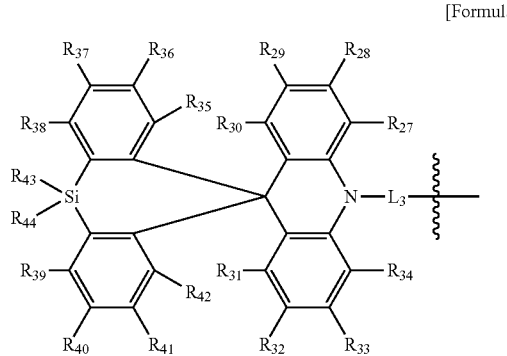

[Formula 4]

in Formulae 2 to 4, Y is a direct linkage, CZ$_1$Z$_2$, NZ$_3$, O, or S,

Z$_1$ to Z$_3$ and R$_9$ to R$_{44}$ are each independently hydrogen atom, deuterium atom, halogen atom, cyano group, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, optionally, R$_{25}$ and R$_{26}$, R$_{43}$ and R$_{44}$, and Z$_1$ and Z$_2$ each two groups independently combine with each other to form a ring, and L$_1$ to L$_3$ are each independently a direct linkage, or substituted or unsubstituted arylene group having 6 to 30 carbon atoms for forming a ring.

2. The polycyclic compound of claim 1, wherein Formula 1 is represented by the following Formula 1-1:

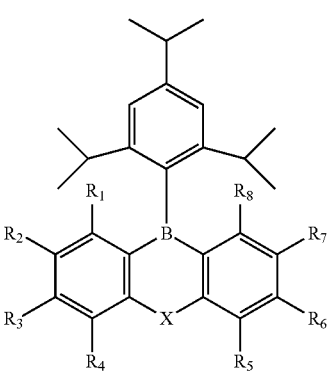

[Formula 1-1]

in Formula 1-1, X and R$_1$ to R$_8$ are as defined in claim 1.

3. The polycyclic compound of claim 1, wherein L$_1$ to L$_3$ are each independently a direct linkage, or substituted or unsubstituted phenylene group.

4. The polycyclic compound of claim 1, wherein Formula 3 is represented by one of the following Formulae 3-1 to 3-4:

5. The polycyclic compound of claim 1, wherein Formula 4 is represented by one of the following Formulae 41 to 4-4:

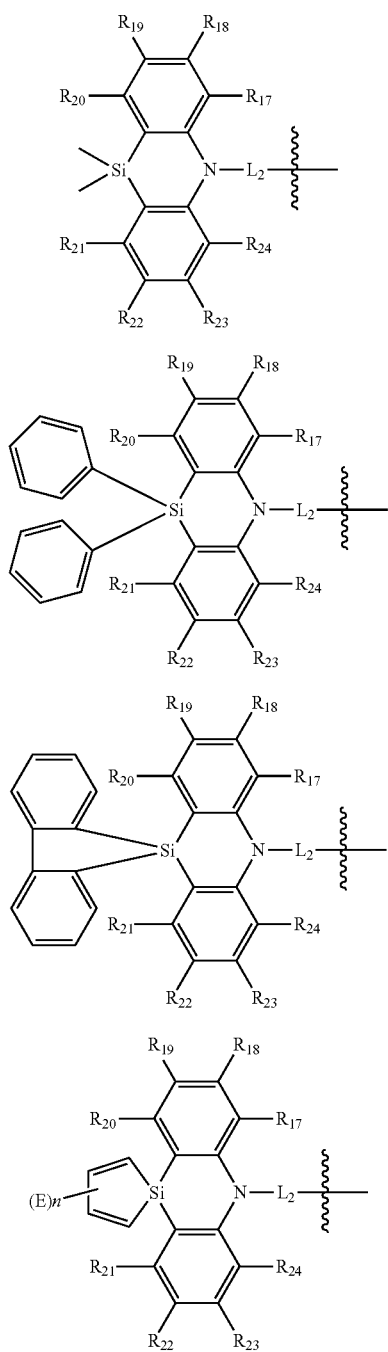

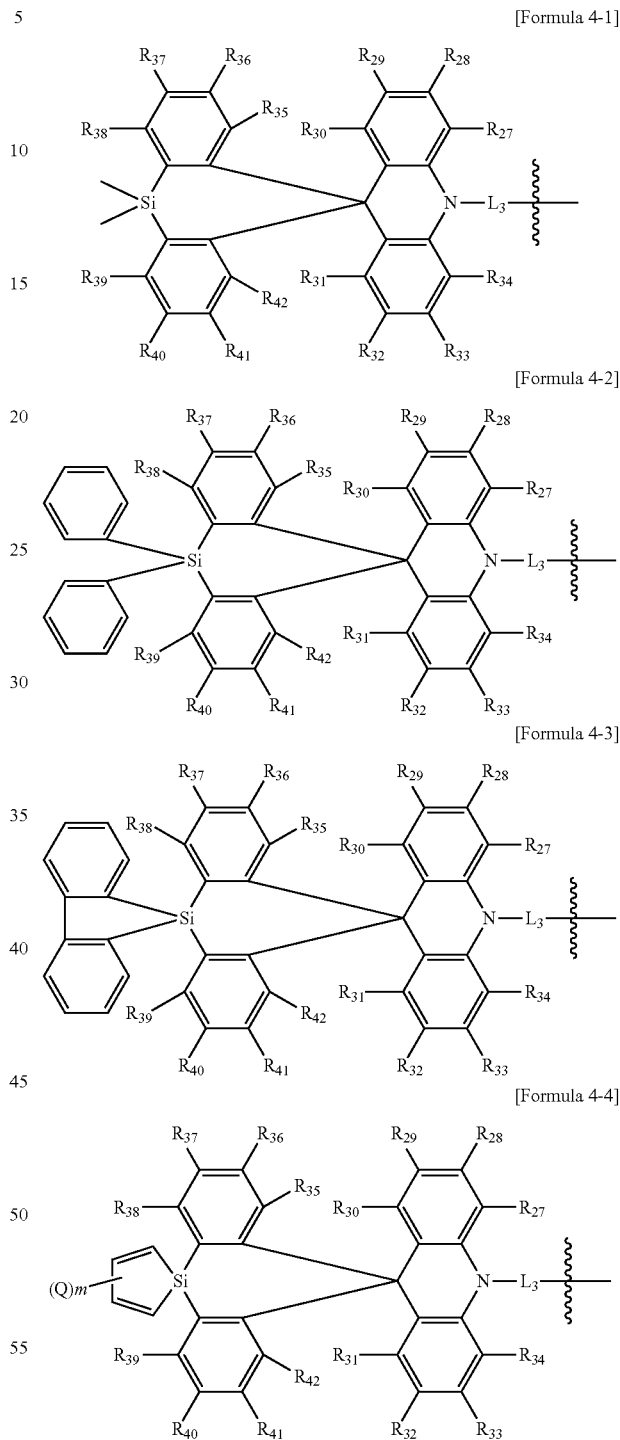

in Formulae 3-1 to 3-4, $L_2$, and $R_{17}$ to $R_{24}$ are as defined in claim 1, E is hydrogen atom, deuterium, atom substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, where E optionally combines with an adjacent group to form a ring, and n is an integer of 0 to 4.

in Formulae 4-1 to 4-4, $L_3$, and $R_{27}$ to $R_{42}$ are as defined in claim 1, Q is hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, Where Q optionally combines with an adjacent group to form a ring, and m is an integer of 0 to 4.

6. The polycyclic compound of claim 1, wherein X is BAr$_1$, and Ar$_1$ is substituted or unsubstituted phenyl group.

7. The polycyclic compound of claim 1, wherein Formula 1 is represented by the following Formula 1-2:

[Formula 1-2]

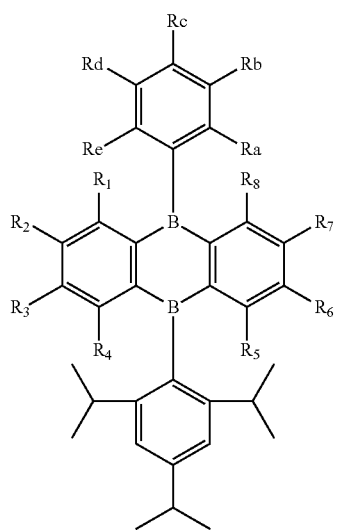

in Formula 1-2, Ra to Re, and R$_1$ to R$_8$ are as defined in claim 1.

8. The polycyclic compound of claim 1, wherein the polycyclic compound represented by Formula 1 is at least one of compounds represented in the following Compound Groups 1 and 3:

[Compound Group 1]

1

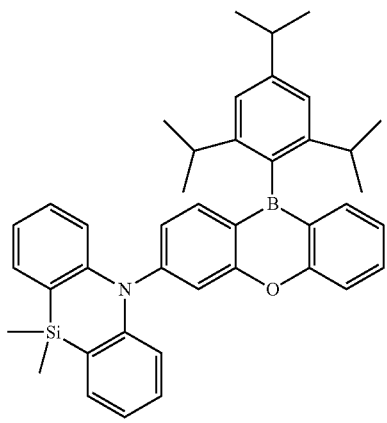

-continued

2

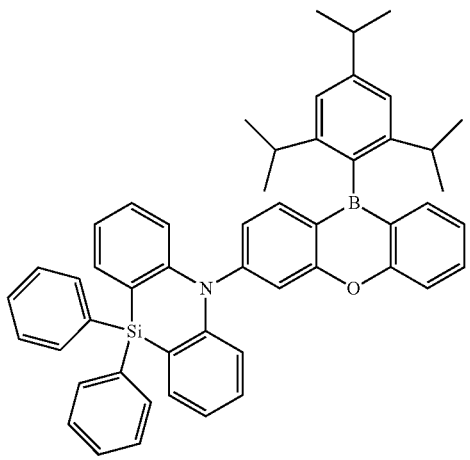

3

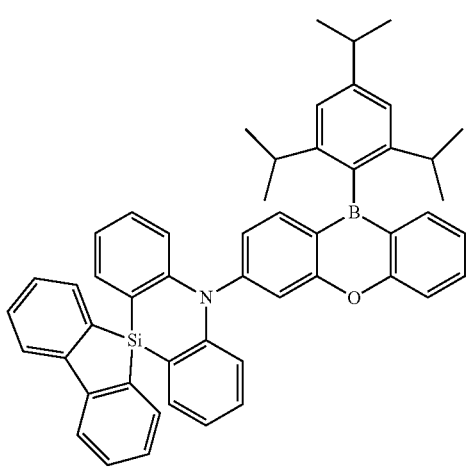

4

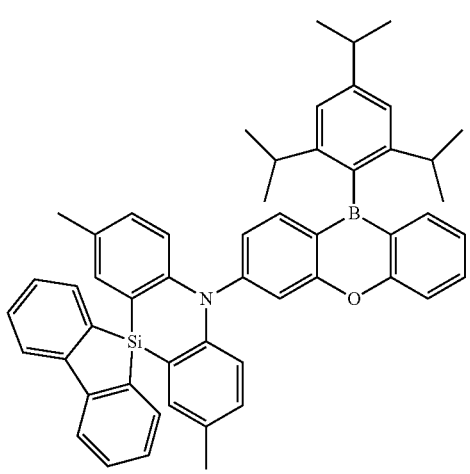

5
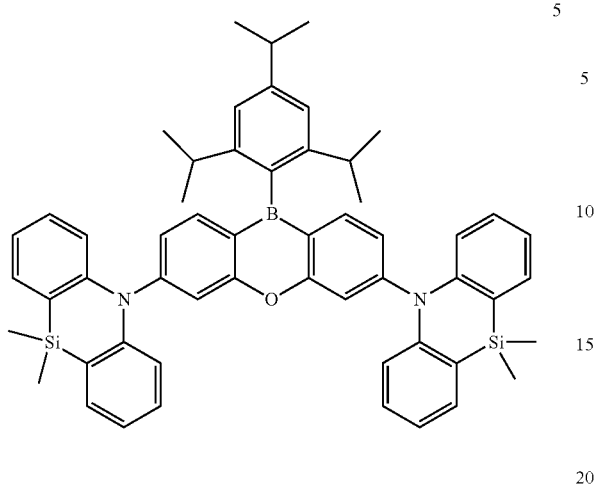
6
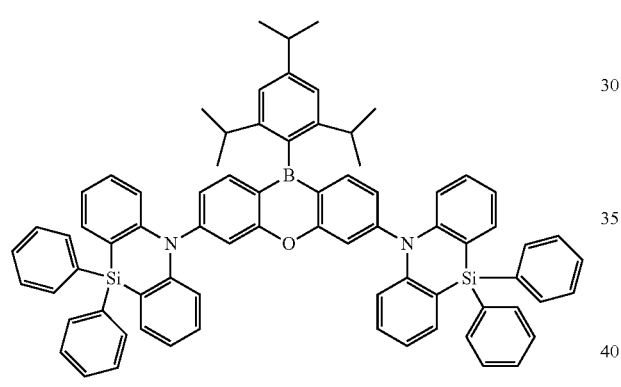
7
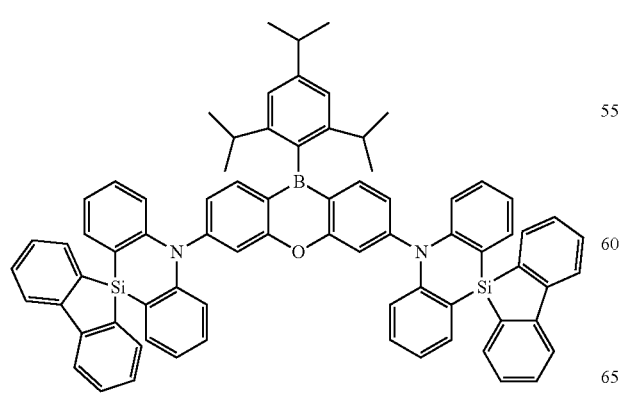
8
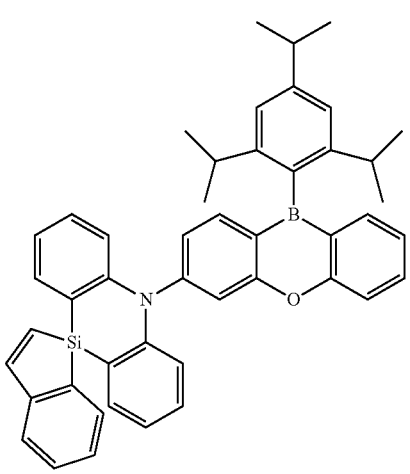
9
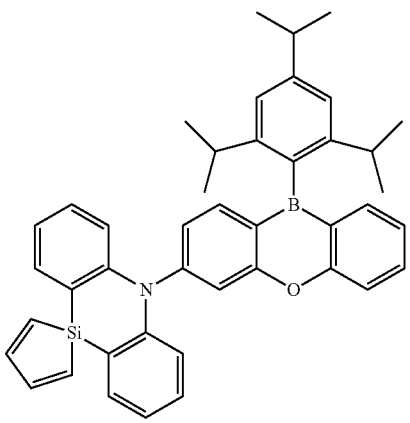
10
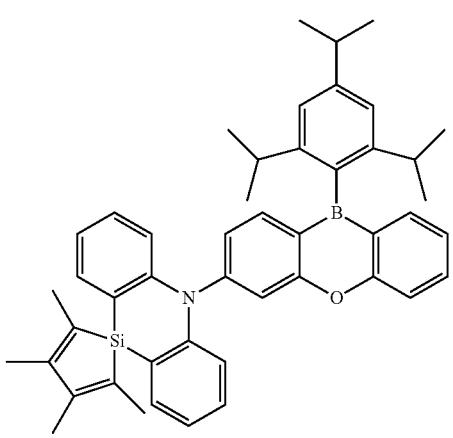

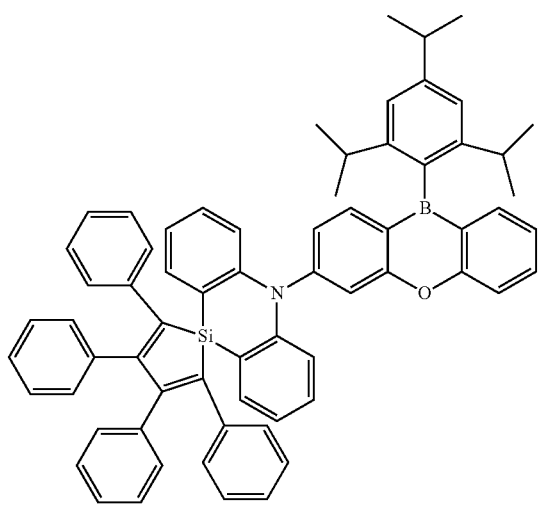
11
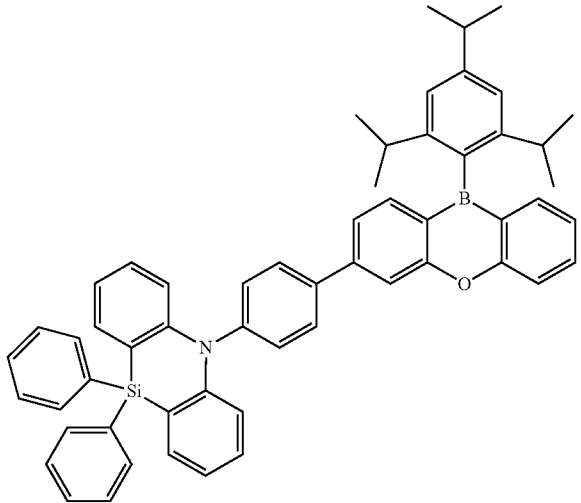
14
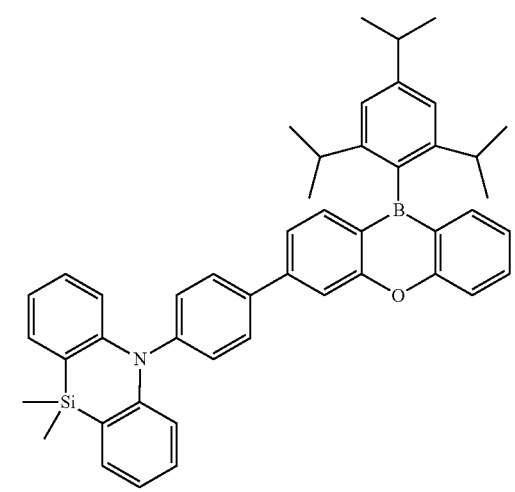
12
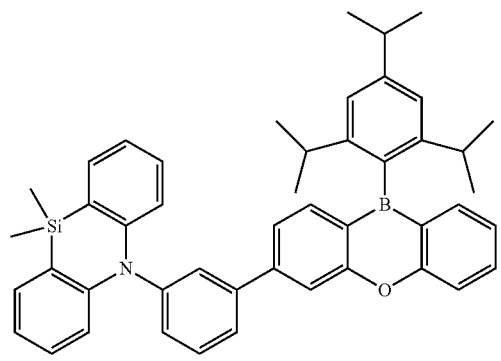
13
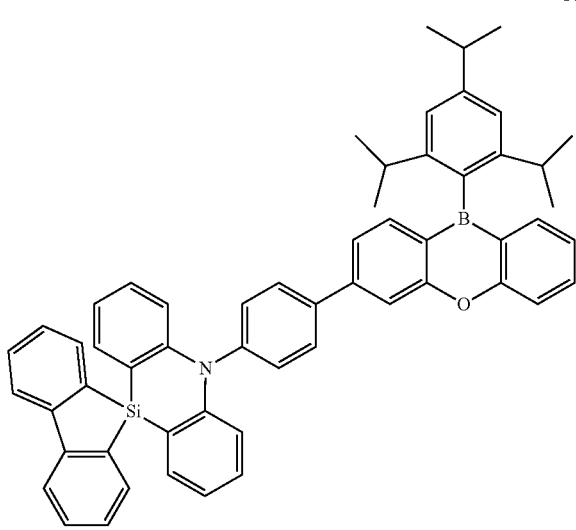
15
16

17
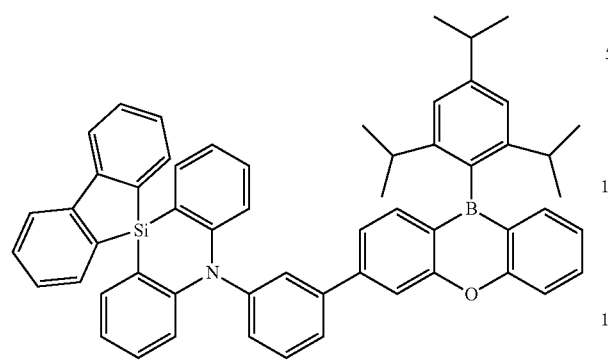
18
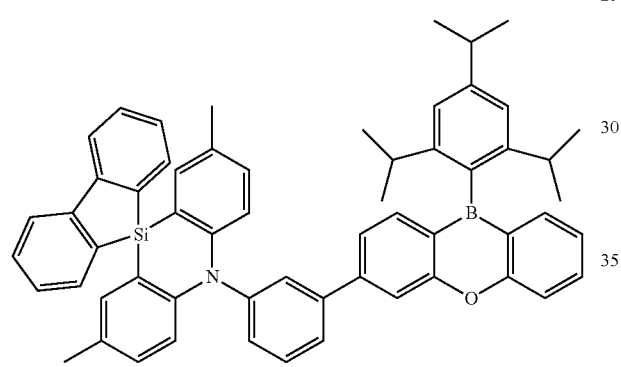
19
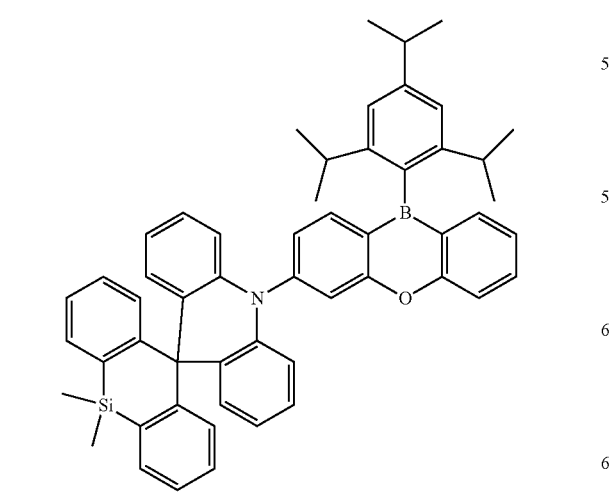
20
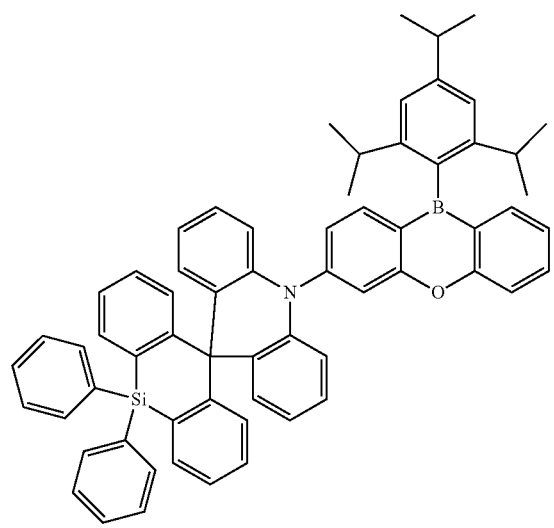
21
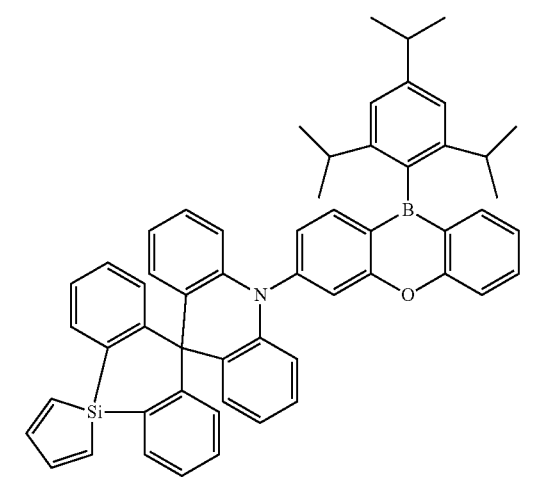

-continued
23
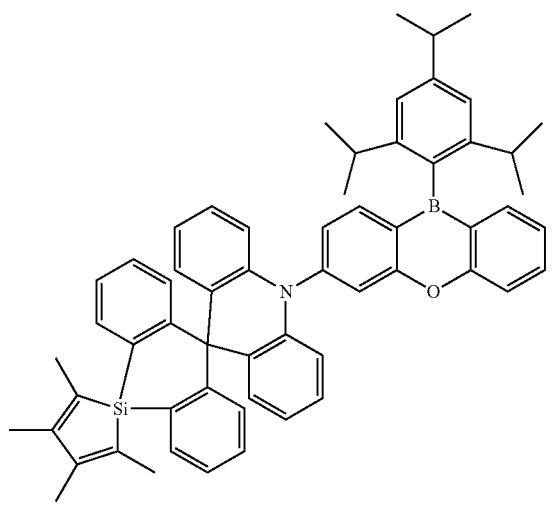
24
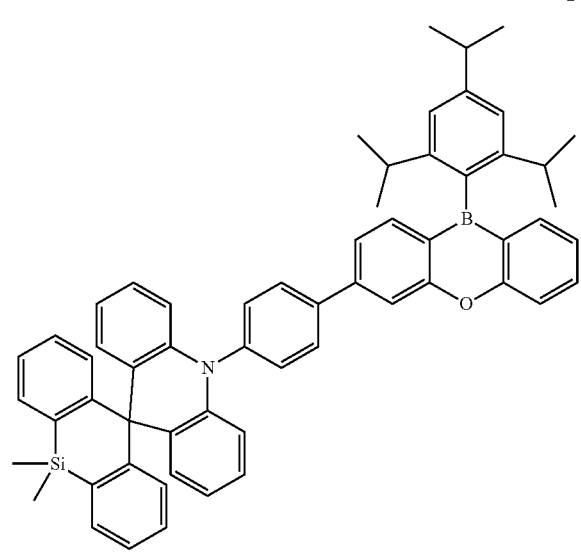
25
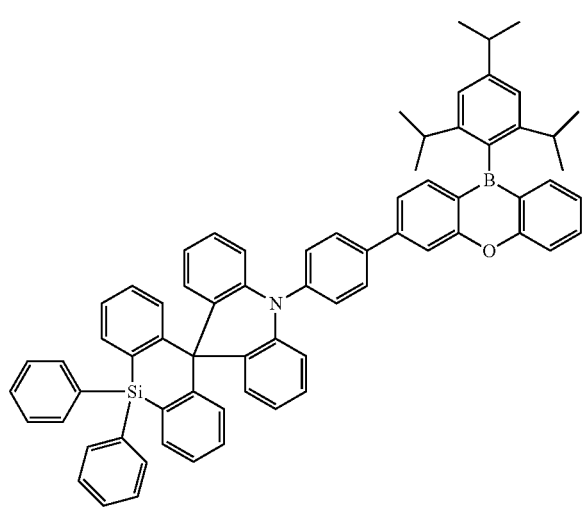
-continued
26
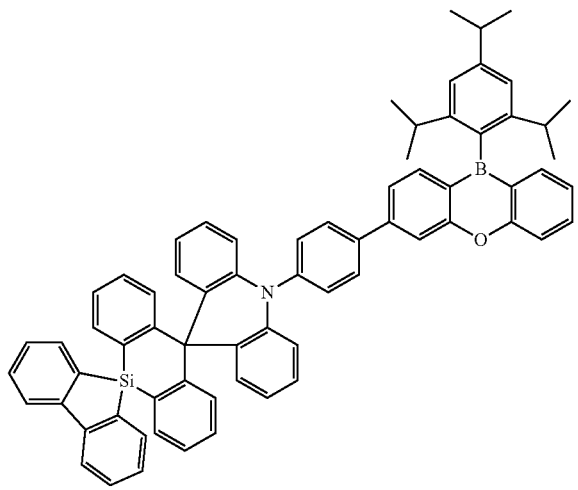
27
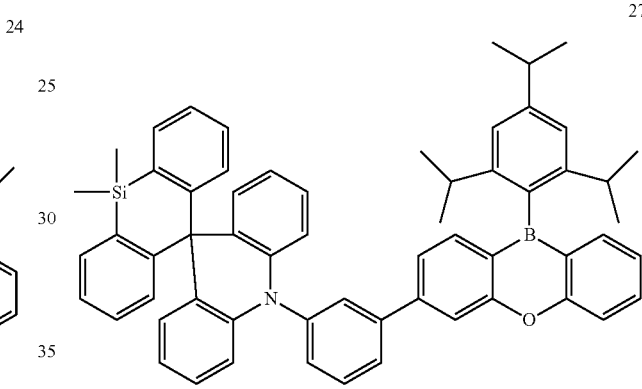
28
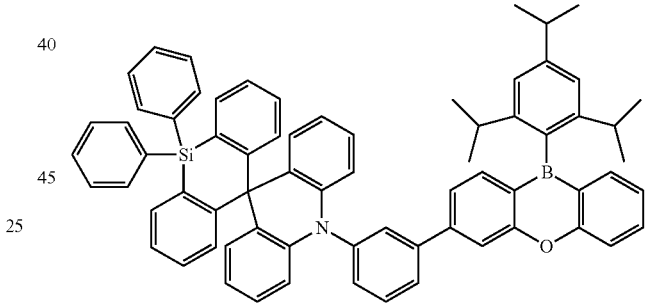
29
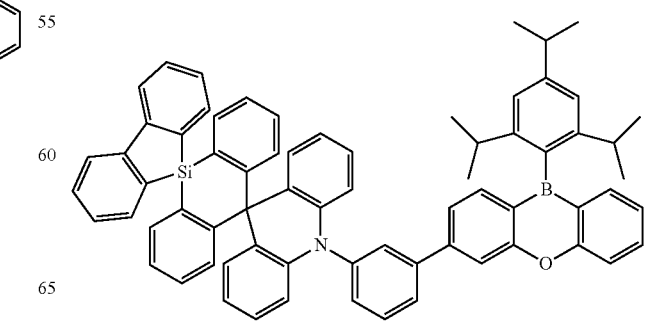

125
-continued
30
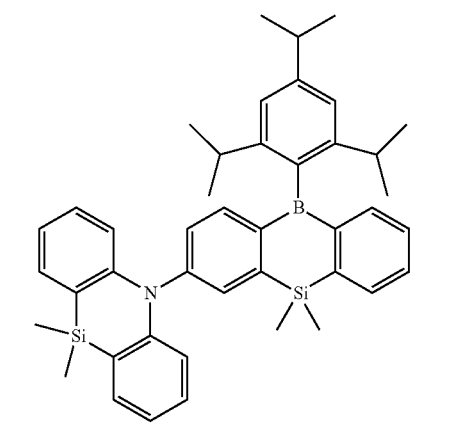
31
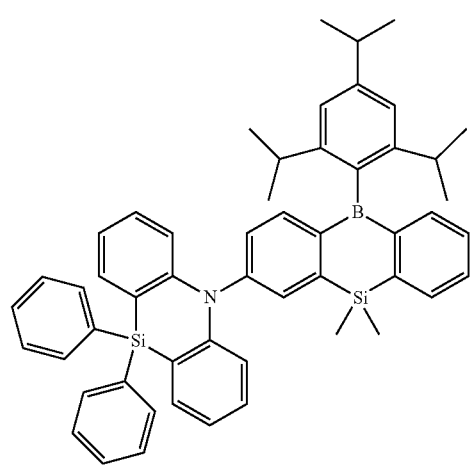
32
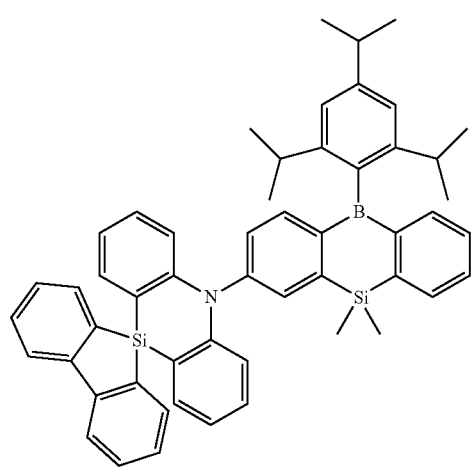
126
-continued
33
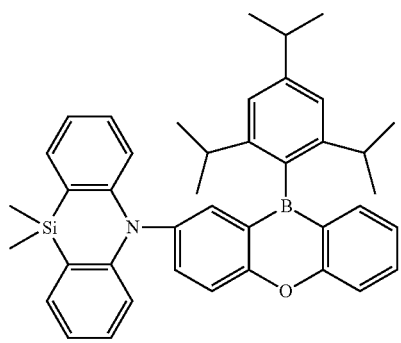
34
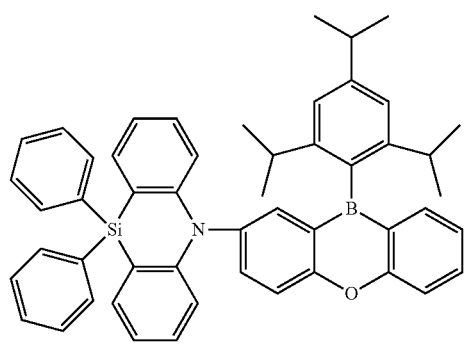
35
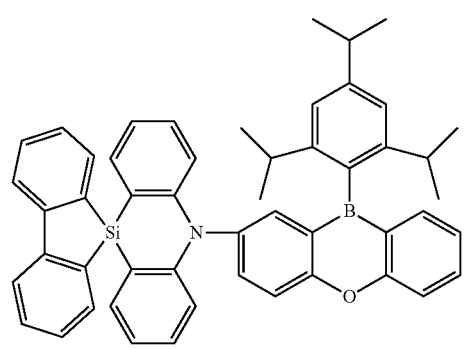
36
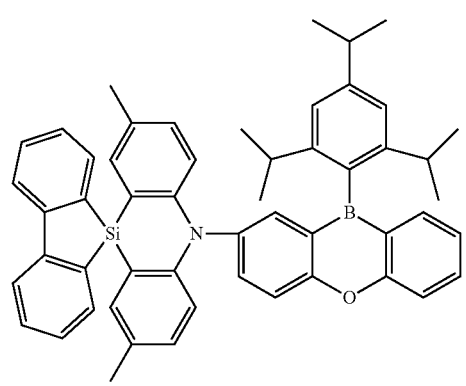

37
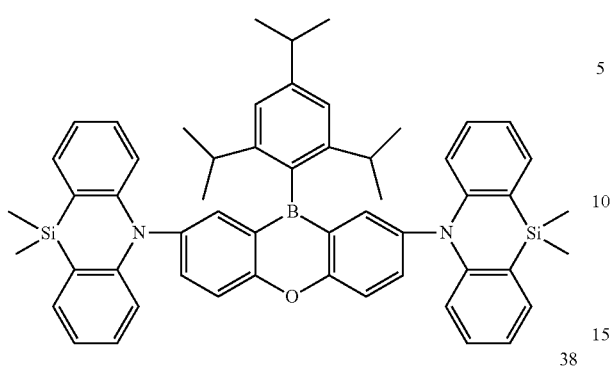
38
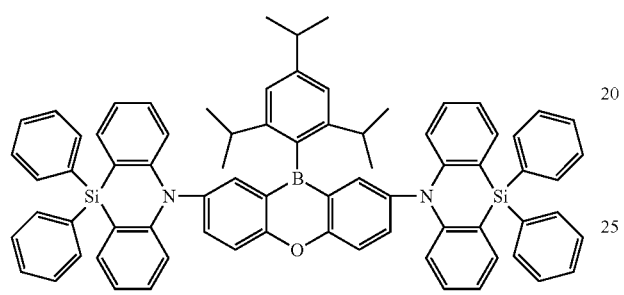
39
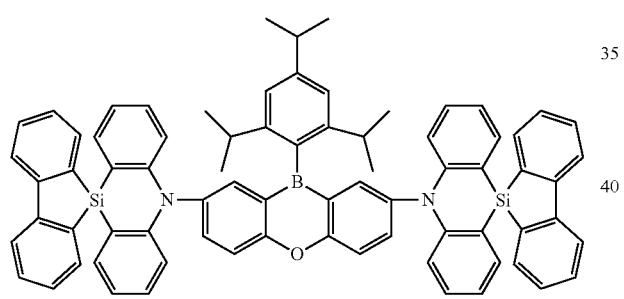
40
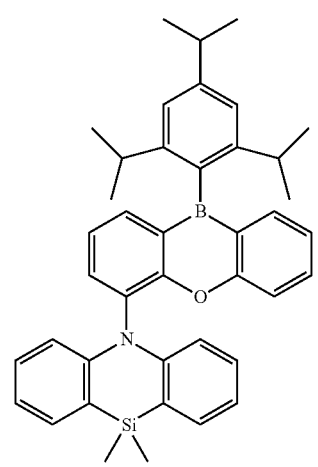
41
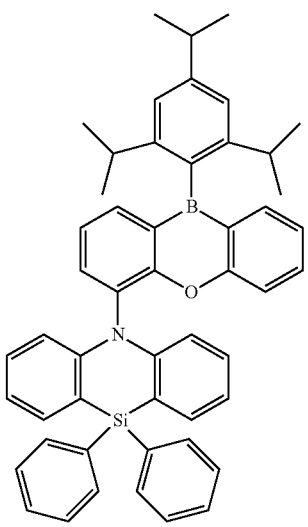
42
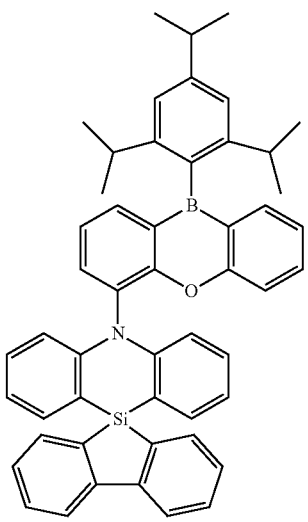
43
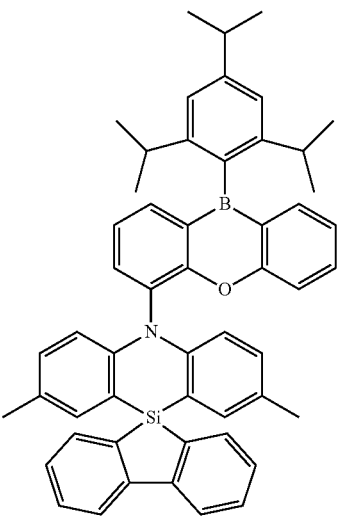

-continued
44
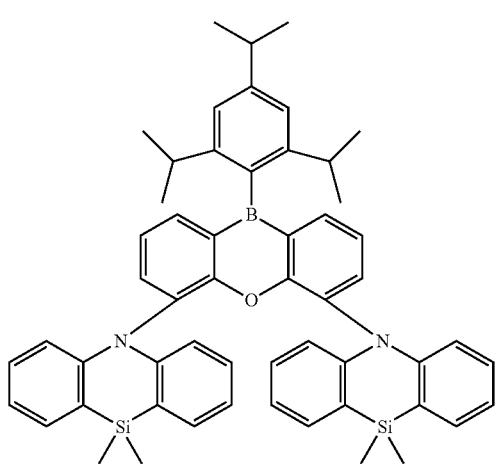
45
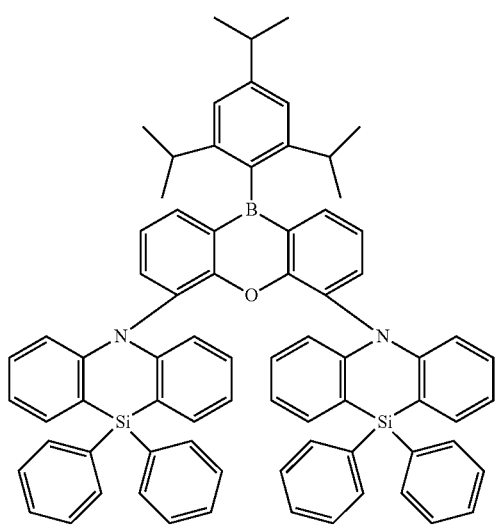
46
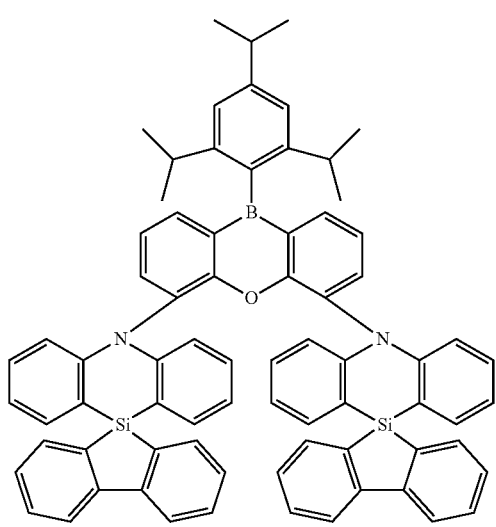
-continued
47
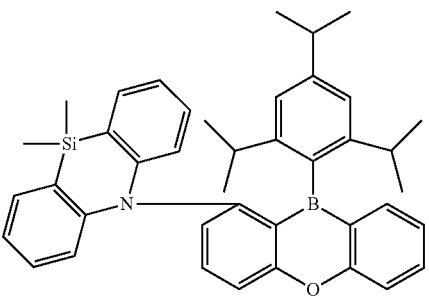
48
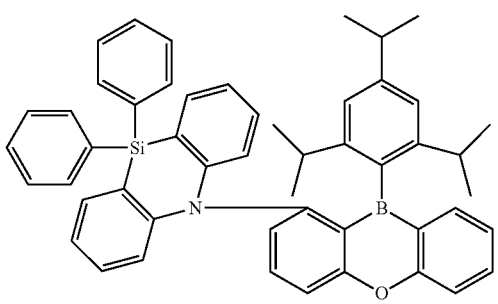
49
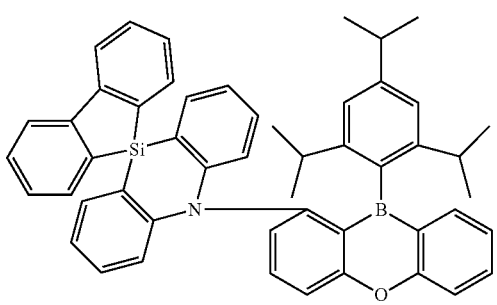
50
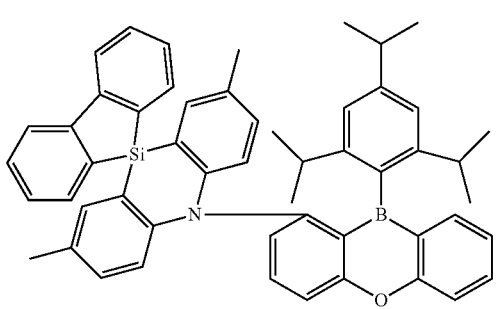
51
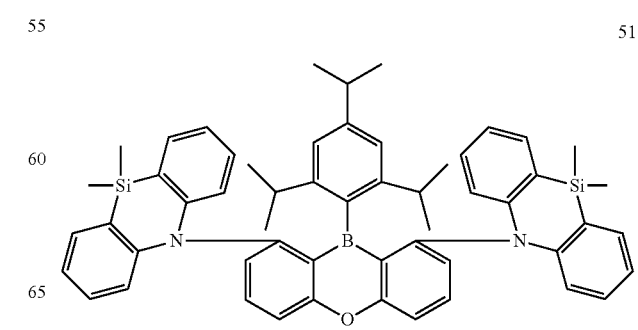

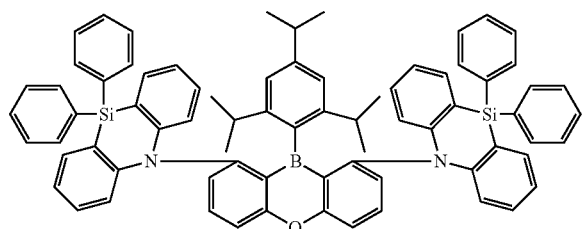
52
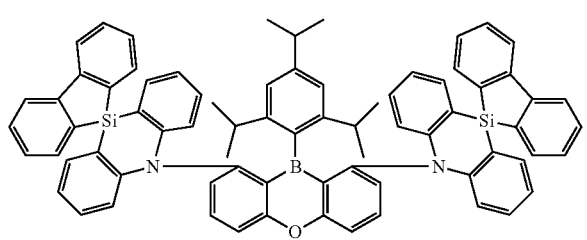
53
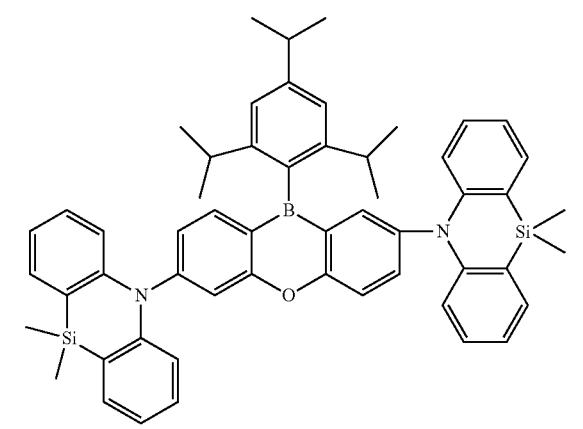
54
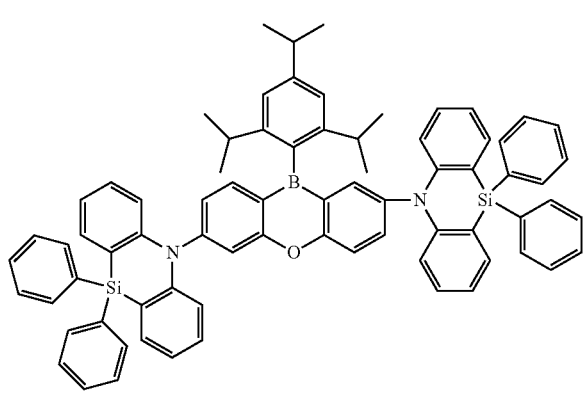
55
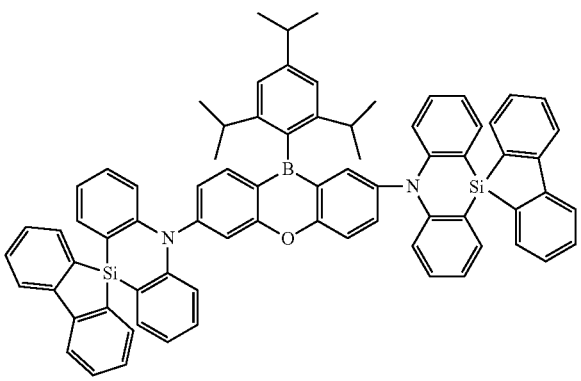
56
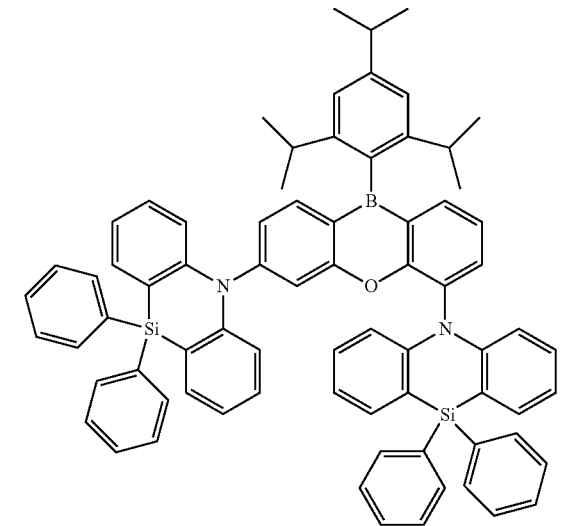
57
58

59
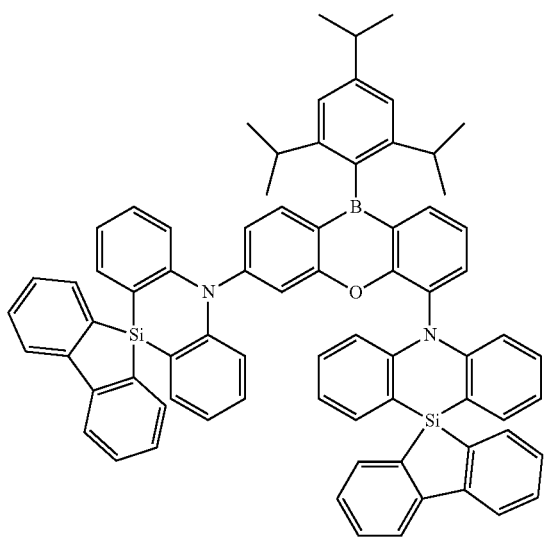
60
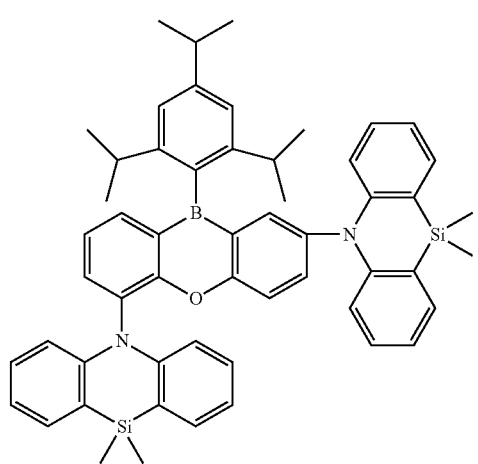
61
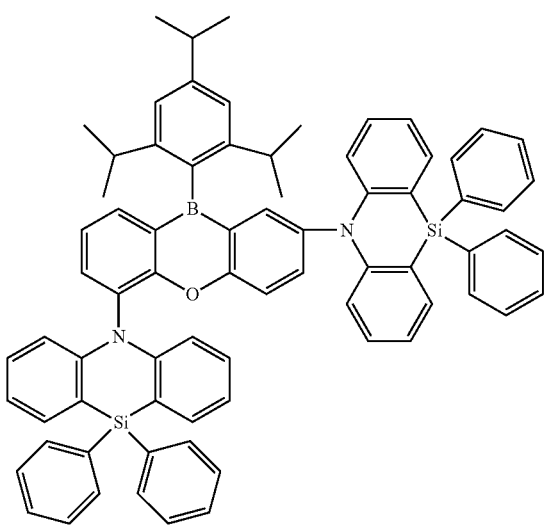
62
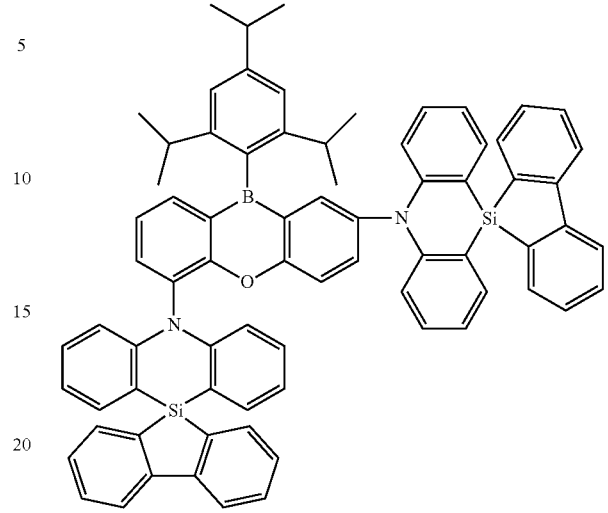
[Compound Group 3]
153
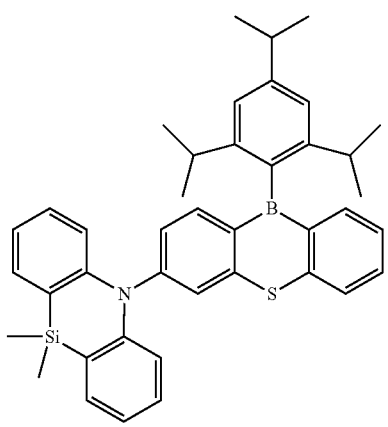
154
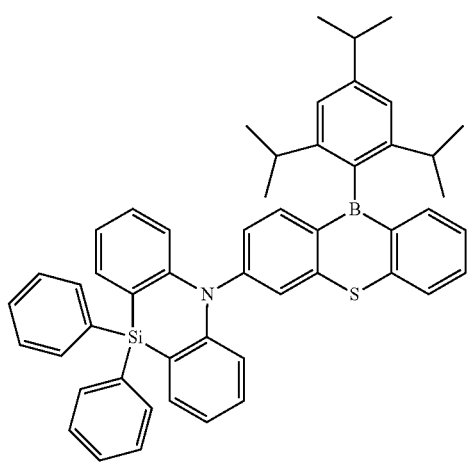

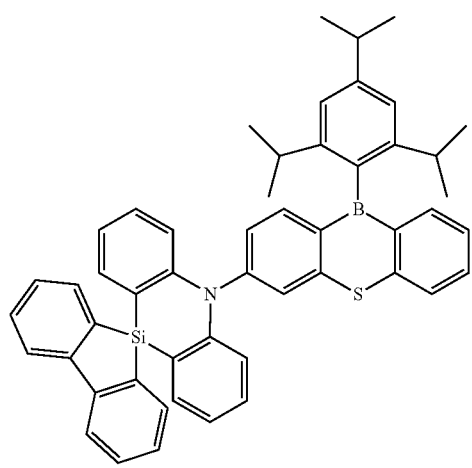
155
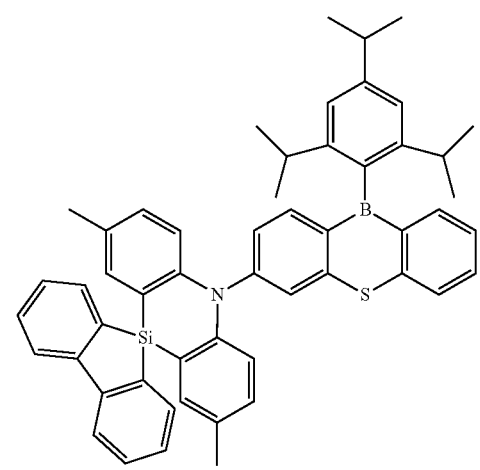
156
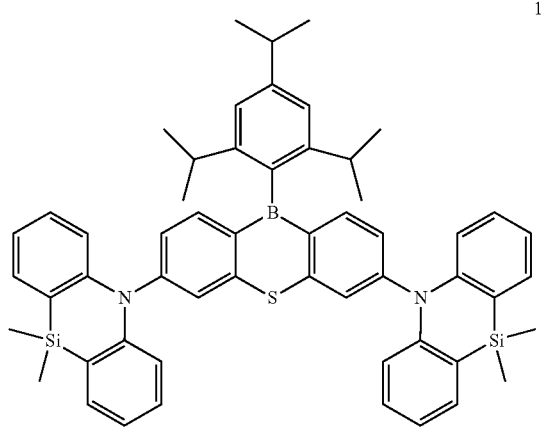
157
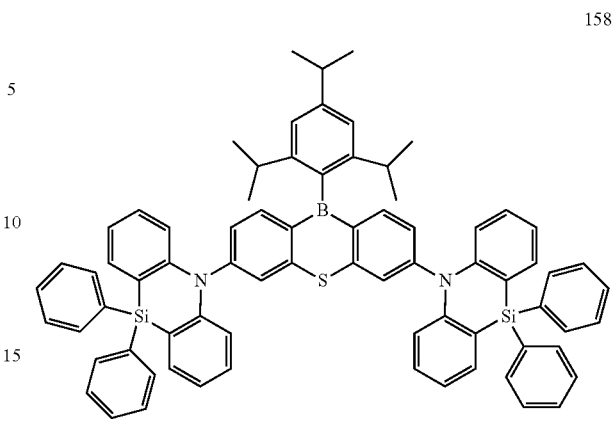
158
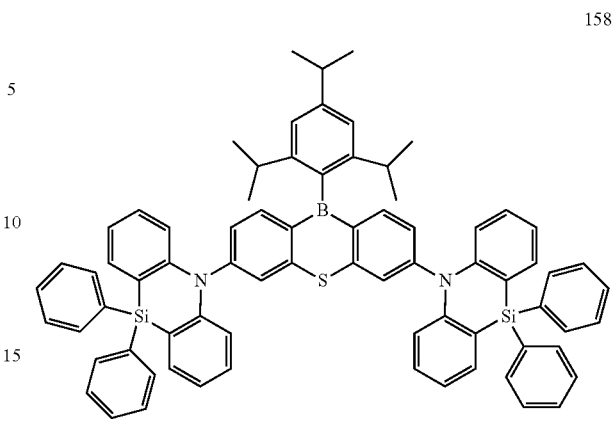
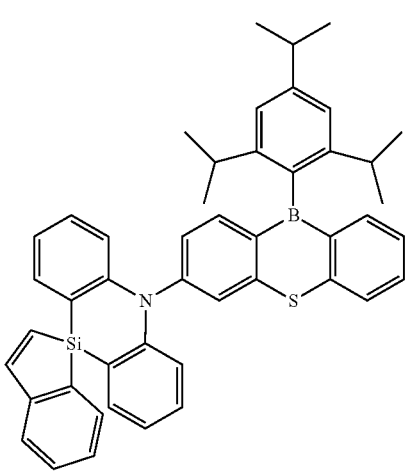
160

161
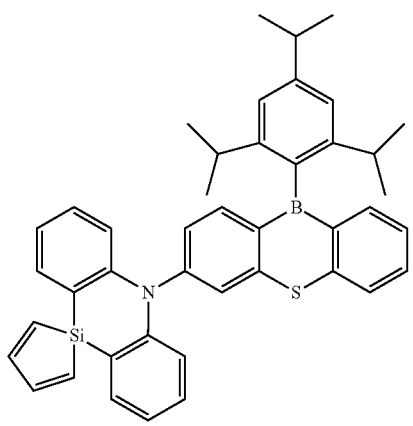
164
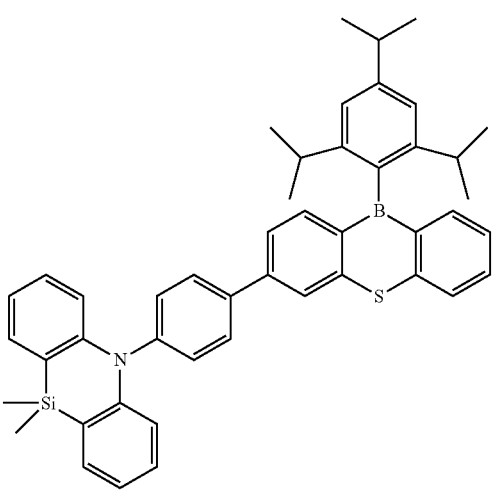
162
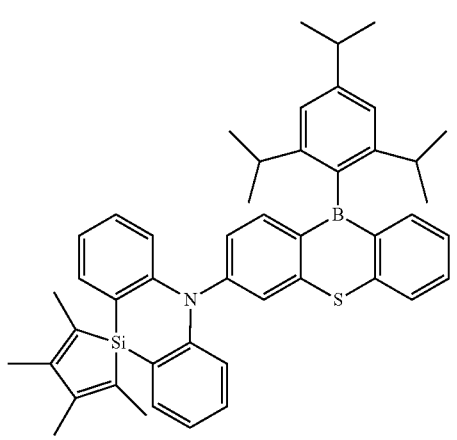
165
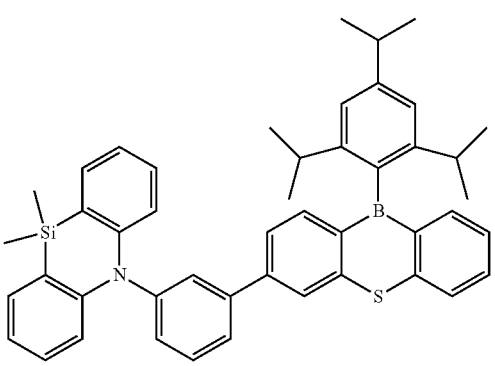
163
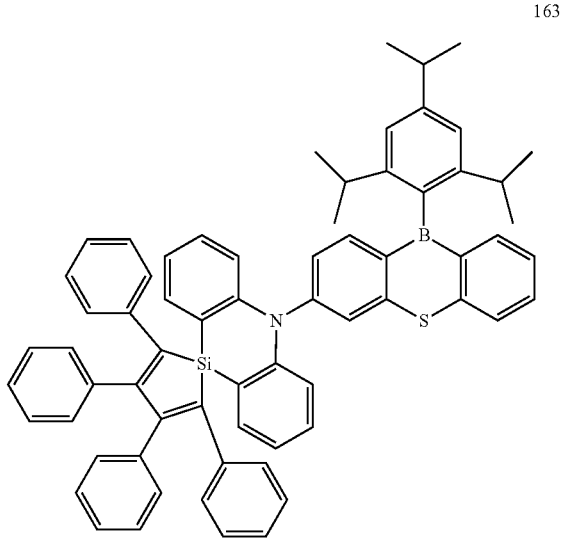
166
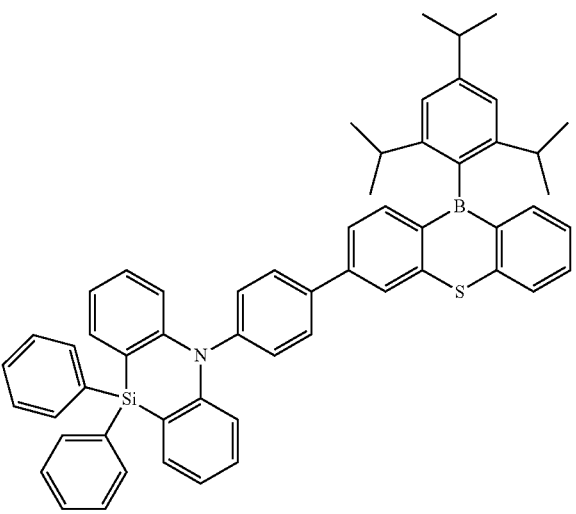

-continued
167
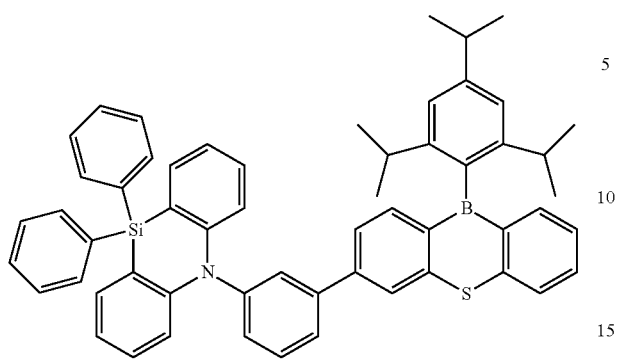
168
171
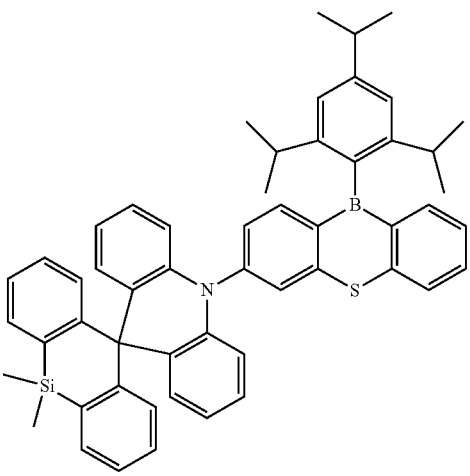
172
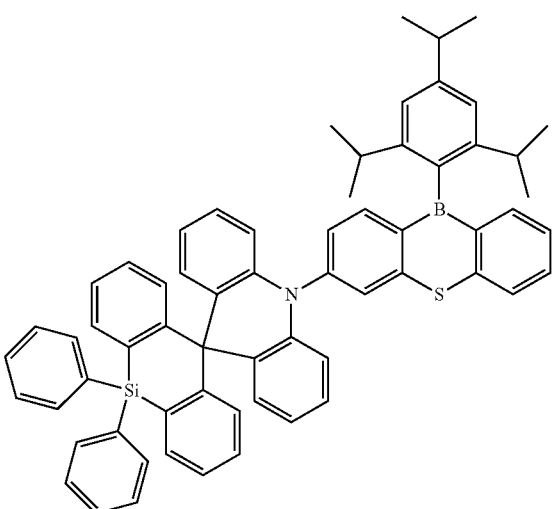
169
170
-continued
173
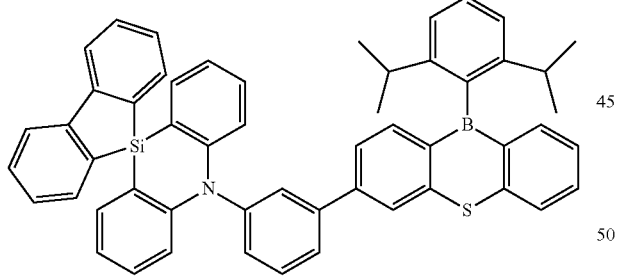
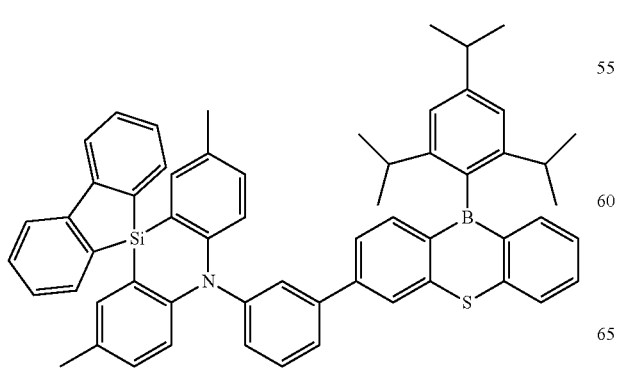

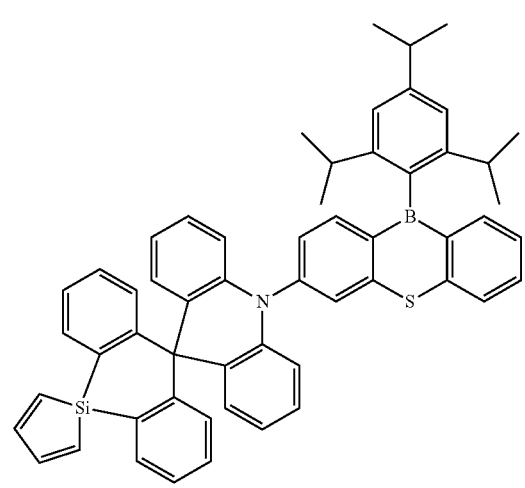
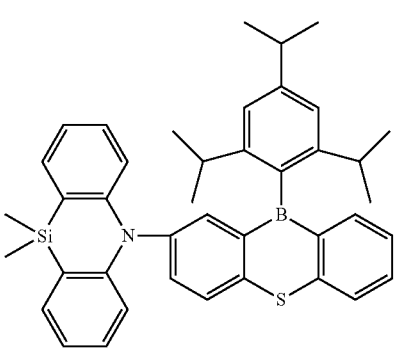
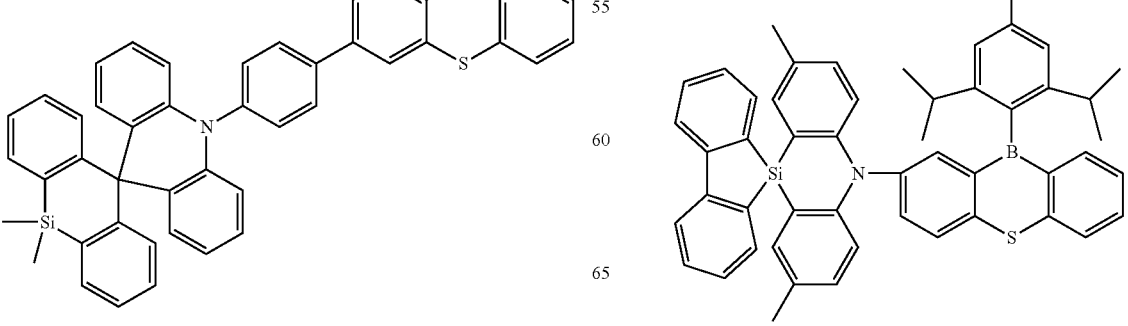

-continued
181
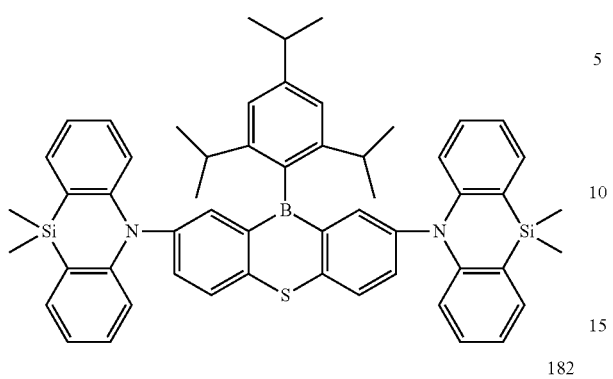
182
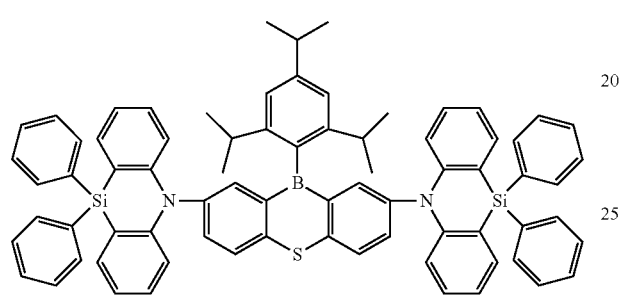
183
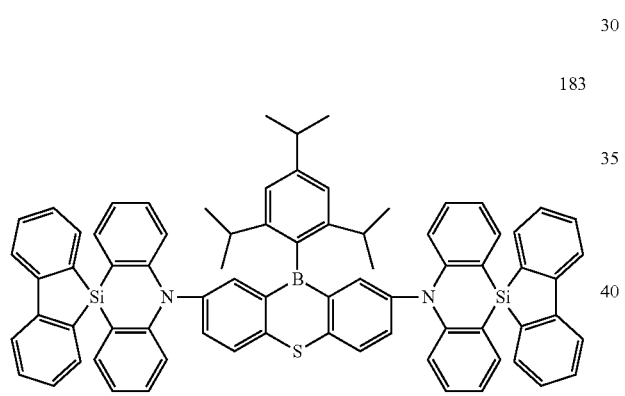
184
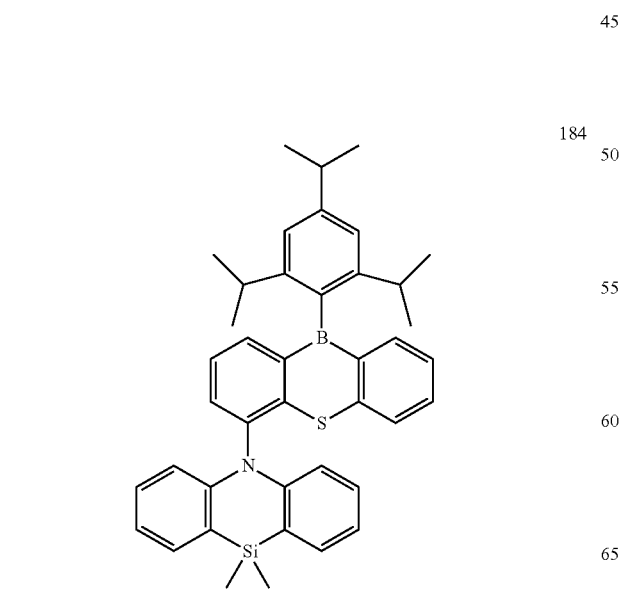
-continued
185
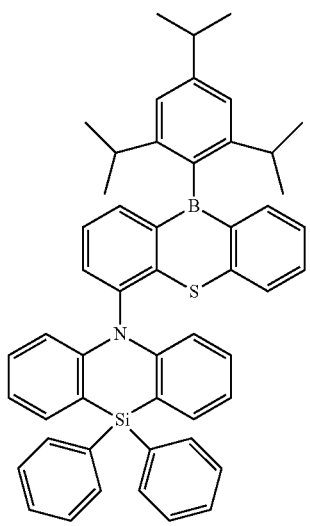
186
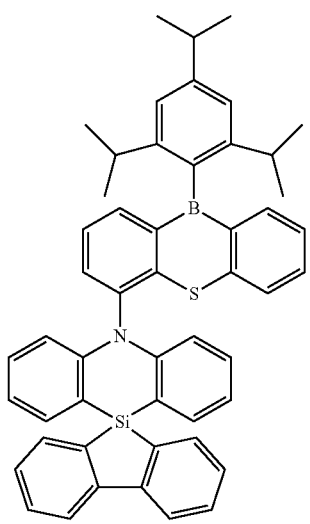
187
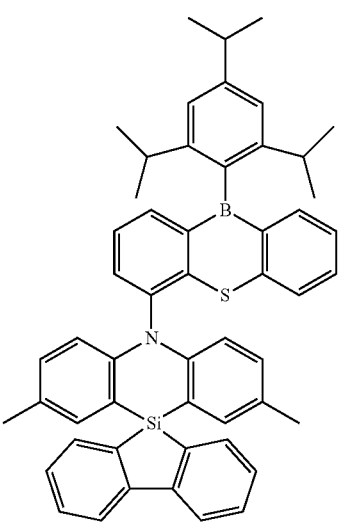

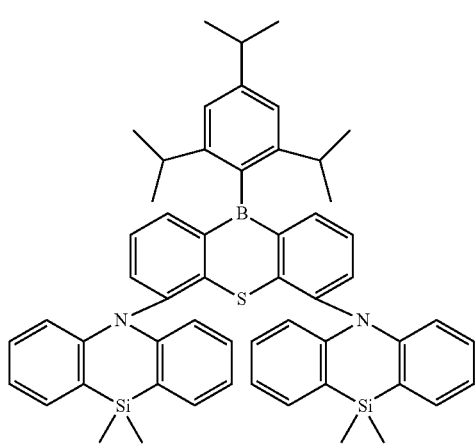
188
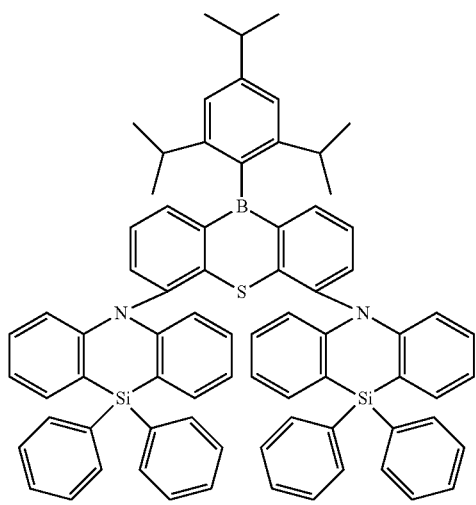
189
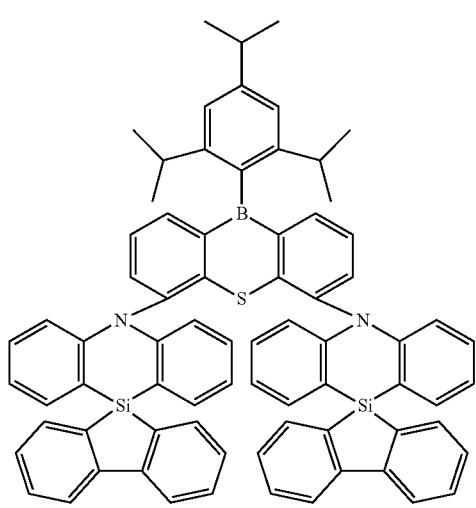
190
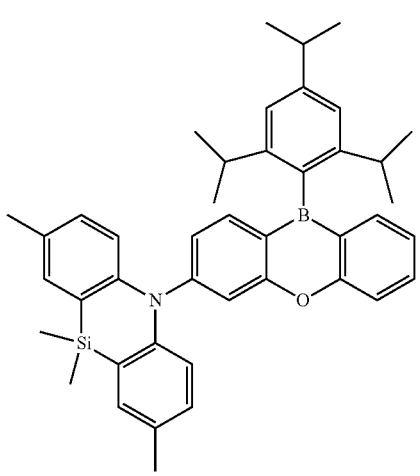
191
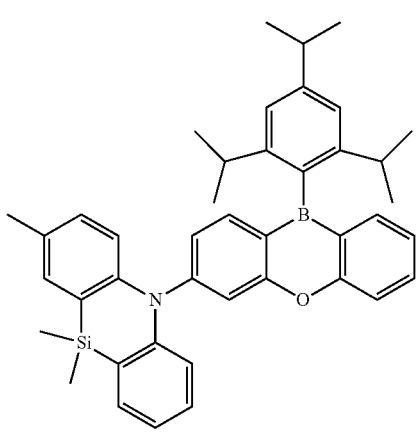
192
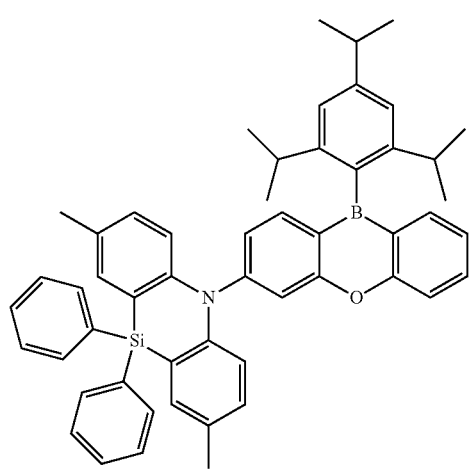
193

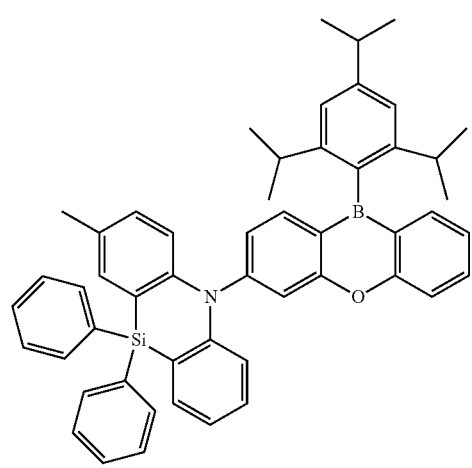
194
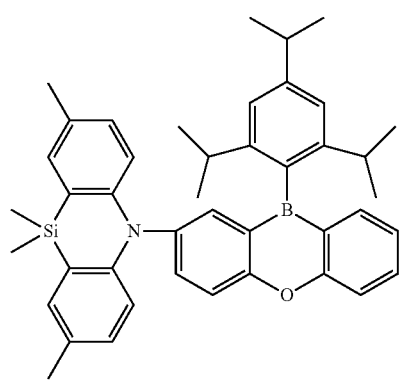
195
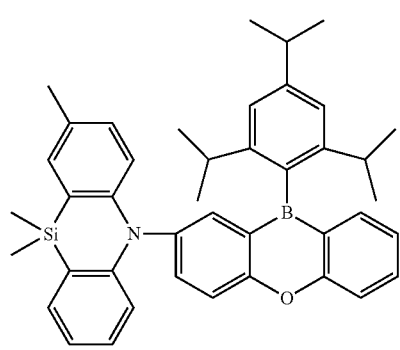
196
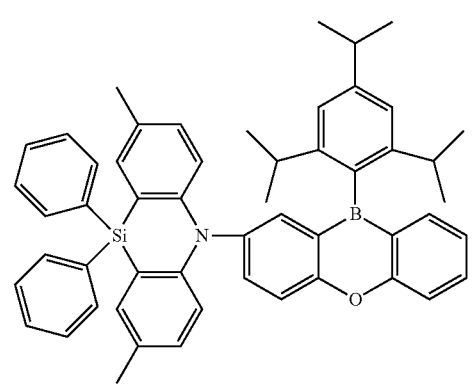
197
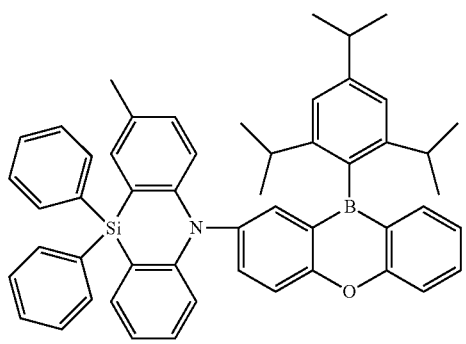
198
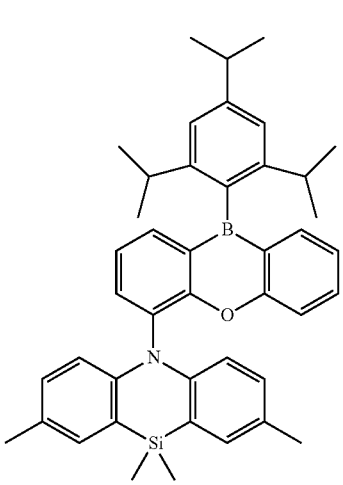
199
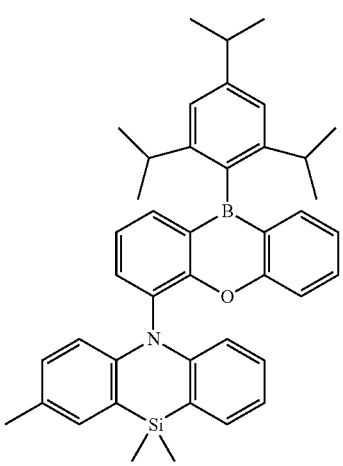
200

149
-continued
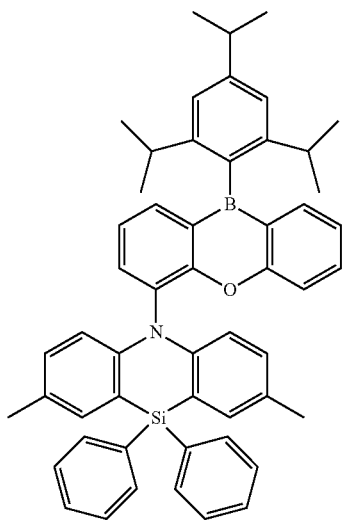
201
150
-continued
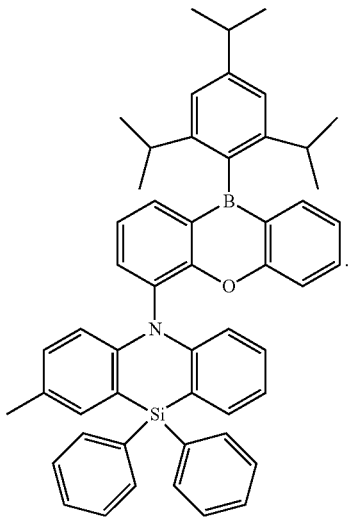
202
9. The polycyclic compound of claim 1, wherein the polycyclic compound represented by Formula 1 is at least one of compounds represented in the following Compound Group 2:
[Compound Group 2]
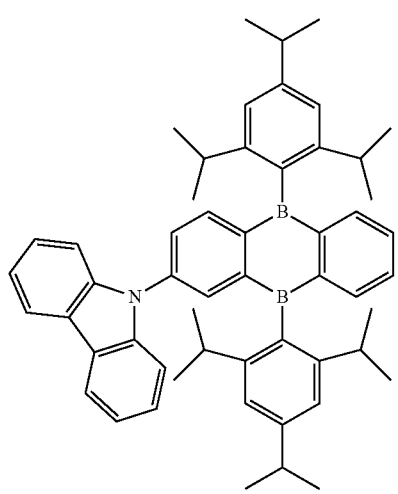
63
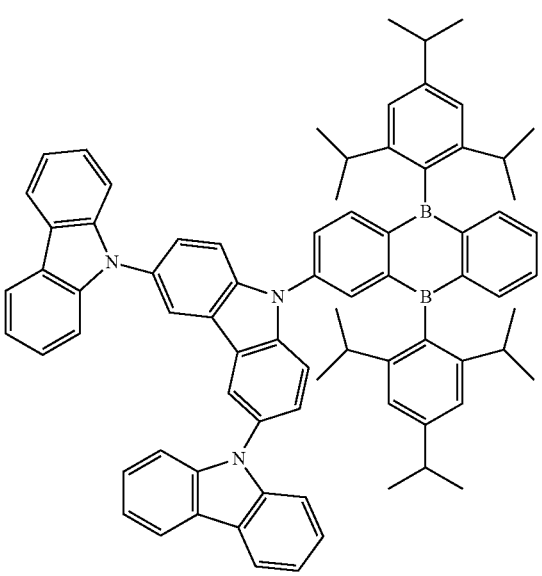
64

151    152
-continued
65
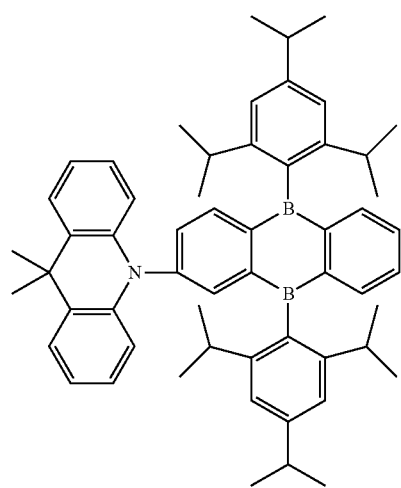
66
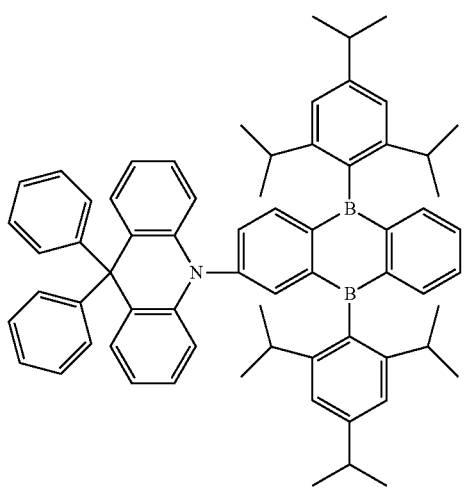
67
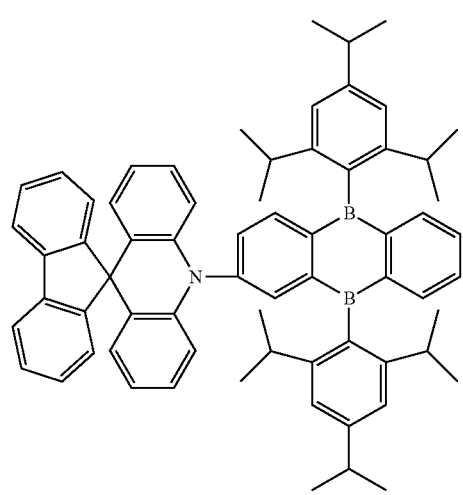
68
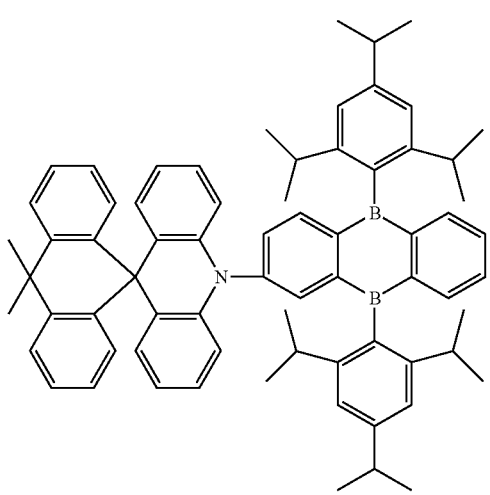
69
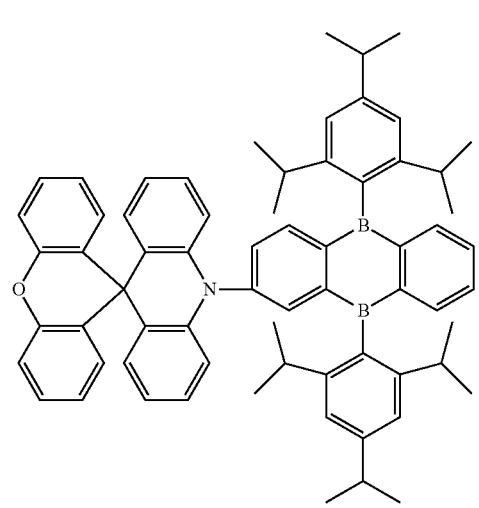
70
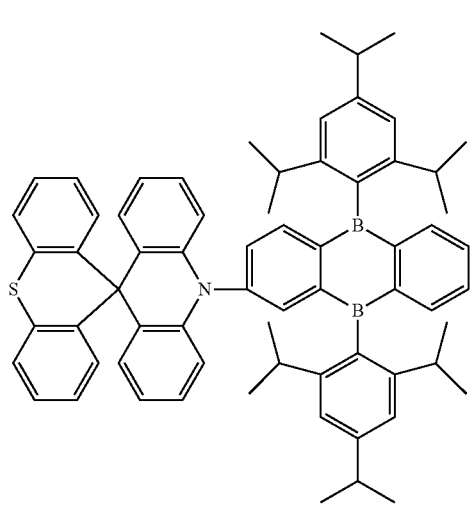

-continued
71
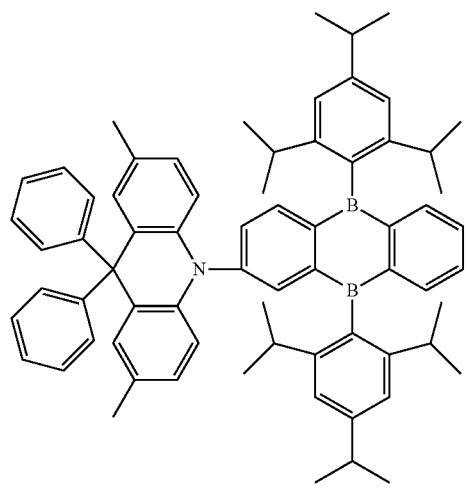
72
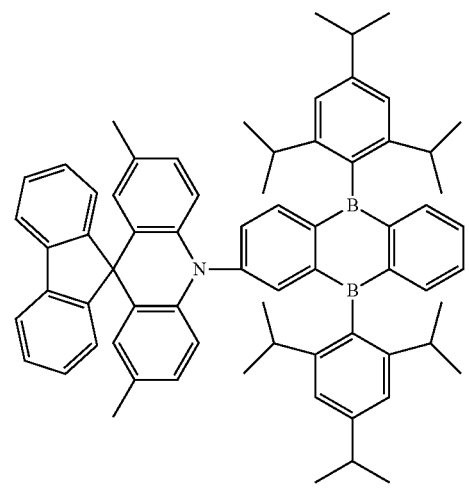
73
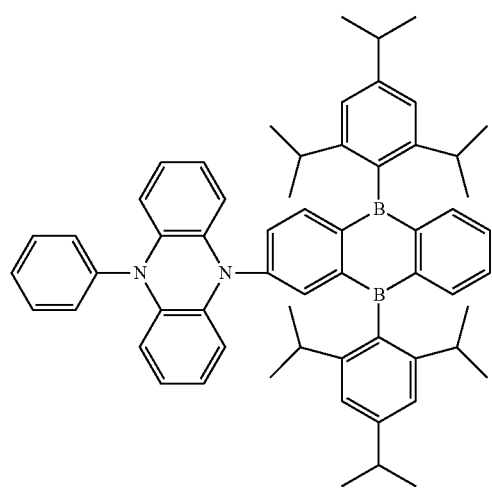
74
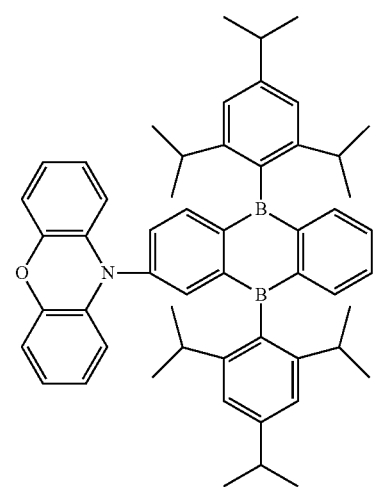
75
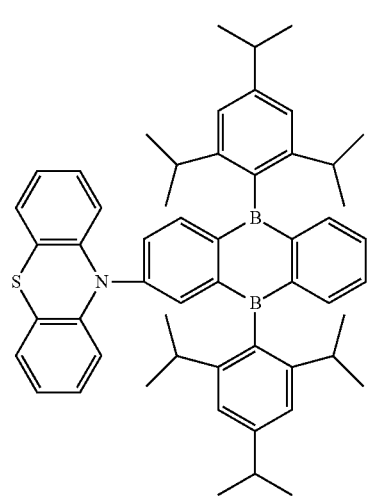
76
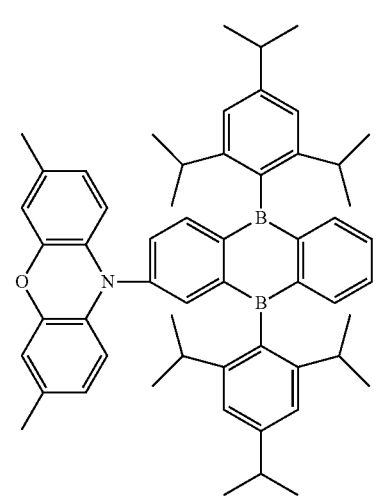

-continued
77
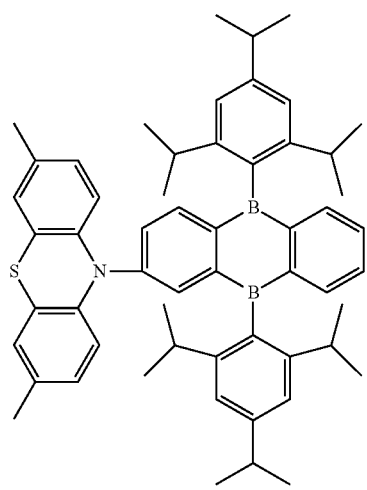
78
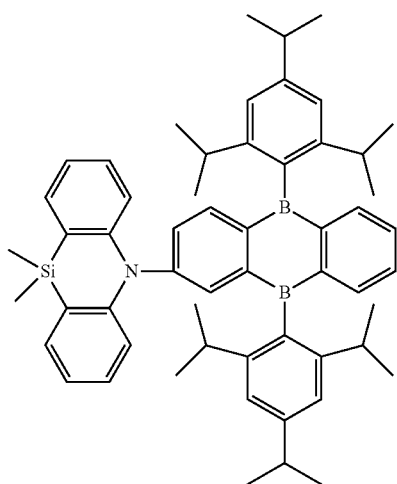
79
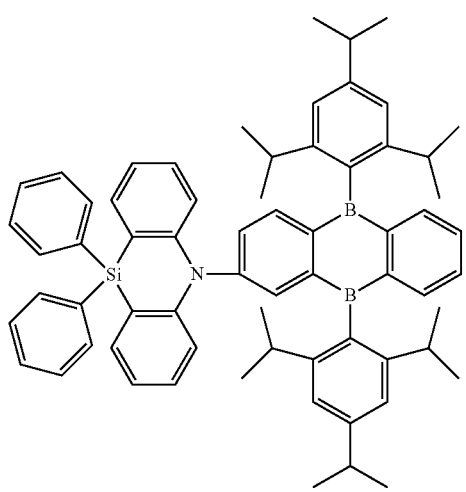
80
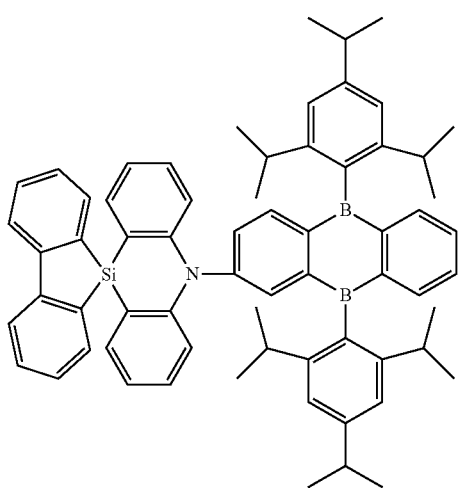
81
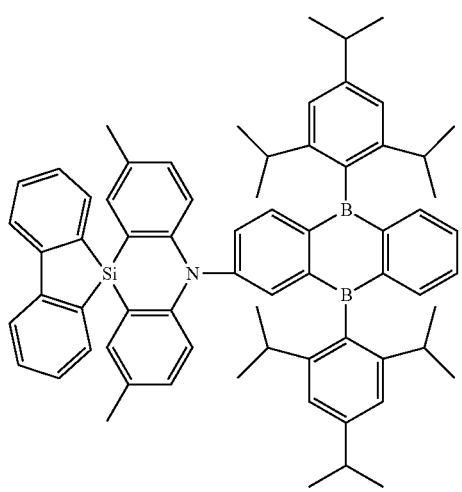
82
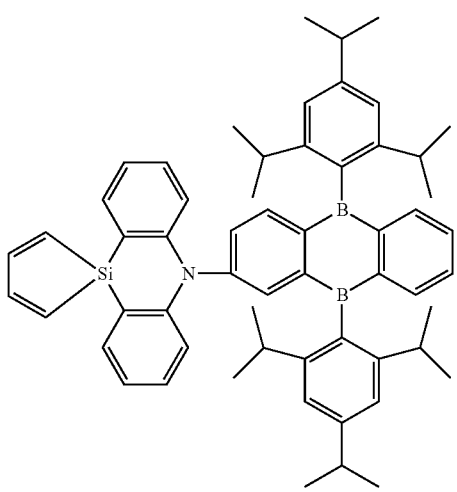

-continued
83
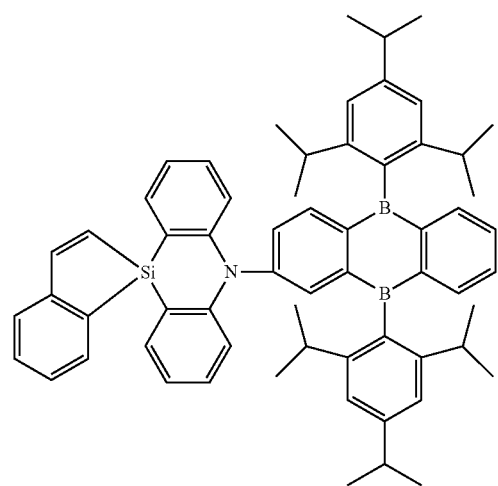
84
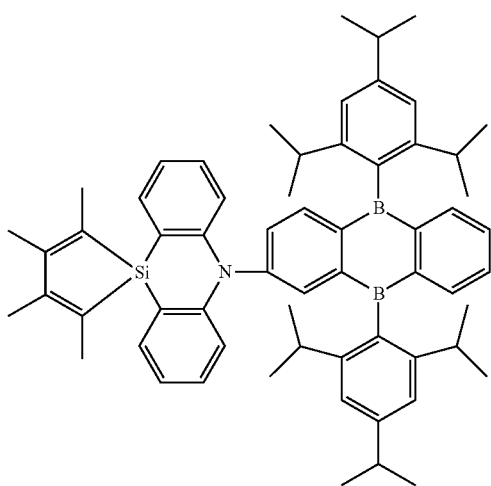
85
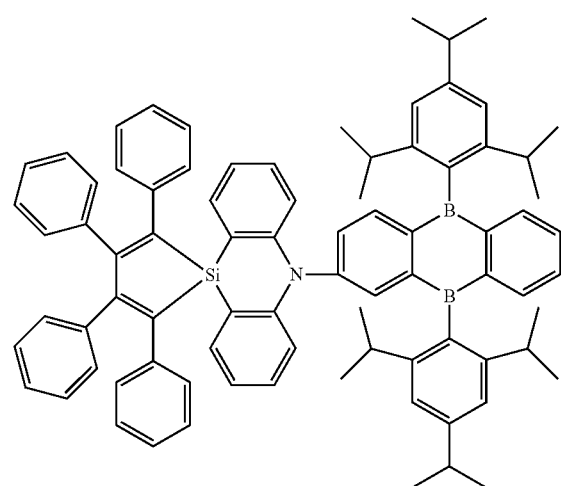
86
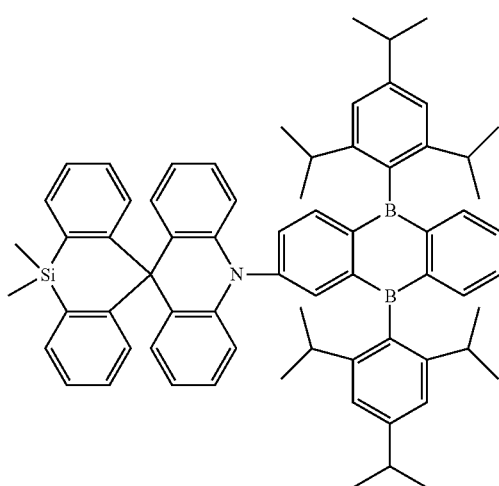
87
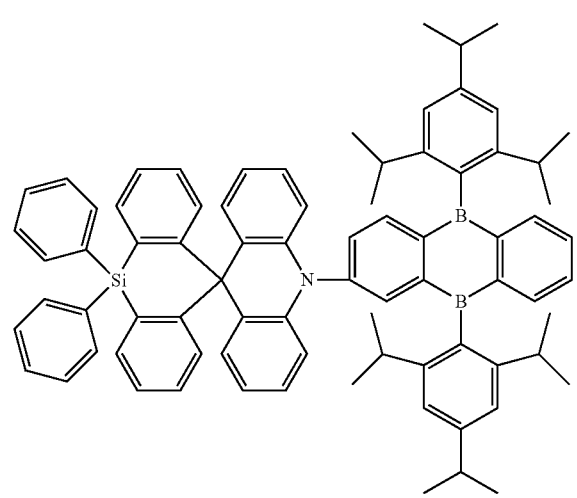
88
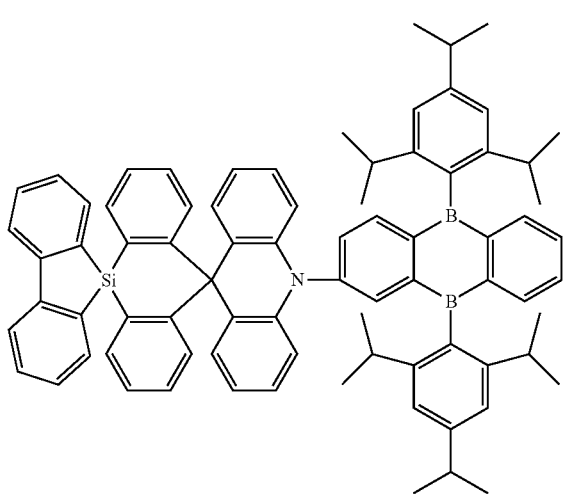

-continued
89
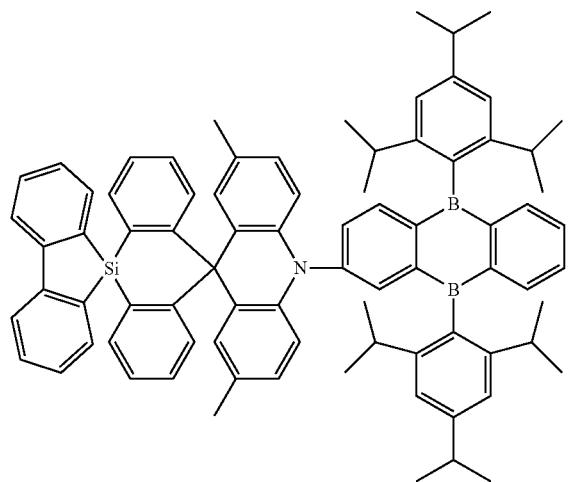
90
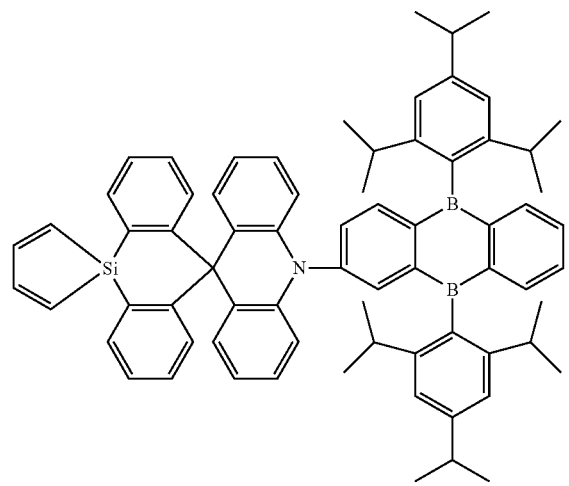
91
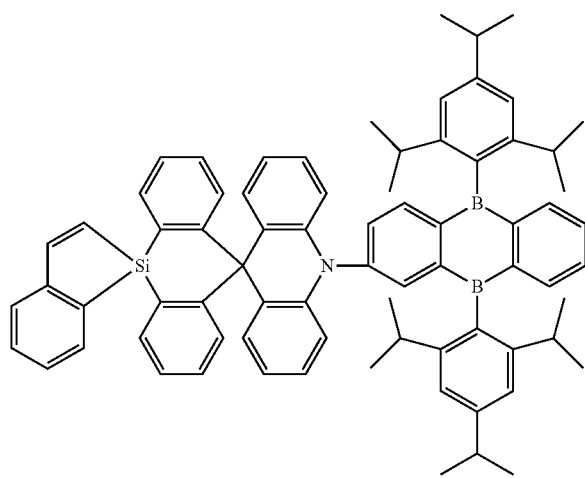
92
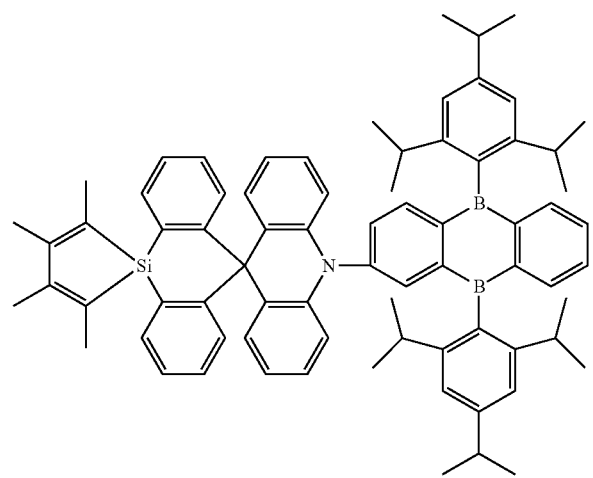
93
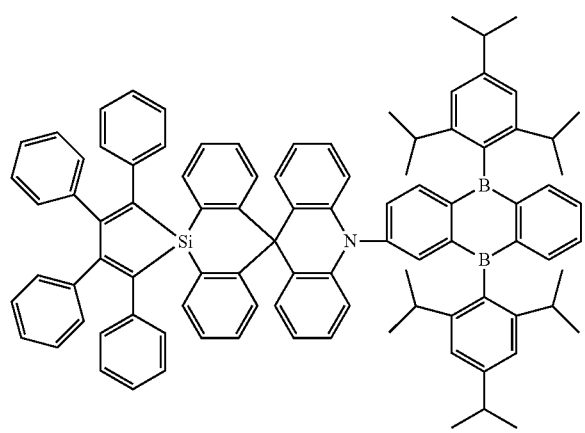
94
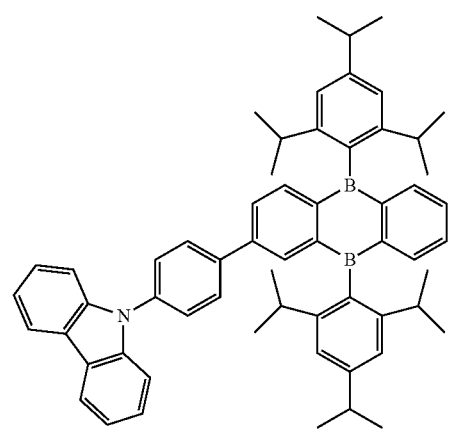

-continued
95
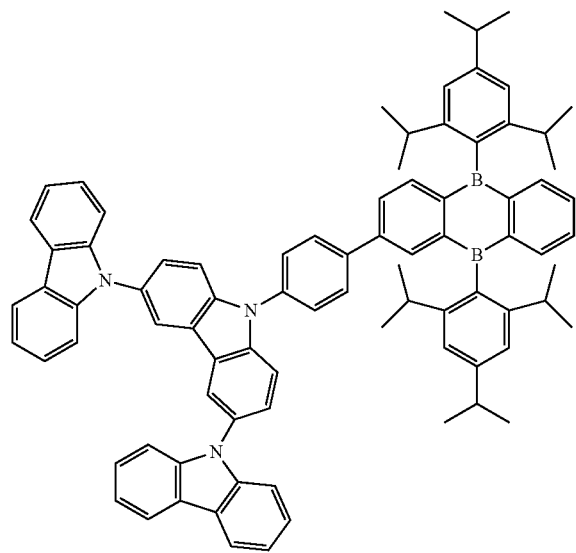
96
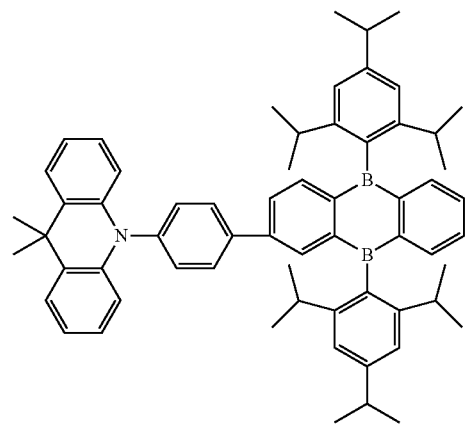
97
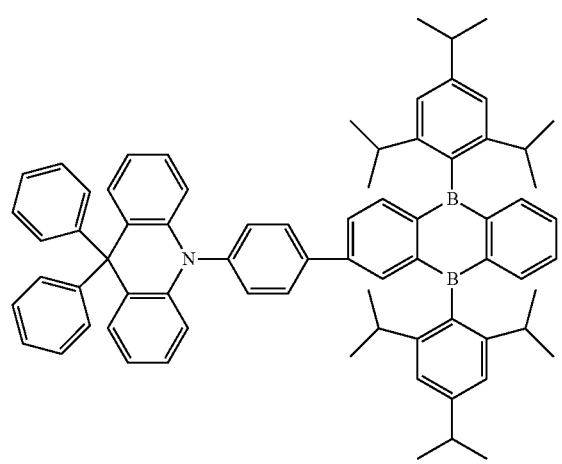
98
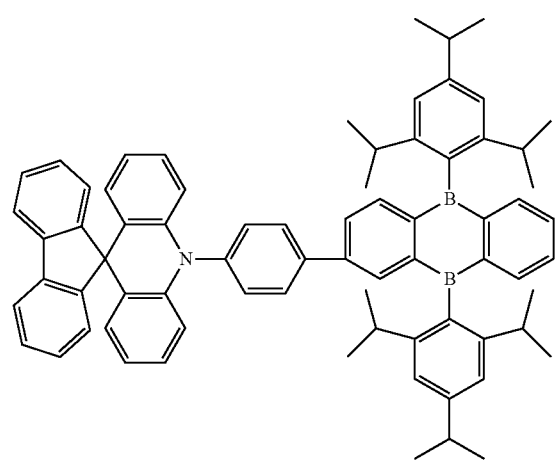
99
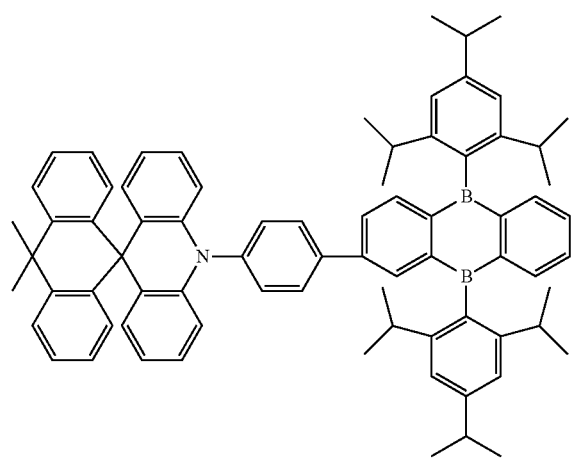
100
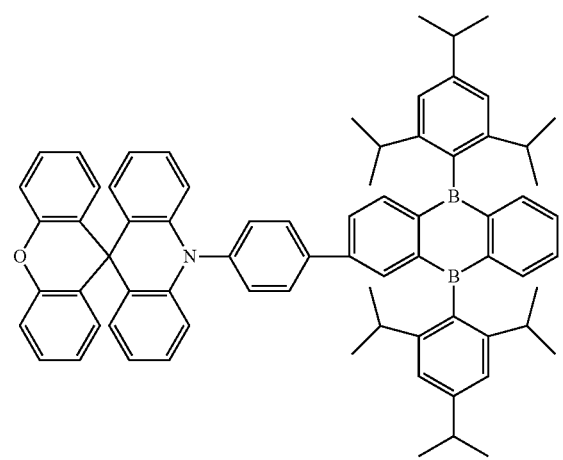

-continued
101
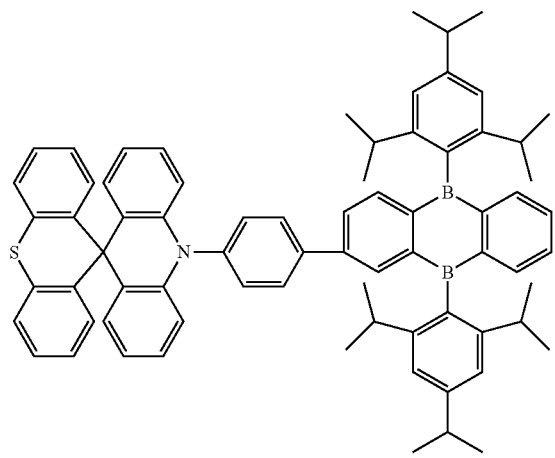
102
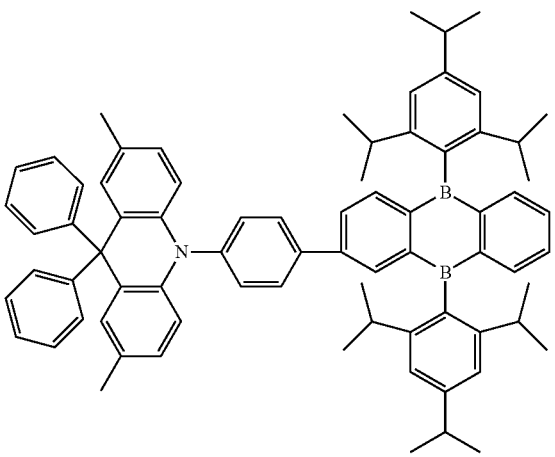
103
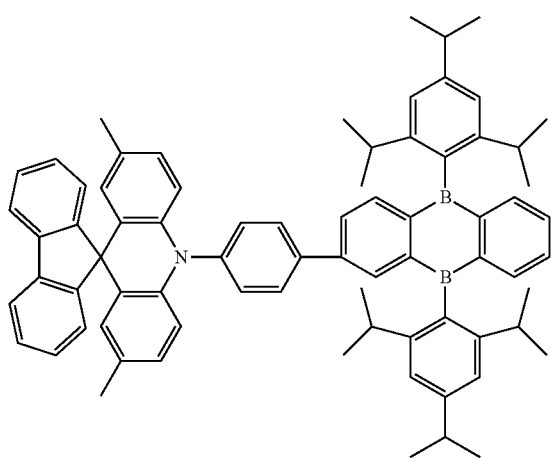
104
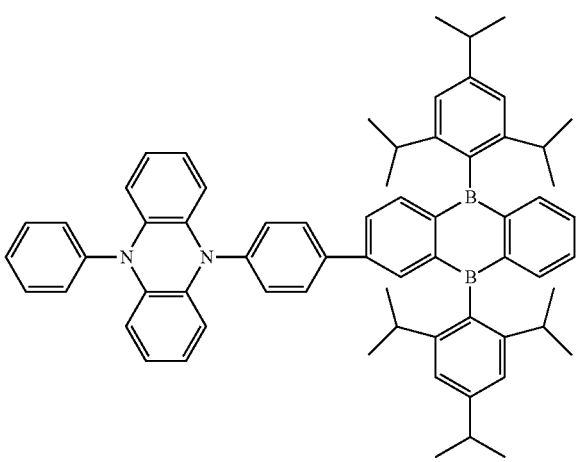
105
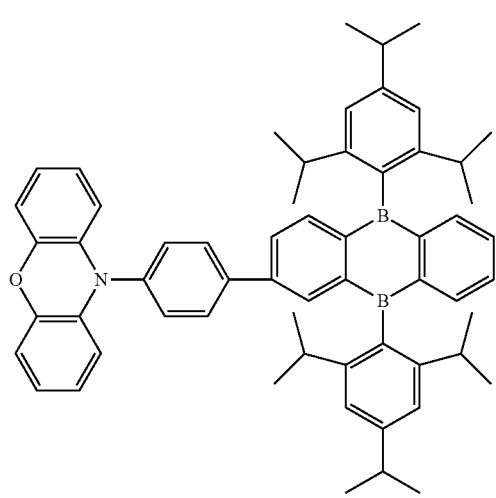
106
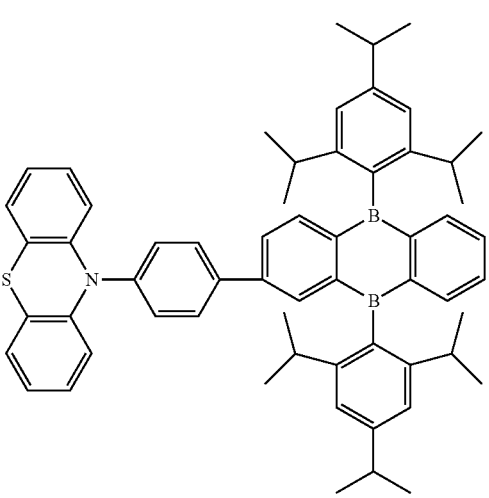

-continued
107
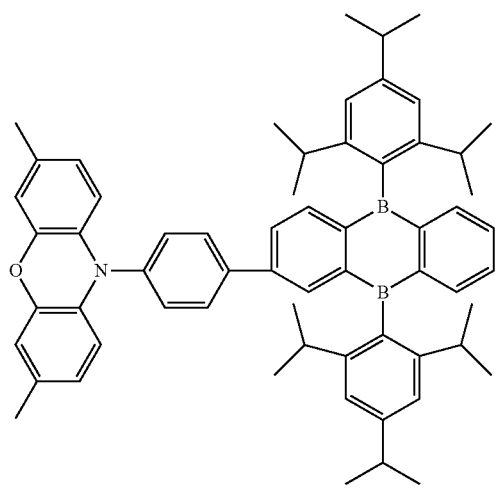
108
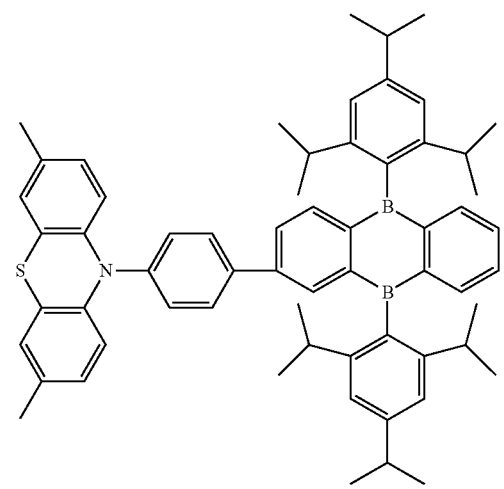
109
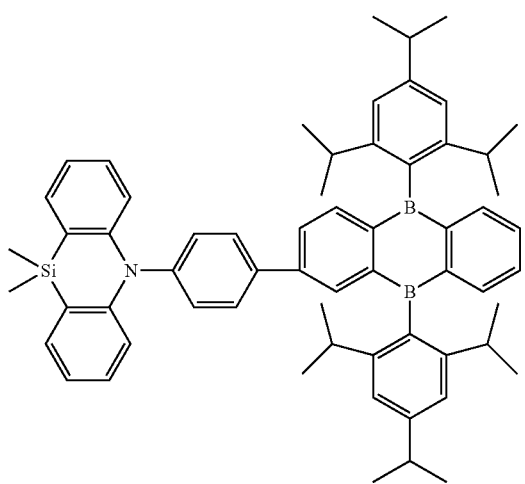
110
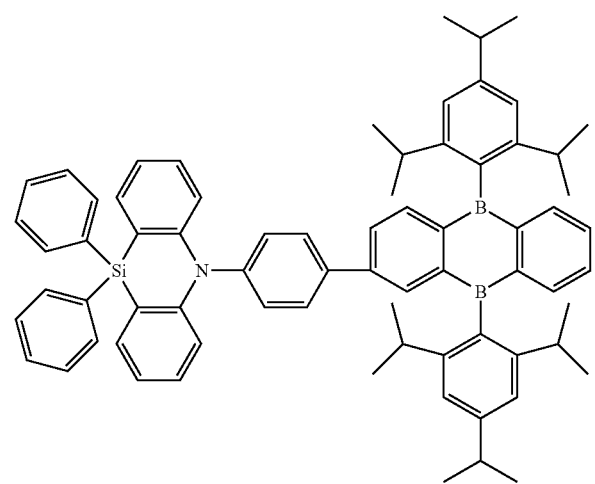
111
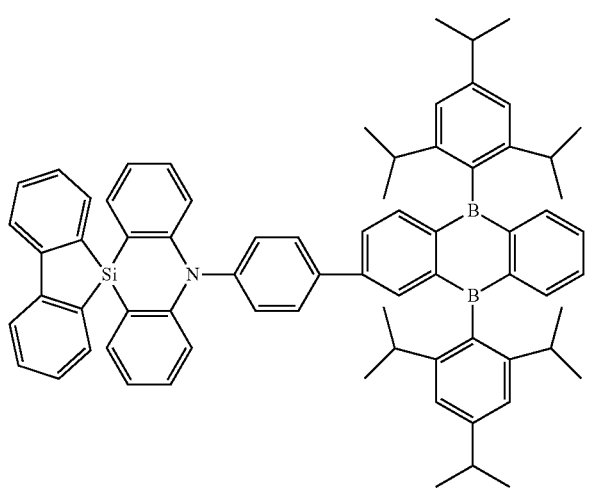
112
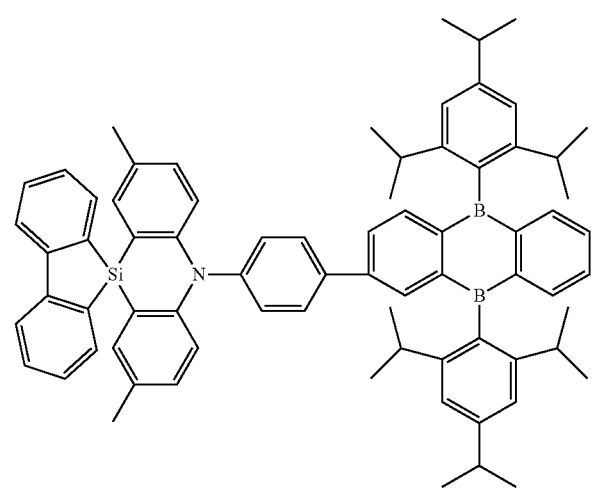

-continued
113
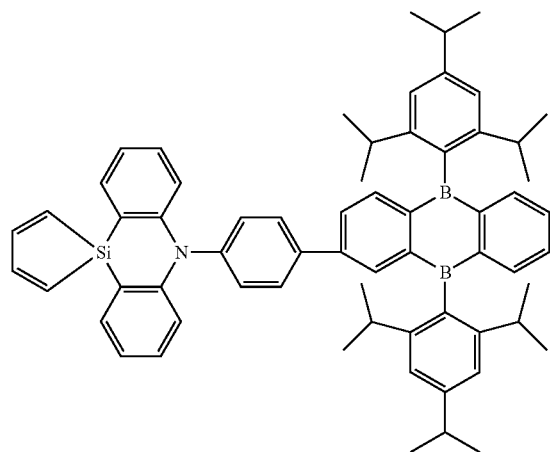
114
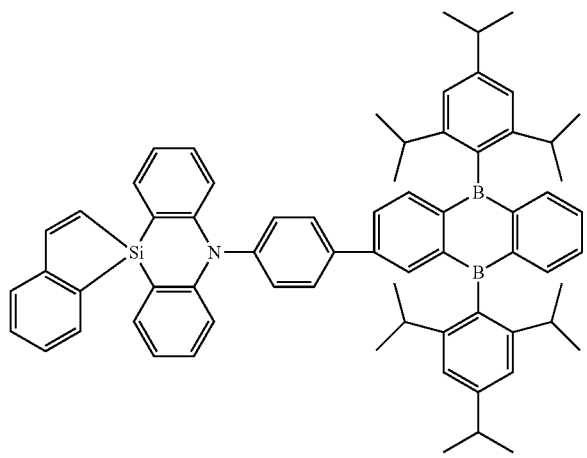
115
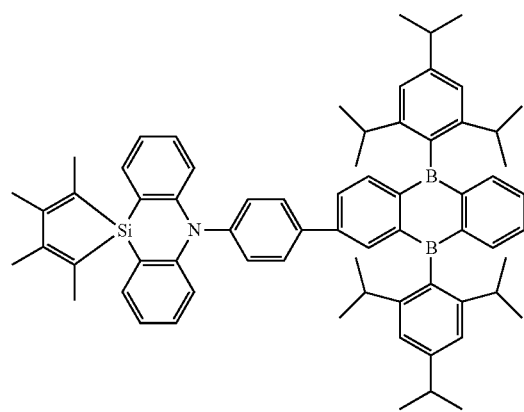
116
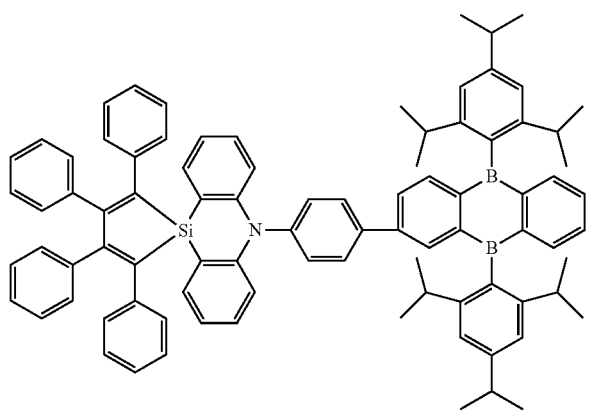
117
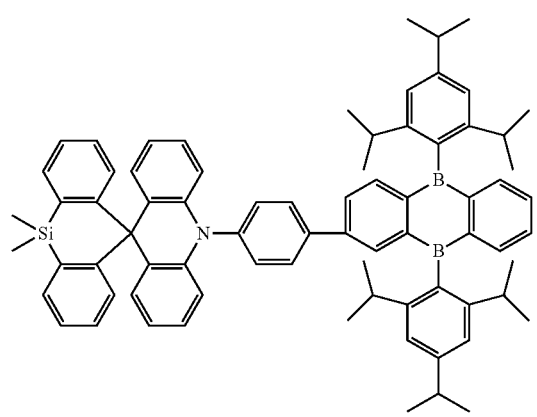
118
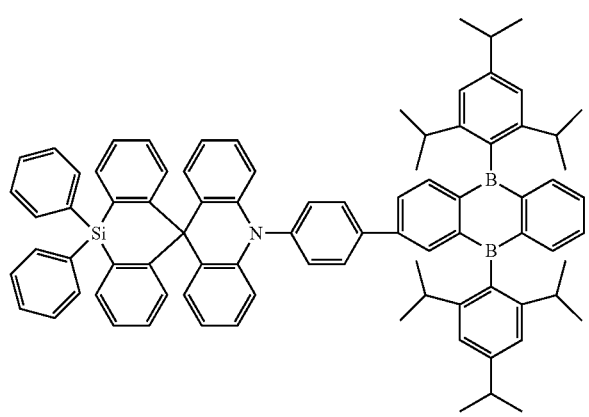

-continued
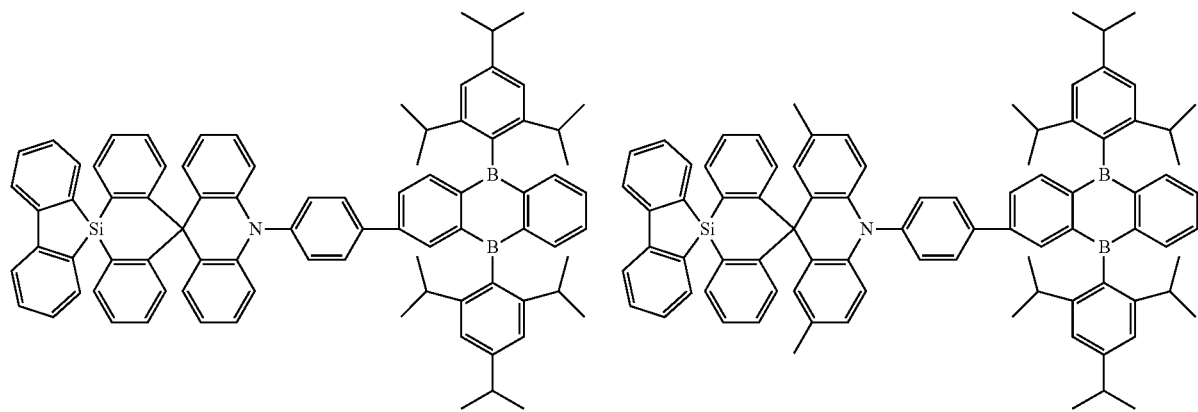
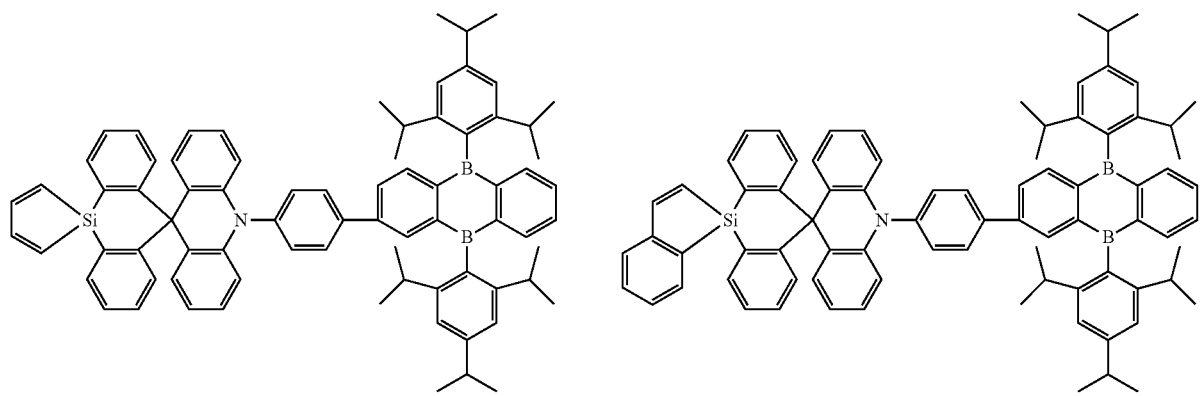
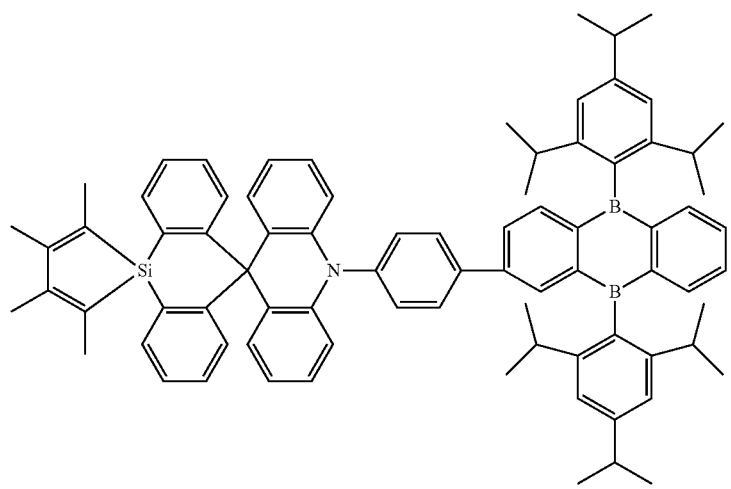

-continued
124
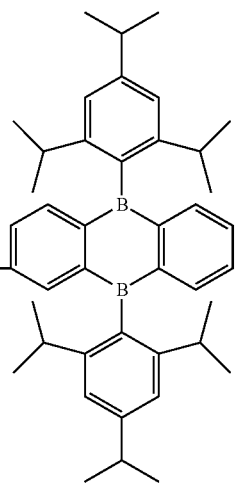
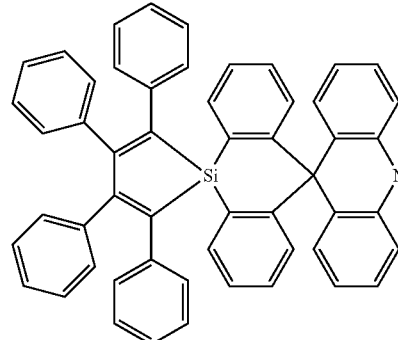
125
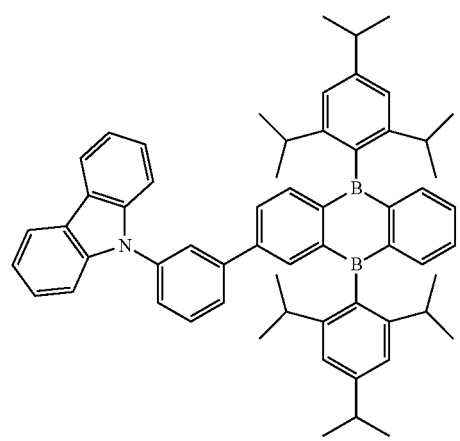
126
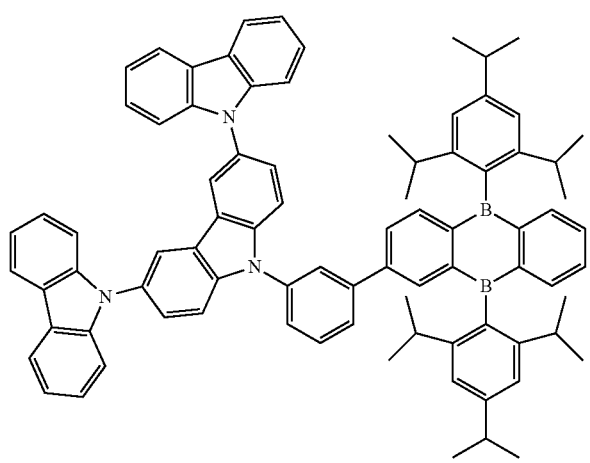
127
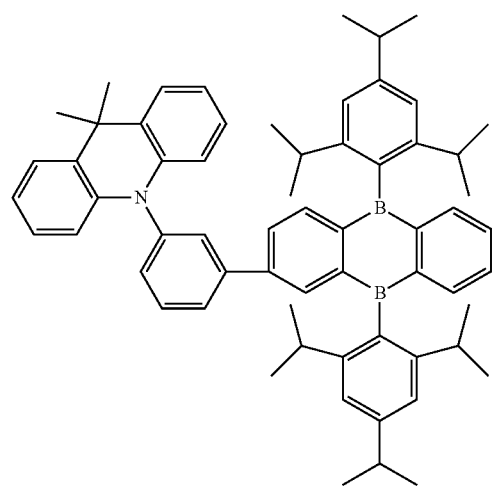
128
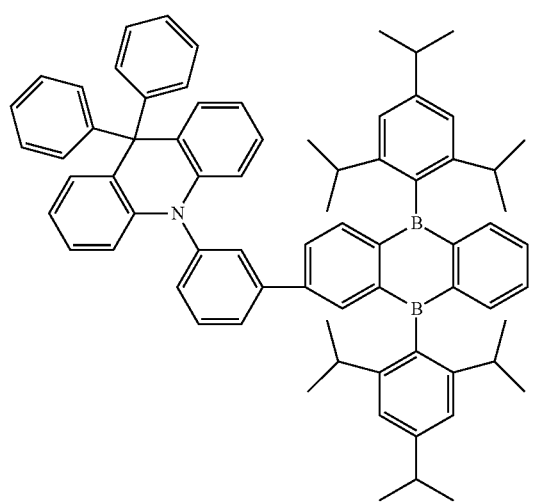

-continued
129
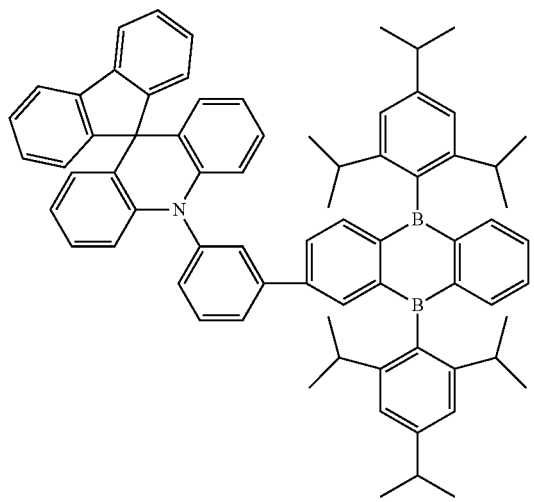
130
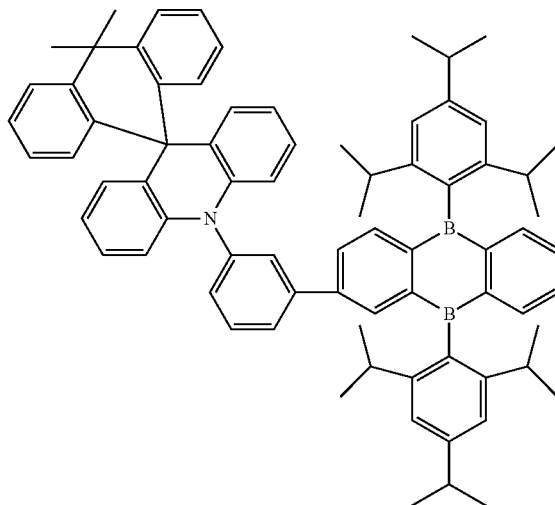
131
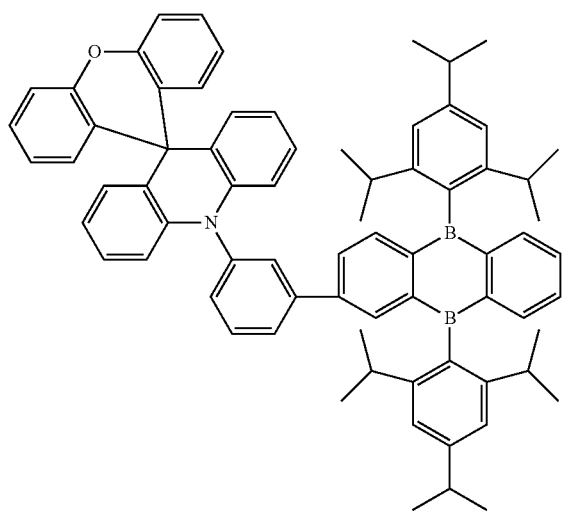
132
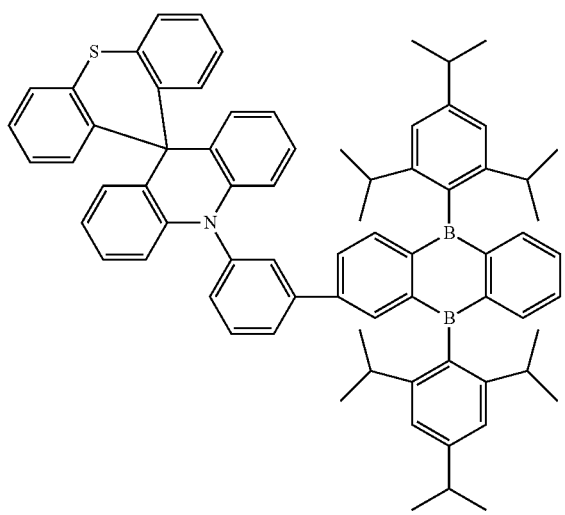
133
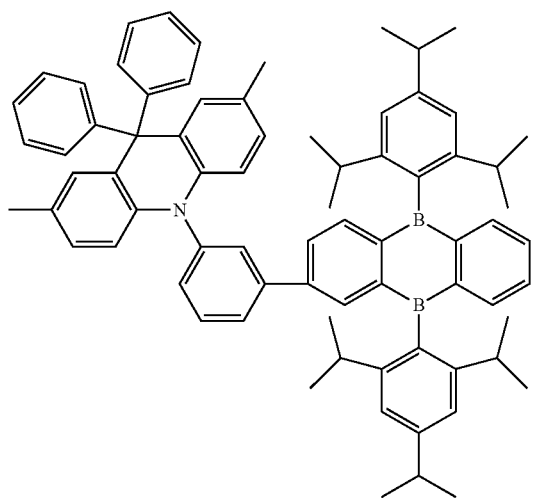
134
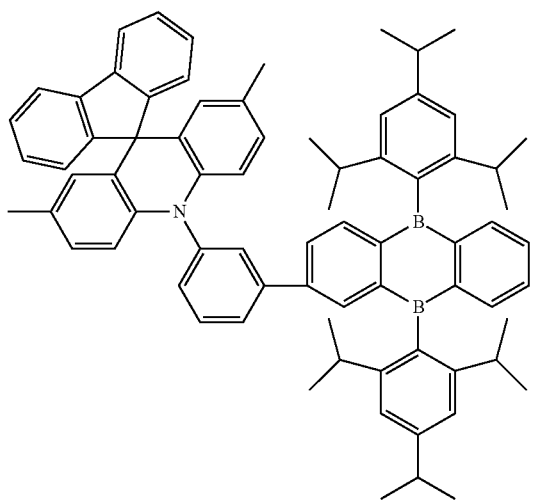

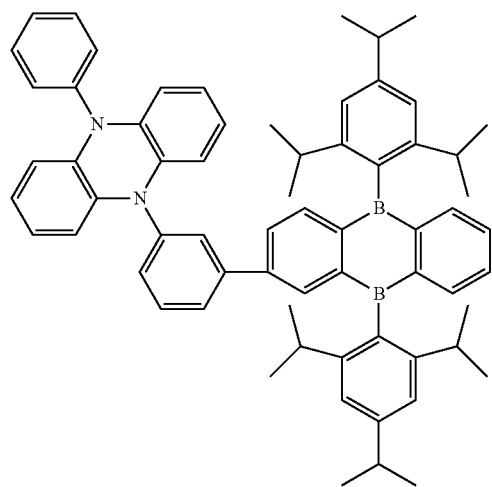
135
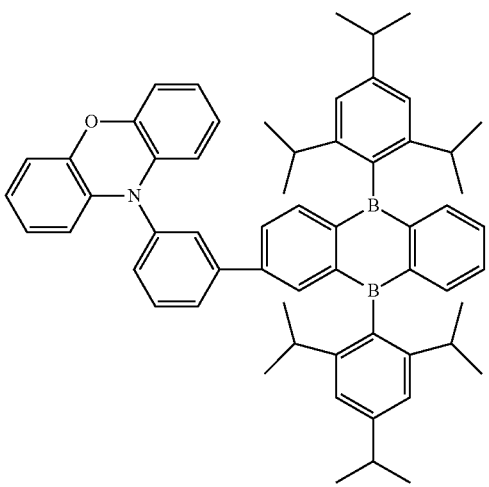
136
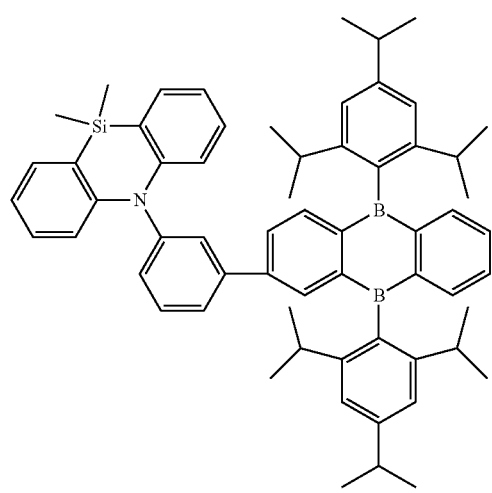
137
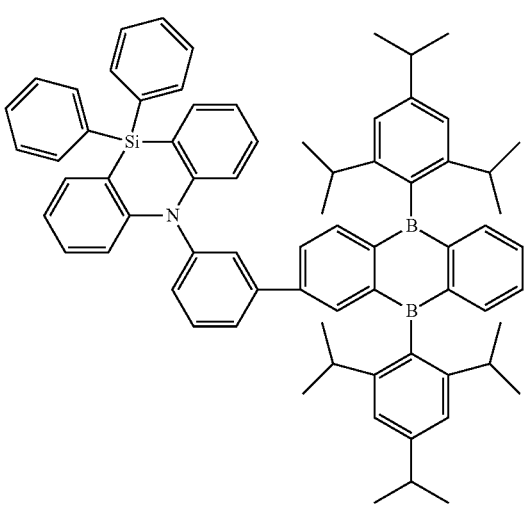
138
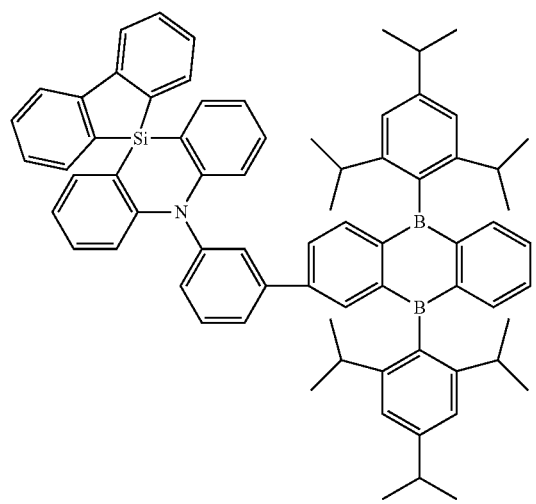
139
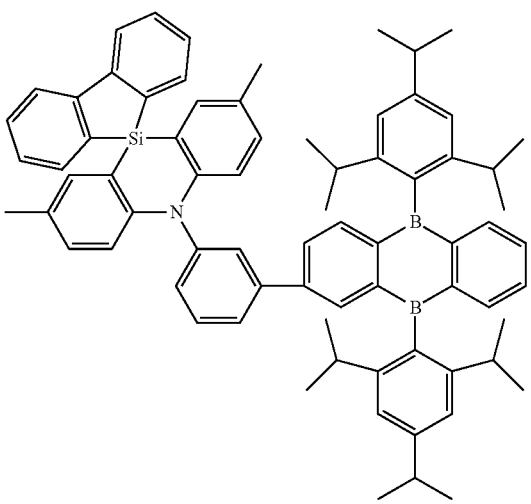
140

141
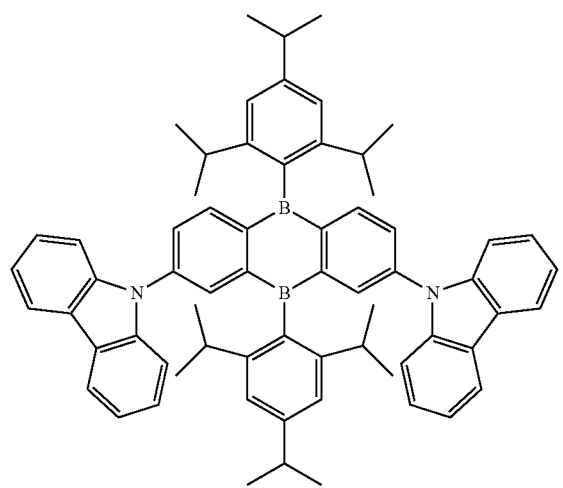
142
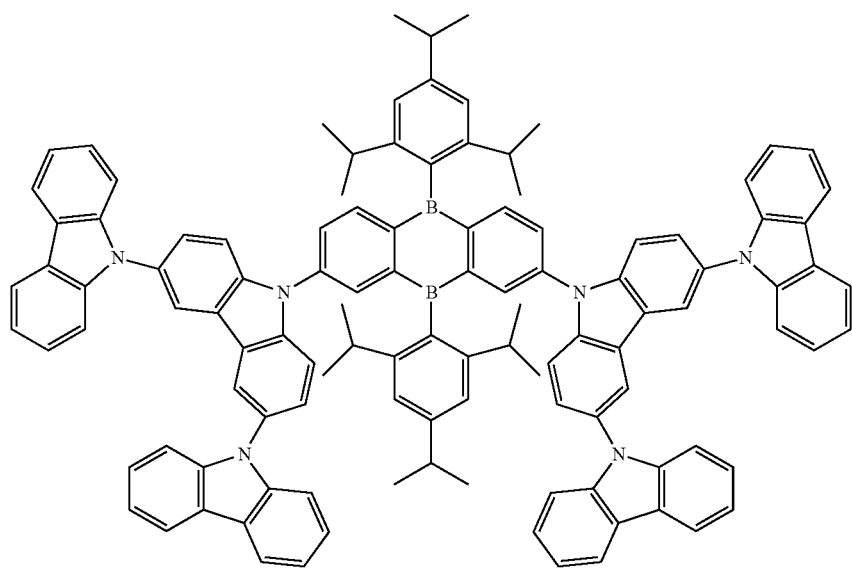
143
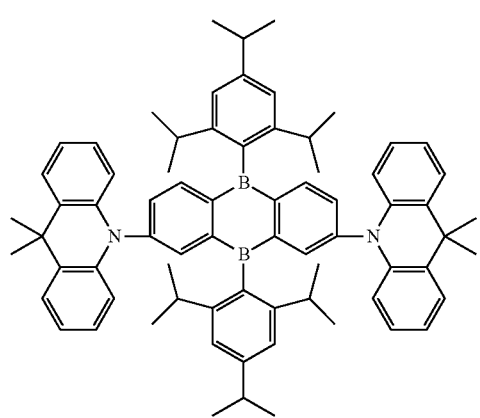
144
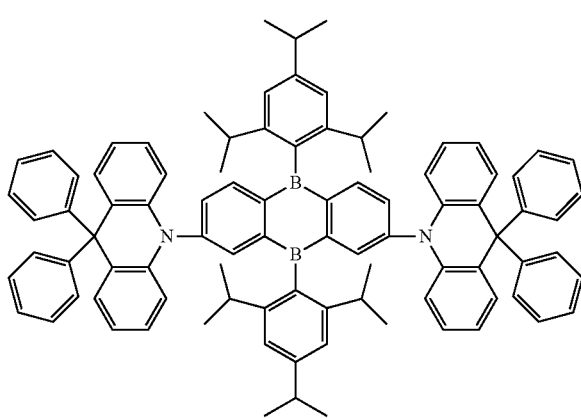

145
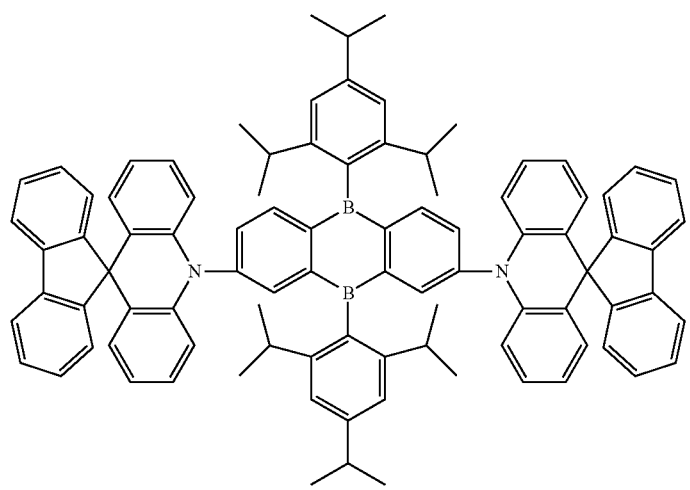
146
147
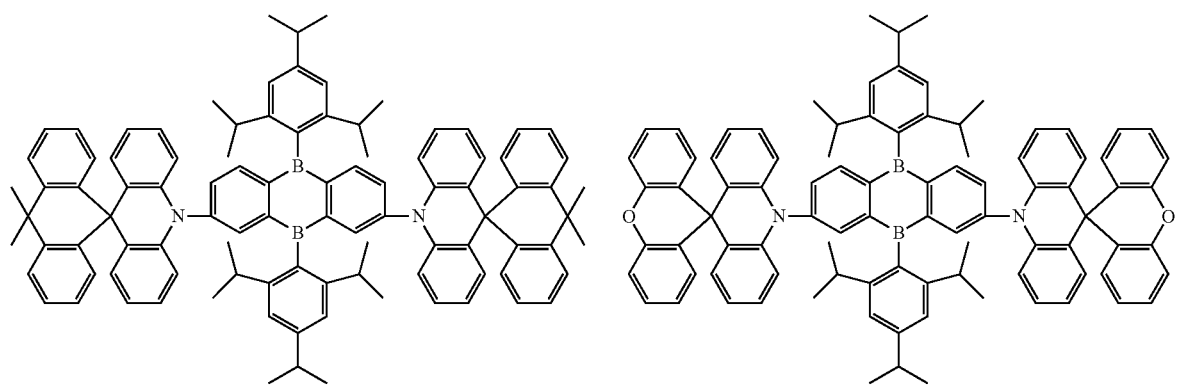
148
149
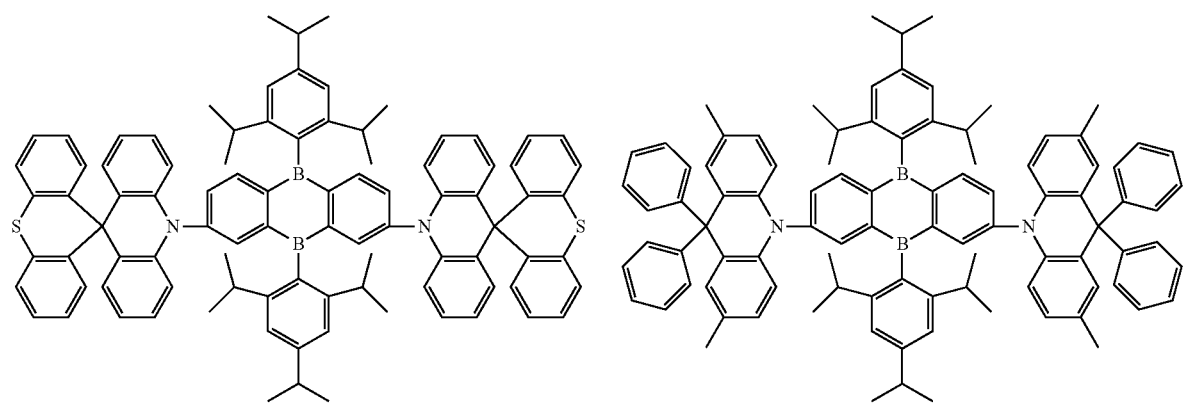

-continued

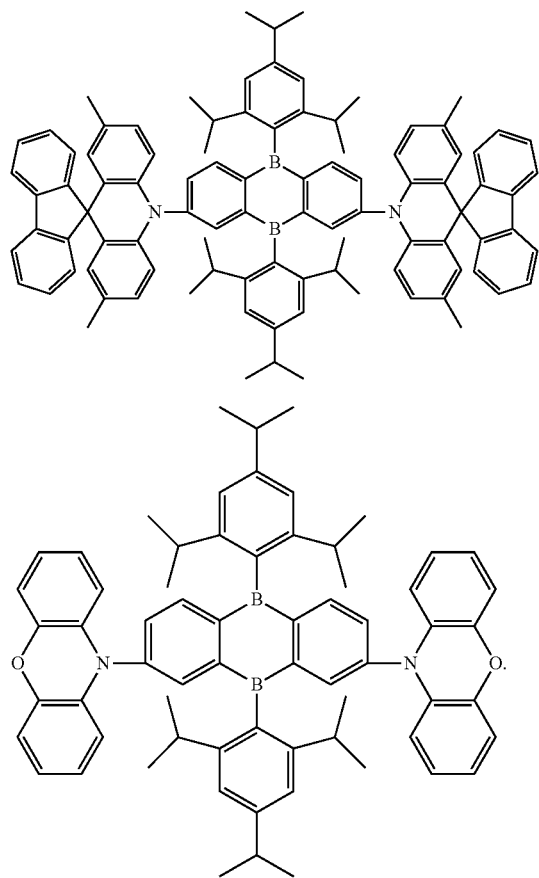

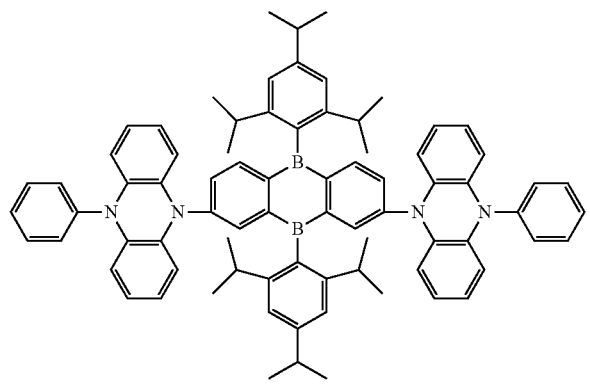

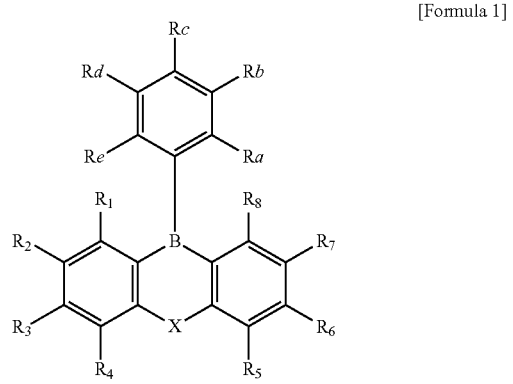

10. An organic electroluminescence device, comprising:
a first electrode;
a hole transport region provided on the first electrode;
an emission layer provided on the hole transport region;
an electron transport region provided on the emission layer; and
a second electrode provided on the electron transport region,
wherein the emission layer comprises a polycyclic compound represented by the following Formula 1:

[Formula 1]

in Formula 1, X is O, SiR'R", S, or $BAr_1$, $Ar_1$ is substituted or unsubstituted aryl group having 6 to 30 carbon atoms for forming a ring, or substituted or unsubstituted heteroaryl group having 2 to 30 carbon atoms for forming a ring, R' and R" are each independently substituted or unsubstituted alkyl group having 1 to 30 carbon atoms, substituted or unsubstituted aryl group having 6 to 30 carbon atoms for forming a ring, or substituted or unsubstituted heteroaryl group having 2 to 30 carbon atoms for forming a ring, Ra to Re, and $R_1$ to $R_8$ are each independently hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, when X is $BAr_1$, at least one of $R_1$ to $R_8$ is represented by one of the following Formulae 2 to 4, when X is O, SiR'R", S, at least one of $R_1$ to $R_8$ is represented by the following Formula 3 or 4:

[Formula 3]

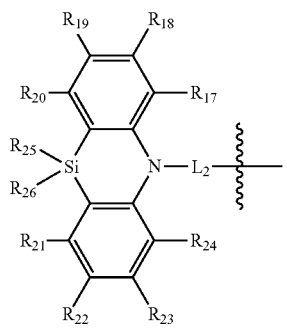

[Formula 4]

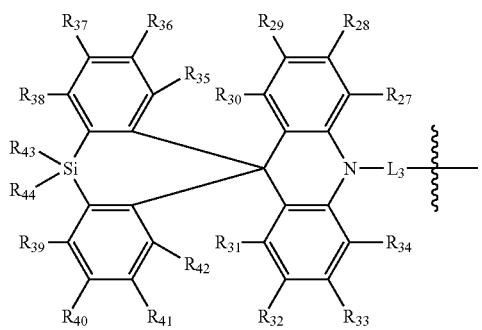

in Formulae 2, Y is a direct linkage, $CZ_1Z_2$, $NZ_3$, O, or S, $Z_1$ to $Z_3$, and $R_9$ to $R_{44}$ are each independently hydrogen atom, deuterium atom, halogen atom, cyano group, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, optionally, $R_{25}$ and $R_{26}$, $R_{43}$ and $R_{44}$, and $Z_1$ and $Z_2$ each two groups independently combine with each other to form a ring, and $L_1$ to $L_3$ are each independently a direct linkage, or substituted or unsubstituted arylene group having 6 to 30 carbon atoms for forming a ring.

11. The organic electroluminescence device of claim 10, wherein the polycyclic compound represented by Formula 1 has an absolute value of about 0.2 eV or less energy gap between a singlet energy level and a triplet energy level.

12. The organic electroluminescence device of claim 10, wherein the polycyclic compound represented by Formula 1 is a material for emitting thermally activated delayed fluorescence.

13. The organic electroluminescence device of claim 10, Wherein Formula 1 is represented by the following Formula 1-1:

[Formula 1-1]

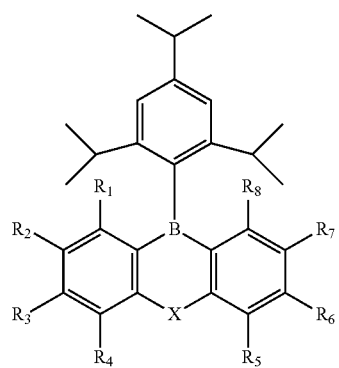

in Formula 14, X, and $R_1$ to $R_8$ are as defined in claim 10.

14. The organic electroluminescence device of claim 10, wherein $L_1$ to $L_3$ are each independently a direct linkage, or substituted or unsubstituted phenylene group.

15. The organic electroluminescence device of claim 10, wherein Formula 3 is represented by one of the following Formulae 3-1 to 3-4:

[Formula 3-1]

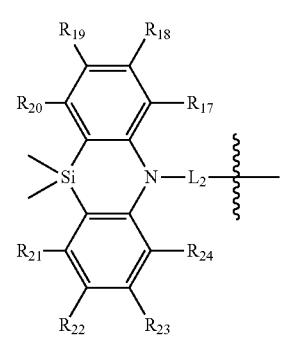

[Formula 3-2]

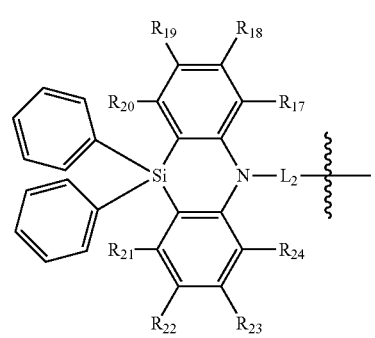

[Formula 3-3]

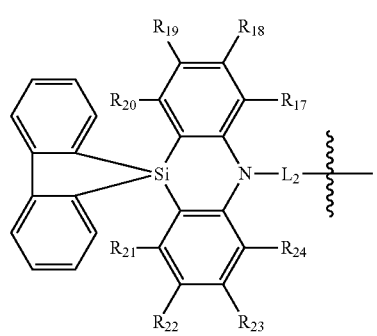

[Formula 3-4]

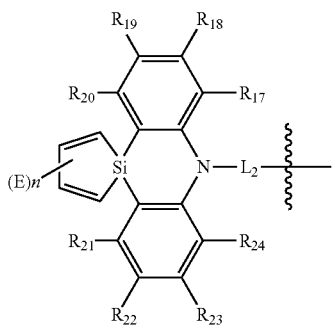

[Formula 4-3]

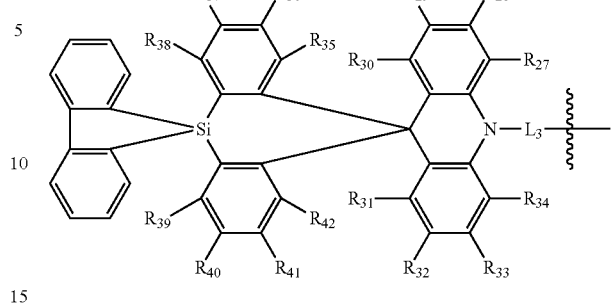

in Formulae 3-1 to 3-4, $L_2$, and $R_{17}$ to $R_{24}$ are as defined in claim 10, E is hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, where E optionally combines with an adjacent group to form a ring, and n is an integer of 0 to 4.

16. The organic electroluminescence device of claim 10, wherein Formula 4 is represented by one of the following Formulae 4-1 to 4-2:

[Formula 4-1]

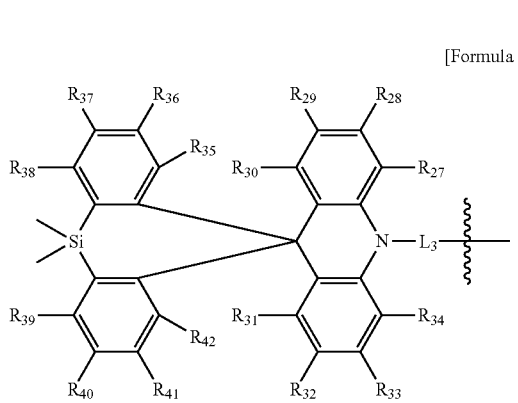

[Formula 4-4]

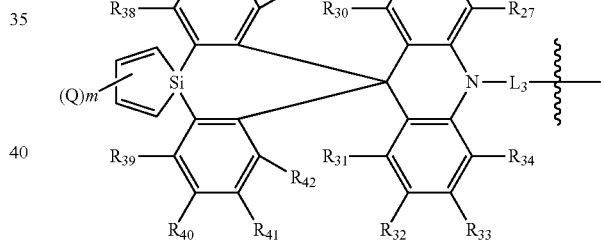

[Formula 4-2]

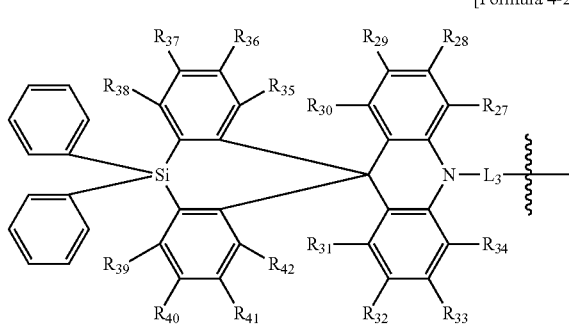

in Formulae 4-1 to 4-4, $L_3$, and $R_{27}$ to $R_{42}$ are as defined in claim 10, Q is hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, where Q optionally combines with an adjacent group to form a ring, and m is an integer of 0 to 4.

17. The organic electroluminescence device of claim 10, wherein X is $BAr_1$, and $Ar_1$ is substituted or unsubstituted phenyl group.

18. The organic electroluminescence device of claim 10, wherein Formula 1 is represented by the following Formula 1-2:

[Formula 1-2]
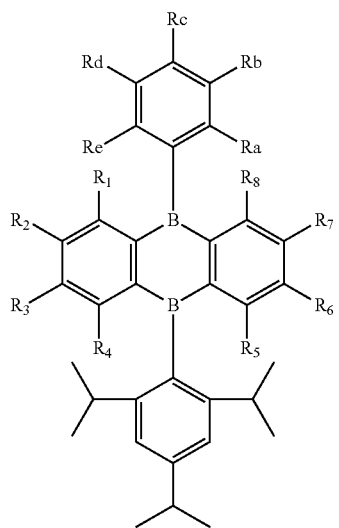
in Formula 1-2, Ra to Re, and $R_1$ to $R_8$ are as defined in claim 10.
19. The organic electroluminescence device of claim 10, wherein the polycyclic compound represented by Formula 1 is at least one of compounds represented in the following Compound Groups 1 and 3:
[Compound Group 1]
1
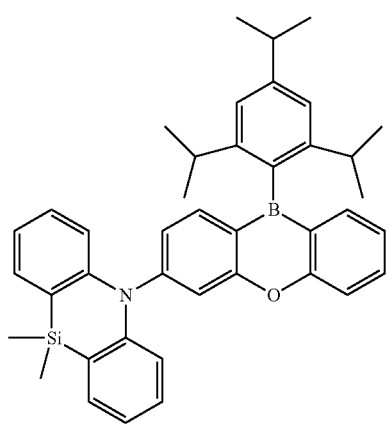
2
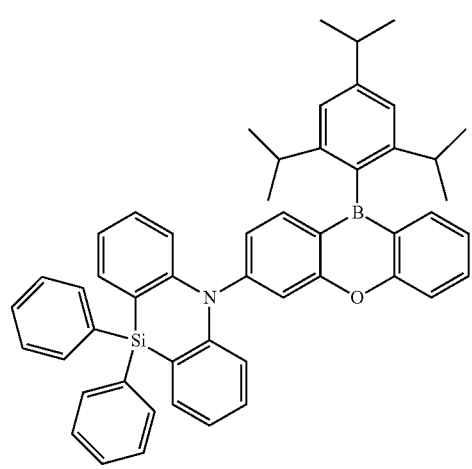
3
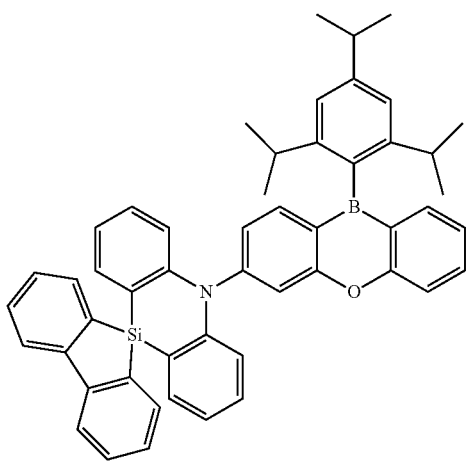
4
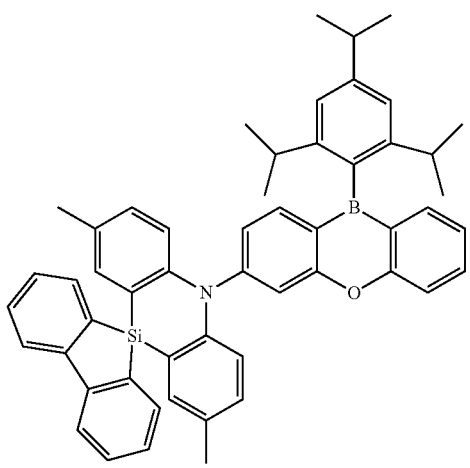
5
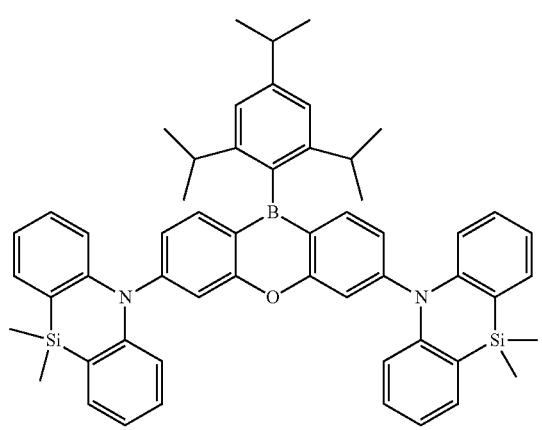

6
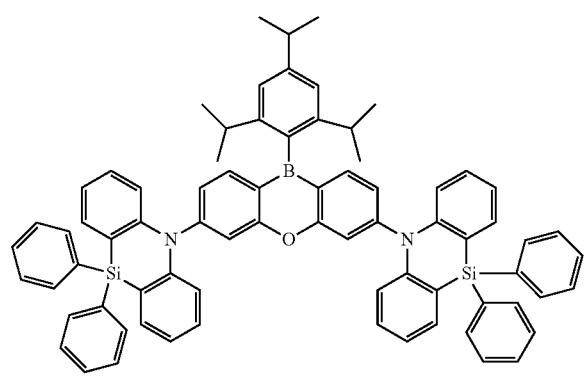
7
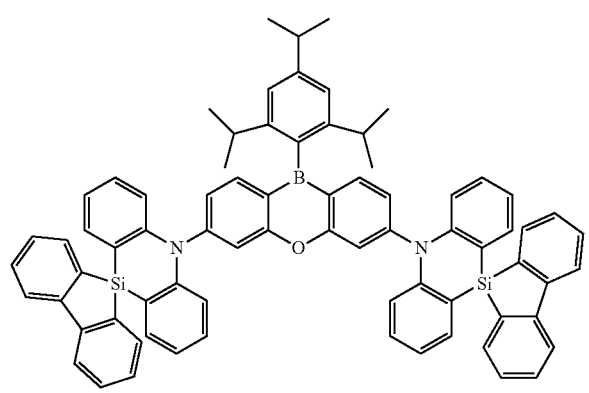
8
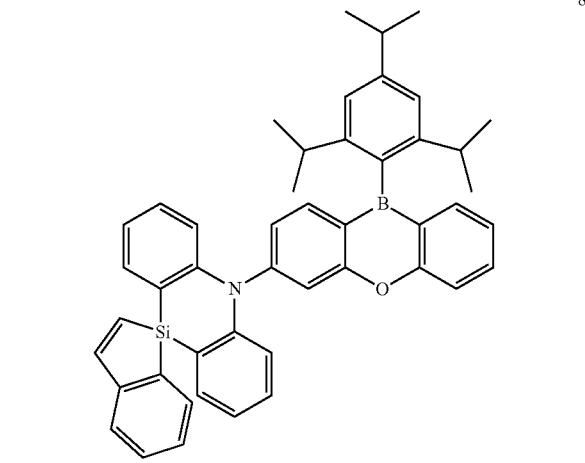
9
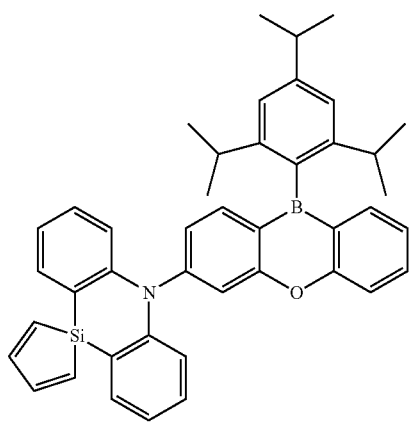
10
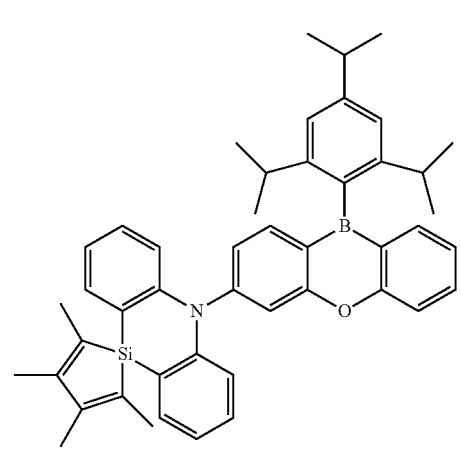
11
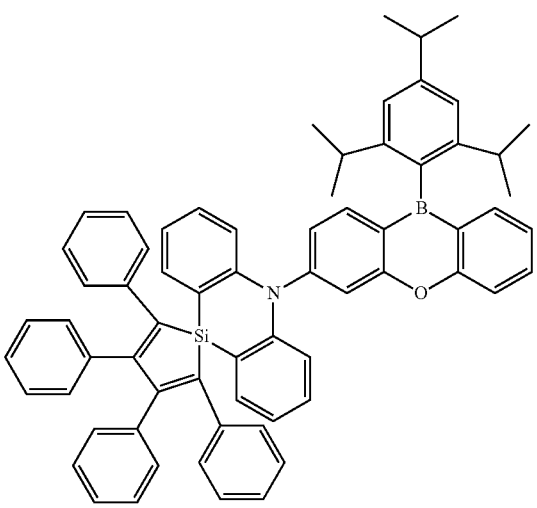

12
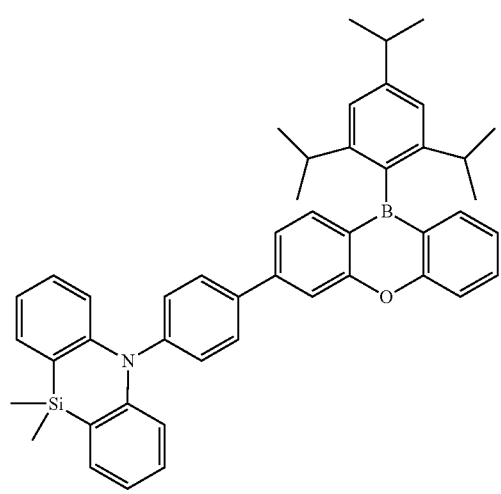
13
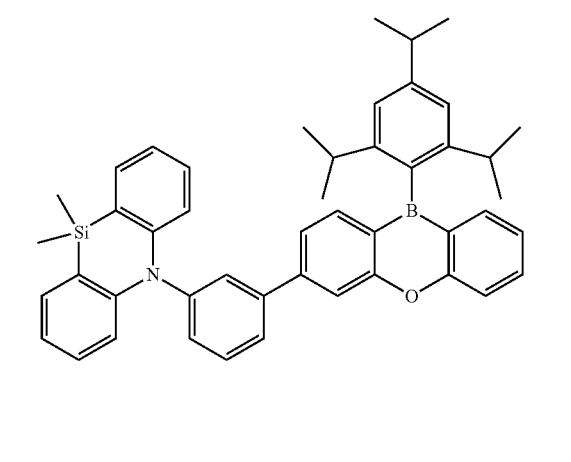
14
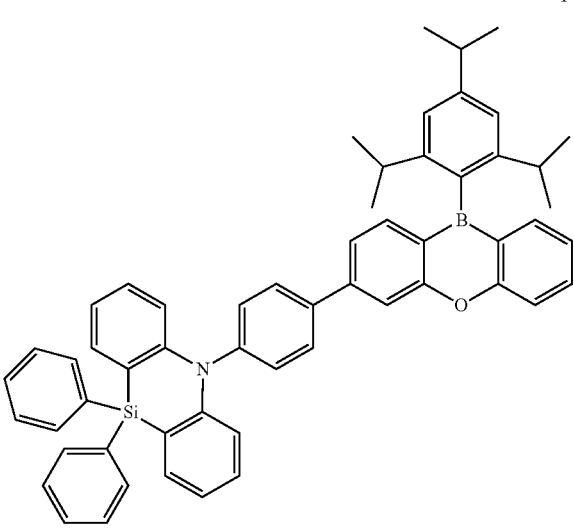
15
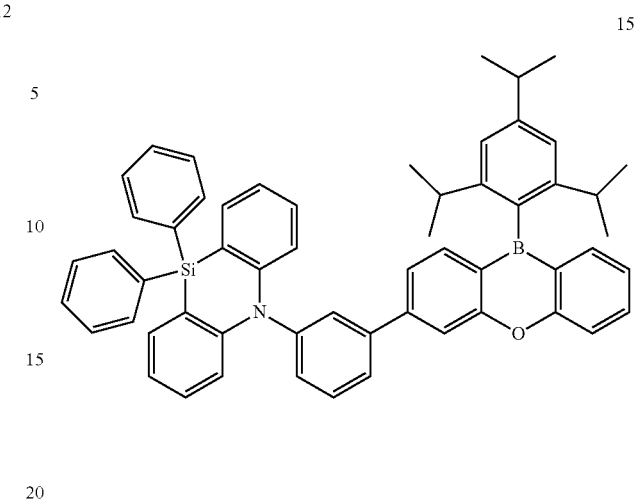
16
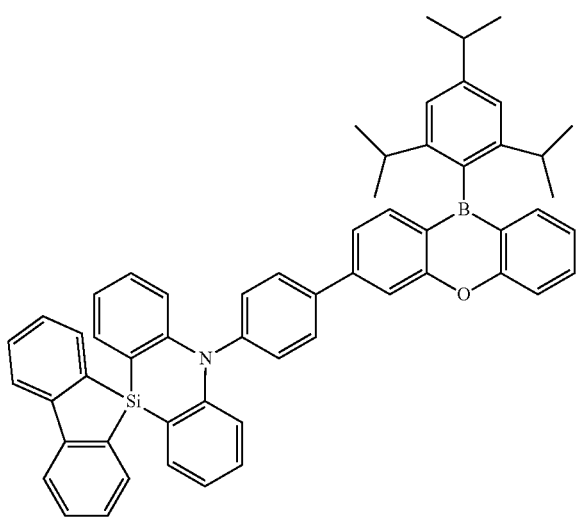
17
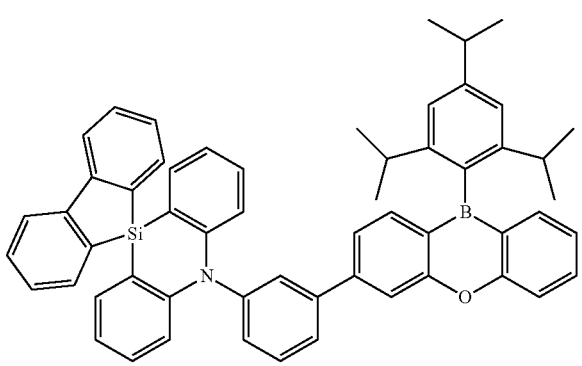

-continued
18
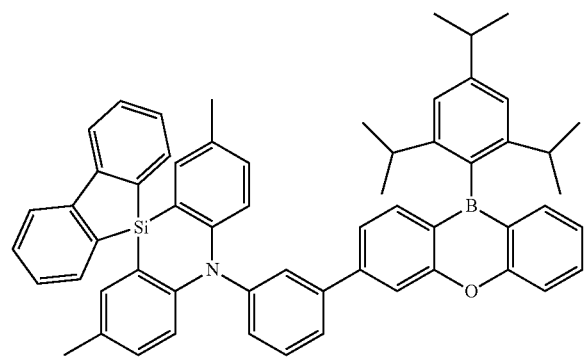
19
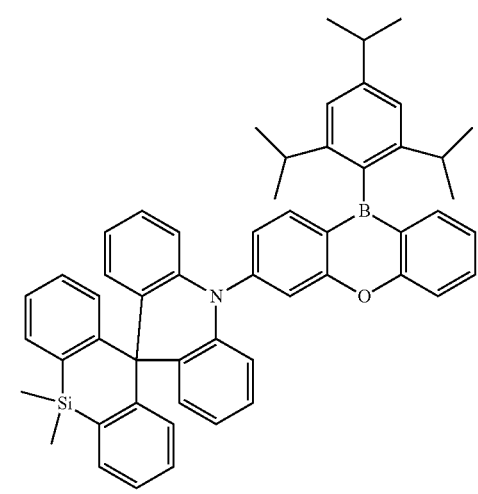
20
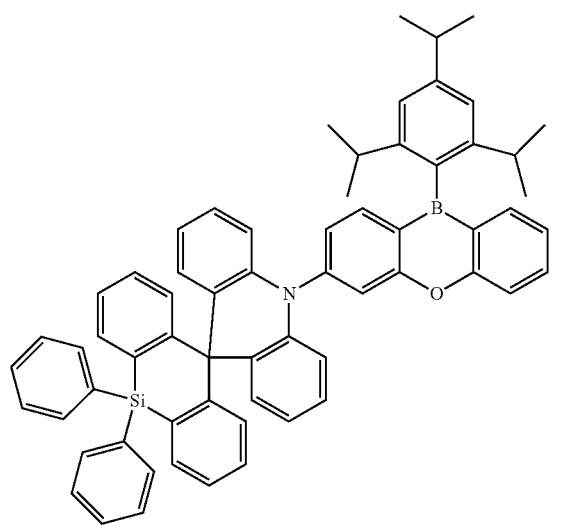
-continued
21
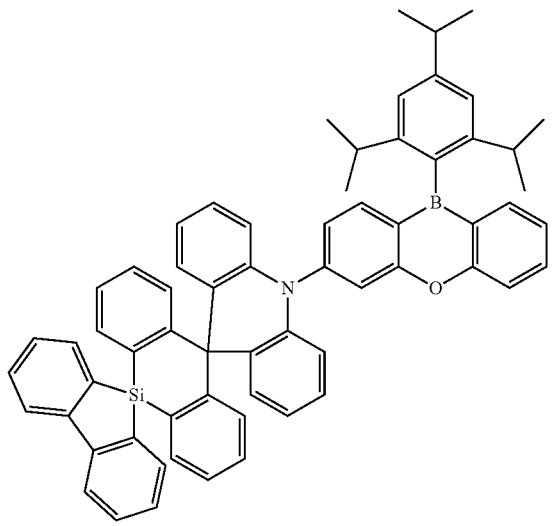
22
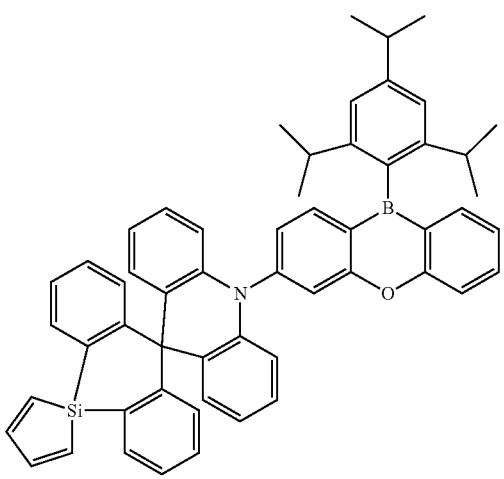
23
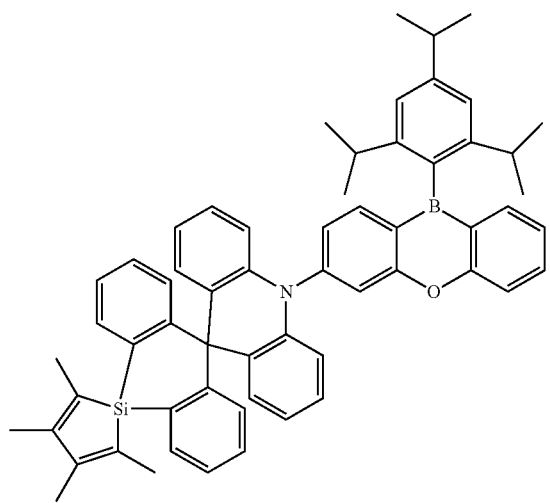

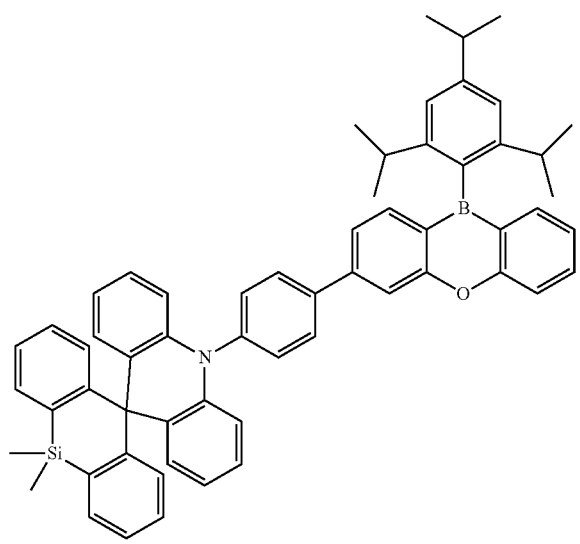
24
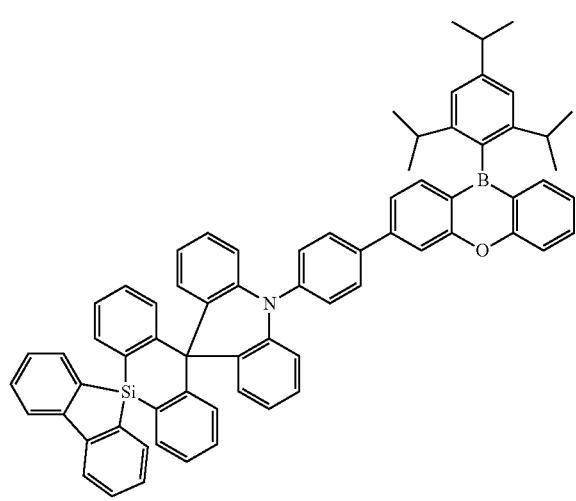
26
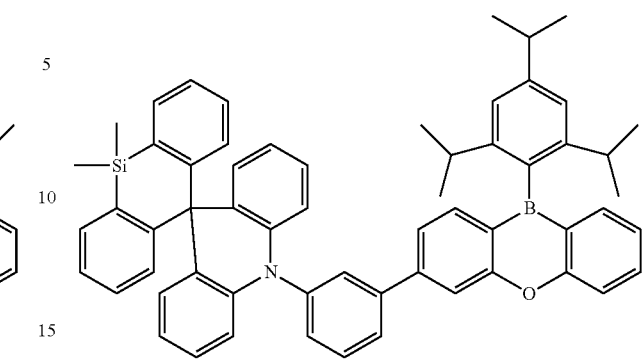
27
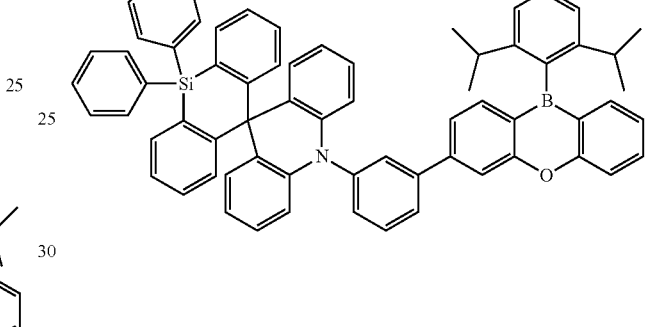
28
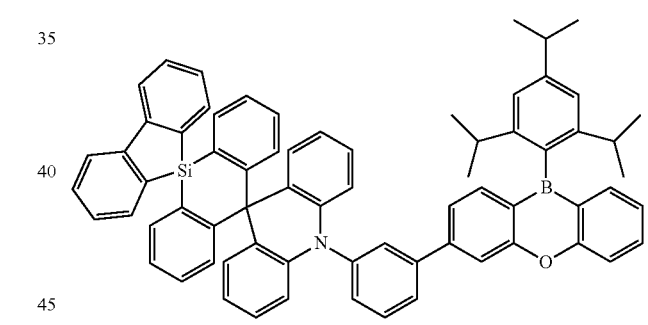
29
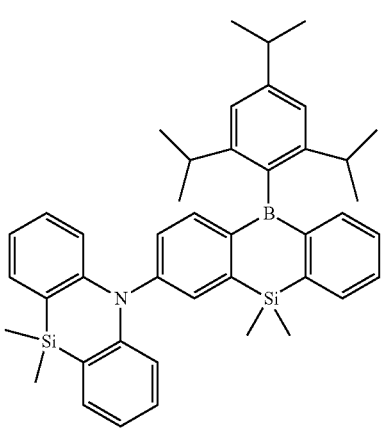
30

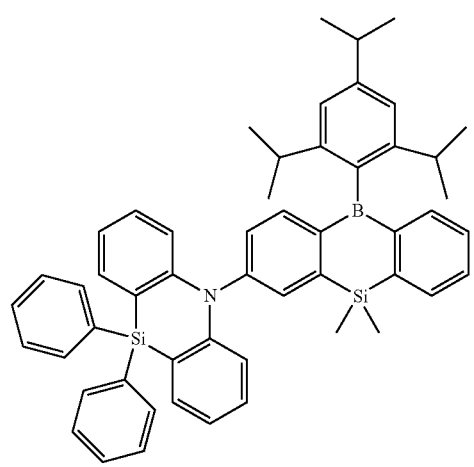
31
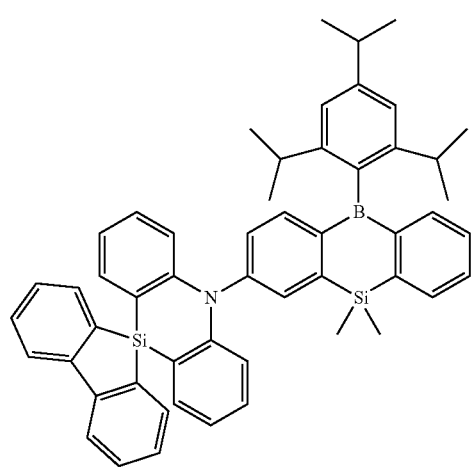
32
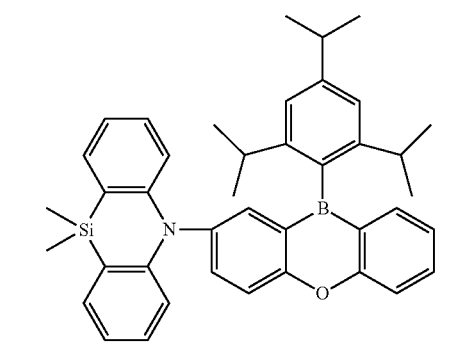
33
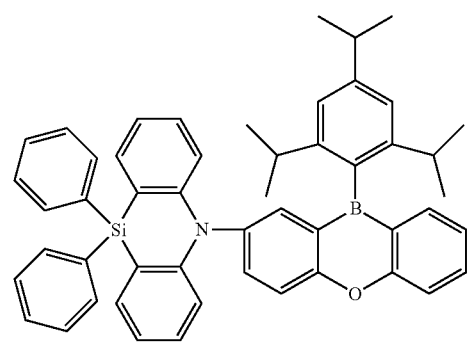
34
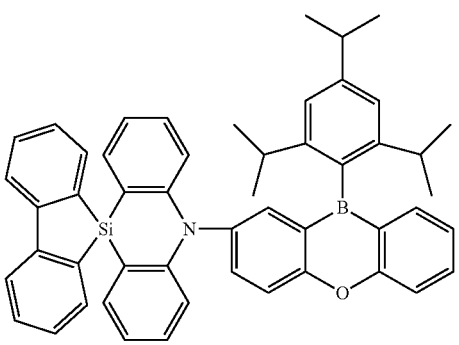
35
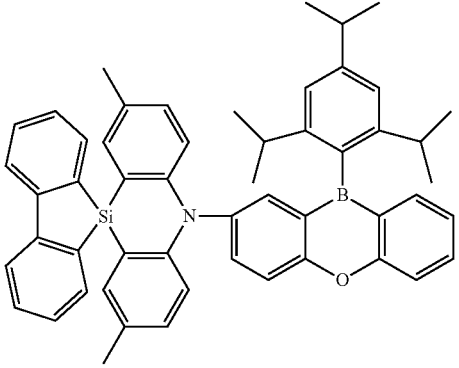
36
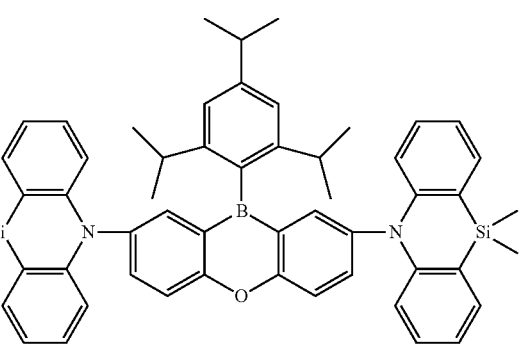
37
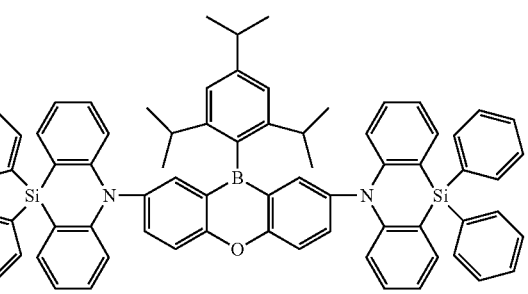
38

199
-continued
39
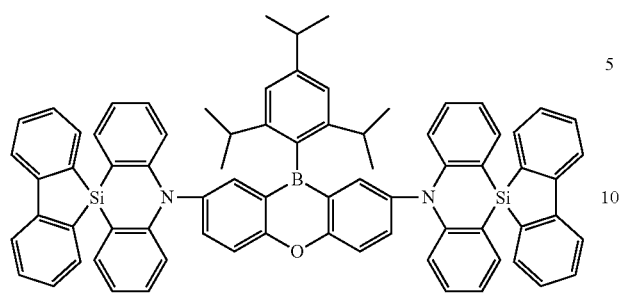
40
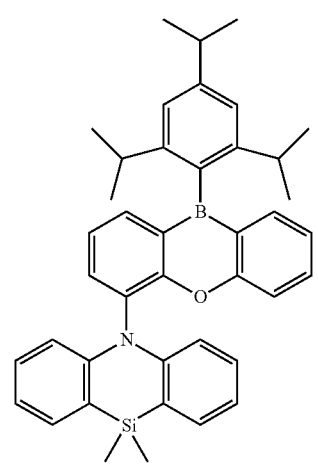
41
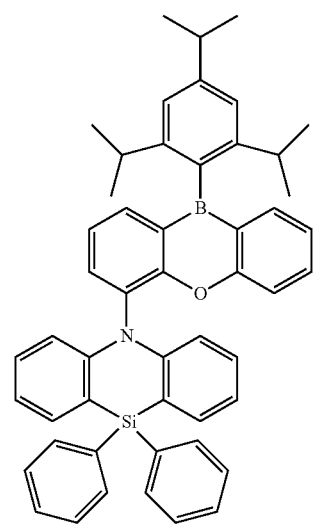
200
-continued
42
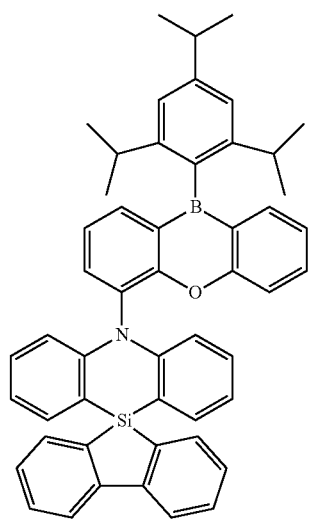
43
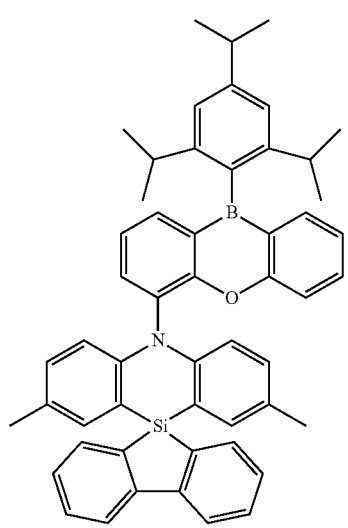
44
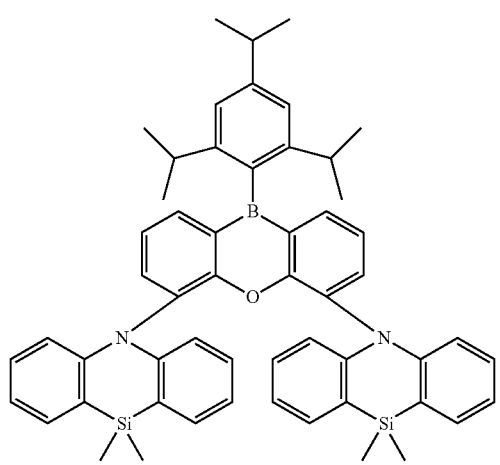

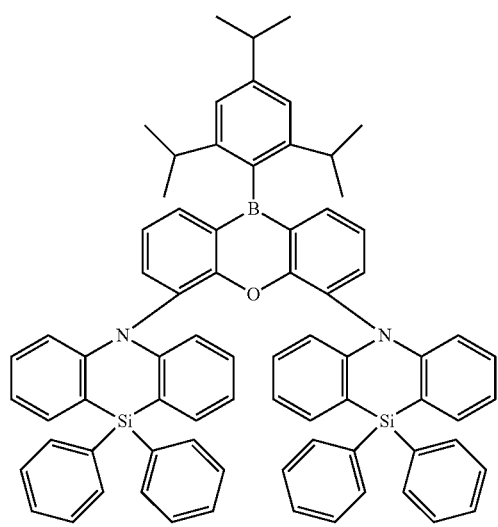
45
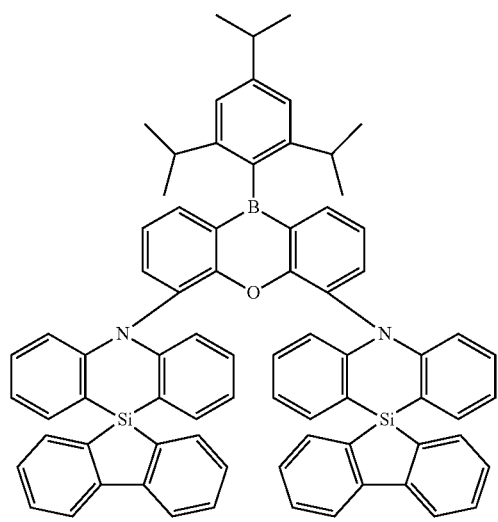
46
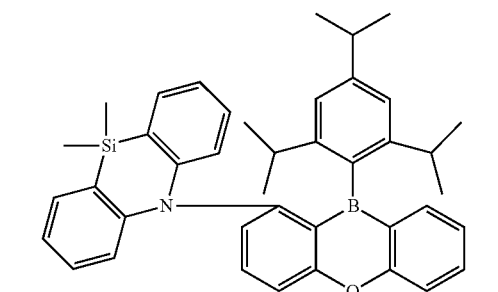
47
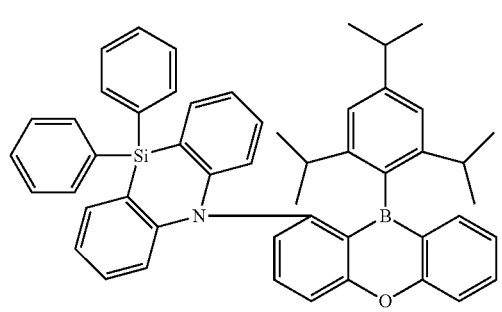
48
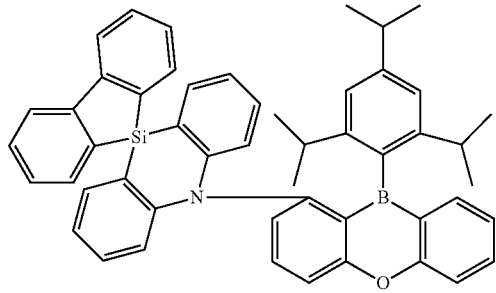
49
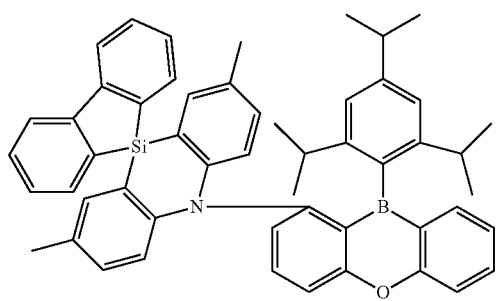
50
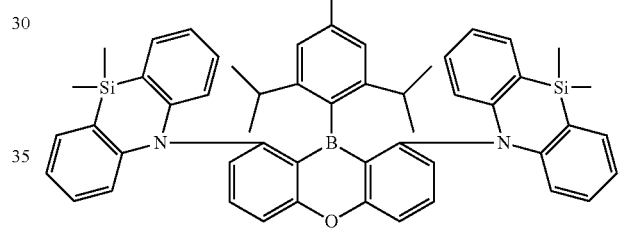
51
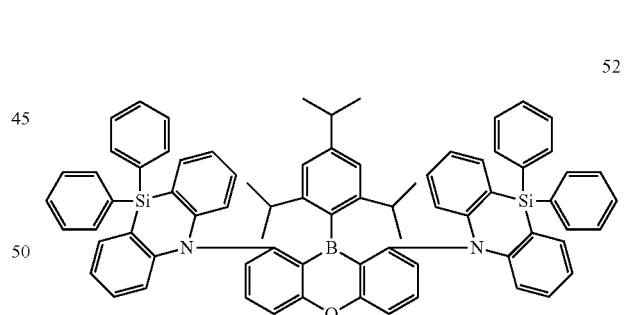
52
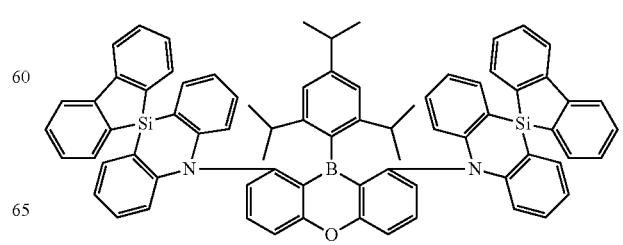
53

203
-continued
54
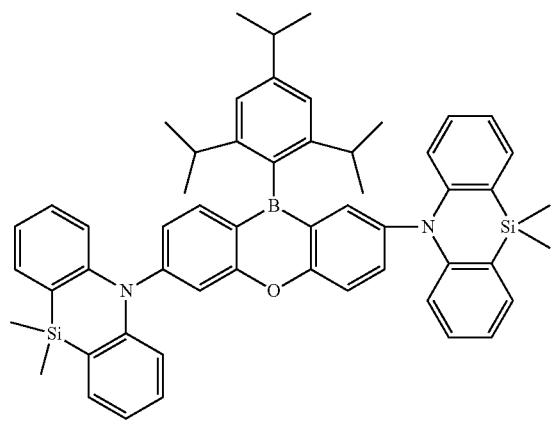
55
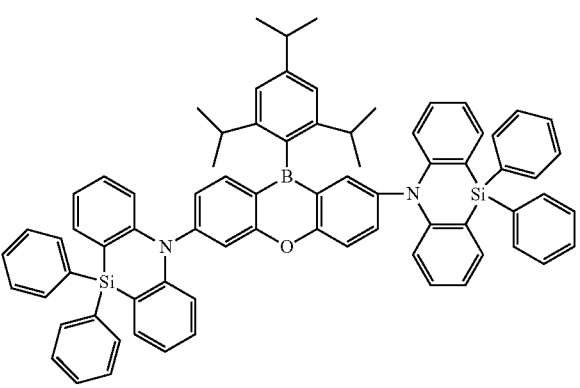
56
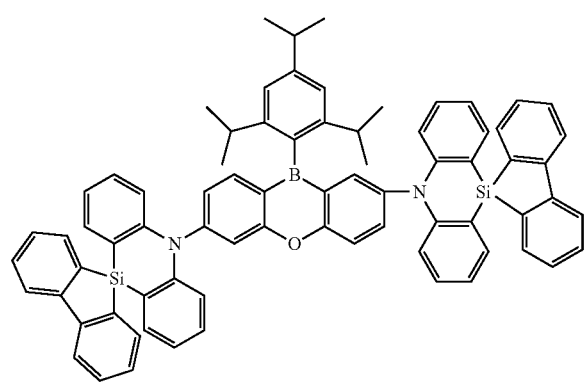
204
-continued
57
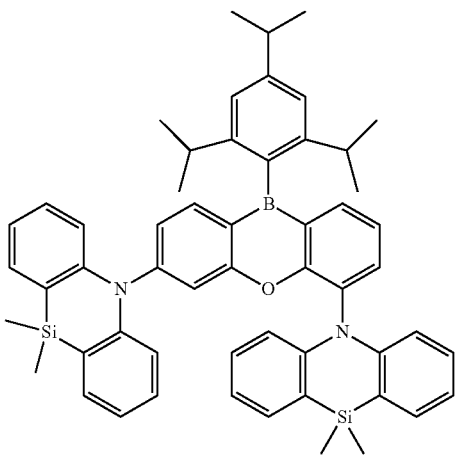
58
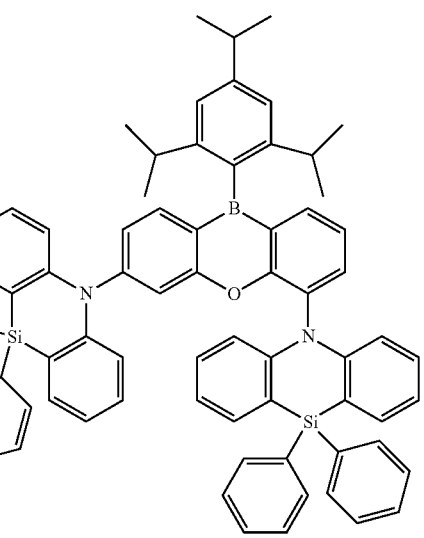
59
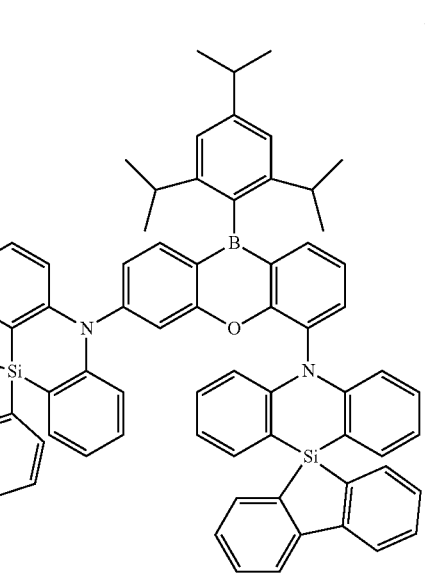

205
-continued
60
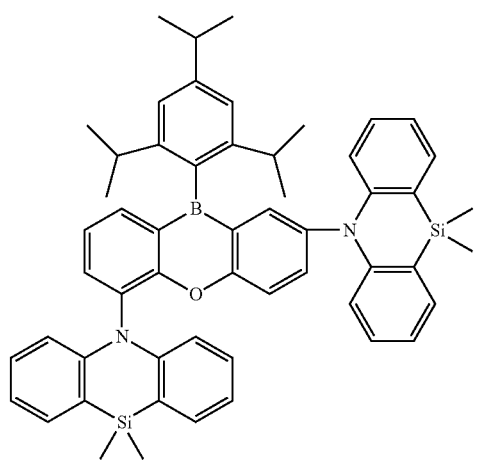
61
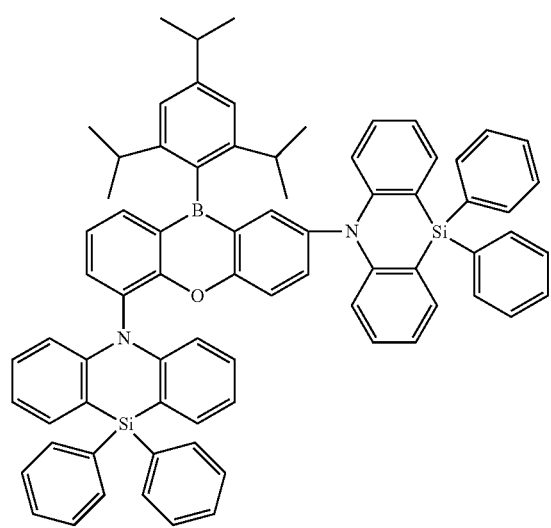
62
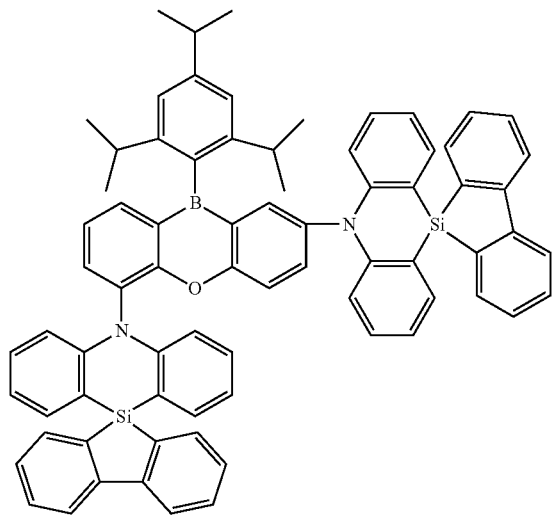
206
-continued
[Compound Group 3]
153
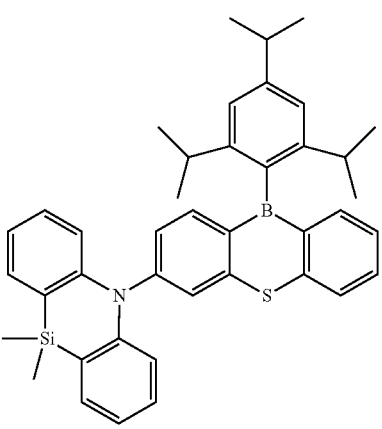
154
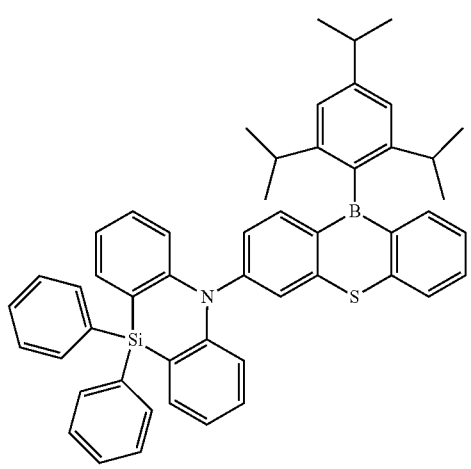
155
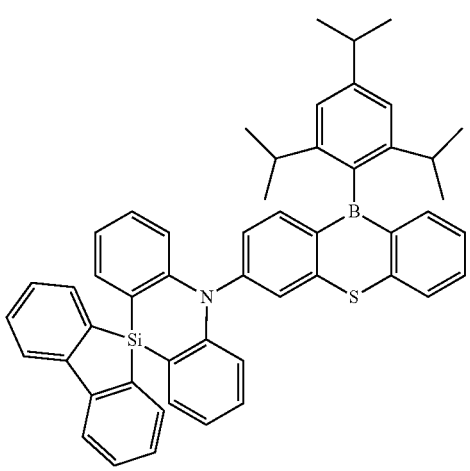

156
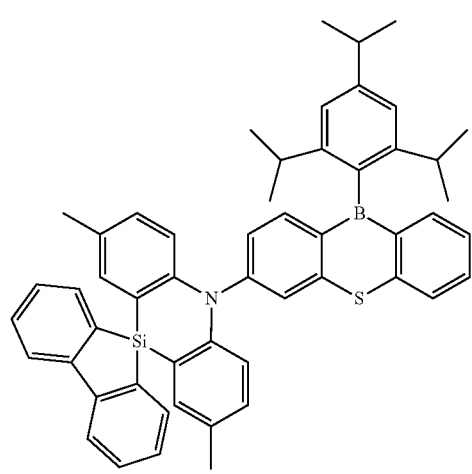
157
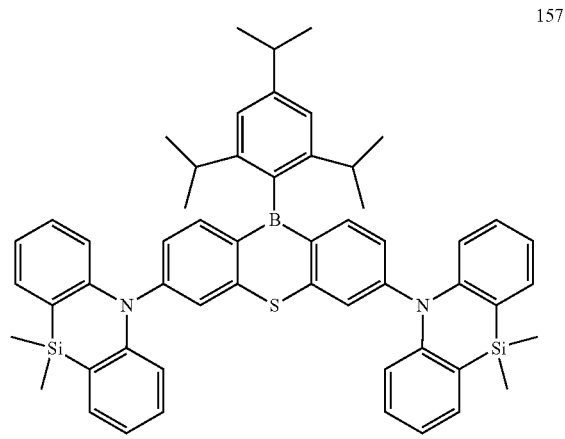
158
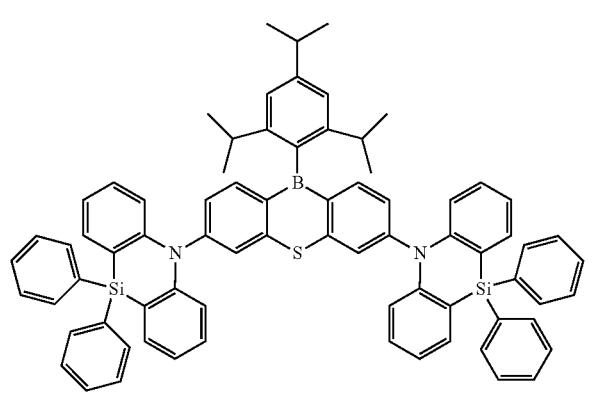
159
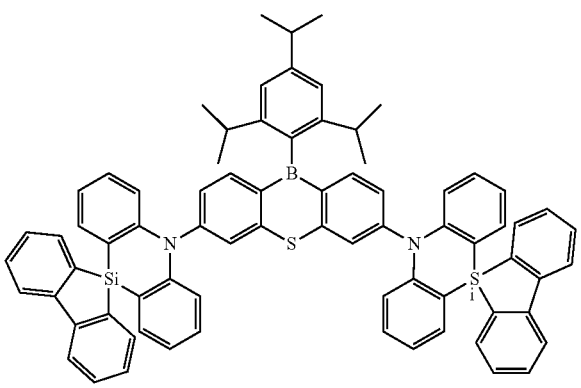
160
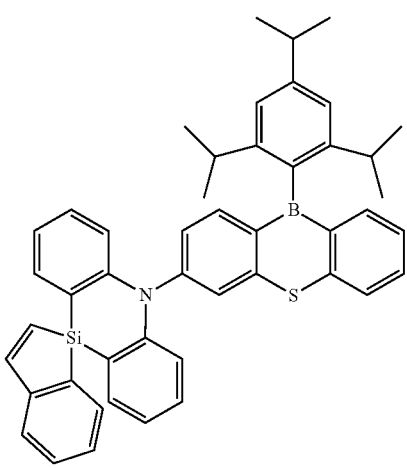
161
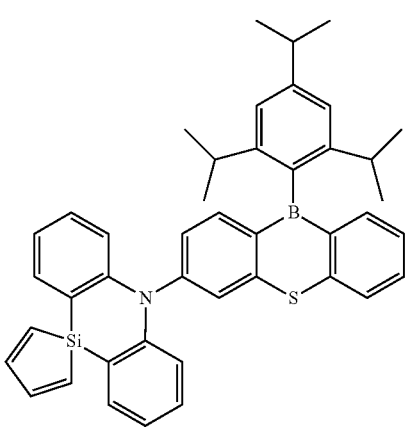

-continued
162
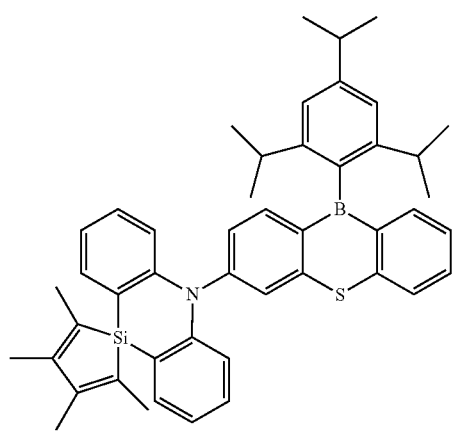
163
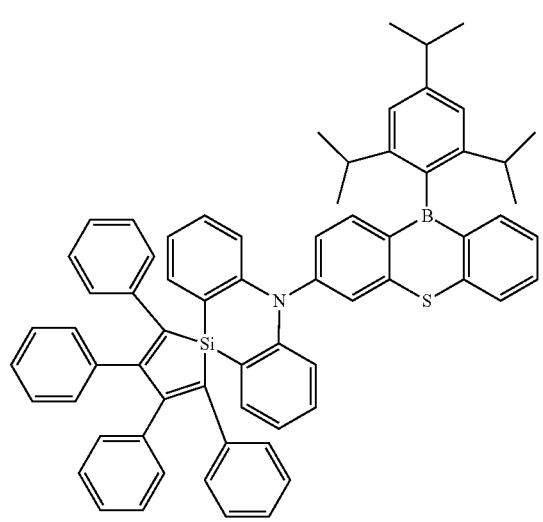
164
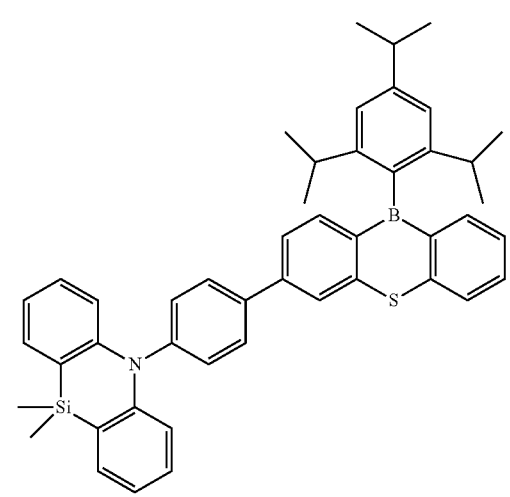
-continued
165
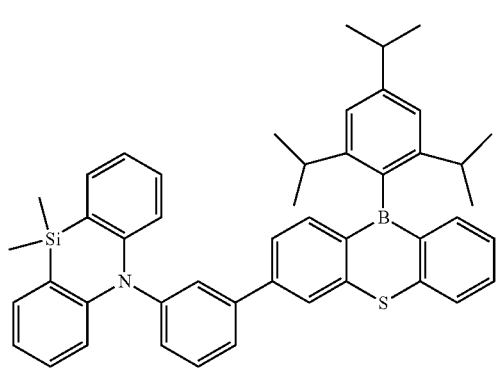
166
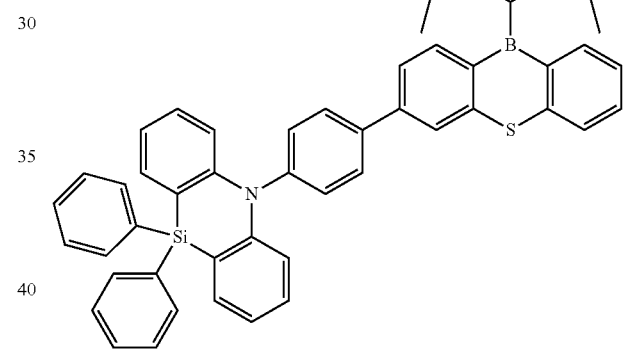
167
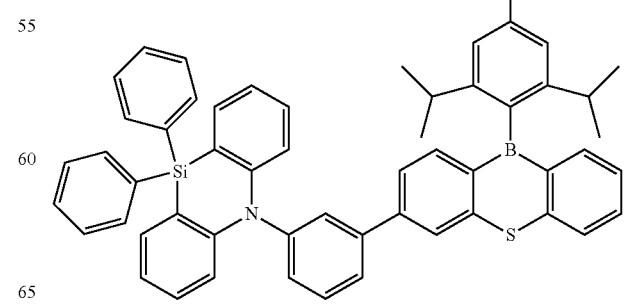

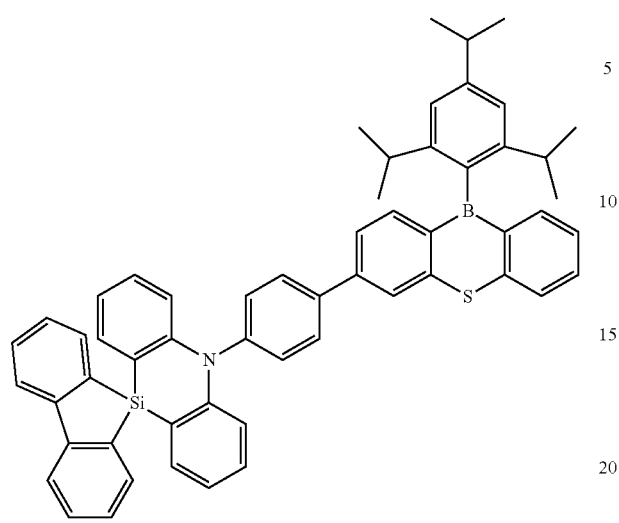
168
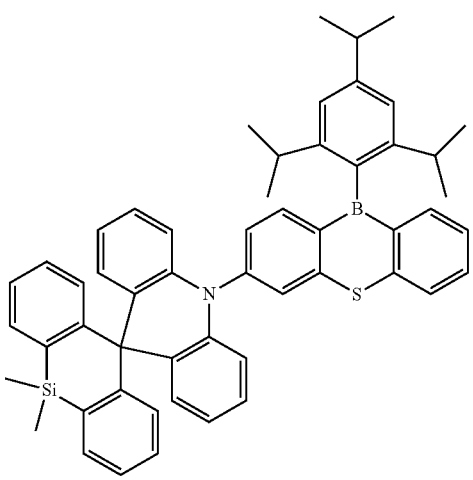
171
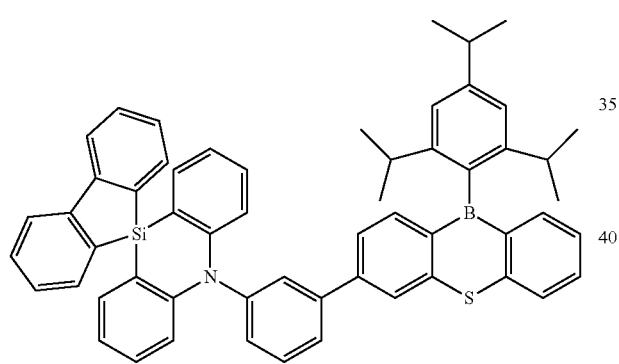
169
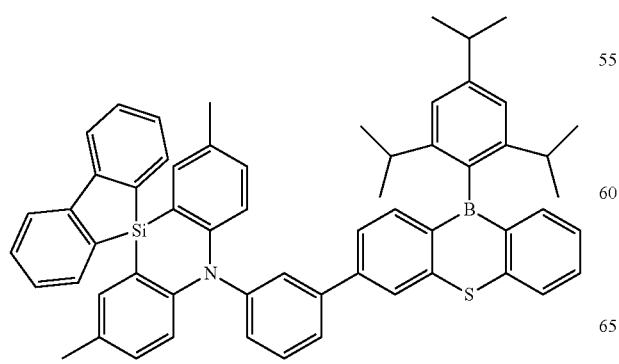
170

174
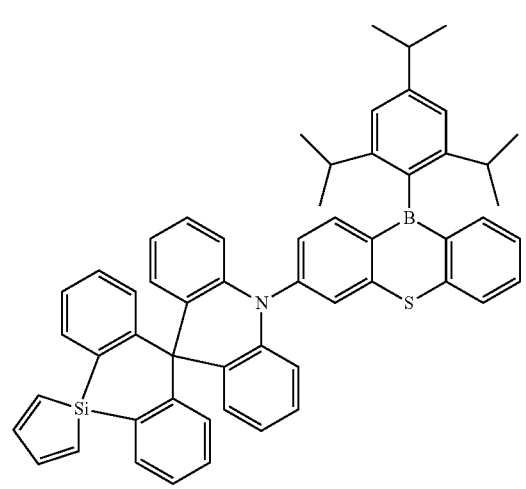
175
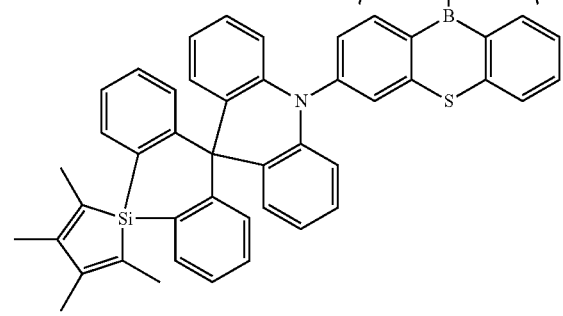
176
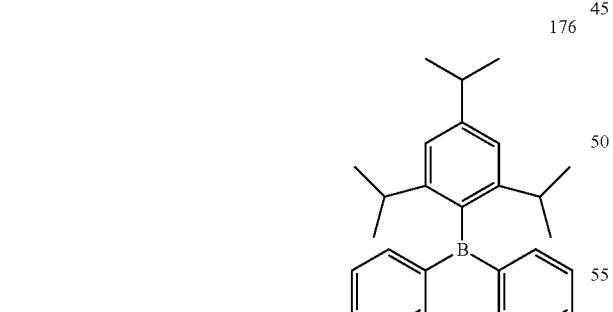
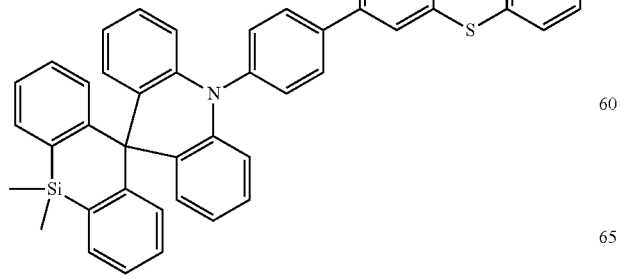
177
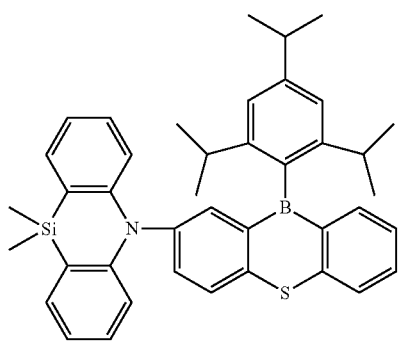
178
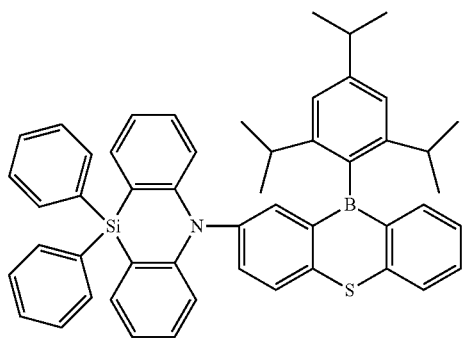
179
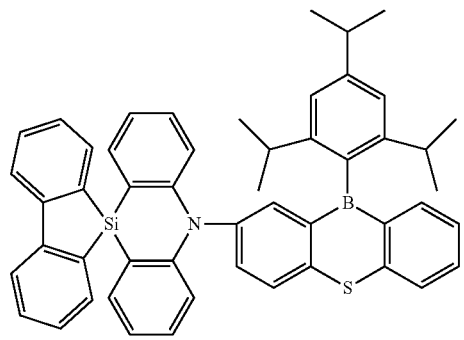
180
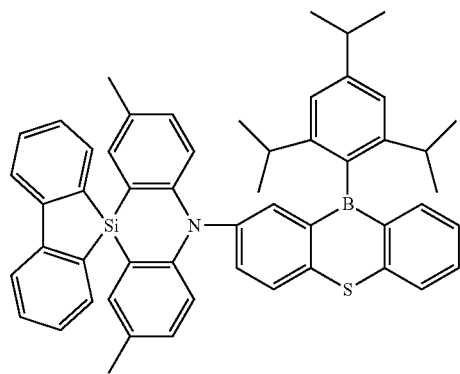

-continued
181
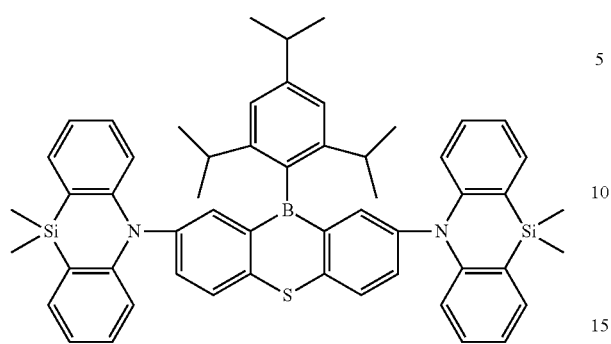
182
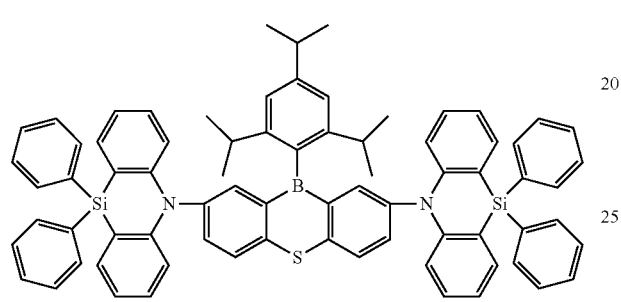
183
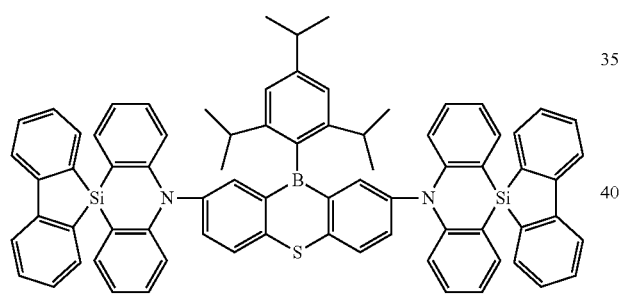
184
185
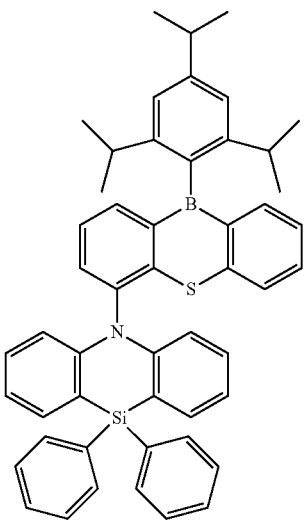
186
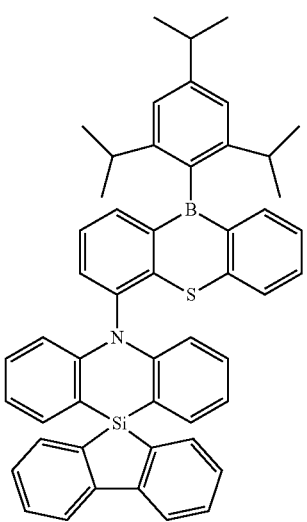
187
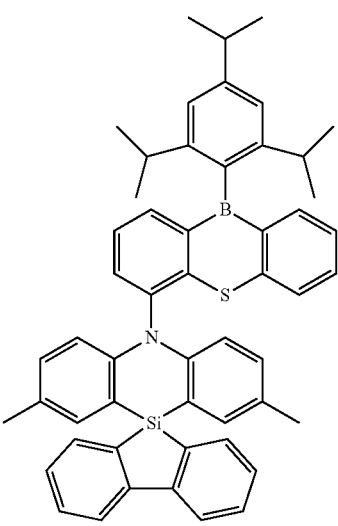

217
-continued
188
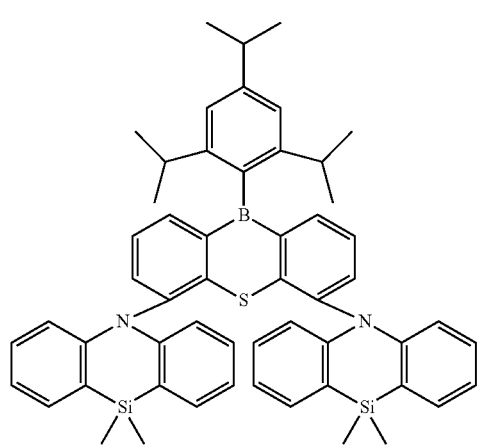
189
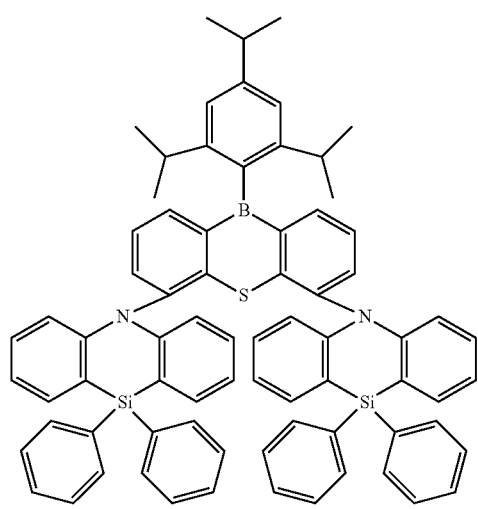
190
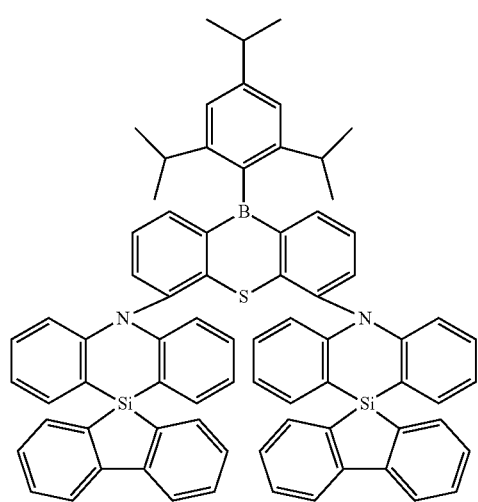
218
-continued
191
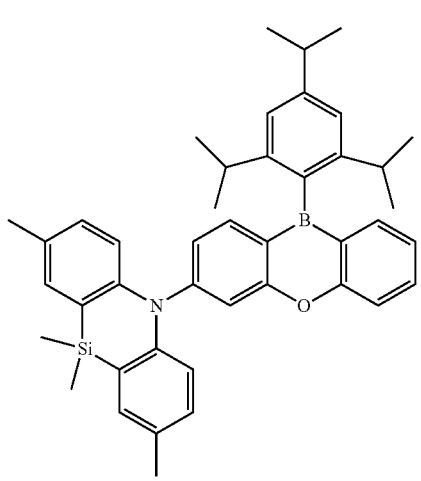
192
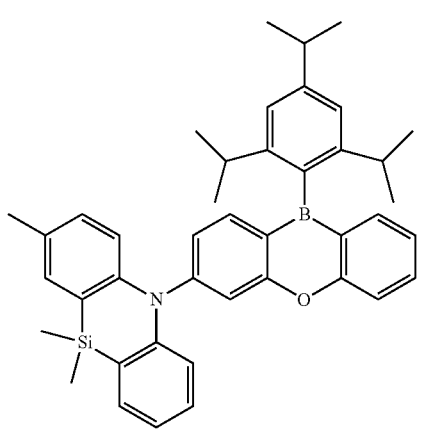
193
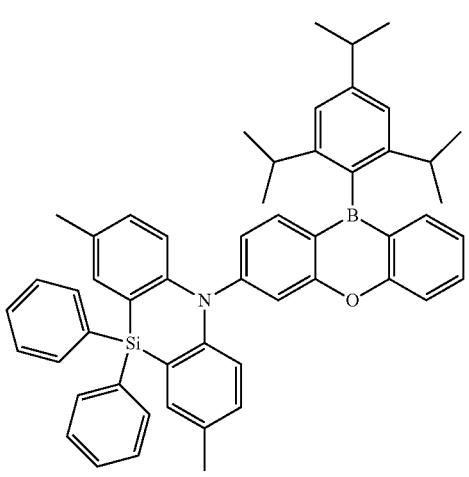

-continued
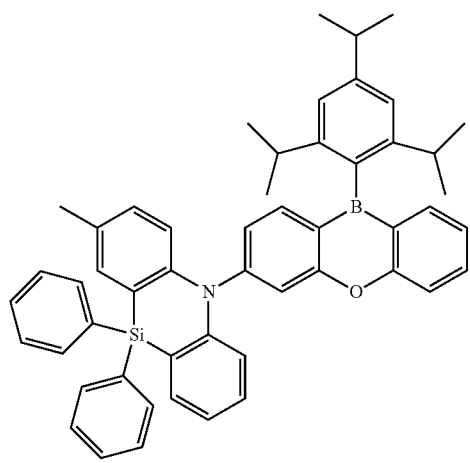
194
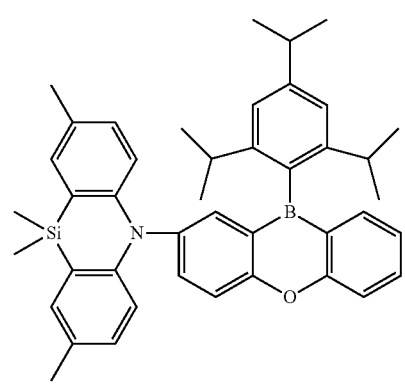
195
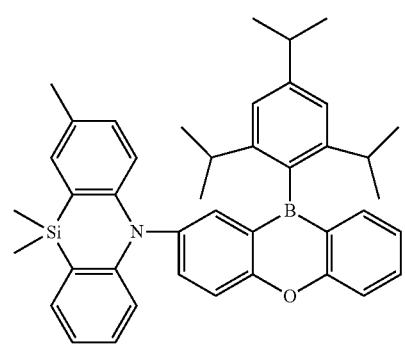
196
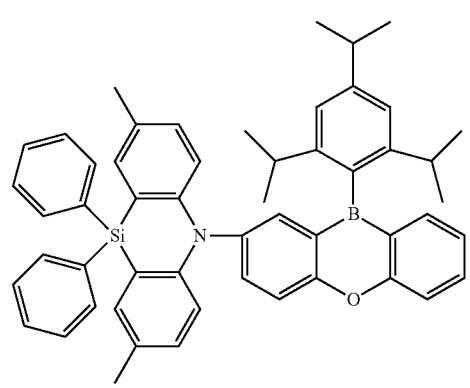
197
-continued
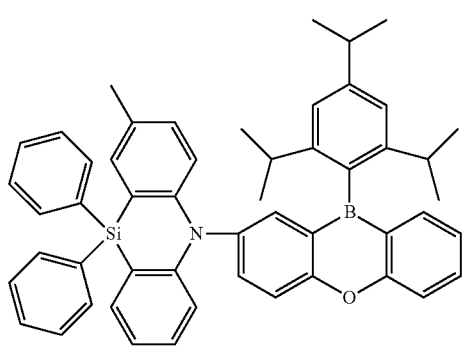
198
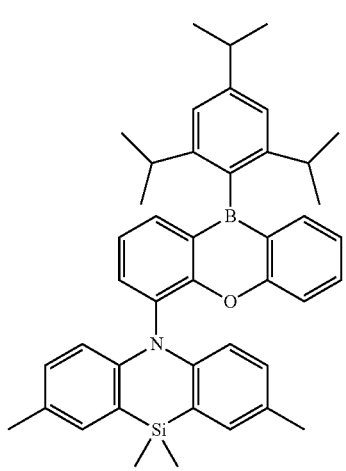
199
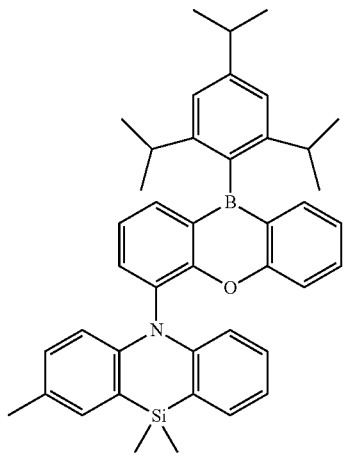
200

221
-continued
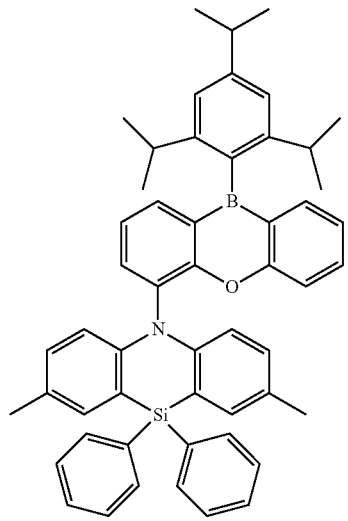
201
222
-continued
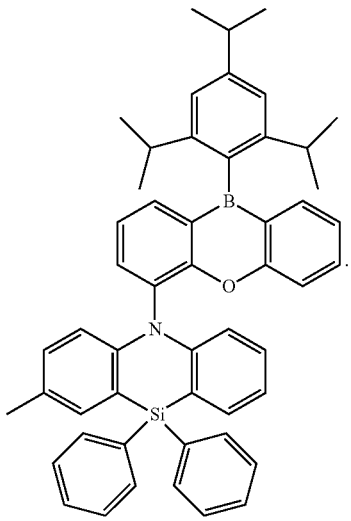
202
20. The organic electroluminescence device of claim 10, wherein the polycyclic compound represented by Formula 1 is at least one of compounds represented in the following Compound Group 2:
[Compound Group 2]
[Compound Group 2]
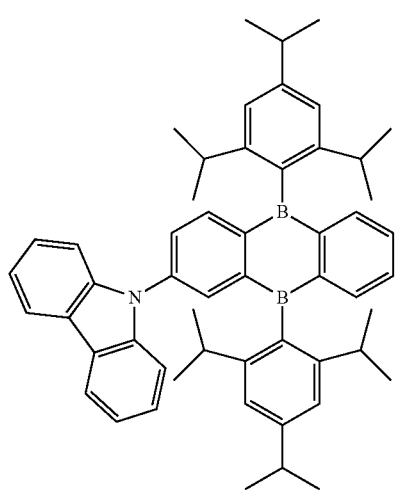
63
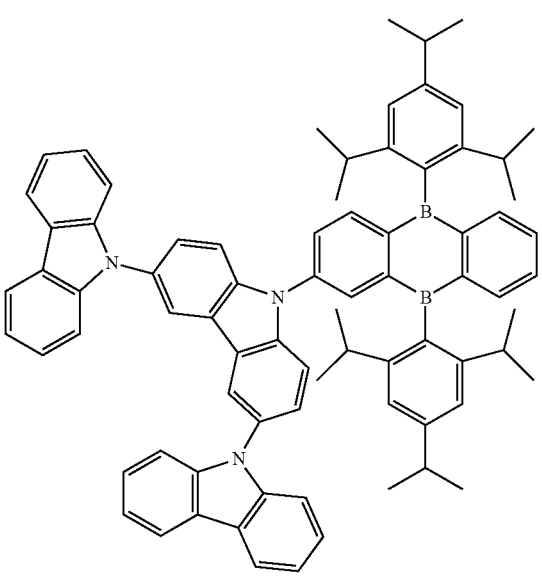
64

-continued
65
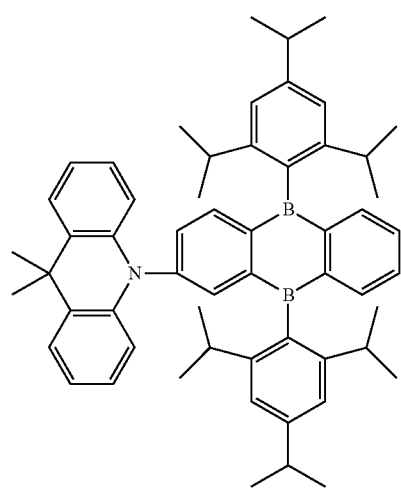
66
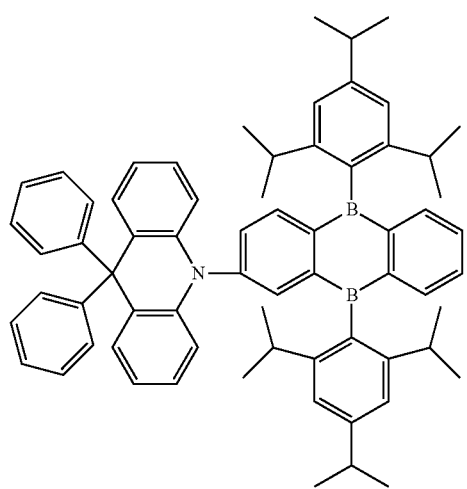
67
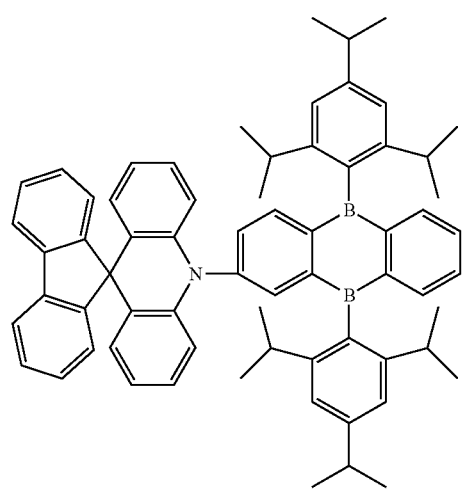
68
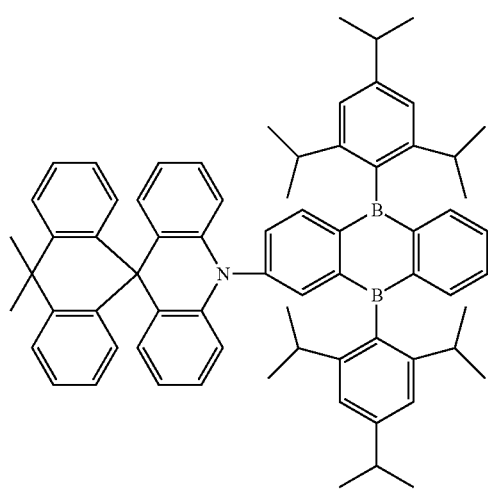
69
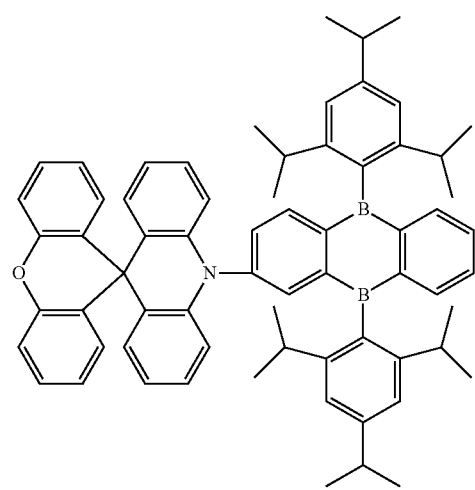
70
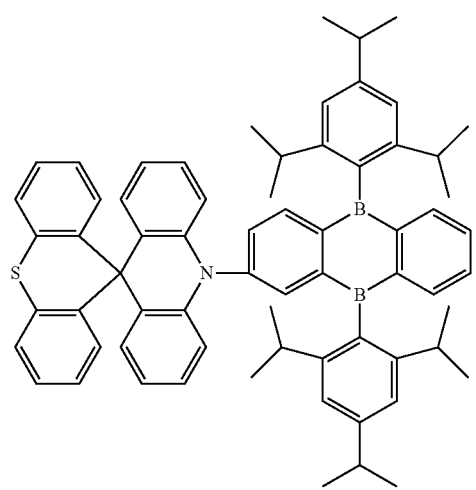

-continued
71
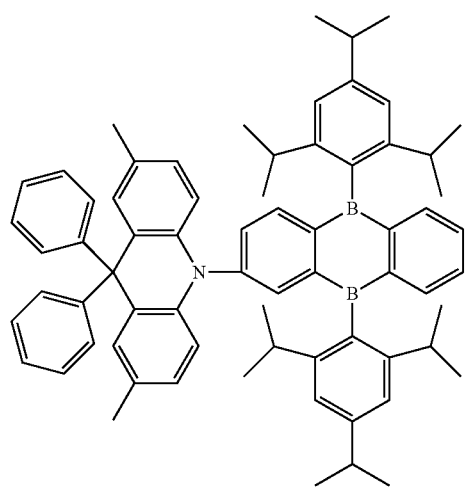
72
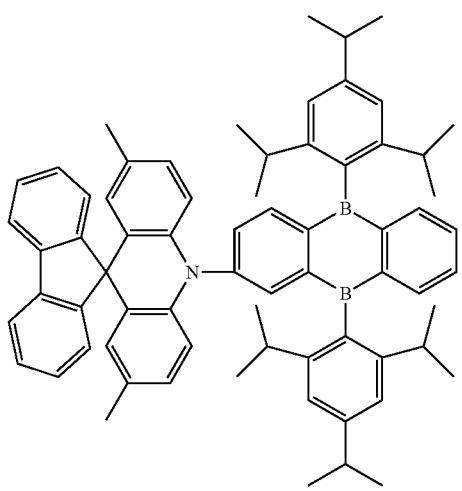
73
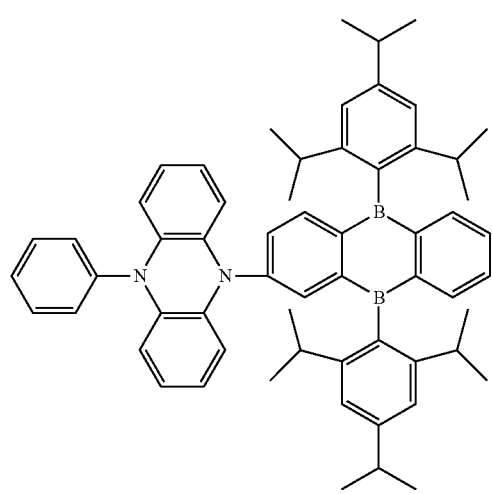
74
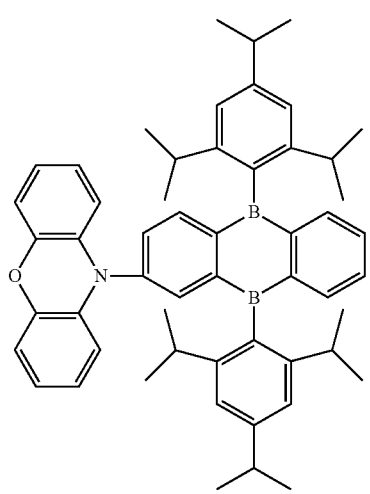
75
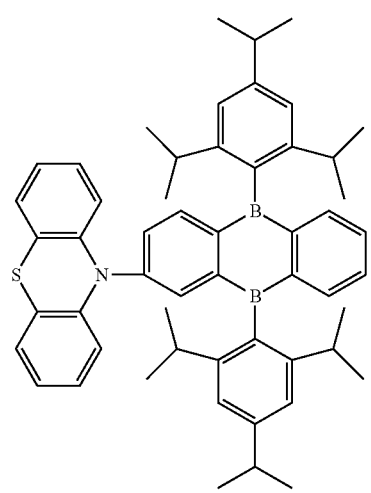
76
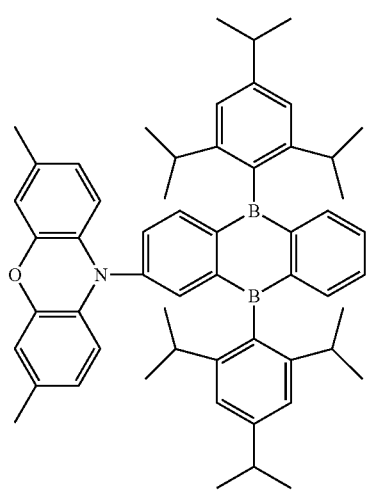

77
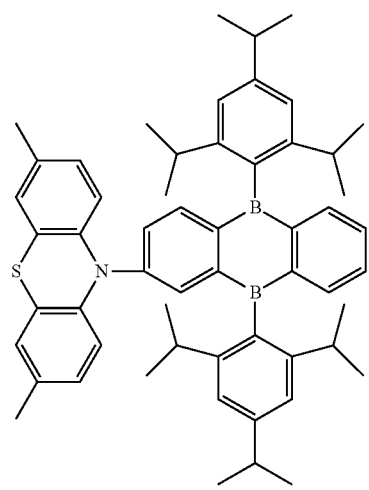
78
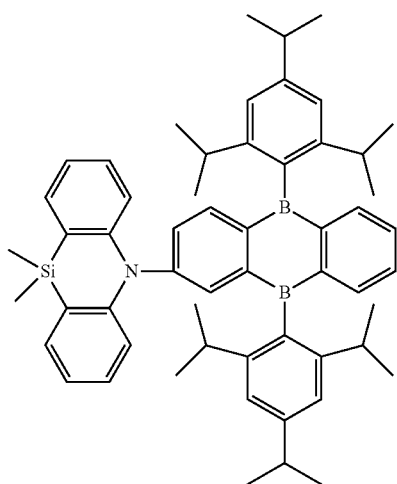
79
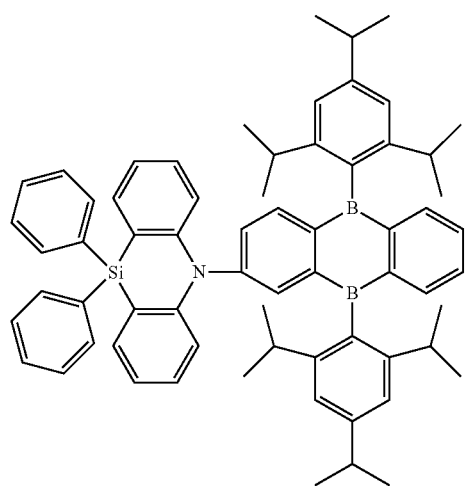
80
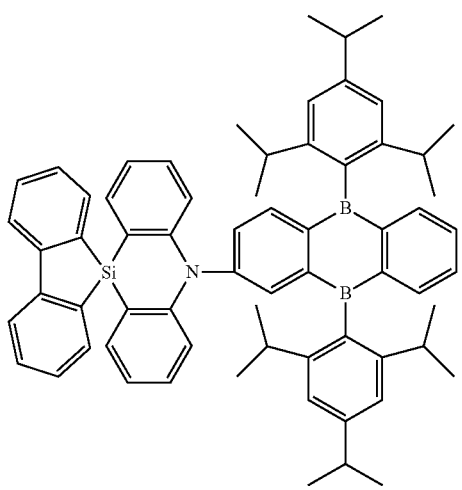
81
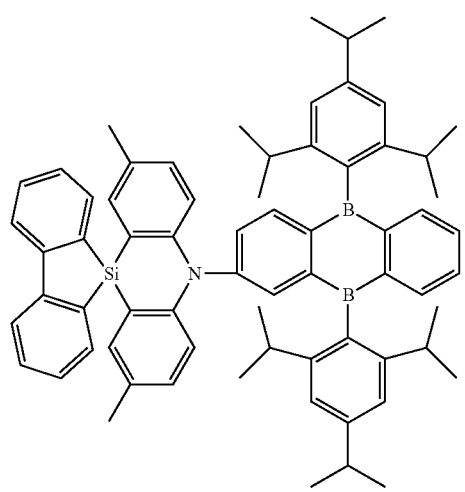
82
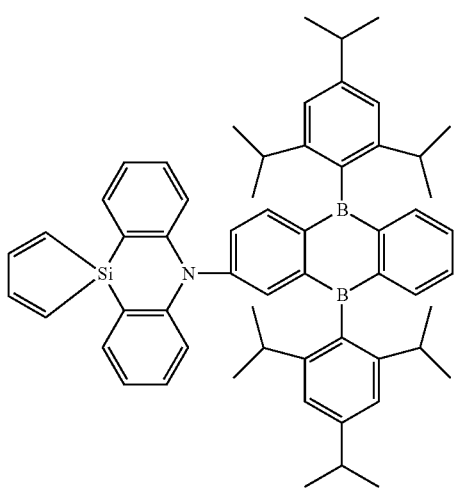

83
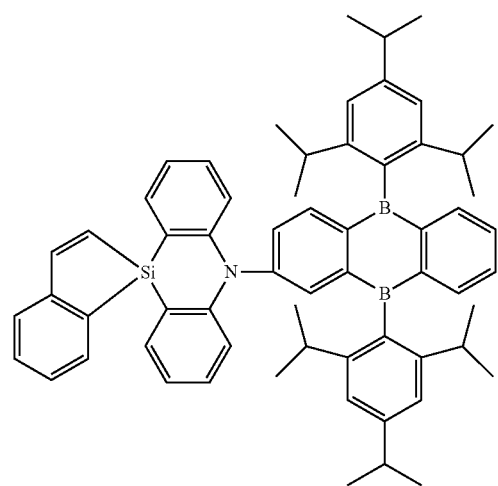
84
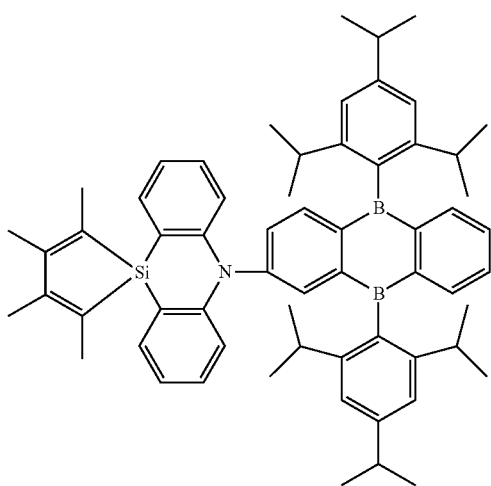
85
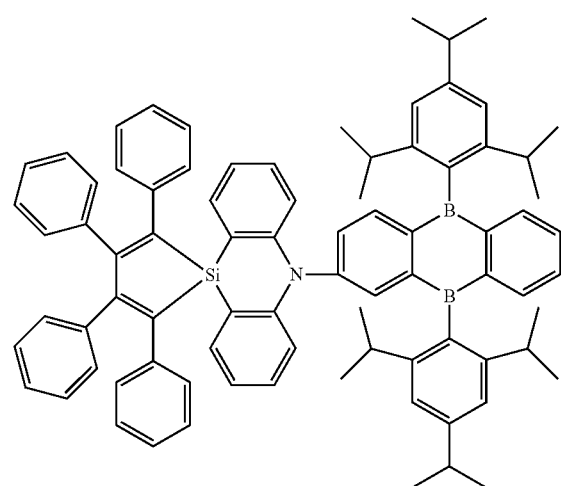
86
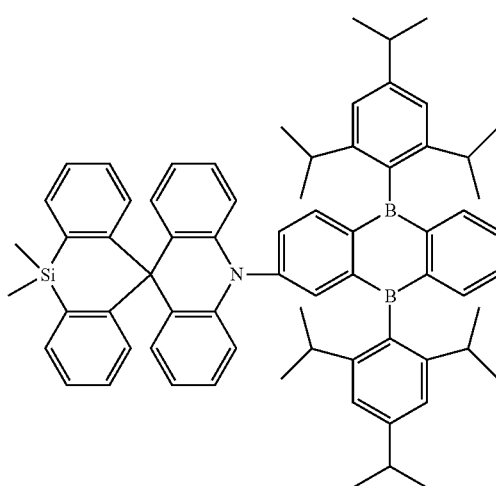
87
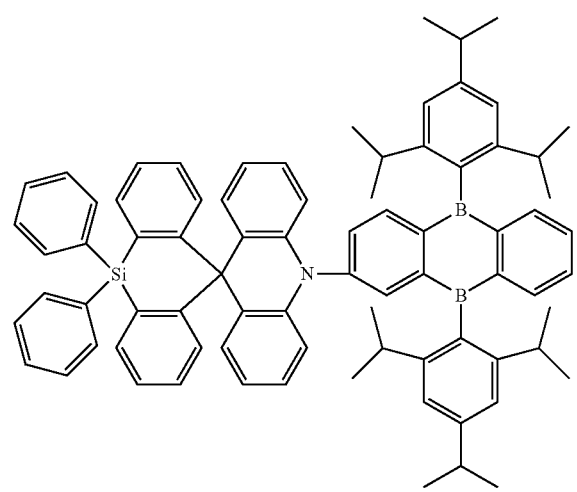
88
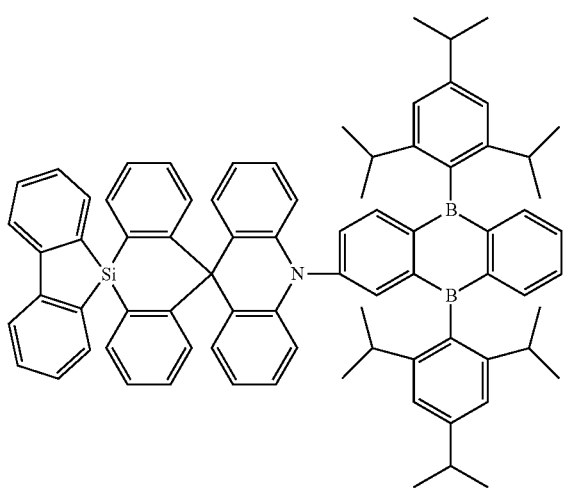

89
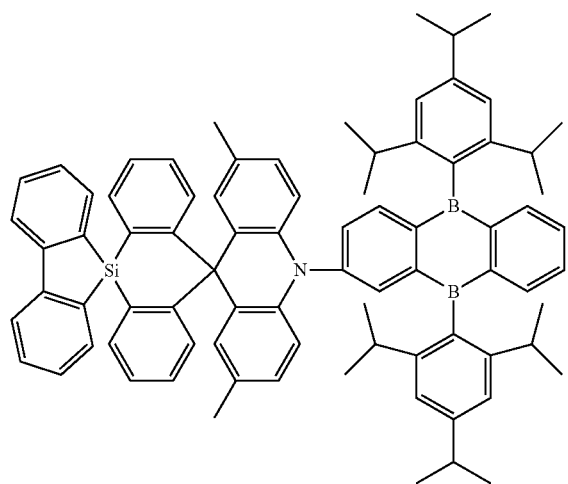
90
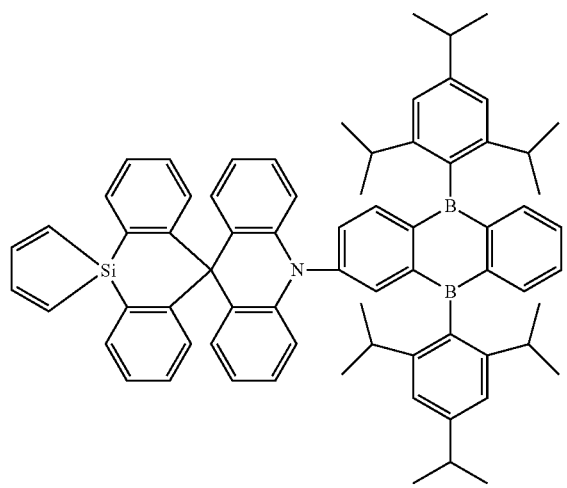
91
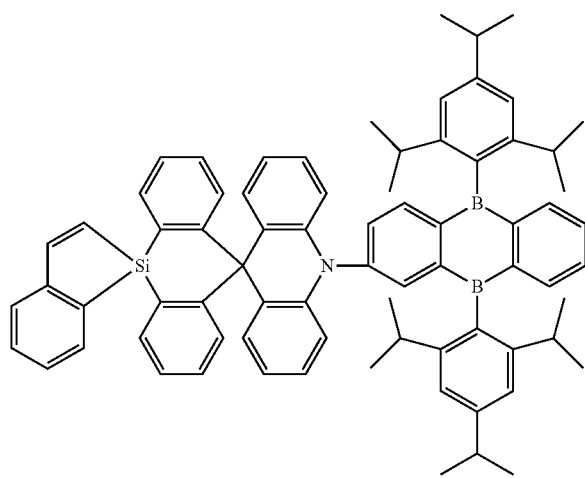
92
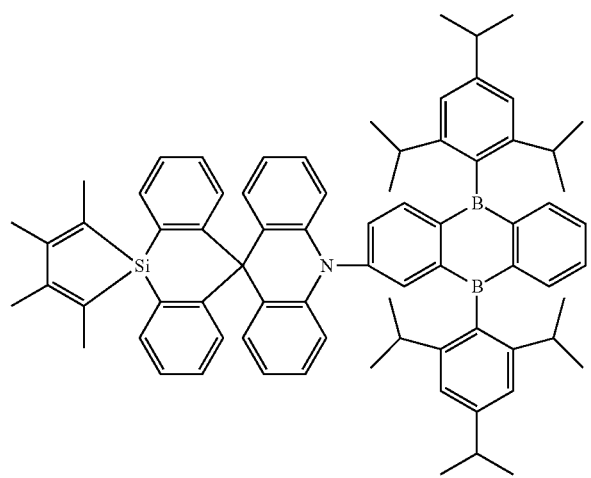
93
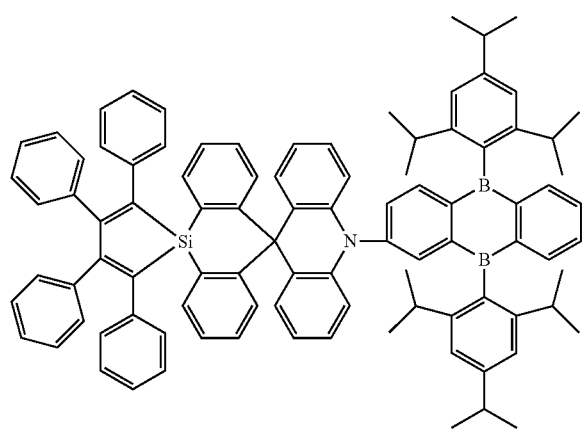
94
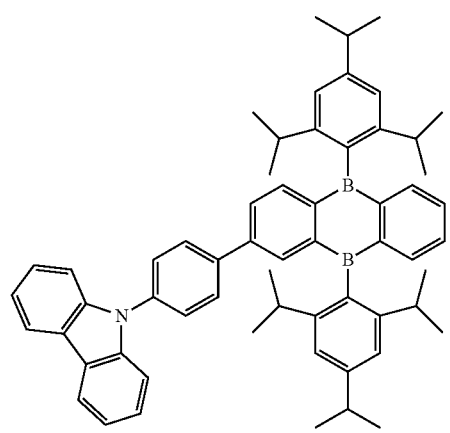

95
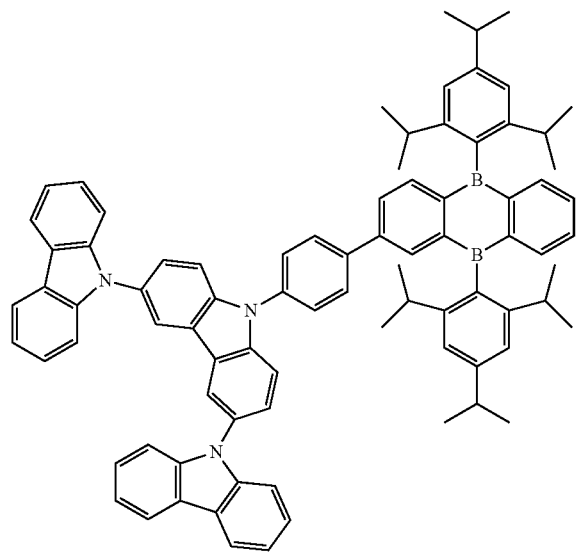
96
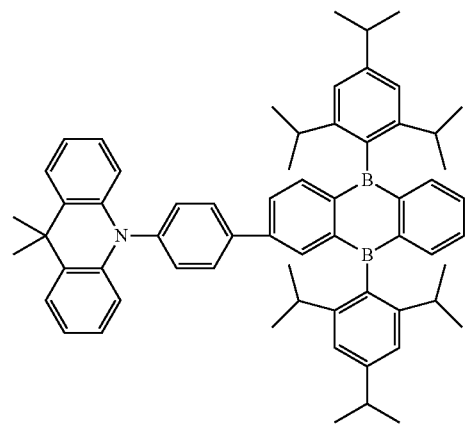
97
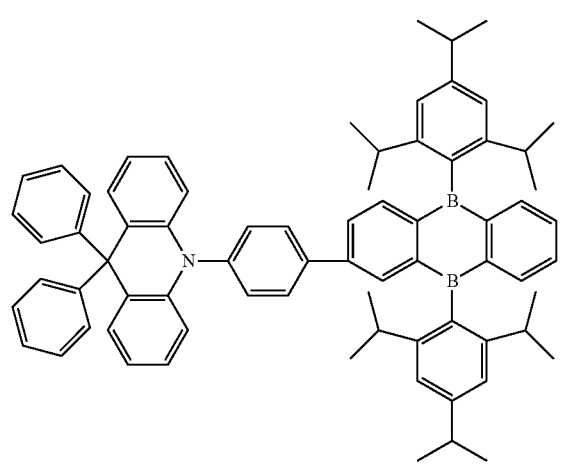
98
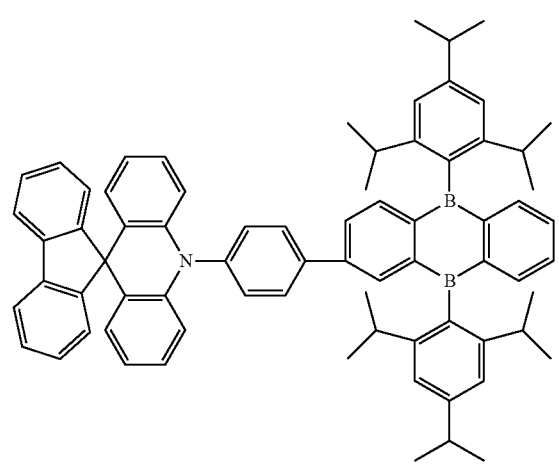
99
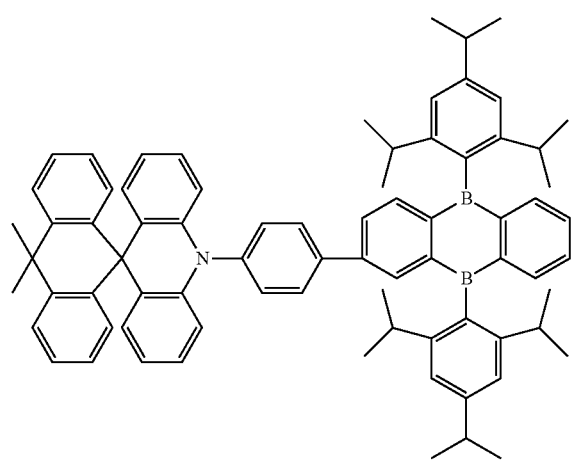
100
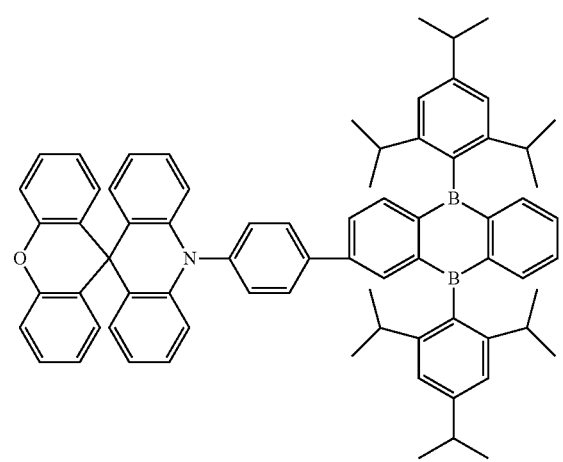

-continued
101
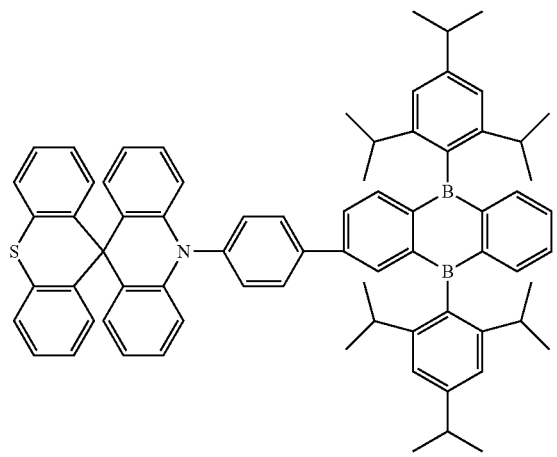
102
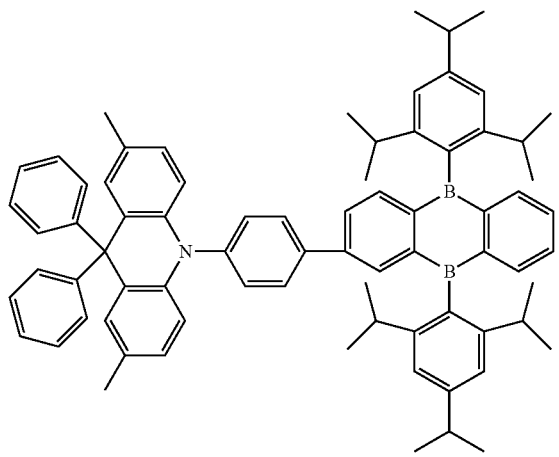
103
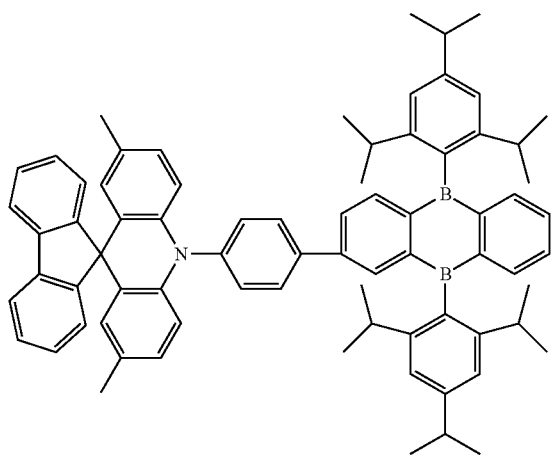
104
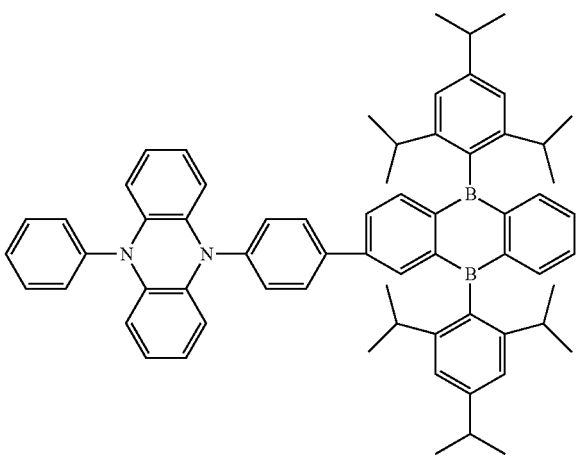
105
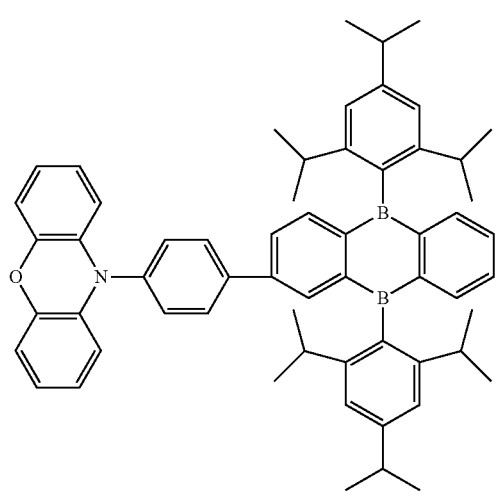
106
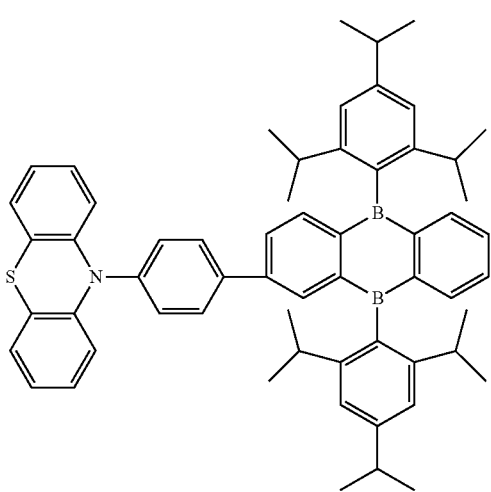

-continued
107
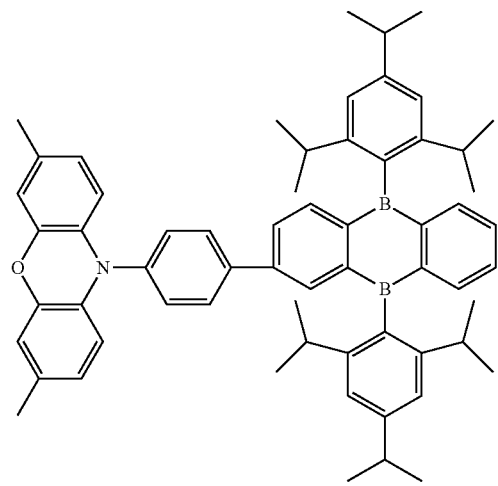
108
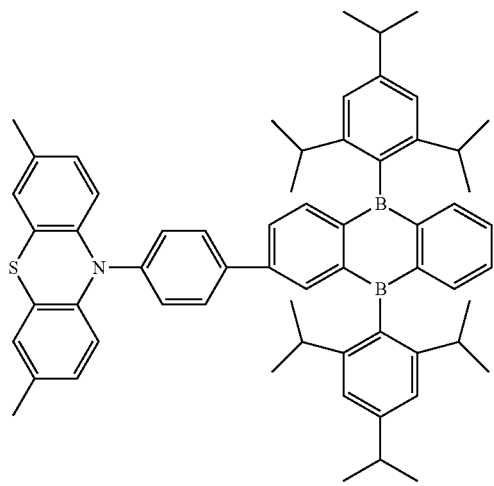
109
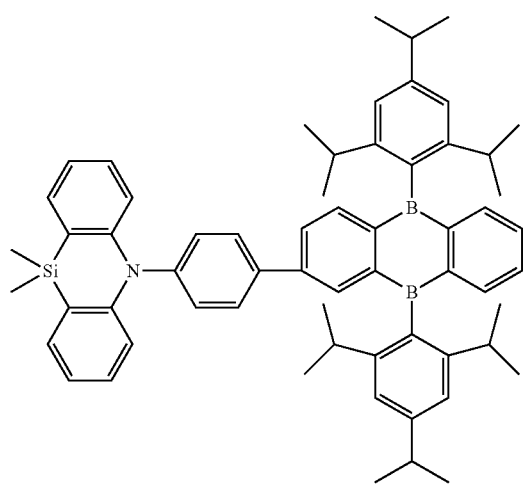
110
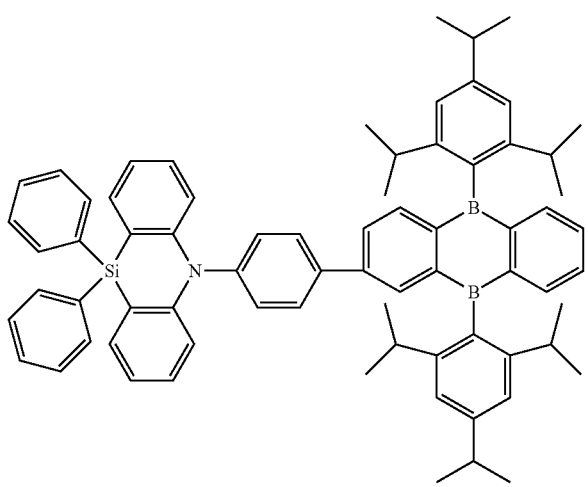
111
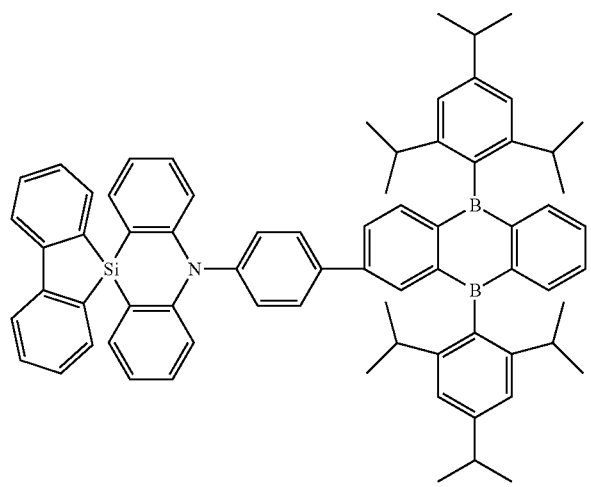
112
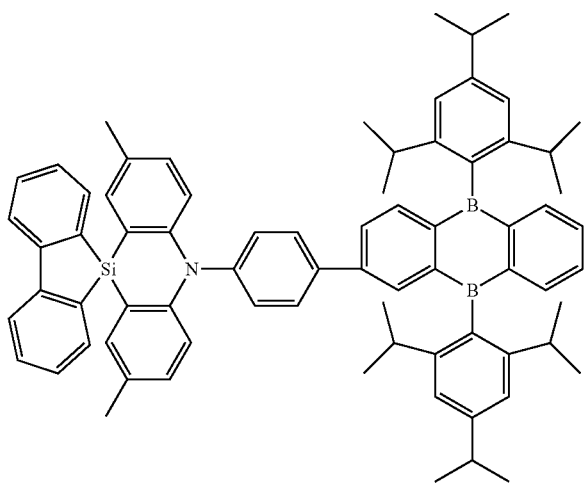

-continued
113
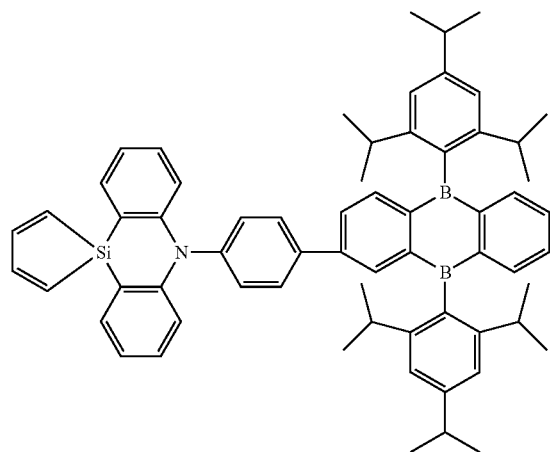
114
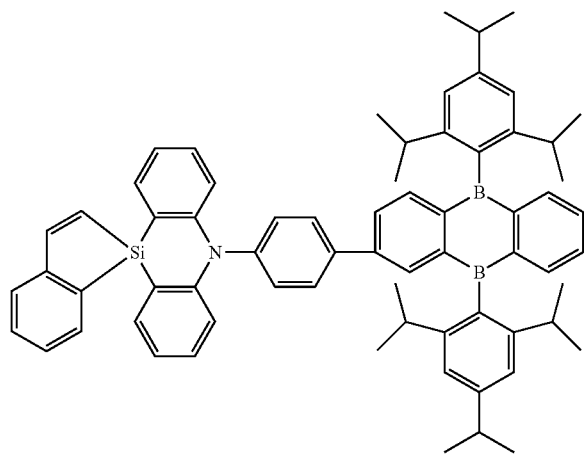
115
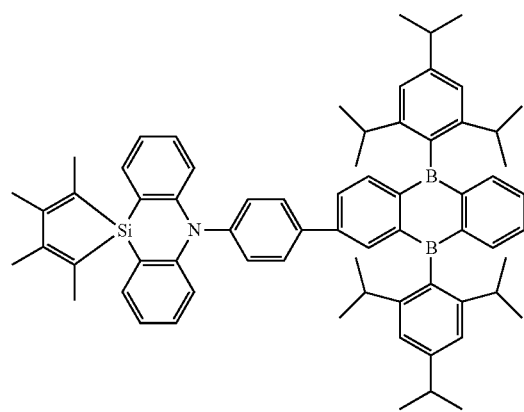
116
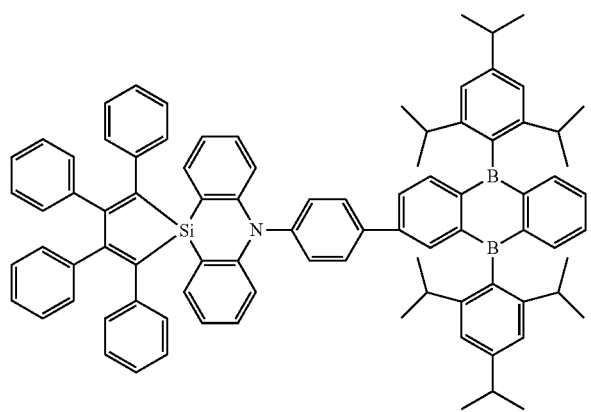
117
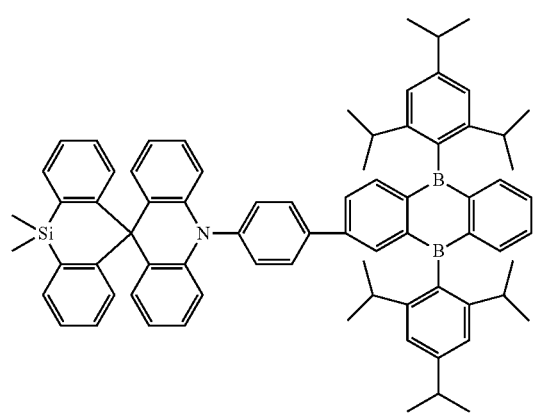
118
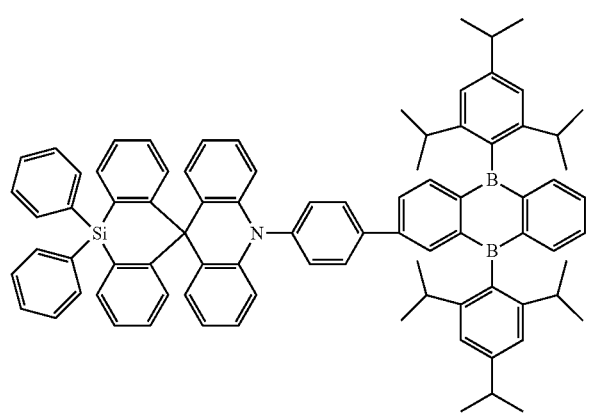

-continued
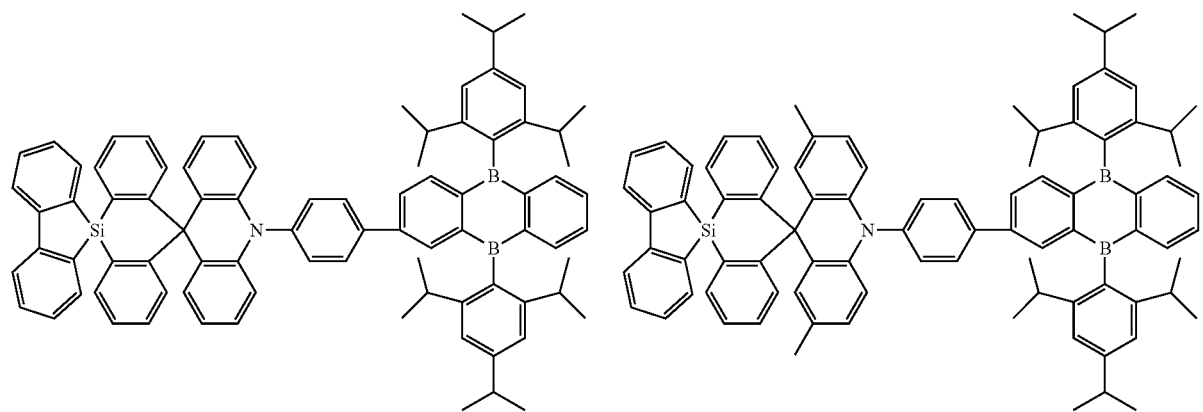
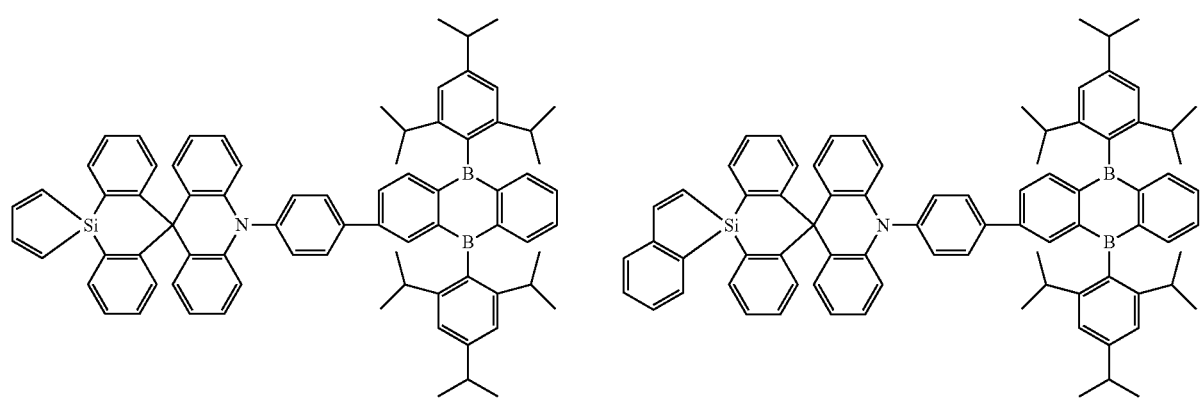
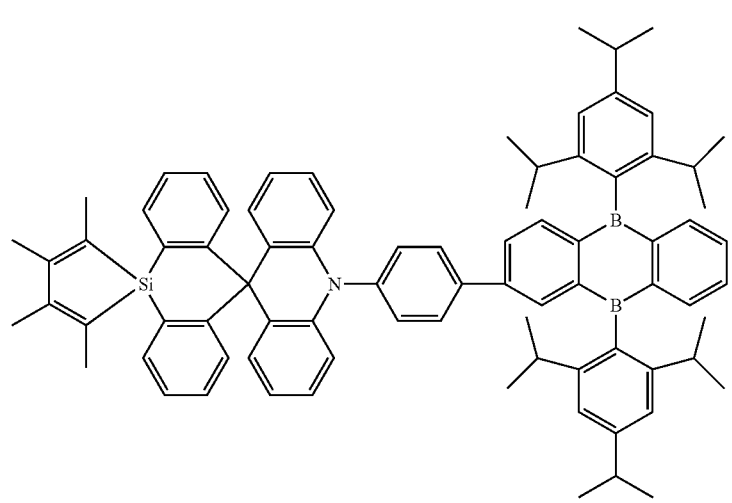

-continued
124
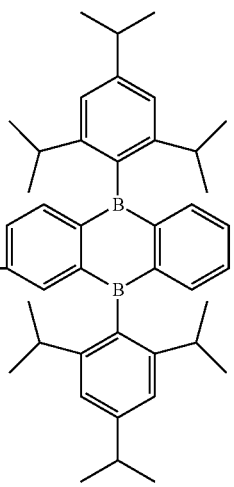
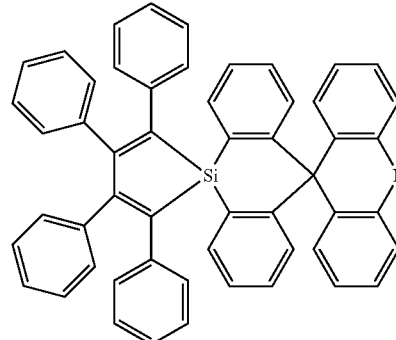
125
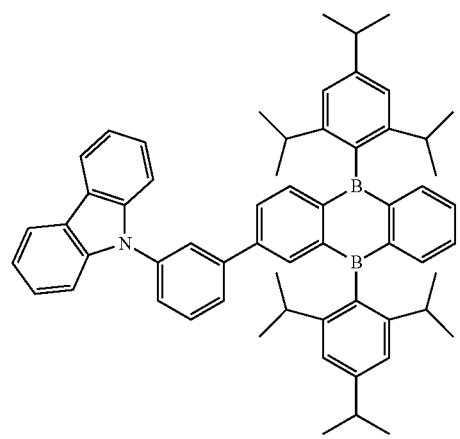
126
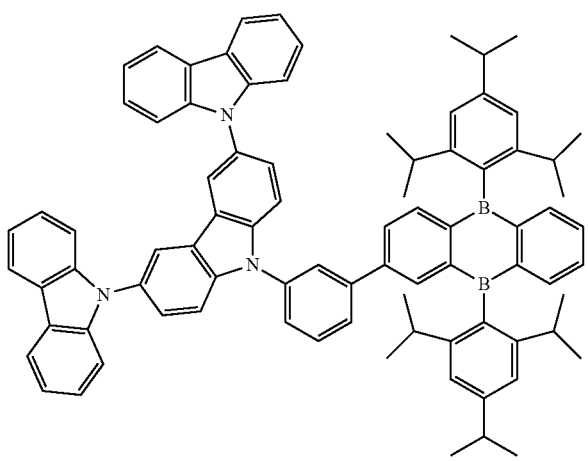
127
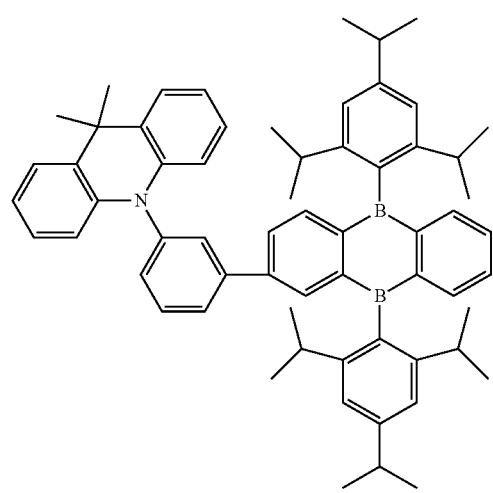
128
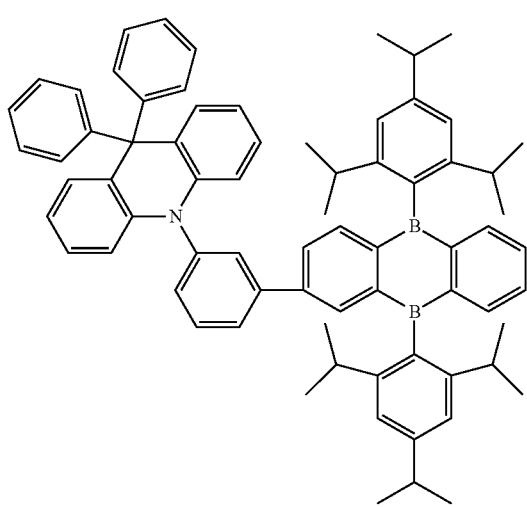

-continued
129
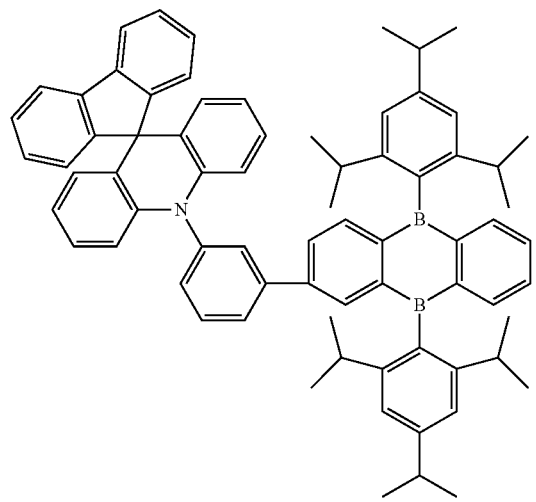
130
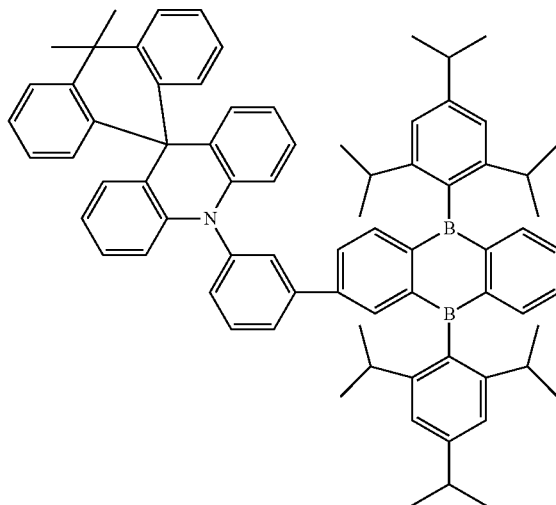
131
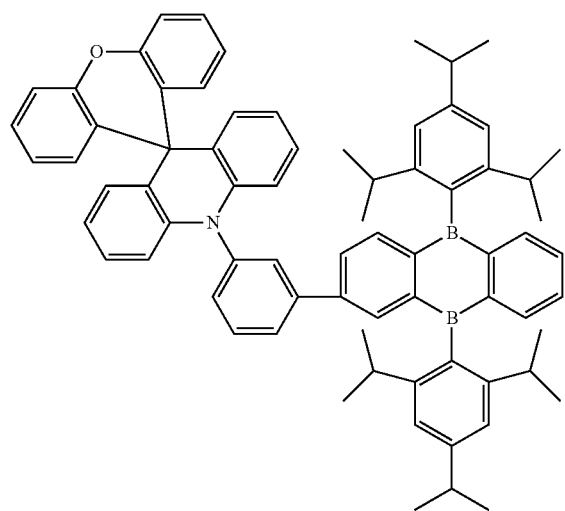
132
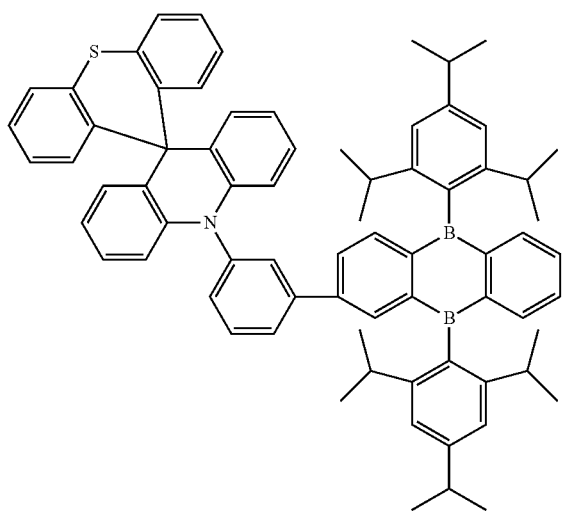
133
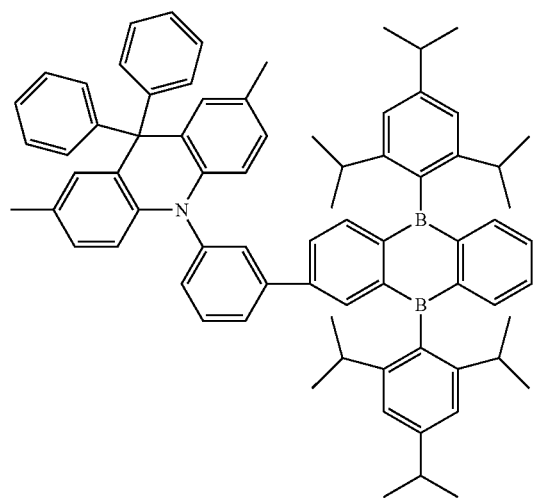
134
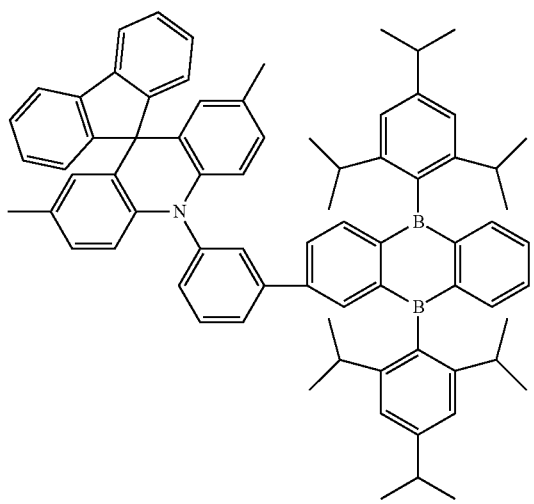

-continued
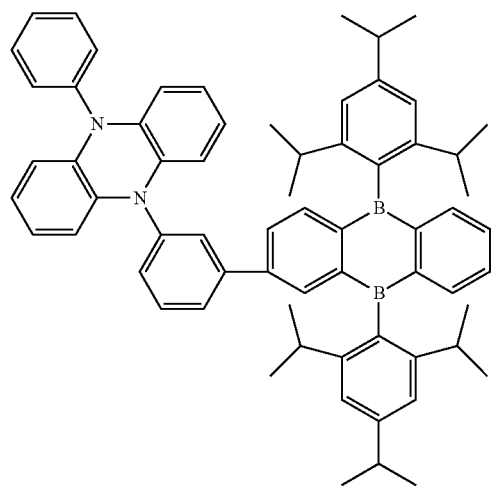
135
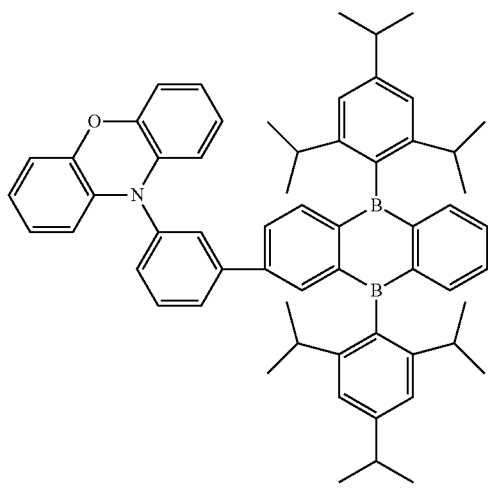
136
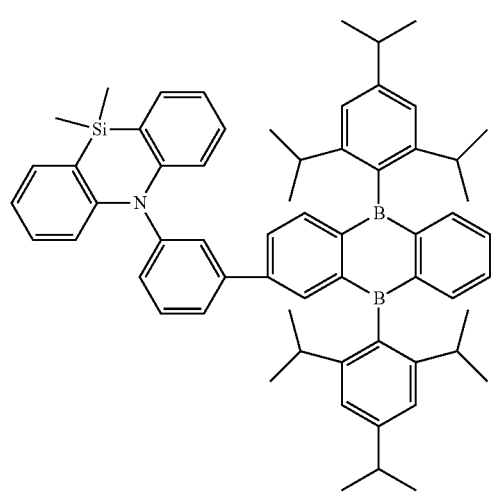
137
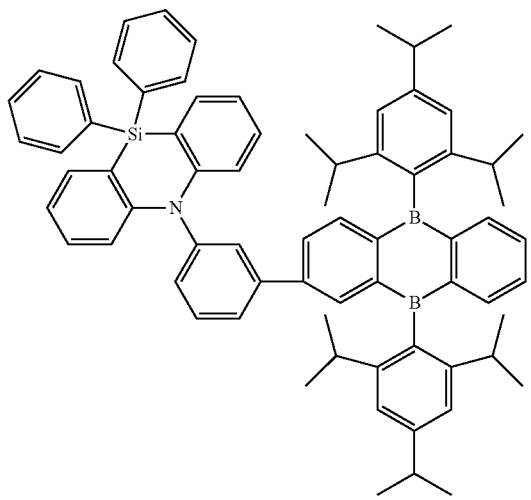
138
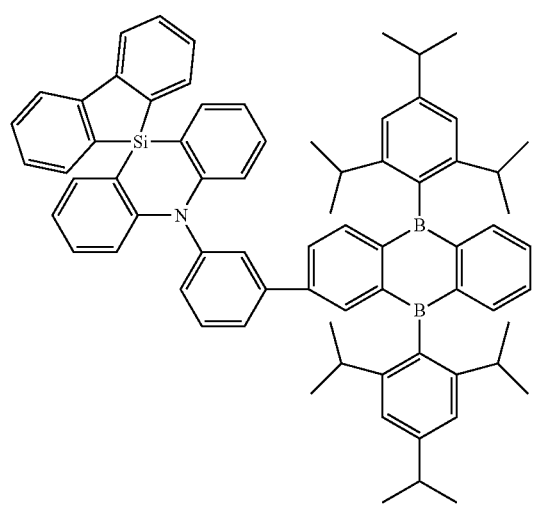
139
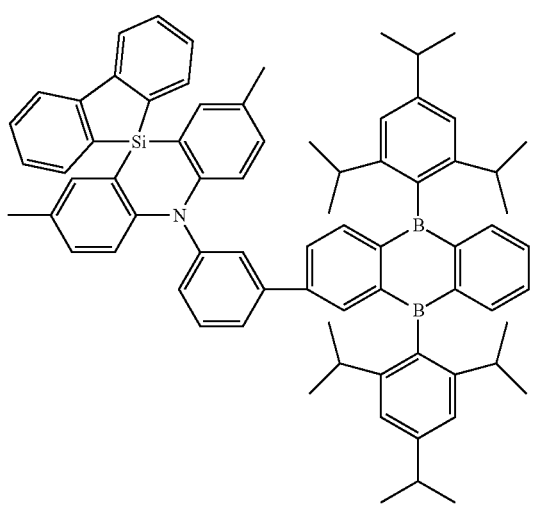
140

249 250
-continued
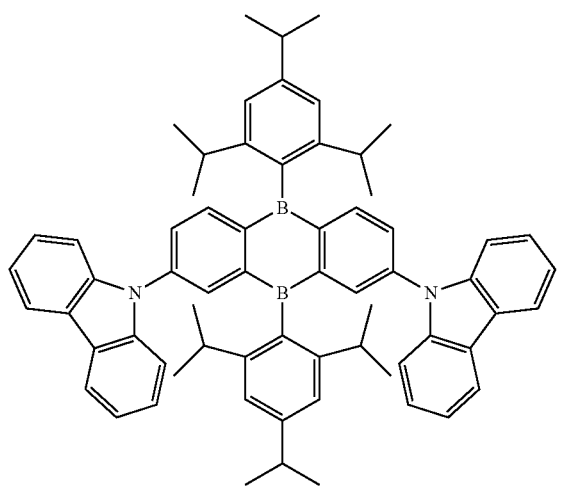
141
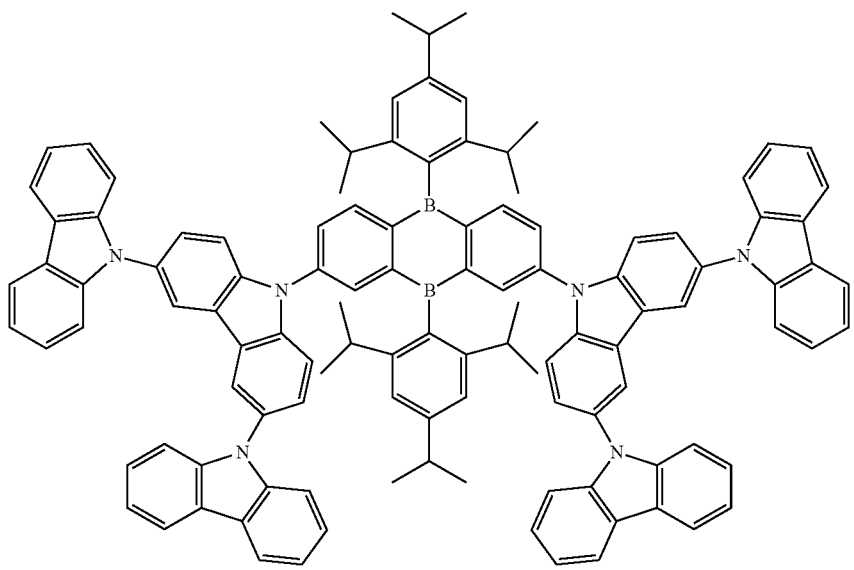
142
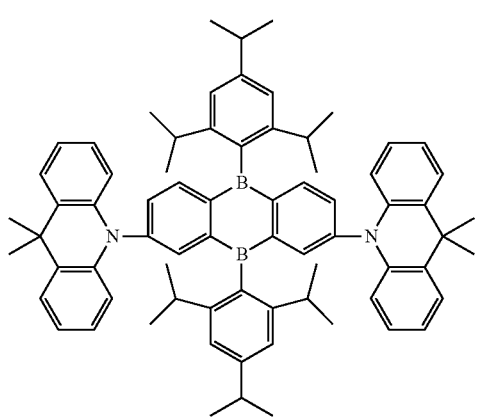
143
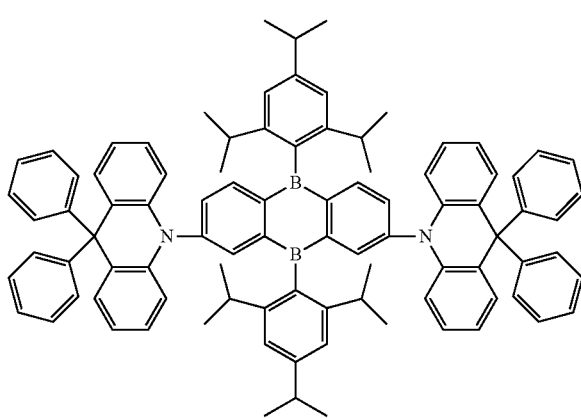
144

145
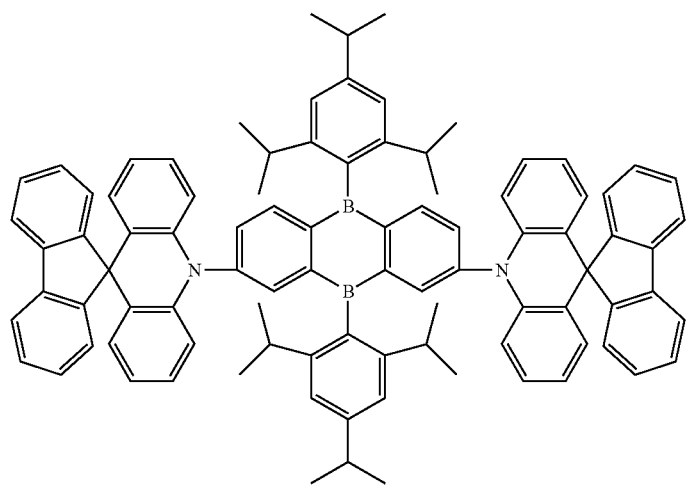
146
147
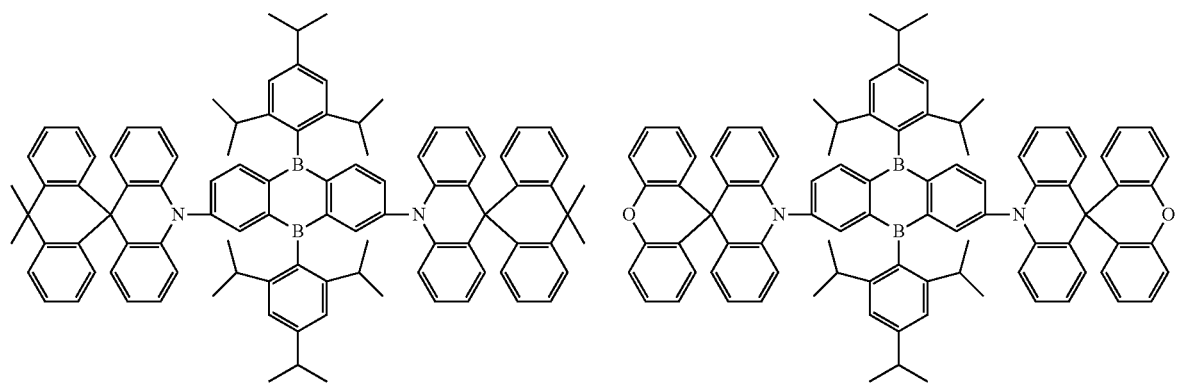
148
149
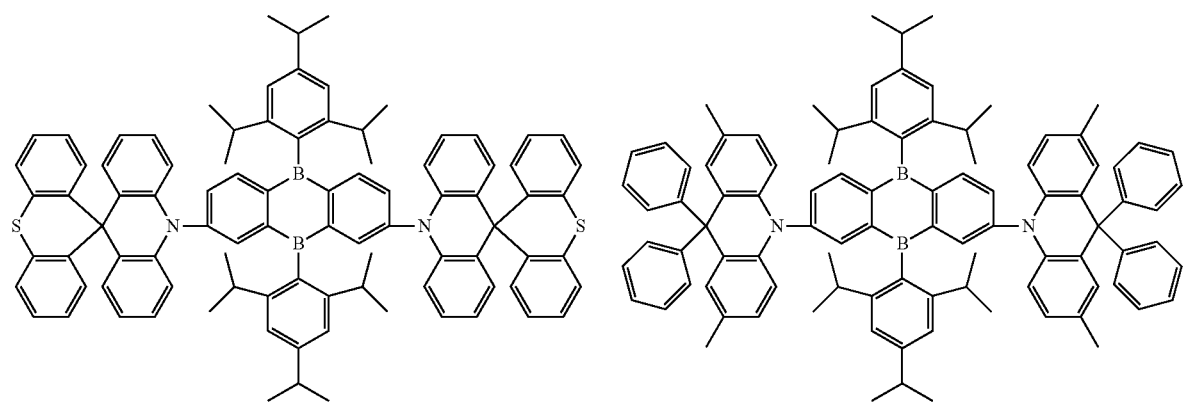

-continued

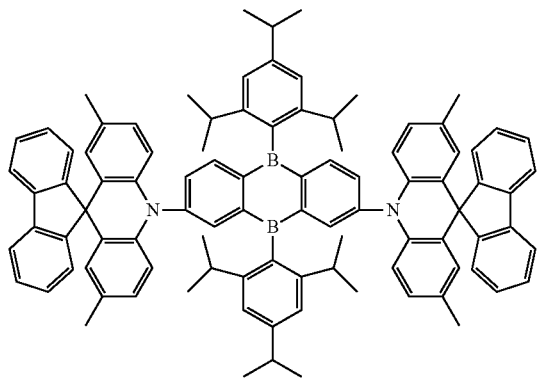

150

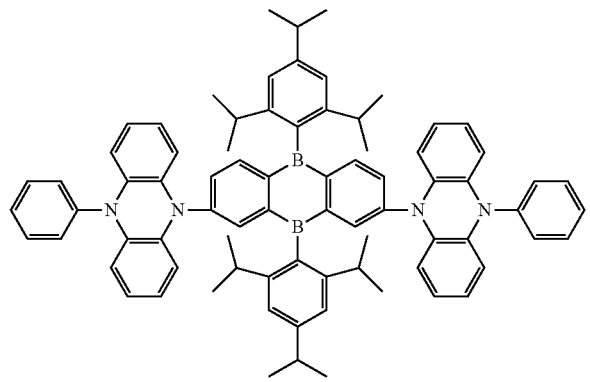

151

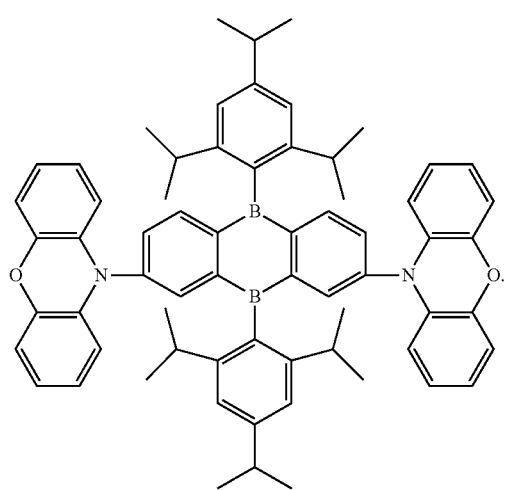

152

21. An organic electroluminescence device, comprising:
a first electrode;
a hole transport region provided on the first electrode;
an emission layer provided on the hole transport region;
an electron transport region provided on the emission layer; and
a second electrode provided on the electron transport region,
wherein the emission layer comprises a polycyclic compound represented by the following Formula 1:

[Formula 1]

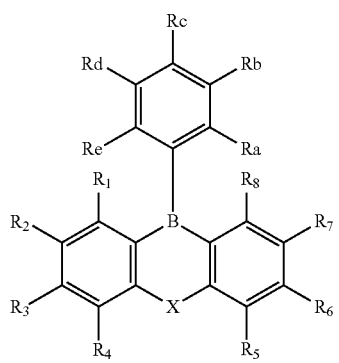

in Formula 1, X is O, SiR'R", S, or $BAr_1$, $Ar_1$ is substituted or unsubstituted aryl group having 6 to 30 carbon atoms for forming a ring, or substituted or unsubstituted heteroaryl group having 2 to 30 carbon atoms for forming a ring, R' and R" are each independently substituted or unsubstituted alkyl group having 1 to 30 carbon atoms, substituted or unsubstituted aryl group having 6 to 30 carbon atoms for forming a ring, or substituted or unsubstituted heteroaryl group having 2 to 30 carbon atoms for forming a ring, Ra to Re, and $R_1$ to $R_8$ are each independently hydrogen atom, deuterium atom, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, at least one of $R_1$ to $R_8$ is represented by the following Formula 2:

[Formula 2]

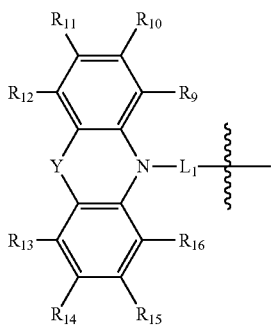

[Formula 3]

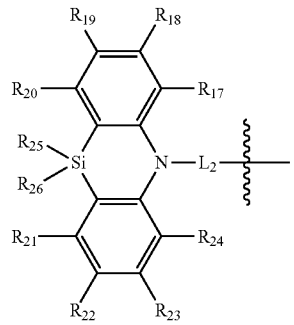

[Formula 4]

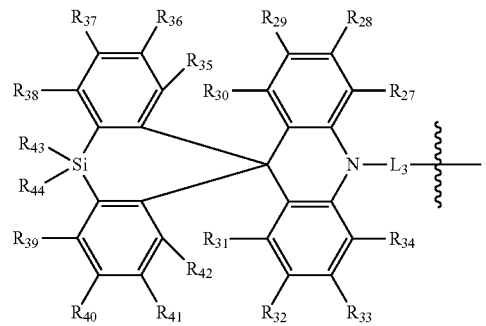

when X is $BAr_1$ in Formulae 2, Y is a direct linkage, $CZ_1Z_2$, $NZ_3$, $SiZ_4Z_5$, O, S or $CZ_6Z_7$ of which $Z_6$ and $Z_7$ combine with each other through Si to form a ring, when X is O, SiR'R", or S, Y is $SiZ_4Z_5$, or $CZ_6Z_7$ of which $Z_6$ and $Z_7$ combine with each other through Si to form a ring, $Z_1$ to $Z_5$, and $R_9$ to $R_{16}$ are each independently hydrogen atom, deuterium atom, halogen atom, cyano group, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, $Z_6$ and $Z_7$ are each independently substituted or unsubstituted phenyl group, optionally, $Z_1$ and $Z_2$, and $Z_4$ and $Z_5$ each two groups independently combine with each other to form a ring, and $L_1$ is a direct linkage, or substituted or unsubstituted arylene group having 6 to 30 carbon atoms for forming a ring.

22. The organic electroluminescence device of claim 21, wherein Formula 2 is represented by the following Formula 3 or 4:

in Formulae 3 and 4, $R_{17}$ to $R_{44}$ are each independently hydrogen atom, deuterium atom, halogen atom, cyano group, substituted or unsubstituted alkyl group having 1 to 10 carbon atoms, substituted or unsubstituted aryl group having 6 to 30 carbon atoms for forming a ring, or substituted or unsubstituted heteroaryl group having 2 to 30 carbon atoms for forming a ring, optionally, $R_{25}$ and $R_{26}$, and $R_{43}$ and $R_{44}$ each two groups independently combine with each other to form a ring, and $L_2$ and $L_3$ are each independently a direct linkage, or substituted or unsubstituted arylene group having 6 to 30 carbon atoms for forming a ring.

23. The organic electroluminescence device of claim 21, wherein the polycyclic compound represented by Formula 1 is a material for emitting thermally activated delayed fluorescence with wavelength from about 440 nm to about 460 nm.

* * * * *